United States Patent
Leung et al.

(10) Patent No.: US 10,939,912 B2
(45) Date of Patent: Mar. 9, 2021

(54) MICROSTRUCTURE-BASED SYSTEMS, APPARATUS, AND METHODS FOR WOUND CLOSURE

(71) Applicant: KitoTech Medical, Inc., Mercer Island, WA (US)

(72) Inventors: Cheuk Yin Paul Leung, Bellevue, WA (US); Ronald J. Berenson, Mercer Island, WA (US)

(73) Assignee: KitoTech Medical, Inc., Seattle, WA (US)

( * ) Notice: Subject to any disclaimer, the term of this patent is extended or adjusted under 35 U.S.C. 154(b) by 0 days.

(21) Appl. No.: 15/446,999

(22) Filed: Mar. 1, 2017

(65) Prior Publication Data
US 2017/0333039 A1    Nov. 23, 2017

Related U.S. Application Data

(60) Provisional application No. 62/402,492, filed on Sep. 30, 2016, provisional application No. 62/302,055, filed on Mar. 1, 2016.

(51) Int. Cl.
*A61B 17/08* (2006.01)
*A61B 17/00* (2006.01)

(52) U.S. Cl.
CPC .......... *A61B 17/08* (2013.01); *A61B 17/083* (2013.01); *A61B 17/085* (2013.01);
(Continued)

(58) Field of Classification Search
CPC .............. A61B 17/064; A61B 17/0642; A61B 17/0644; A61B 17/08; A61B 17/083;
(Continued)

(56) References Cited

U.S. PATENT DOCUMENTS

| 345,541 A | * | 7/1886 | Reichardt | A61B 17/085 |
| | | | | 606/216 |
| 2,472,009 A | * | 5/1949 | Gardner | A61B 17/08 |
| | | | | 606/215 |

(Continued)

FOREIGN PATENT DOCUMENTS

| AU | 767122 | 10/2003 |
| AU | 2004200303 | 2/2004 |

(Continued)

OTHER PUBLICATIONS

Francesko and Tzanov, "Chitin, Chitosan and Derivatives for Wound Healing and Tissue Engineering," Adv Biochem Engin/Biotechnol (2011); 125: 1-27.

(Continued)

*Primary Examiner* — Dianne Dornbusch
(74) *Attorney, Agent, or Firm* — Schwegman Lundberg & Woessner, P.A.

(57) ABSTRACT

Systems, apparatus, and methods related to wound closure devices comprising one or more microstructures are described herein. In some embodiments, the wound closure devices include a backing and a microstructure array. The microstructure array may include a first portion, a second portion, and a bridge portion. The first portion and the second portion each include one or more microstructures configured to penetrate tissue. Additionally, the first portion and the second portion each include one or more expandable portions such that the wound closure device is configured to expand in length. The wound closure device is configured to grip tissue surrounding a wound to either close the wound or secure the tissue in place.

23 Claims, 54 Drawing Sheets

(52) U.S. Cl.
CPC ............... *A61B 2017/00004* (2013.01); *A61B 2017/00862* (2013.01); *A61B 2017/081* (2013.01)

(58) Field of Classification Search
CPC .......... A61B 17/085; A61B 2017/0641; A61B 2017/0645; A61B 2017/081; A61B 2017/088
See application file for complete search history.

(56) References Cited

U.S. PATENT DOCUMENTS

| | | | |
|---|---|---|---|
| 2,575,205 A * | 11/1951 | Brown | A45D 44/22 606/204.35 |
| 2,619,084 A * | 11/1952 | Brown | A45D 44/22 606/204.35 |
| 2,669,747 A * | 2/1954 | Detaranto | A47J 43/18 452/176 |
| 3,068,869 A * | 12/1962 | Sheiden | A61B 17/08 606/216 |
| 3,473,528 A * | 10/1969 | Mishkin | A61B 17/58 606/54 |
| 3,613,679 A * | 10/1971 | Bijou | A61F 13/00059 602/75 |
| 3,931,821 A * | 1/1976 | Kletschka | A61B 17/0466 606/233 |
| 4,430,998 A | 2/1984 | Harvey et al. | |
| 4,535,772 A * | 8/1985 | Sheehan | A61B 17/085 606/217 |
| 4,637,380 A * | 1/1987 | Orejola | A61B 17/08 606/216 |
| 4,762,260 A | 8/1988 | Richards et al. | |
| 4,803,078 A | 2/1989 | Sakai et al. | |
| 5,047,047 A * | 9/1991 | Yoon | A61B 17/083 606/213 |
| 5,531,790 A * | 7/1996 | Frechet | A61B 90/02 606/1 |
| 5,843,123 A * | 12/1998 | Brazeau | A61B 17/085 606/213 |
| 5,916,224 A * | 6/1999 | Esplin | A61B 17/1146 606/151 |
| 5,968,097 A * | 10/1999 | Frechet | A61B 90/02 606/187 |
| 6,168,596 B1 * | 1/2001 | Wellisz | A61B 17/688 606/151 |
| 6,254,624 B1 * | 7/2001 | Oddsen | A61B 17/08 606/150 |
| 6,256,533 B1 | 7/2001 | Yuzhakov et al. | |
| 6,312,612 B1 | 11/2001 | Sherman et al. | |
| 6,334,856 B1 * | 1/2002 | Allen | A61B 5/14514 128/898 |
| 6,379,324 B1 | 4/2002 | Gartstein et al. | |
| 6,451,240 B1 | 9/2002 | Sherman et al. | |
| 6,471,715 B1 * | 10/2002 | Weiss | A61B 17/04 606/216 |
| 6,471,903 B2 | 10/2002 | Sherman et al. | |
| 6,503,231 B1 | 1/2003 | Prausnitz et al. | |
| 6,537,264 B1 * | 3/2003 | Cormier | A61M 37/0015 600/575 |
| 6,565,532 B1 | 5/2003 | Yuzhakov et al. | |
| 6,589,202 B1 | 7/2003 | Powell | |
| 6,611,707 B1 | 8/2003 | Prausnitz et al. | |
| 6,652,478 B1 | 11/2003 | Gartstein et al. | |
| 6,712,839 B1 * | 3/2004 | Lonne | A61B 17/085 606/233 |
| 6,743,211 B1 | 6/2004 | Prausnitz et al. | |
| 6,931,277 B1 | 8/2005 | Yuzhakov et al. | |
| 6,960,193 B2 | 11/2005 | Rosenberg | |
| 7,060,192 B2 | 6/2006 | Yuzhakov et al. | |
| 7,144,495 B2 | 12/2006 | Teodorczyk et al. | |
| 7,160,312 B2 * | 1/2007 | Saadat | A61B 5/4238 606/153 |
| 7,172,615 B2 * | 2/2007 | Morriss | A61B 90/02 606/215 |
| 7,226,439 B2 | 6/2007 | Prausnitz et al. | |
| 7,344,499 B1 | 3/2008 | Prausnitz et al. | |
| 7,416,541 B2 | 8/2008 | Yuzhakov et al. | |
| 7,455,681 B2 * | 11/2008 | Wilke | A61B 17/0466 606/216 |
| 7,510,566 B2 | 3/2009 | Jacobs et al. | |
| 7,626,070 B2 | 12/2009 | Propp | |
| 7,658,728 B2 | 2/2010 | Yuzhakov | |
| 7,683,234 B2 | 3/2010 | Gurtner et al. | |
| 7,686,829 B2 * | 3/2010 | Elliott | A61B 17/08 606/216 |
| 7,785,301 B2 * | 8/2010 | Yuzhakov | A61M 37/0015 604/272 |
| 7,806,266 B2 | 10/2010 | Hagino et al. | |
| 8,049,058 B2 | 11/2011 | Propp | |
| 8,053,624 B2 | 11/2011 | Propp | |
| 8,063,263 B2 * | 11/2011 | Gurtner | A61K 47/67 602/41 |
| 8,157,839 B2 * | 4/2012 | Riskin | A61B 17/083 606/214 |
| 8,168,850 B2 | 5/2012 | Gurtner et al. | |
| 8,183,428 B2 | 5/2012 | Gurtner et al. | |
| 8,250,729 B2 | 8/2012 | Lee et al. | |
| 8,388,631 B2 * | 3/2013 | Oostman, Jr. | A61B 17/0206 606/133 |
| 8,389,791 B2 | 3/2013 | Gurtner et al. | |
| 8,397,973 B1 | 3/2013 | Hausen | |
| 8,414,548 B2 | 4/2013 | Yuzhakov | |
| 8,540,672 B2 | 9/2013 | Mcallister | |
| 8,663,275 B2 * | 3/2014 | O'Malley | A61B 17/02 606/216 |
| 8,777,987 B2 * | 7/2014 | Herrmann | B26F 3/08 606/228 |
| 8,852,214 B2 * | 10/2014 | Kubiak | A61B 17/1146 606/151 |
| 8,894,683 B2 * | 11/2014 | Weadock | A61B 17/0401 606/213 |
| 9,050,086 B2 * | 6/2015 | Belson | A61B 17/085 |
| 9,089,328 B2 * | 7/2015 | Belson | A61B 17/08 |
| 9,358,376 B2 | 6/2016 | Altarac | |
| 9,392,965 B2 * | 7/2016 | Tenney | A61B 5/1072 |
| 9,414,840 B2 * | 8/2016 | Fleischmann | A61B 17/08 |
| 9,427,309 B2 * | 8/2016 | Kubiak | A61F 2/0811 |
| 9,993,620 B2 * | 6/2018 | Le | A61M 25/02 |
| 10,219,804 B2 * | 3/2019 | Linder | A61F 2/0811 |
| 10,492,780 B2 * | 12/2019 | Gross | A61B 17/0485 |
| 2001/0051815 A1 * | 12/2001 | Esplin | A61B 17/0401 606/232 |
| 2002/0082543 A1 | 6/2002 | Park et al. | |
| 2002/0133129 A1 | 9/2002 | Arias et al. | |
| 2002/0168290 A1 | 11/2002 | Yuzhakov et al. | |
| 2002/0193754 A1 * | 12/2002 | Cho | A61M 37/0015 604/272 |
| 2003/0028087 A1 | 2/2003 | Yuzhakov et al. | |
| 2003/0028125 A1 | 2/2003 | Yuzhakov et al. | |
| 2003/0065360 A1 | 4/2003 | Jacobs et al. | |
| 2003/0074021 A1 * | 4/2003 | Morriss | A61B 90/02 606/215 |
| 2003/0176890 A1 * | 9/2003 | Buckman | A61B 17/08 606/213 |
| 2003/0212344 A1 | 11/2003 | Yuzhakov et al. | |
| 2004/0010276 A1 * | 1/2004 | Jacobs | A61B 17/064 606/153 |
| 2004/0138705 A1 | 7/2004 | Heino et al. | |
| 2005/0049549 A1 * | 3/2005 | Wong | A61B 10/0064 604/46 |
| 2005/0119694 A1 * | 6/2005 | Jacobs | A61B 17/064 606/213 |
| 2005/0143713 A1 | 6/2005 | Delmore et al. | |
| 2005/0148921 A1 | 7/2005 | Hsu | |
| 2005/0197699 A1 * | 9/2005 | Jacobs | A61F 2/0811 623/13.14 |
| 2005/0261631 A1 | 11/2005 | Clarke et al. | |
| 2006/0058842 A1 * | 3/2006 | Wilke | A61M 1/0088 606/213 |

(56) References Cited

U.S. PATENT DOCUMENTS

| | | | |
|---|---|---|---|
| 2006/0093658 A1* | 5/2006 | Sathyan | A61K 9/0021 424/448 |
| 2006/0228320 A1 | 10/2006 | Minami et al. | |
| 2007/0021779 A1* | 1/2007 | Garvin | A61B 17/08 606/216 |
| 2007/0191761 A1 | 8/2007 | Boone et al. | |
| 2007/0225676 A1 | 9/2007 | Prausnitz et al. | |
| 2007/0282374 A1* | 12/2007 | Sogard | A61B 17/10 606/219 |
| 2007/0288040 A1* | 12/2007 | Ferree | A61F 2/442 606/151 |
| 2007/0293815 A1* | 12/2007 | Chan | A61M 37/0015 604/46 |
| 2007/0299388 A1* | 12/2007 | Chan | A61M 37/0015 604/46 |
| 2008/0009825 A1 | 1/2008 | Ringsred et al. | |
| 2008/0051723 A1 | 2/2008 | Laermer et al. | |
| 2008/0183144 A1 | 7/2008 | Trautman et al. | |
| 2008/0195035 A1 | 8/2008 | Frederickson et al. | |
| 2008/0262543 A1 | 10/2008 | Bangera et al. | |
| 2008/0275409 A1 | 11/2008 | Kane et al. | |
| 2009/0099437 A1 | 4/2009 | Yuzhakov | |
| 2009/0131846 A1 | 5/2009 | Gurtner et al. | |
| 2009/0216326 A1* | 8/2009 | Hirpara | A61B 17/1146 623/13.14 |
| 2009/0312597 A1* | 12/2009 | Bar | A61B 17/00234 600/37 |
| 2010/0048744 A1 | 2/2010 | Park et al. | |
| 2010/0137679 A1* | 6/2010 | Lashinski | A61B 17/0401 600/37 |
| 2010/0193997 A1 | 8/2010 | Frederickson et al. | |
| 2010/0256568 A1 | 10/2010 | Frederickson et al. | |
| 2010/0274283 A1 | 10/2010 | Kirsch et al. | |
| 2010/0305473 A1 | 12/2010 | Yuzhakov | |
| 2010/0312191 A1 | 12/2010 | Allen et al. | |
| 2011/0288565 A1* | 11/2011 | Kubiak | A61B 17/1146 606/151 |
| 2012/0029434 A1 | 2/2012 | Kobayashi et al. | |
| 2012/0046586 A1 | 2/2012 | Gurtner et al. | |
| 2012/0184916 A1 | 7/2012 | Kobayashi et al. | |
| 2012/0203253 A1* | 8/2012 | Kubiak | A61F 2/0811 606/151 |
| 2013/0123806 A1 | 5/2013 | Howlett et al. | |
| 2013/0218083 A1 | 8/2013 | Yuzhakov | |
| 2015/0032204 A1* | 1/2015 | Johansson | A61M 25/09 623/2.11 |
| 2015/0250476 A1* | 9/2015 | Feezor | A61B 17/06166 606/144 |
| 2015/0305739 A1* | 10/2015 | Rolandi | A61B 17/08 606/221 |
| 2016/0095592 A1 | 4/2016 | Levinson et al. | |
| 2017/0119371 A1* | 5/2017 | Mims | A61B 17/0469 |

FOREIGN PATENT DOCUMENTS

| | | |
|---|---|---|
| CA | 2510389 | 12/1999 |
| CA | 2330207 | 8/2005 |
| CA | 2376128 | 1/2009 |
| CN | 109069155 | 12/2018 |
| EP | 0286657 | 10/1988 |
| EP | 1183065 | 3/2002 |
| EP | 1281352 | 2/2003 |
| EP | 1284121 | 2/2003 |
| EP | 1391716 | 2/2004 |
| EP | 1598011 | 11/2005 |
| EP | 1360931 | 1/2006 |
| EP | 1360933 | 7/2006 |
| EP | 1360932 | 1/2007 |
| EP | 1086214 | 5/2007 |
| EP | 1973479 | 10/2008 |
| EP | 2209417 | 7/2010 |
| EP | 1183064 | 12/2012 |
| EP | 1183066 | 12/2012 |
| EP | 1834589 | 12/2012 |
| EP | 1904158 | 7/2013 |
| JP | 2003-533326 A | 11/2003 |
| WO | 8801955 | 4/1988 |
| WO | 0074764 | 12/2000 |
| WO | 0074765 | 12/2000 |
| WO | 0074766 | 12/2000 |
| WO | 0167944 | 9/2001 |
| WO | 0191846 | 12/2001 |
| WO | WO 2002/072189 A2 | 9/2002 |
| WO | 2005123173 | 12/2005 |
| WO | 2006016364 | 2/2006 |
| WO | WO 2006/124671 A2 | 11/2006 |
| WO | 2007002523 | 1/2007 |
| WO | 2007081430 | 7/2007 |
| WO | WO 2007/127976 A2 | 11/2007 |
| WO | WO 2008/019051 A2 | 2/2008 |
| WO | WO 2008/020632 A1 | 2/2008 |
| WO | 2008067290 | 6/2008 |
| WO | 2009048687 | 4/2009 |
| WO | WO 2010/124712 A1 | 11/2010 |
| WO | 2010140760 | 12/2010 |
| WO | WO 2011/016230 A1 | 2/2011 |
| WO | 2012170497 | 12/2012 |
| WO | 2013042723 | 3/2013 |
| WO | 2013096026 | 6/2013 |
| WO | WO 2013/188884 A1 | 12/2013 |
| WO | WO 2017/151806 A1 | 9/2017 |

OTHER PUBLICATIONS

International Search Report and Written Opinion dated Aug. 13, 2013 in International Application No. PCT/US2013/046181, 8 pages.

International Search Report and Written Opinion dated Jul. 25, 2017 in International Application No. PCT/US2017/020258, 18 pages.

International Preliminary Report on Patentability dated Dec. 16, 2014 in International Application No. PCT/US2013/046181, 6 pages.

Lawton et al., "Novel Haemostatic Dressings," JR Army Med Corps (2009); 155(4): 309-314.

Lee et al., "β-Chitin-based wound dressing containing silver sulfurdiazine." Journal of Materials Science: Materials in Medicine (2000); 11(12): 817-823. (Abstract).

Mahdavi et al., "A biodegradable and biocompatible gecko-inspired tissue adhesive." Proceedings of the National Academy of Sciences (2008); 105(7): 2307-2312.

Sugamori et al., "Local hemostatic effects of microcrystalline partially deacetylated chitin hydrochloride." J Biomed Mater Res, (2000); 49(2): 225-232. (Abstract).

Yusof et al., "Preparation and characterization of chitin beads as a wound dressing precursor." Journal of Biomedica Materials Research (2001); 54(1): 59-68. (Abstract).

Zhong et al., "A Chitin Nanofiber Ink for Airbrushing, Replica Molding, and Microcontact Printing of Self-assembled Macro-, Micro-, and Nanostructures." Adv Materials (2011); 23(41): 4776-4781.

Zhong et al., "A facile bottom-up route to self-assembled biogenic chitin nanofibers." Soft Matter (2010); 6(21): 5298-5301.

"International Application Serial No. PCT US2017 020258, International Preliminary Report on Patentability dated Sep. 13, 2018", 14 pgs.

"European Application Serial No. 177114444.4, Response filed Apr. 9, 2019 to Communication Pursuant to Rules 161(1) and 162 EPC dated Oct. 16, 2018", 22 pgs.

Rajabi, Mina, "Flexible and Stretchable Microneedle Patches with Integrated Rigid Stainless Steel Microneedles for Transdermal Biointerfacing", PLOS One Doi: 10.1371, (Dec. 9, 2016), 13 pgs.

"European Application Serial No. 17711444.4, Notification Regarding Rule 164 and Article 94(3) EPC mailed Dec. 20, 2019", 10 pages.

* cited by examiner

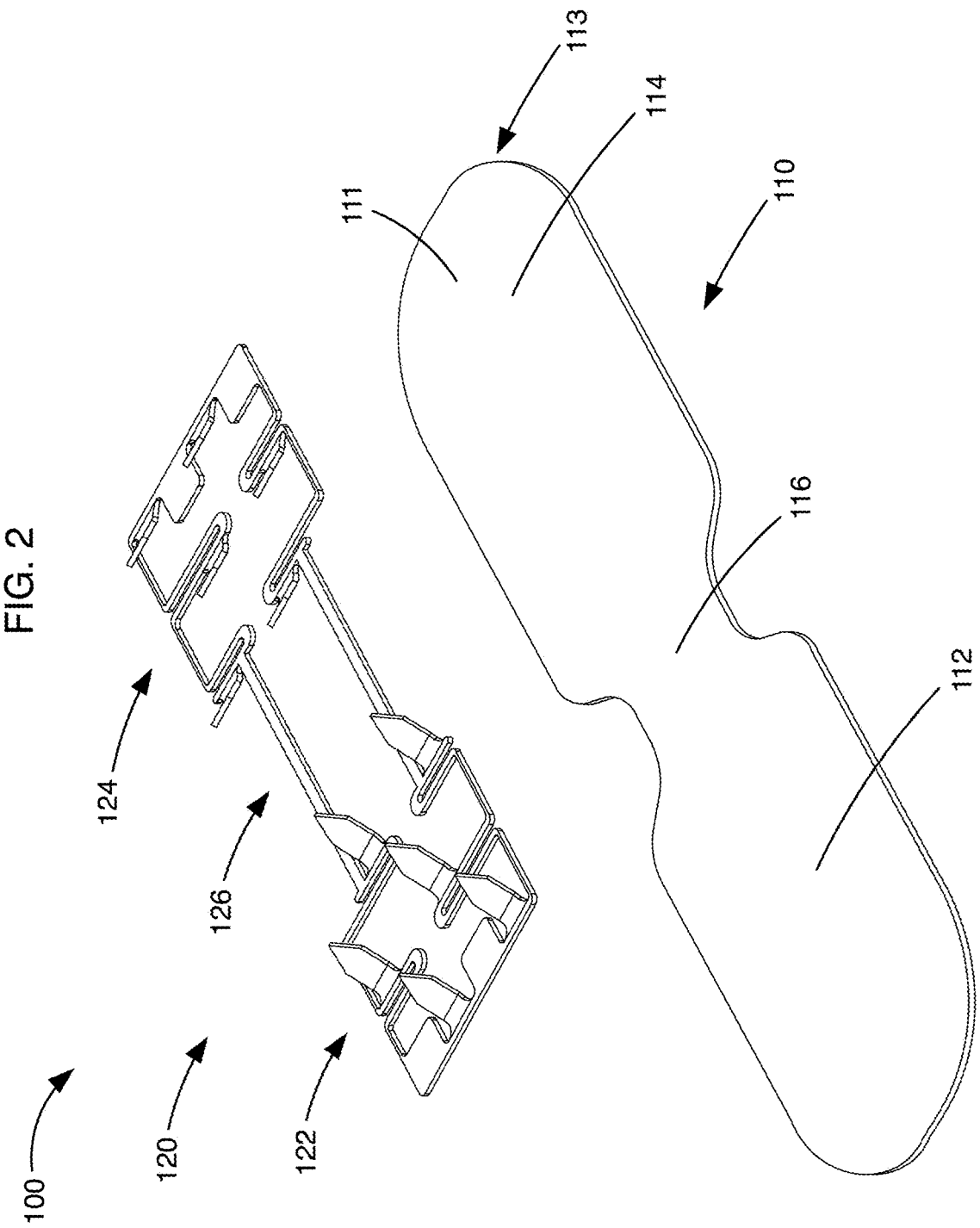

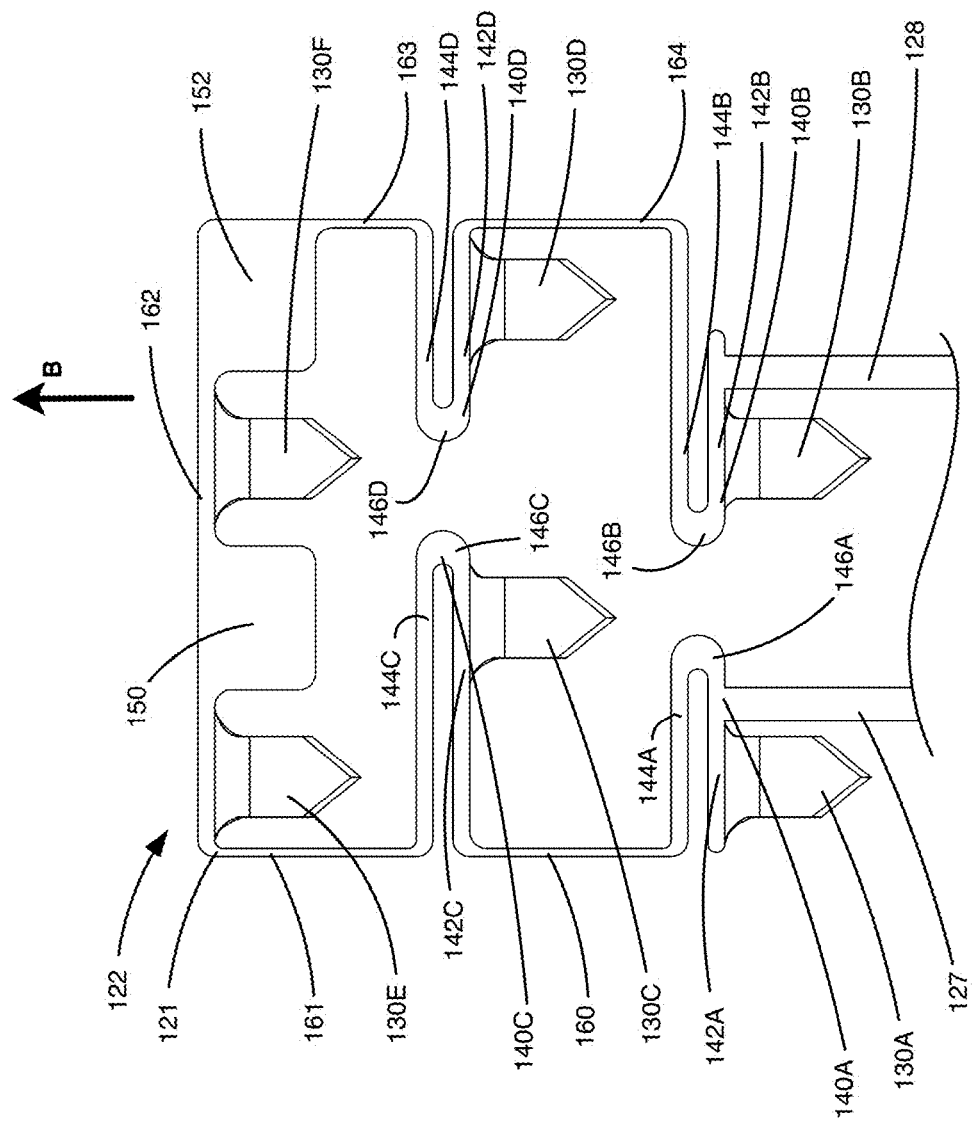

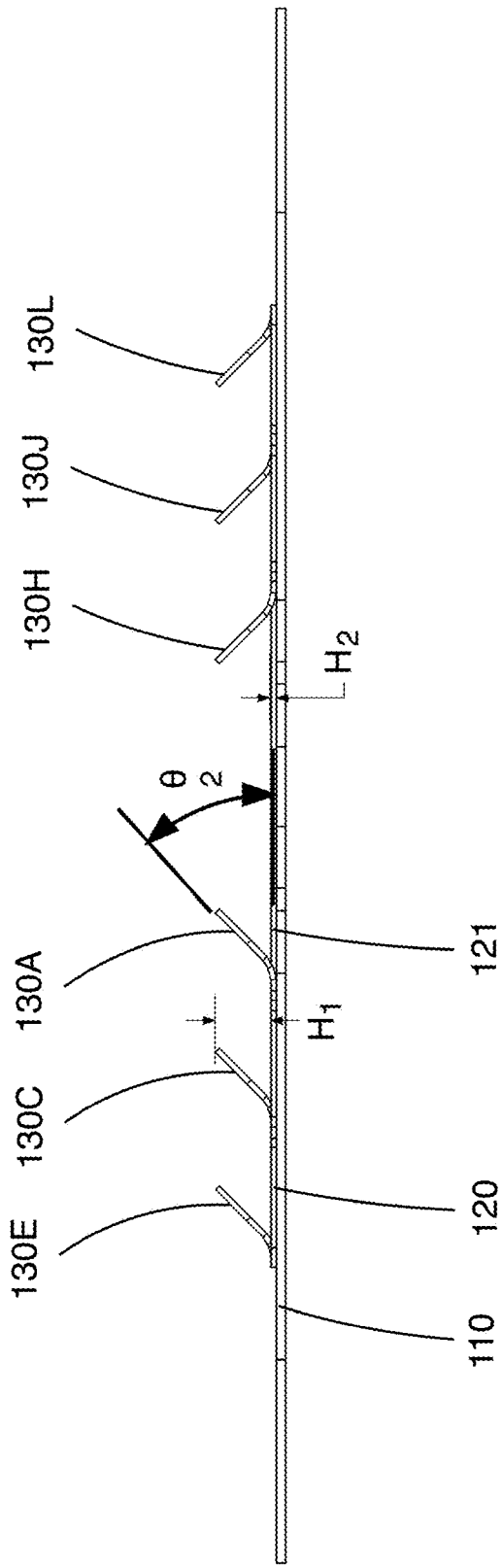
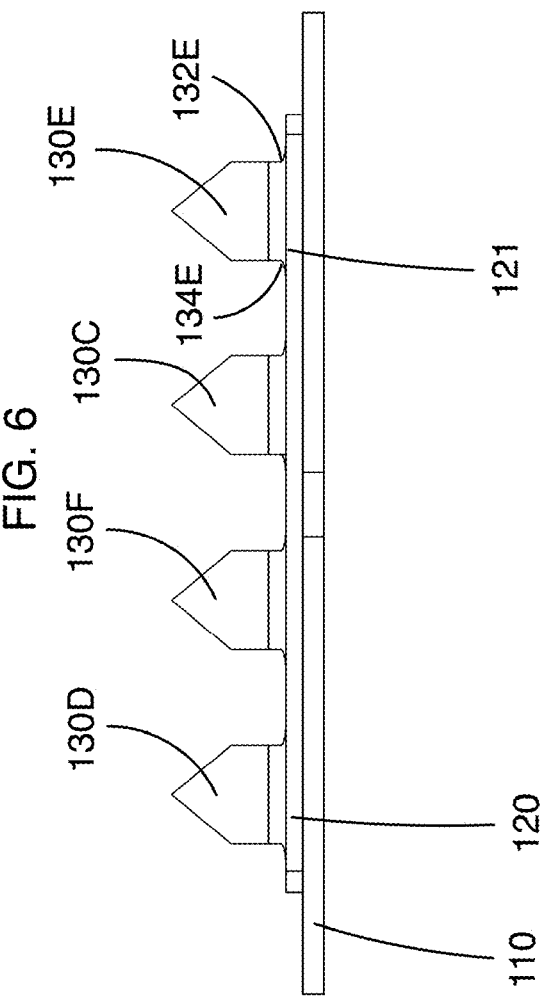

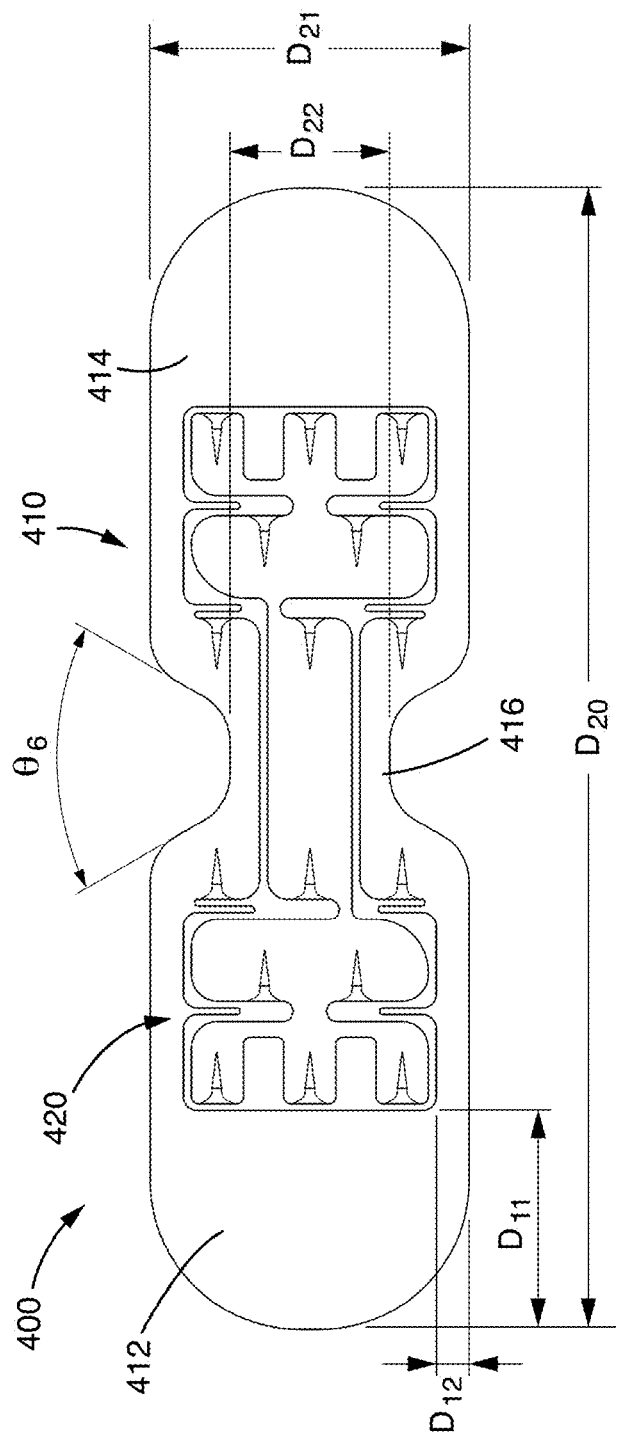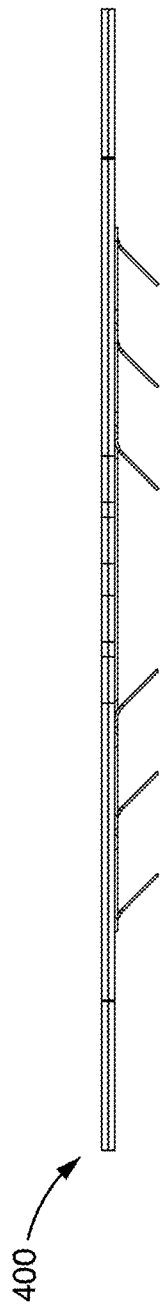

FIG. 16
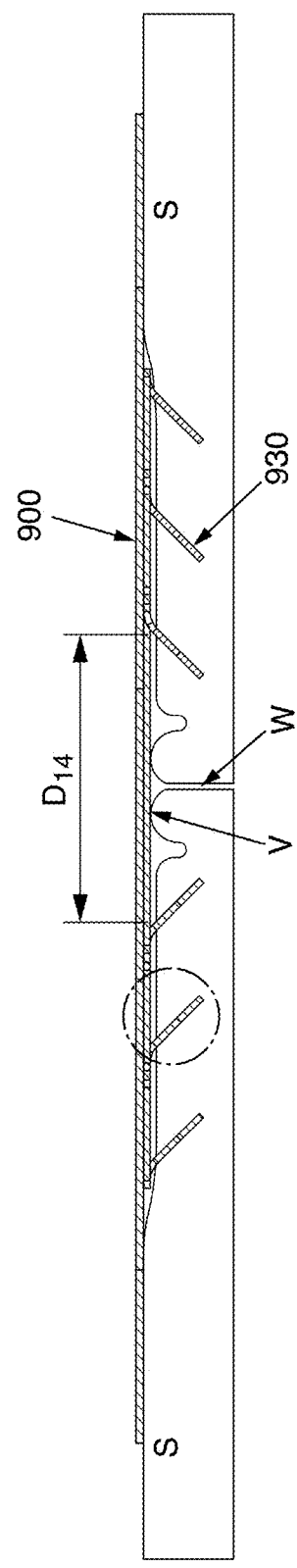
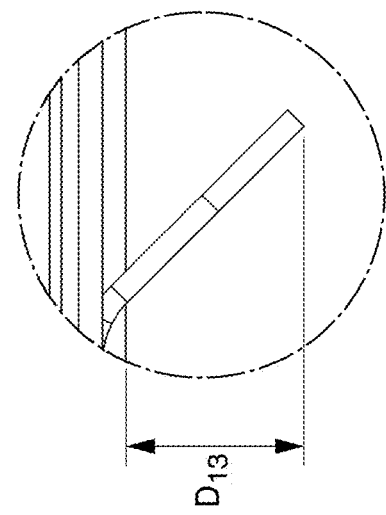

FIG. 20
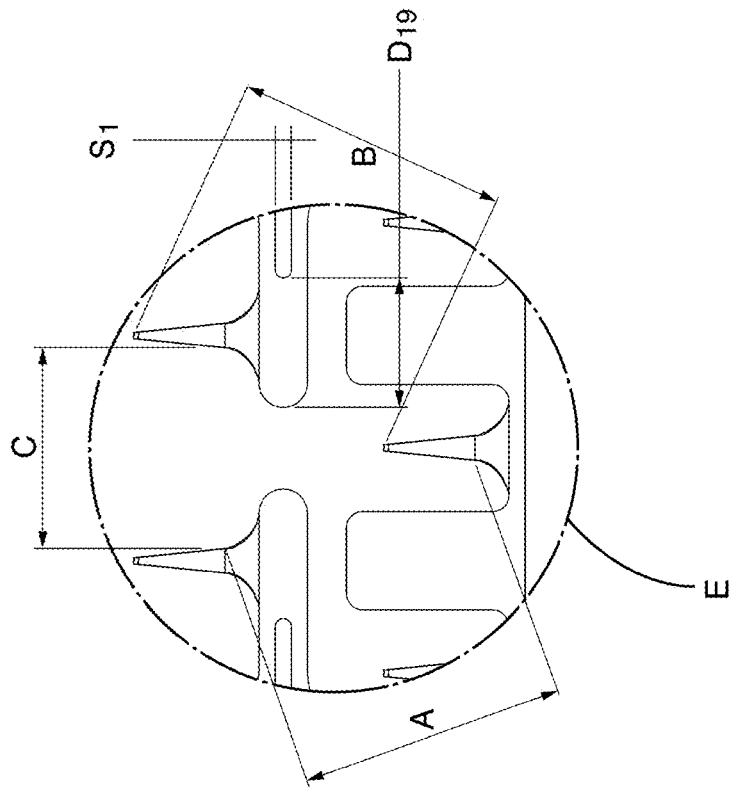
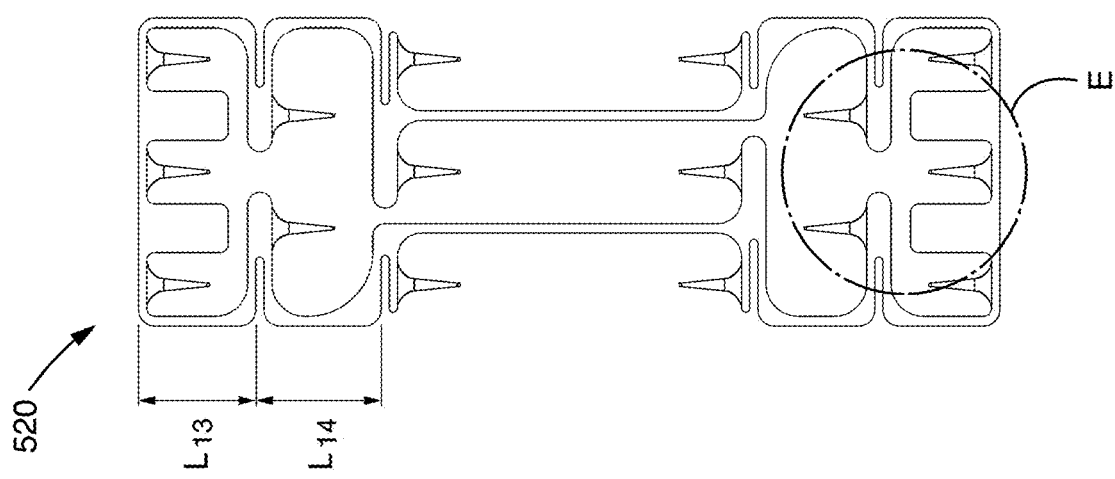

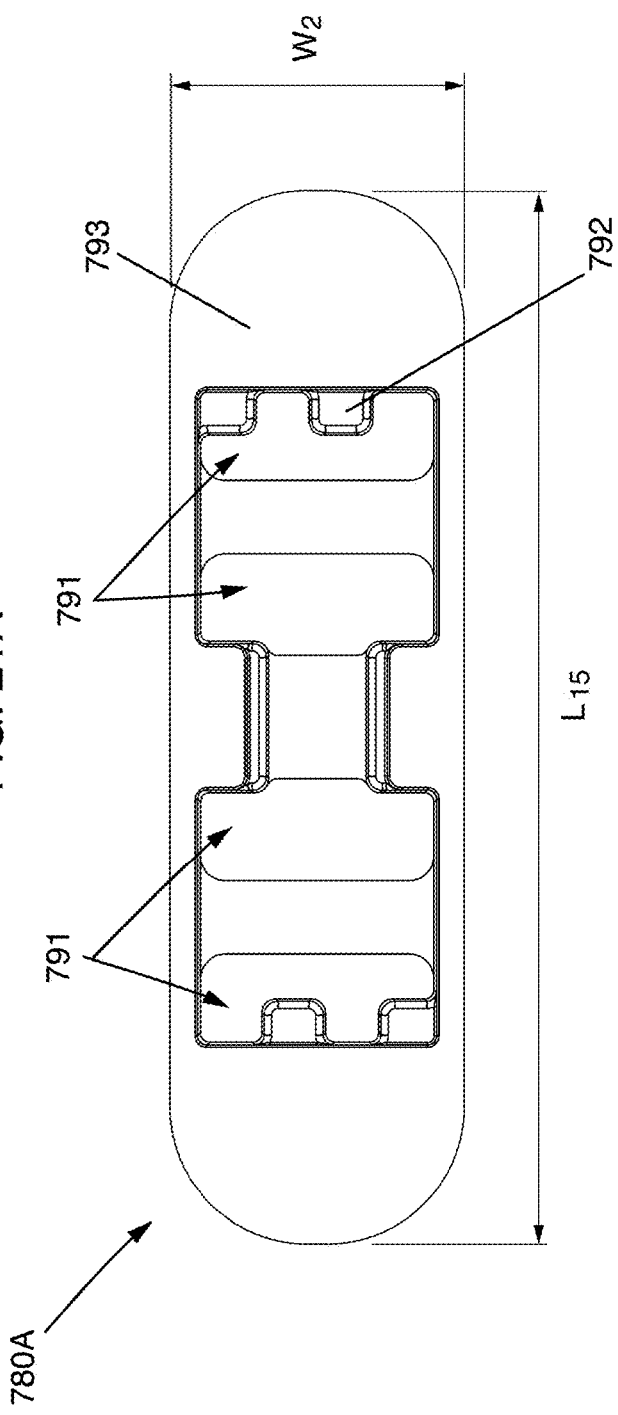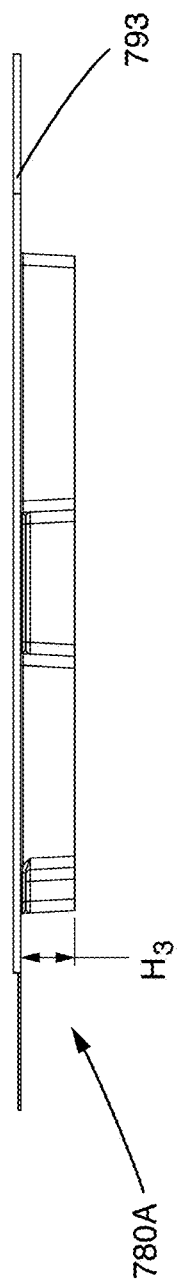

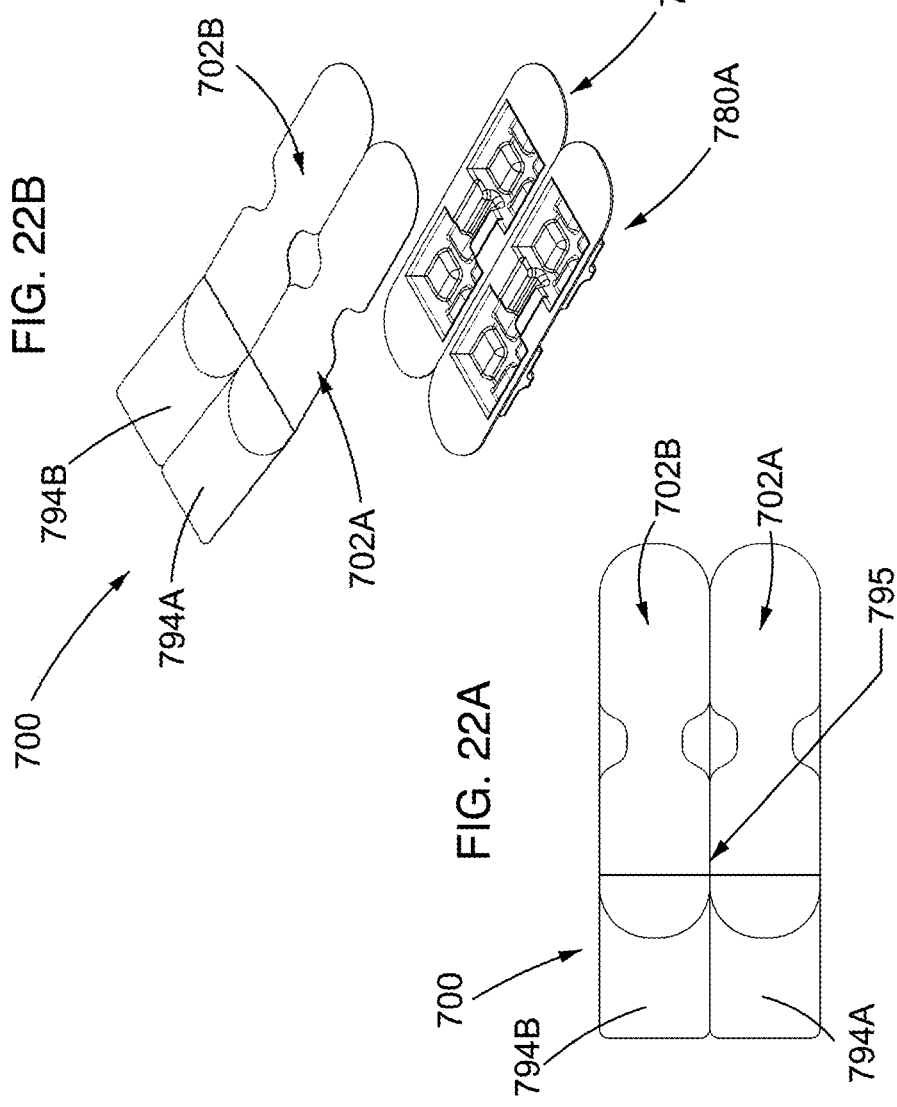

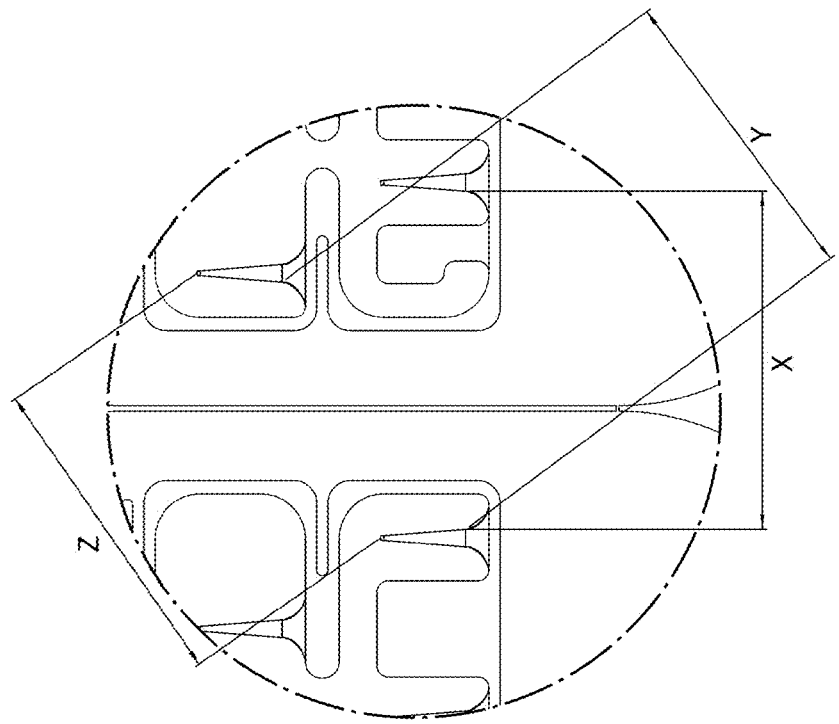
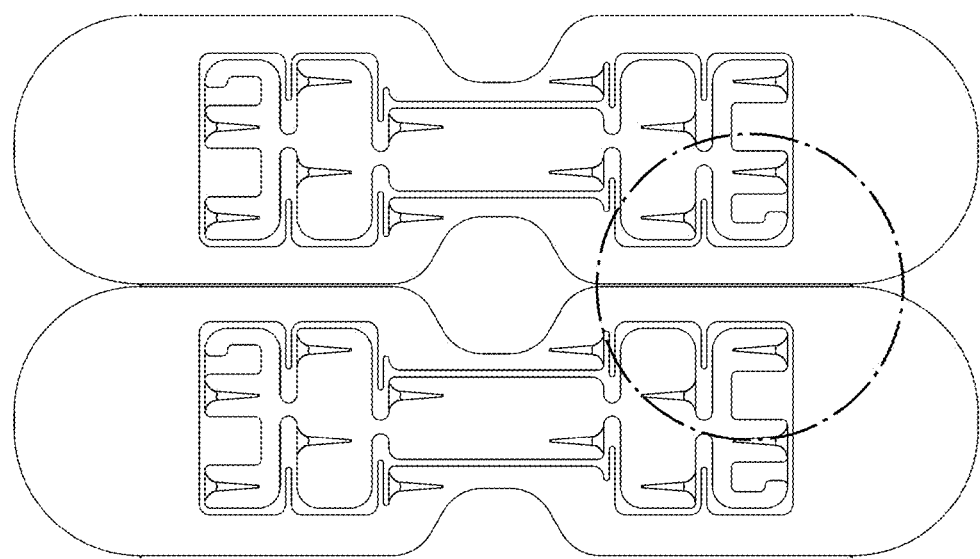
FIG. 23

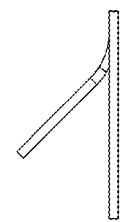
FIG. 29C
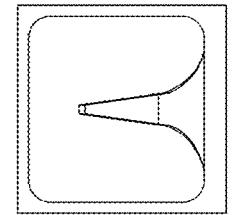
FIG. 29A
FIG. 29B
FIG. 28C
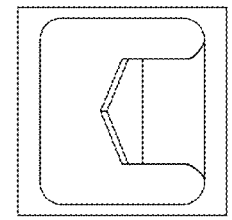
FIG. 28A
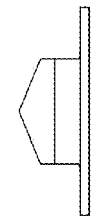
FIG. 28B
FIG. 27C
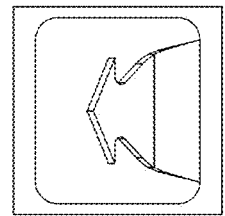
FIG. 27A
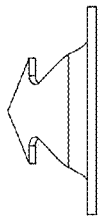
FIG. 27B

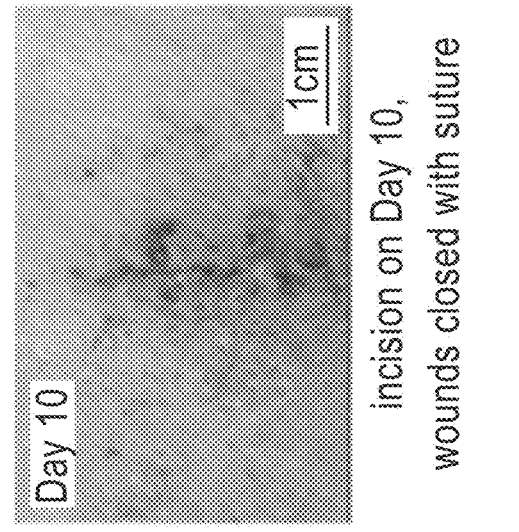
FIG. 30C
incision on Day 10, wounds closed with suture
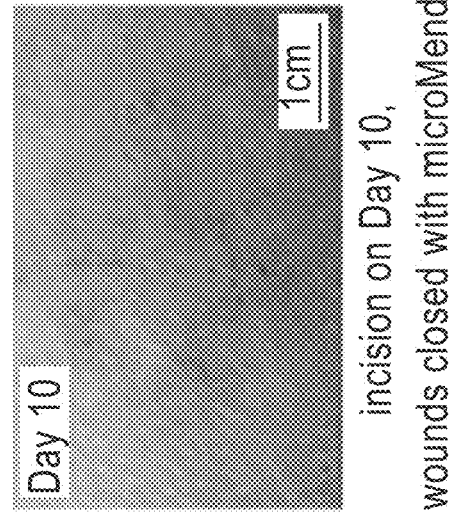
FIG. 30E
incision on Day 10, wounds closed with microMend
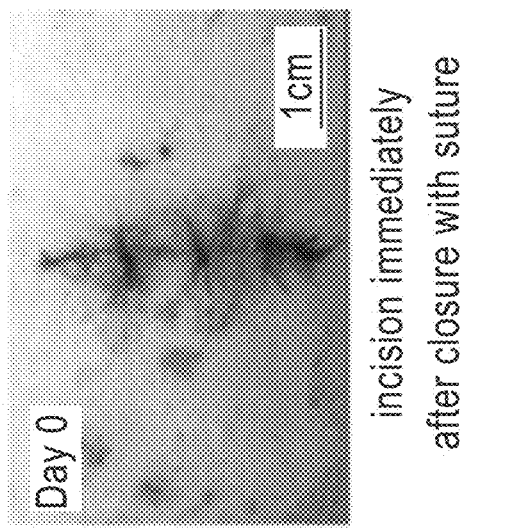
FIG. 30B
incision immediately after closure with suture
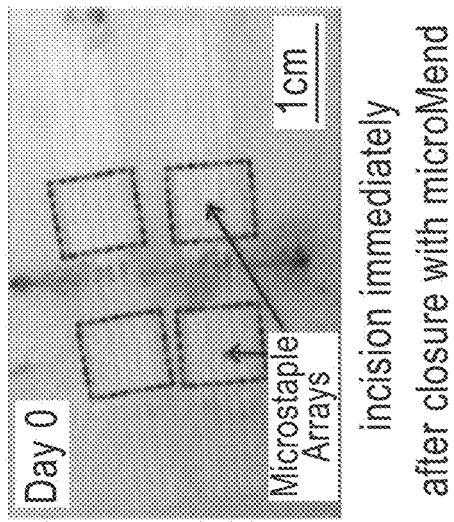
FIG. 30D
incision immediately after closure with microMend
FIG. 30A
3cm, Full-thickness incision prior to wound closure

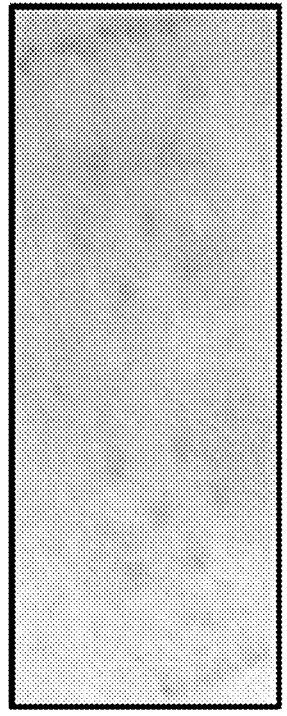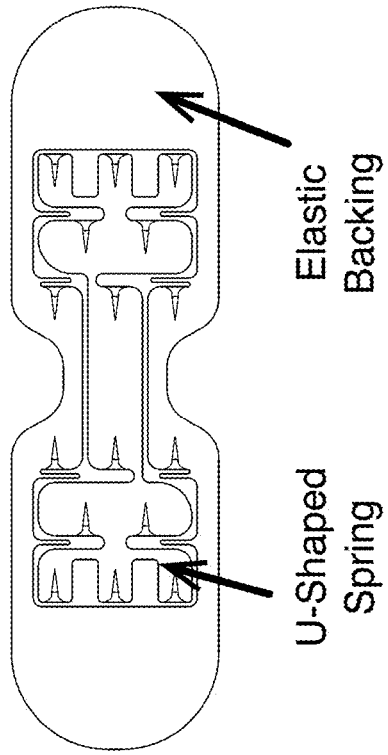
FIG. 31A
FIG. 31B
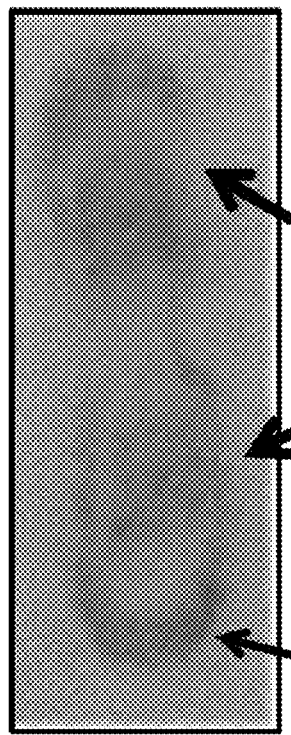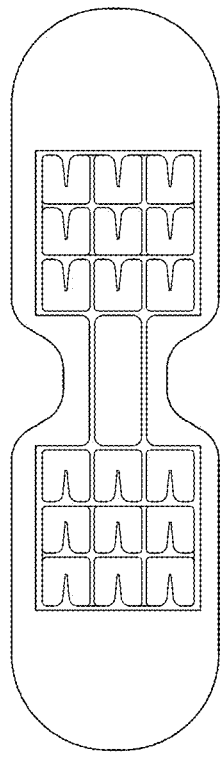

DETAIL A
SCALE 16 : 1

NOTES:
1. ALL DIMENSIONS IN mm, UNLESS OTHERWISE SPECIFIED
2. MATERIAL: STAINLESS STEEL 316 SHEET 0.008" THICK

SCALE: 4:1

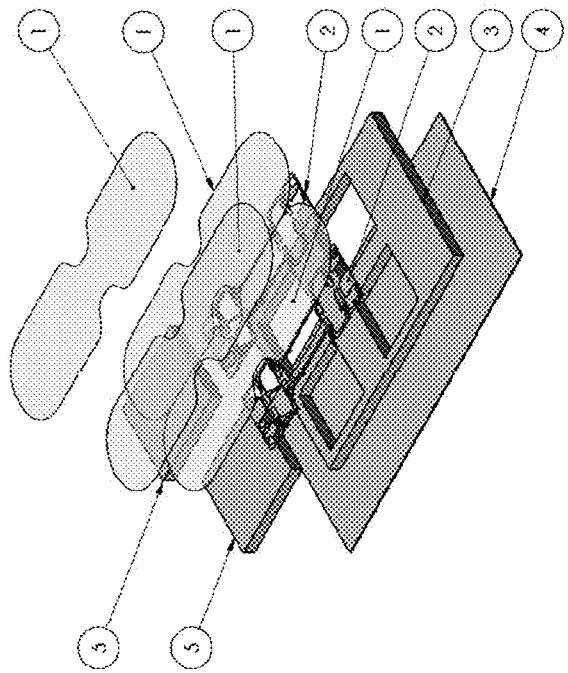

| ITEM NO. | PART NUMBER | DESCRIPTION | QTY. |
|---|---|---|---|
| 1 | PN0923151PL | BACKING FILM | 4 |
| 2 | (SEE NOTES) | BRIDGED MICROSTAPLE ARRAY | 6 |
| 3 | PN0923153PL | FOAM SPACER BASE | 1 |
| 4 | PN0104161PL | PACKAGING BASE CARD | 1 |
| 5 | PN0910151PL | FOAM TAB | 2 |

NOTES

ITEM 1 - MATERIAL: DERMAMED 4034 4.0MIL

ITEM 2 - ALIGN AT CENTER OF ITEM 1 IN ORIENTATION SHOWN

ITEM 2 - CONFIGURATIONS:
1. PN1123151PL; 6-STAPLE 1.05MM
2. PN1123152PL; 6-STAPLE 1.5MM
3. PN1208151PL; 6-STAPLE 0.76MM
4. PN1201151PL; 8-STAPLE 1.05MM
5. PN1201152PL; 8-STAPLE 1.5MM
6. PN1208152PL; 8-STAPLE 0.76MM
7. PN1206151PL; 6-STAPLE 1.05MM 2.8X
8. PN1206152PL; 6-STAPLE 1.5MM 2.8X
9. PN1209151PL; 6-STAPLE 0.76MM 2.8X
10. PN1207151PL; 8-STAPLE 1.05MM 2.8X
11. PN1207152PL; 8-STAPLE 1.5MM 2.8X
12. PN1209152PL; 8-STAPLE 0.76MM 2.8X

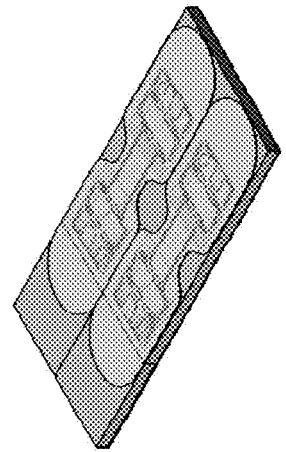

SCALE: 2:1

FIG. 33B

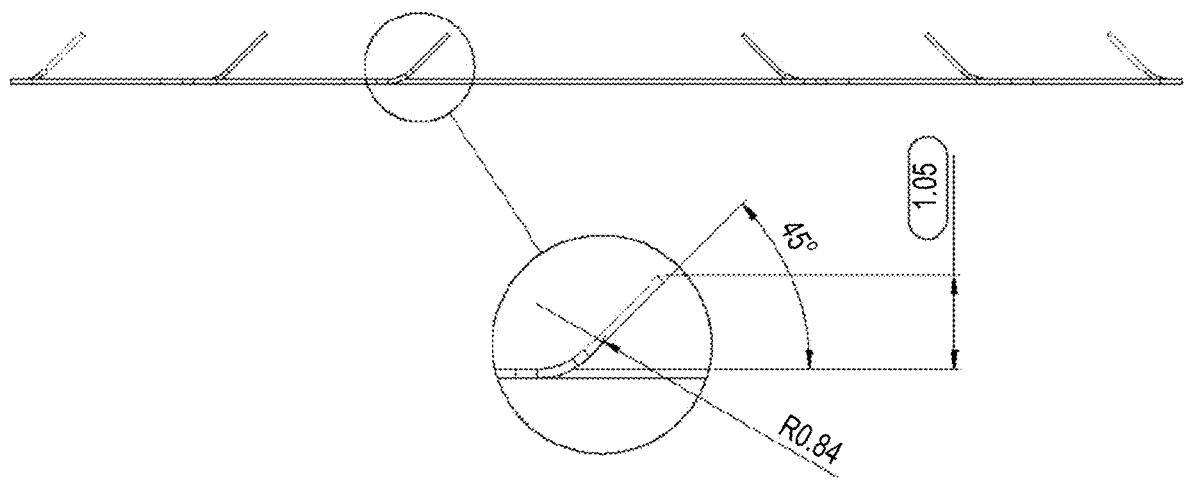
NOTES
1. ALL DIMENSIONS IN mm, UNLESS OTHERWISE SPECIFIED
2. MATERIAL: STAINLESS STEEL 316 SHEET 0.004" THICK
3. REFER TO DXF / CAD FILE FOR DETAILS
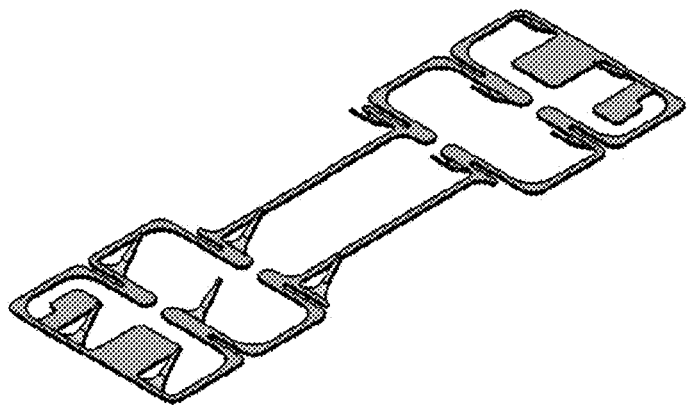
SCALE: 1:1
FIG. 35A Average Tensile Strength (Day 20) = 63N/25mm or 30N/12mm
(26% higher than Inelastic Devices at 24N/12mm)

| ITEM NO. | PART NUMBER | DESCRIPTION | Default/QTY. |
|---|---|---|---|
| 1 | PN0426163PL | FOAM SPACER BASE | 1 |
| 2 | PN0104161PL | PACKAGING BASE CARD | 1 |
| 3 | PN1125151PL | MICROSTAPLE ARRAY | 2 |
| 4 | PN0923151PL | BACKING FILM | 2 |
| 5 | PN0426162PL | FOAM TAB | 2 |

NOTES:
1. ITEM 3 - ALIGN AT CENTER OF ITEM 4 IN ORIENTATION SHOWN
2. ITEM 4 - MATERIAL: DERMAMED DM-4034 4.0MIL

NOTES:
1. MATERIAL:
   DERMAMED4001 1.0MIL - CONFIG.A
   BP 3428R 1.0MIL - CONFIG B
   BP 3428R 1.0MIL - CONFIG C
   BP M102 PUR FILM 3.5MIL - CONFIG D
   DERMAMED 4034 4.0MIL - CONFIG E
2. ALL DIMENSIONS IN MM. UNLESS OTHERWISE SPECIFIED

SCALE: 4:1

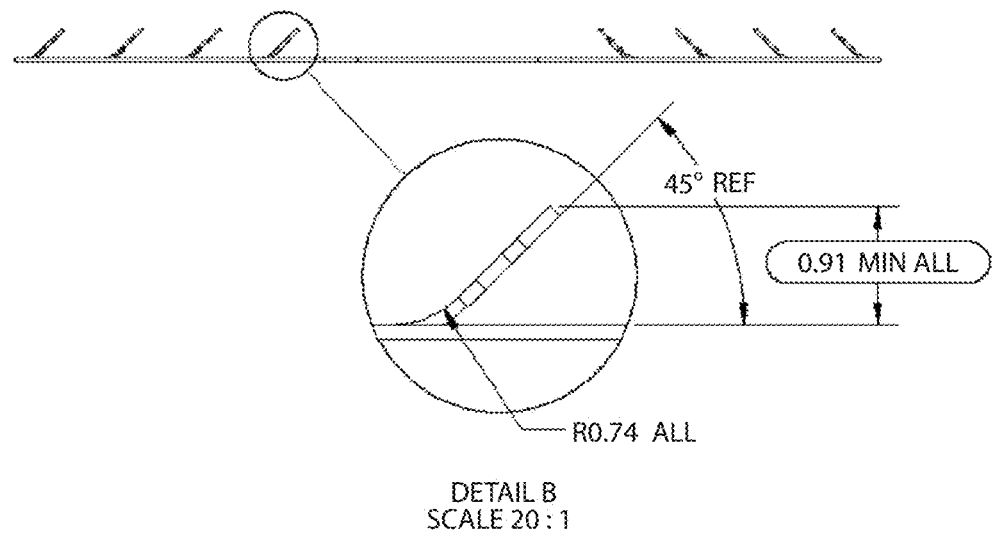
NOTES:
1. ALL DIMENSIONS IN mm, UNLESS OTHERWISE SPECIFIED
2. MATERIALS: STAINLESS STEEL 316 SHEET 0.004" THK
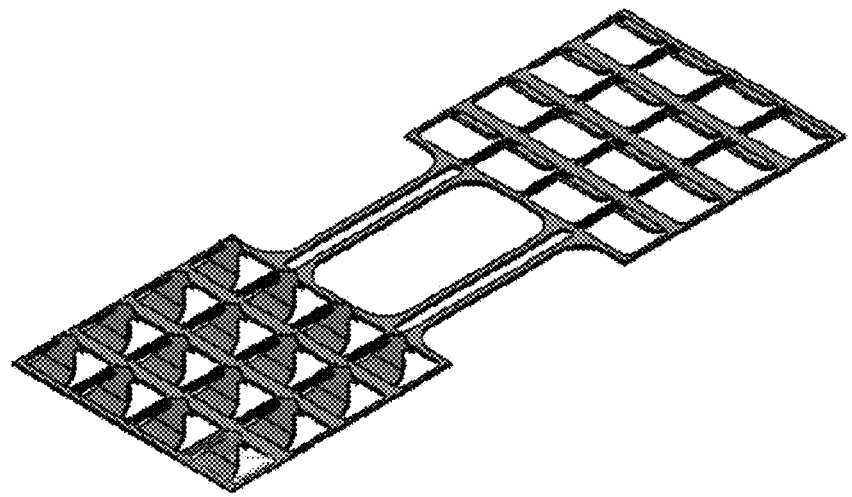
FIG. 41A

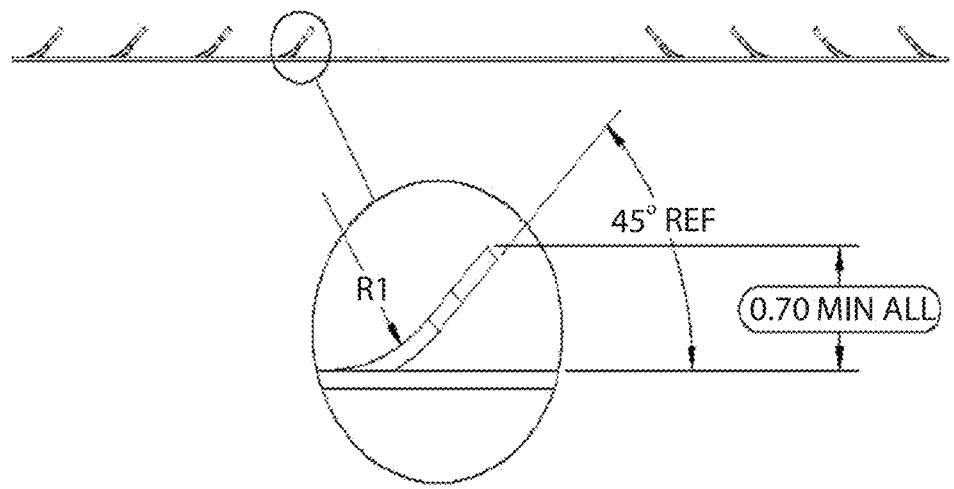
DETAIL A
SCALE 25 : 1
NOTES:
1. ALL DIMENSIONS IN mm, UNLESS OTHERWISE SPECIFIED
2. MATERIALS: STAINLESS STEEL 316 SHEET 0.004" THK
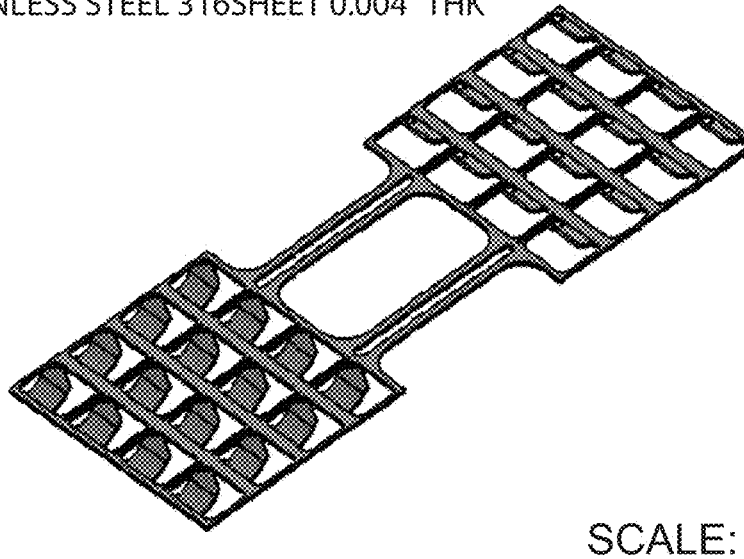
SCALE: 4:1
FIG. 42A

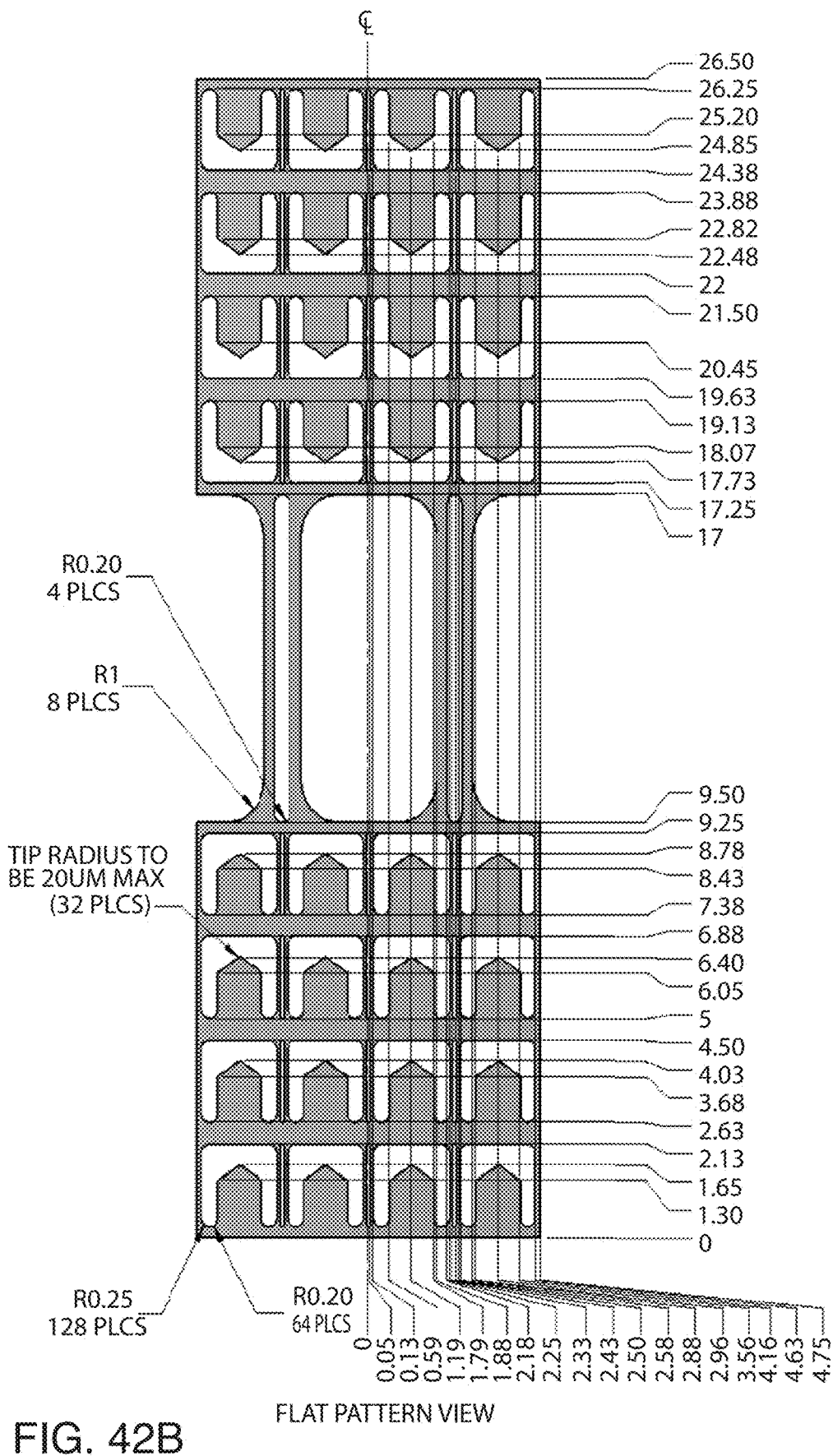
FIG. 42B  FLAT PATTERN VIEW

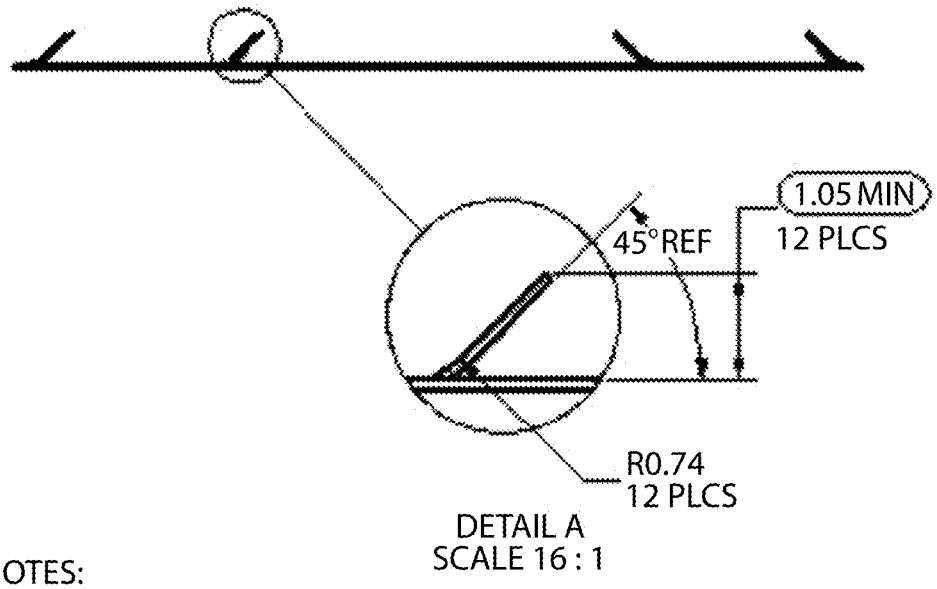
NOTES:
1. ALL DMENSIONS IN mm, UNLESS OTHERWISE SPECIFIED
2. MATERIALS: STAINLESS STEEL 316 SHEET 0.004" THICK
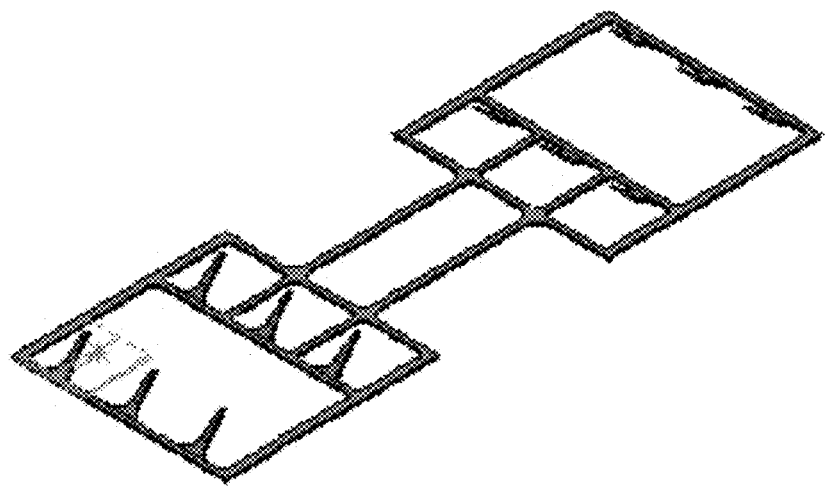
SCALE: 1:1
FIG. 43A

MICROSTRUCTURE-BASED SYSTEMS, APPARATUS, AND METHODS FOR WOUND CLOSURE

CROSS REFERENCE TO RELATED APPLICATIONS

This application claims priority to U.S. Provisional Application No. 62/402,492, filed on Sep. 30, 2016, and U.S. Provisional Application No. 62/302,055, filed on Mar. 1, 2016, each of which is herein incorporated by reference in its entirety.

BACKGROUND

Embodiments described herein relate generally to systems, apparatus, and methods for wound closure, and in particular to wound closure using one or more microstructures.

Existing devices, compositions, and methods for closing and treating a wound may range from simple over-the-counter products, such as dressings, wraps, bandages, adhesive bandages, butterfly strips, and surgical tape, to more specialized products, such as sutures and staples, depending on the type and severity of the wound, the skill of the caregiver, etc. Although sutures and staples can be quite effective at closing wounds, proper application requires a trained specialist. Additionally, the application of sutures or staples is an invasive and painful procedure that frequently requires the use of an anesthetic. Furthermore, these procedures can leave unsightly scars, both from secondary insertion holes and from varying tensions applied to the laceration or surgical incision as a result of variations in suture or staple spacing and depth. For sutures, tension also can vary depending how tightly the suture is tied. Moreover, these skin closure techniques necessitate follow-up visits to a hospital or doctor's office for removal of the sutures or staples. This can be a problem not only for scheduled removal, but an even bigger issue if infection occurs since it requires removal of the sutures or sutures to reopen and clean the wound. Additionally, simply covering the wound with a bandage, such as an adhesive bandage, a butterfly closure strip, or surgical tape, is usually not sufficient to close more severe or deeper wounds, such as dermal wounds, because the adhesives used to attach devices such as adhesive bandages, butterfly closure strips, and surgical tape are not adequate to close these wounds without detaching or creep. Skin moisture adds to the problem by further reducing adherence of the adhesive-based bandage to the skin, which may lead to the premature release of the bandage from the skin and wound site before closure of the wound and proper healing. Also, the adhesive can induce symptomatic allergic and inflammatory reactions.

Therefore, a need exists for wound closure devices that enable more effective wound closure and/or that minimize scarring. Additionally, there is a need for a wound closure device that is easily applied and removed.

SUMMARY

The inventors have recognized and appreciated that systems, apparatus, and methods related to wound closure devices comprising one or more microstructures are described herein. In some embodiments, an apparatus includes a backing and a microstructure array. The microstructure array may include a first portion, a second portion, and a bridge portion. The first portion and the second portion each include one or more microstructures configured to grasp tissue. Additionally, the first portion and the second portion may each include one or more expandable portions such that the wound closure device is configured to stretch or elongate in length. The wound closure devices disclosed herein are improvement over traditional wound closure methods (e.g., sutures), and may result in various improvements including improved wound closure, wound healing, and improved cosmesis.

In some embodiments, the wound closure device comprises: a microstructure, the array comprising a plurality of microstructure portions connected by at least one bridge portion, each of the plurality of microstructure portions comprising at least one microstructure for securing the array to the tissue such that at least one bridge portion overlays the wound, and at least one of the plurality of microstructure portions comprising at least one structure with spring characteristics.

In some embodiments, the wound closure device comprises: a microstructure, the array comprising a plurality of microstructure portions, each of the plurality of microstructure portions comprising at least one microstructure for securing the array to the tissue such that at least one bridge portion overlays the wound, and at least one of the plurality of microstructure portions comprising at least one structure with spring characteristics.

In some embodiments, the present disclosure presents a wound closure device comprising: a microstructure array, the array comprising a plurality of microstructure portions connected by at least one bridge portion, each of the plurality of microstructure portions comprising at least one microstructure for securing the array to the tissue such that at least one bridge portion overlays the wound, and at least one of the plurality of microstructure portions comprising at least one structure with spring characteristics.

In some embodiments, the present disclosure presents a wound closure device comprising: a microstructure array, the array comprising at least one microstructure portion, wherein each of the at least one microstructure portions comprise at least one microstructure for securing the array to the tissue, and at least one of the at least one microstructure portions comprise at least one structure with spring characteristics.

In some embodiments, the microstructure portion comprises at least one structure with spring characteristics. In some embodiments, the microstructure portions comprise at least one of 2, 3, 4, 5, 6, 7, 8, 9, and 10 structures with spring characteristics.

In some embodiments, the expandability of at least one structure comprised on the microstructure portion has spring characteristics that range from about 100.2% to about 105.0% in at least one direction.

In some embodiments, at least one structure with spring characteristics comprised on the microstructure portion has an approximate shape comprising at least one of a congruent V-shape, a congruent U-shape, a congruent S-shape, a congruent I-shape, a congruent H-shape, a congruent C-shape, a congruent X-shape, a congruent Y-shape, a congruent M-shape, a congruent N-shape, a congruent T-shape, a congruent W-shape, and a congruent Z-shape. In some embodiments, the approximate shape of at least one structure with spring characteristics comprises a plurality of congruent U-shapes. In some embodiments, the plurality of congruent U-shapes are oriented to a serpentine shape. In some embodiments, a geometry of the expandable portions is partly or completely made up of singles, multiples, combinations and/or mirror images of the congruent shapes.

In some embodiments, the at least one structure with spring characteristics comprises a first arm portion, a second arm portion, and a curved portion connecting the first arm portion and the second arm portion, the curved portion for operating as a rotational axis such that the first arm rotates relative to the second arm when a force moves the first arm away from the second arm.

In some embodiments, the expandability of at least one structure with spring characteristics is substantially derived from at least one of (i) a geometry of at least one structure with spring characteristics and/or (ii) a material property of at least one structure with spring characteristics.

In some embodiments, a material property of at least one structure with spring characteristics is elasticity.

In some embodiments, a spring constant of at least one structure with spring characteristics ranges from about 0.5 N/mm to about 10 N/mm.

In some embodiments, a spring constant of the wound closure device ranges from about 0.5 N/mm to about 10 N/mm.

In some embodiments, the wound closure device comprises at least one structure with spring characteristics comprising a spring constant selected for at least one of a particular type of wound, a particular type of tissue, a period of wound closure time, a period of healing time, a degree of inflammation associated with the device, a degree of inflammation associated with the wound, a degree of wound eversion, a degree of scarring associated with the wound, and a degree of postinflammatory hyperpigmentation associated with the microstructure array.

In some embodiments, each of the plurality of microstructure portions comprises a plurality of microstructures for securing the array to the tissue. In some embodiments, the number of microstructures on a first portion of the plurality of microstructure portions is equal to the number of microstructures on a second portion of the plurality of microstructure portions. In some embodiments, the number of microstructures on a first portion of the plurality of microstructure portions differs from the number of microstructures on a second portion of the plurality of microstructure portions. In some embodiments, the number of microstructures on a microstructure portion of the plurality of microstructure portions is at least one of 2, 3, 4, 5, 6, 7, 8, 9, and 10 microstructures.

In some embodiments, the microstructure array comprises a support base.

In some embodiments, the wound closure device comprises at least one microstructure that is at least one of (i) integrally formed with the support base and (ii) connected to the support base such that at least one microstructure projects from the support base.

In some embodiments, the wound closure device comprises at least one microstructure portion of the plurality of microstructure portions that is at least one of (i) integrally formed with the support base and (ii) connected to the support base.

In some embodiments, the wound closure device comprises at least one structure with spring characteristics that is at least one of (i) integrally formed with the support base and (ii) connected to the support base.

In some embodiments, the wound closure device comprises at least one bridge portion that is at least one of (i) integrally formed with the support base and (ii) connected to the support base.

In some embodiments, the microstructure array comprises at least one of a polymer, a metal, a biomaterial, a biodegradable material, and a non-biodegradable material. In some embodiments, the microstructure array comprises at least one of aluminum, titanium, and stainless steel. In some embodiments, the microstructure array comprises a 300 series stainless steel alloy. In some embodiments, the microstructure array comprises 316 stainless steel.

In some embodiments, the microstructure array defines at least one aperture.

In some embodiments, the wound closure device comprises at least one microstructure that extends at an angle relative to the microstructure array. In some embodiments, the angle is from about 10 degrees to about 90 degrees. In some embodiments, the angle is about 45 degrees.

In some embodiments, the wound closure device comprises at least one microstructure that is angled toward at least one bridge portion. In some embodiments, the wound closure device comprises at least one microstructure that is angled toward at least one bridge portion, such that at least one microstructure is angled toward a wound upon application of the device.

In some embodiments, the wound closure device comprises at least one microstructure that is at least one of a microstaple, a microbarb, a microneedle, a microblade, a microanchor, a microhook, a microfishscale, a micropillar, and a microhair.

In some embodiments, the wound closure device comprises at least one microstructure that has a trapezoidal profile.

In some embodiments, the wound closure device comprises at least one microstructure that has a tip with a width of less than about 200 μm.

In some embodiments, the microstructure array comprises from about 2 microstructures to about 50 microstructures. In some embodiments, the microstructures are positioned on the plurality of microstructure portions in a staggered arrangement. In some embodiments, the tip-to-tip distance separating each microstructure on a given microstructure portion from its nearest microstructure ranges from about 0.5 mm to about 15 mm. In some embodiments, the base-to-tip distance separating each microstructure in a given microstructure portion from its nearest microstructure ranges from about 0.5 mm to about 15 mm.

In some embodiments, the wound closure device comprises a density of microstructures on the array that is selected for at least one of a particular type of wound, a particular type of tissue, a period of wound closure time, a period of healing time, a degree of inflammation associated with the device, a degree of postinflammatory hyperpigmentation associated with the wound, a degree of wound eversion, a degree of scarring associated with the wound, and a degree of postinflammatory hyperpigmentation associated with the microstructure array.

In some embodiments, the microstructure array comprises at least one microstructure that has a height H1 of about 0.1 mm to about 8 mm. In some embodiments, the height or vertical displacement H1 is from about 0.5 mm to about 2 mm. In some embodiments, the height or vertical displacement H1 of the microstructure is about 1.05 mm. In some embodiments, the at least one microstructure has a height or vertical displacement H1 of about 1.5 mm.

In some embodiments, the wound closure device comprises at least one of a base-to-tip length, a base width, and a tip width of the at least one microstructure that is selected for a degree of pain associated with application of the device.

In some embodiments, at least a portion of the wound closure device comprises elasticity.

In some embodiments, the at least one bridge portion comprised on the wound closure device comprises elasticity. In some embodiments, at least one bridge portion comprised on the wound closure device is substantially inelastic.

In some embodiments, the plurality of microstructure portions comprised on the wound closure device comprise elasticity and the at least one bridge portion comprised on the wound closure device is substantially inelastic.

In some embodiments, the at least one bridge portion extends longitudinally. In some embodiments, the wound closure device comprises a plurality of bridge portions extending longitudinally. In some embodiments, the at least one bridge portion comprises two bridge portions extending longitudinally. In some embodiments, the at least one bridge portion has a width from about 0.5 mm to about 100 mm. In some embodiments, the width of the at least one bridge portions is from about 1 mm to about 50 mm. In some embodiments, the width of the at least one bridge portions is from about 3 mm to about 20 mm. In some embodiments, the at least one bridge portion has a length that is from about 1 mm to about 50 mm. In some embodiments, the at least one bridge portion has a length that is from about 3 mm to about 30 mm. In some embodiments, the at least one bridge portion has a length that is from about 5 mm to about 25 mm.

In some embodiments, the wound closure device comprises a backing. In some embodiments, the backing is at least one of breathable, stretchable, flexible, and elastic. In some embodiments, the backing is at least one of permeable, semi-permeable, and impermeable. In some embodiments, the backing is at least one of transparent and opaque. In some embodiments, the backing comprises at least one of medical tape, white cloth tape, surgical tape, tan cloth medical tape, silk surgical tape, clear tape, hypoallergenic tape, silicone, elastic silicone, polyurethane, elastic polyurethane, polyethylene, elastic polyethylene, rubber, latex, Gore-Tex, plastic, plastic components, polymer, biopolymer, woven material, non-woven material, and natural material. In some embodiments, the backing comprises a polyurethane-based film. In some embodiments, the backing has a shape comprising at least one of a circle, oval, ellipse, square, rectangle, triangle, diamond, butterfly, and hourglass. In some embodiments, at least one edge of the backing is rounded to reduce unintentional delamination. In some embodiments, the backing comprises at least one layer of a backing material. In some embodiments, the backing comprises at least two layers of a backing material. In some embodiments, the at least two layers are of the same backing material.

In some embodiments, the microstructure array comprises a support base. In some embodiments, the microstructure array comprises a support base that is affixed to a backing. In some embodiments, the microstructure array comprises a support base that is affixed to a backing via adhesive. In some embodiments, the adhesive is a medical grade adhesive. In some embodiments, the adhesive is selected for at least one of high shear strength, high tack, high peel strength, and long term wear. In some embodiments, the adhesive is selected for high shear strength.

In some embodiments, the wound closure device comprises a tab. In some embodiments, the wound closure device comprises a tab attached to the backing. In some embodiments, the wound closure device comprises a tab attached to the backing, wherein the tab configured to improve at least one of removing the device from its packaging and applying the device to the tissue. In some embodiments, the tab has a dimension at least as wide as the device. In some embodiments, the tab has a thickness of about 100 µm. In some embodiments, the tab comprises at least one of a metal, a plastic, and a foam.

In some embodiments, the microstructure array comprises a support base a backing, and at least one tab, wherein the support base is affixed to the backing via adhesive, and wherein a tab is positioned at least one end of the device; wherein, optionally, the tab is in partial contact with the adhesive.

In some embodiments, the wound closure device comprises a tension indicator. In some embodiments, the tension indicator indicates when the device is properly applied.

In some embodiments, the wound closure device comprises at least one microstructure with a base width and a tip width, wherein the base width is larger than the tip width.

In some embodiments, the tissue the wound closure device is applied to is skin.

In some embodiments, the present disclosure presents a package comprising: at least one wound closure device comprising a microstructure array, the array comprising a plurality of microstructure portions connected by at least one bridge portion, each of the plurality of microstructure portions comprising at least one microstructure for securing the array to the tissue such that the at least one bridge portion overlays the wound, at least one of the plurality of microstructure portions comprising at least one structure with spring characteristics for expanding with movement of the tissue; and at least one thermoformed spacer for protecting at least one wound closure device.

In some embodiments, the present disclosure provides a wound closure device comprising:
  a. a microstructure array, the array comprising: a first microstructure portion connected to a second microstructure portion via a bridge portion that is substantially inelastic; wherein:
    i. the bridge portion comprises two longitudinally extending portions, each of which are connected to the first and the second microstructure portions; and
    ii. each of the first and the second microstructure portions comprise (a) at least one structure with spring characteristics and (b) at least one microstructure for securing the array to tissue; and
  b. a backing affixed to the microstructure array via adhesive.

In some embodiments, the microstructure array of the preceding paragraph is produced monolithically. In some embodiments, the microstructure array of the preceding paragraph comprises or consists of 316 stainless steel. In some embodiments, the wound closure device of the preceding paragraph comprises at least 2 structures with spring characteristics on each of the first and the second microstructure portions. In some embodiments, each of the first and the second microstructure portions comprised on the microstructure array of the preceding paragraph each comprise six microstructures (thus the device comprises twelve microstructures). In some embodiments, each of the first and the second microstructure portions comprised on the microstructure array of the preceding paragraph each comprise eight microstructures (thus the device comprises 16 microstructures). In some embodiments, the microstructures are all angled towards a wound (i.e., the microstructure tips are angled towards the bridge portion, e.g., as shown in FIG. 5). In some embodiments, the wound closure device of the preceding paragraph comprises a polyurethane backing.

In some embodiments, the present disclosure provides a wound closure device, wound closure system, or wound closure packaging according to a figure provided herein.

For example, in some embodiments, the present disclosure provides a wound closure device as shown in FIGS. 1-7.

In some embodiments, the present disclosure provides a wound closure system as shown in FIGS. 10-13.

In some embodiments, the present disclosure provides a wound closure system as shown in FIG. 14.

In some embodiments, the present disclosure provides a wound closure system as shown in one of FIG. 22, FIG. 33, and FIG. 39.

In some embodiments, the present disclosure provides a wound closure system as shown in FIGS. 44-47 (wherein the wound closure system further comprises the microstructure array of FIG. 35).

In some embodiments, the present disclosure provides a wound closure device as shown in FIG. 24

In some embodiments, the present disclosure provides a wound closure device as shown in FIG. 26

In some embodiments, the present disclosure provides a wound closure device as shown in FIG. 31.

In some embodiments, the present disclosure provides a microstructure array bridge portion comprising: one or more longitudinally extending portions attached to or integrally connected to (i) two or more of microstructure arrays or (ii) two or more microstructure array portions comprised on a single microstructure array, characterized in that the bridge portion is substantially inelastic. In some embodiments, the microstructure array bridge portion comprises two longitudinally extending portions. In some embodiments, the microstructure array bridge portion comprises more than two longitudinally extending portions. In some embodiments, the microstructure array bridge portion comprises two microstructure array portions. In some embodiments, the microstructure array bridge portion comprises two microstructure array portions integrally connected to the bridge portion. In some embodiments, the one or more of the microstructure array portions comprise at least one structure with spring characteristics. In some embodiments, each of the microstructure array portions comprise at least one structure with spring characteristics. In some embodiments, each of the microstructure array portions comprise at least two microstructure. In particular embodiments, each of microstructure array portions comprise 6 or 8 microstructures. In some embodiments, the microstructure array bridge portion further comprising a backing attached to the bridge portion. In some embodiments, the backing is also attached to the microstructure array portions.

In some embodiments, the present disclosure provides a microstructure array comprising one or more microstructure portions comprising at least one microstructure, wherein at least one of the one or more microstructure portions comprises at least one structure with spring characteristics. In some embodiments, the microstructure array comprises two or at least two microstructure portions. In some embodiments, each of the microstructure portions comprised on the microstructure array comprises at least one of 2, 3, 4, 5, 6, 7, 8, 9, 10, 11, 12, 13, 14, 15, or more structures with spring characteristics. In some embodiments, the expandability of at least one such structure with spring characteristics ranges from about 100.2% to about 105.0% in at least one direction. In some embodiments, the at least one structure with spring characteristics has an approximate shape comprising at least one of a congruent V-shape, a congruent U-shape, a congruent S-shape, a congruent I-shape, a congruent H-shape, a congruent C-shape, a congruent X-shape, a congruent Y-shape, a congruent M-shape, a congruent N-shape, a congruent T-shape, a congruent W-shape, and a congruent Z-shape. In particular embodiments, the approximate shape of the at least one structure with spring characteristics comprises a plurality of congruent U-shapes. In some embodiments, the the plurality of congruent U-shapes are oriented to a serpentine shape. In some embodiments, the microstructure array comprise at least one structure with spring characteristics that comprises a first arm portion, a second arm portion, and a curved portion connecting the first arm portion and the second arm portion, the curved portion for operating as a rotational axis such that the first arm rotates relative to the second arm when a force moves the first arm away from the second arm. In some embodiments, the expandability of the at least one structure with spring characteristics is substantially derived from at least one of (i) a geometry of at least one structure with spring characteristics and/or (ii) a material property of at least one structure with spring characteristics. In some embodiments, the at least one structure with spring characteristics comprises a material property of elasticity. In some embodiments, the geometry of the expandable portions is partly or completely made up of singles, multiples, combinations and/or mirror images of the congruent shapes. In some embodiments, a spring constant of at least one structure with spring characteristics ranges from about 0.5 N/mm to about 10 N/mm. In some embodiments, a spring constant of the device ranges from about 0.5 N/mm to about 10 N/mm. In some embodiments, the microstructure comprises two or more array portions connected or integrally connected together via a bridge portion. In some embodiments, the bridge portion comprises two or at least two microstructure portions. In some embodiments, the microstructure array further comprising a backing.

The wound closure devices of the present invention are suitable for treating internal and external wounds alike. In some embodiments, the wound closure devices are applied to a subject's skin; and in other embodiments the wound closure devices are applied to a subject's tissue {e.g., internal tissue). Accordingly, the wound closure devices of the present invention find utility in a variety of settings including, but not limited to, the treatment of wounds in urgent care settings {e.g., surgery or trauma centers including emergency rooms, operating rooms, ambulances battlefields, and sites of accidents); in hospitals and clinics; in over the counter settings {e.g., for use at home).

In some embodiments, the wound closure devices of the present invention have alternative utilities. For example, the devices disclosed herein may also be used in cosmetics, wherein microstructures, as described herein, may be used to penetrate the skin producing skin rejuvenation via acute injury resulting in stimulating the dermis and collagen formation inducing effects achieved with cosmetic laser procedures and skin rollers made of microneedles. This achieves improvement in the appearance of the skin by reducing wrinkles and increasing skin volume. In contrast to cosmetic laser procedures, application of the wound closure devices do not produce symptomatic inflammation resulting in pain, redness, swelling and temporary disfigurement; symptoms which can present for up to a few days after the laser procedure. In contrast to rollers made of microneedles, the wound closure devices can be applied to regions of the skin that are not easily accessible to microneedles, such as between the nose and mouth. In addition, our wound closure devices can be applied and left in place overnight or for days potentially providing more stimulation to the dermis than is achieved with short-term treatment with a microneedle roller. Finally, the wound closure device generates more uniform distribution of holes in the skin than can be achieved with a microneedle roller which is rolled onto the skin surface.

In some instances, components of the various devices are designed, accordingly to the specifications disclosed herein, to specifically optimize a device for treating a particular wound, tissue type, or location of the body. Accordingly, various specifications, e.g., the microstructure type, geometry, size, specifications, spacing within an array, array structure, number of arrays, location of arrays, dimension of arrays, isthmus, materials of the various components, etc., may in some instances be carefully chosen to design a wound closure device e.g., to treat a specific type of wound, or for treatment of any wound located on a particular type of tissue or location on the patient. For example, but not to be limited in any way, treatment of wounds on the palm or back may need longer needles than would be required to treat a wound on the face, due to the inherent variety of skin thickness that exists in these (and other) different sites of the body. In addition, the treatment of wounds may require shorter needles in patients, who are elderly or have chronic medical conditions or skin conditions, or patients treated with drugs, such as steroids, that are known to result in thinning of the skin. As such, the wound closure devices may comprise any suitable shape and size to adequately cover a variety of wounds. Additionally, the devices may be of any length or width suitable to cover a single wound, or optionally a plurality of wounds (such as, e.g., a tape bandage).

In some embodiments, the present disclosure provides a method of treating the wound with any one or more wound closure devise disclosed herein, the method comprising affixing a first end of the device to the tissue directly adjacent to one side of the wound; optionally stretching the device across the wound; then affixing a second end of the device to the tissue directly adjacent to the other side of the wound. In some embodiments, the wound is closed by the application of the device. In some embodiments, the closed wound is everted due to the action of the device. In some embodiments, the affixing is executed by placing the device in the desired position with the tips of the microstructures being oriented in contact with the tissue to which the device is meant to be affixed; applying pressure to the back of the microstructure array by pushing down on the base or backing directly behind the microstructures so as to induce the insertion of the microstructures into the tissue. In some embodiments, the affixing is executed using a roll-on handheld dispenser. In some embodiments, the method of treating the wound with any one or more wound closure devise disclosed herein further comprising covering the device with a cover after application of the device.

It should be appreciated that all combinations of the foregoing concepts and additional concepts discussed in greater detail below (provided such concepts are not mutually inconsistent) are contemplated as being part of the inventive subject matter disclosed herein, and any of the embodiments provided herein may be combined with one another (provided such combination is not mutually inconsistent). In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 2 is an exploded isometric view of the microstructure array (top) and the wound backing (bottom) for the wound closure device of FIG. 1.

FIG. 3 is a top view of a portion of the microstructure array of the wound closure device of FIG. 1.

FIG. 5 is a side view of the wound closure device of FIG. 1.

FIG. 6 is a front view of the wound closure device of FIG. 1.

FIGS. 15A and 15B are a top view and a side view, respectively, of a wound closure device according to an embodiment.

FIGS. 16 and 17 are cross-sectional illustrations of a subject's skin with a wound closure device applied across the wound, according to an embodiment.

FIG. 20 is a top view of a microstructure array according to an embodiment.

FIGS. 21A and 21B are a top view and a side view, respectively, of a spacer according to an embodiment.

FIG. 22A is a top view of a wound closure system according to an embodiment in a first configuration.

FIG. 22B is an isometric view of the wound closure system of FIG. 22A in a second configuration.

FIG. 22C is an isometric view of the wound closure system of FIG. 22A in a third configuration.

FIG. 23 is a top view of a wound closure device according to an embodiment.

FIGS. 27A, 27B, and 27C are a top view, a front view, and a side view, respectively, of a barbed microstructure, according to an embodiment.

FIGS. 28A, 28B, and 28C are a top view, a front view, and a side view, respectively, of a bladed microstructure, according to an embodiment.

FIGS. 29A, 29B, and 29C are a top view, a front view, and a side view, respectively, of a microneedle shaped microstructure, according to an embodiment.

FIGS. 30A, 30B, 30C, 30D, and 30E shows examples of wounds closed with either non-extendable wound closure devices (n=10 wounds) or sutures (n=2 wounds) immediately after incision (Day 0) or 10 days later. FIG. 30A shows an incision wound prior to closure. FIG. 30B shows an incision after closure with suture. FIG. 30D shows an incision after closure with microMend. FIG. 30C shows the suture closed incision on Day 10. FIG. 30E shows the microMend closed incision on Day 10.

FIGS. 31A and 31B demonstrate elimination of inflammation with microMend devices comprising extendable microstructure arrays. FIG. 31A shows inflammation induced by a non-extendable microMend device. FIG. 31B shows reduced inflammation induced by an extendable microMend device as compared to the result in FIG. 31A.

FIG. 33A-1, FIG. 33A-2 and FIG. 33B show design parameters of the microMend devices utilized in porcine pre-clinical Study 2 and Study 4. FIGS. 33A-1 and 33A-2 show design parameters of the expandable microstructure array included on the microMend devices utilized in pre-clinical Study 2 and Study 4 (Example 3). FIG. 33B shows how various different microMend devices, including the devices utilized in porcine pre-clinical Study 2 and Study 4 (Example 3), were assembled and packaged. Reference numbers 1-5 on the right hand side of the figure refer to the item numbers shown in the table in the upper left corner of the figure. The notes to the left of the drawing indicate various different configurations of the devices.

FIGS. 35A and 35B show design parameters of the microstructure array included on the microMend devices utilized in porcine pre-clinical Study 3 (Example 3) and in the human clinical study (Example 5). The microMend devices utilized in the porcine pre-clinical study were assembled and packaged as shown in FIG. 33B and the devices utilized in the human clinical study were assembled and packaged as shown in FIG. 39.

FIG. 36A shows the wounds immediately after surgery. FIG. 36B shows the wounds immediately after closure with the microMend devices. FIG. 36C shows the wounds 20 days post-surgery.

FIG. 38A shows the wound before closure. FIG. 38B shows the wound immediately after closure. FIG. 38C shows the wound 7 days after closure, immediately after device removal. FIG. 38D shows the wound two weeks after device removal (i.e., 3 weeks after closure).

As shown in FIG. 39, this backing (4) is affixed to the microstructure array (3) to create the microstructure wound device (i.e., a microMend device).

FIGS. 41A and 41B show design parameters of the non-expandable microstructure array included on the microMend devices utilized in the preliminary human clinical study described in Example 5. This same microstructure array was utilized in Device B from the tensile study described in Example 6. The devices were assembled and packaged as shown in FIG. 39.

FIGS. 42A and 42B show design parameters of the non-expandable microstructure array included on microMend Device A utilized in the tensile study described in Example 6. The devices were assembled and packaged as shown in FIG. 39.

FIGS. 43A and 43B show design parameters of the non-expandable microstructure array included on microMend Device C utilized in the tensile study described in Example 6. The devices were assembled and packaged as shown in FIG. 39.

FIG. 48 shows trocar wounds (port site wounds) made using a standard laparoscopic instrument in the lateral dorsal surface of both sides of the abdomen of subject female Yorkshire swine.

DETAILED DESCRIPTION

Definitions

Figure 1:
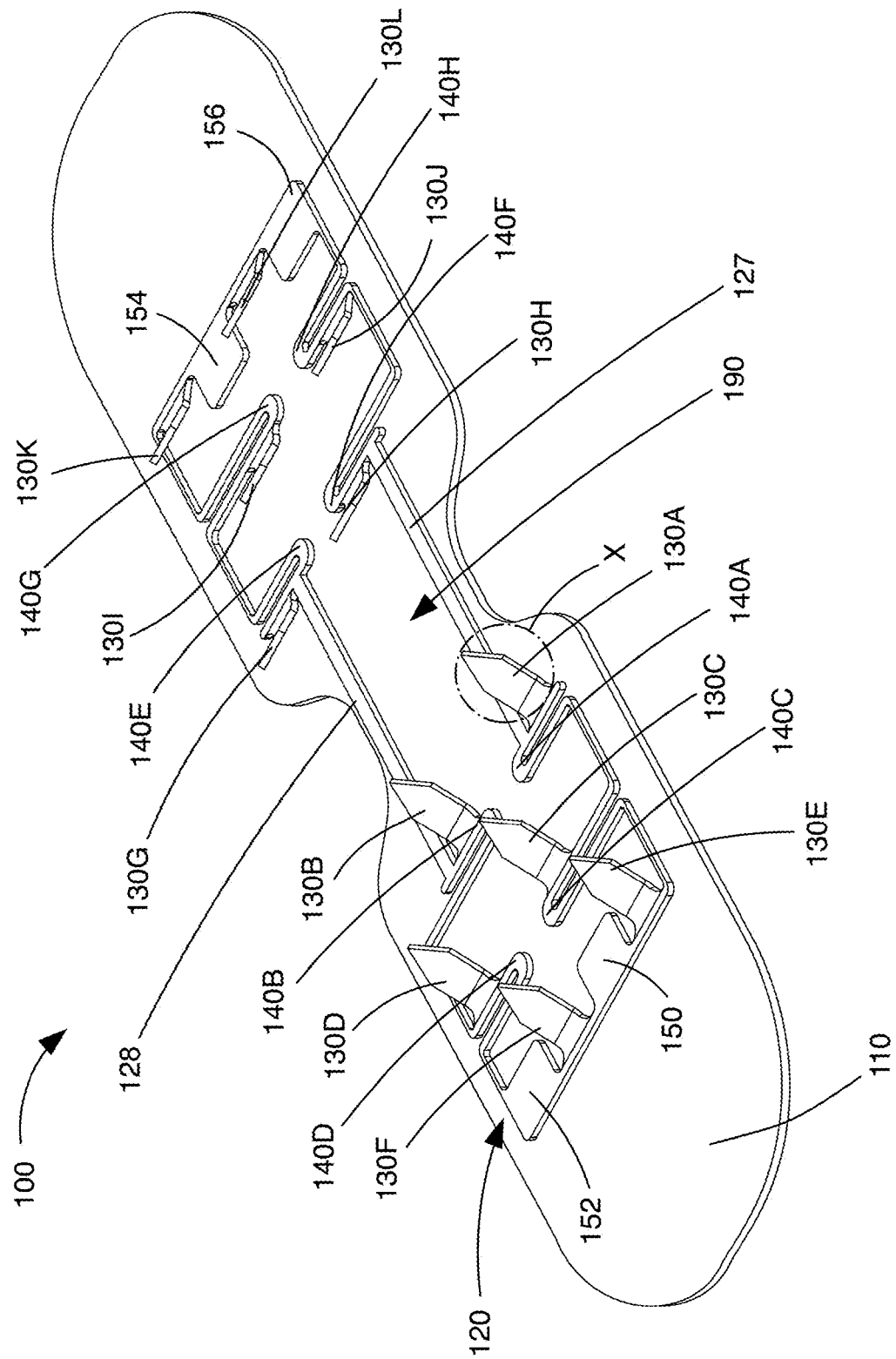
FIG. 1 is an isometric view of a wound closure device according to one embodiment of the present invention.

All definitions, as defined and used herein, should be understood to control over dictionary definitions, definitions in documents incorporated by reference, and/or ordinary meanings of the defined terms.

As used herein and unless otherwise indicated, the terms "a" and "an" are taken to mean "one", "at least one" or "one or more". Unless otherwise required by context, singular terms used herein shall include pluralities and plural terms shall include the singular.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Reference to the term "e.g." is intended to mean "e.g., but not limited to" and thus it should be understood that whatever follows is merely an example of a particular embodiment, but should in no way be construed as being a limiting example. Unless otherwise indicated, use of "e.g." is intended to explicitly indicate that other embodiments have been contemplated and are encompassed by the present invention.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

Figure 46:
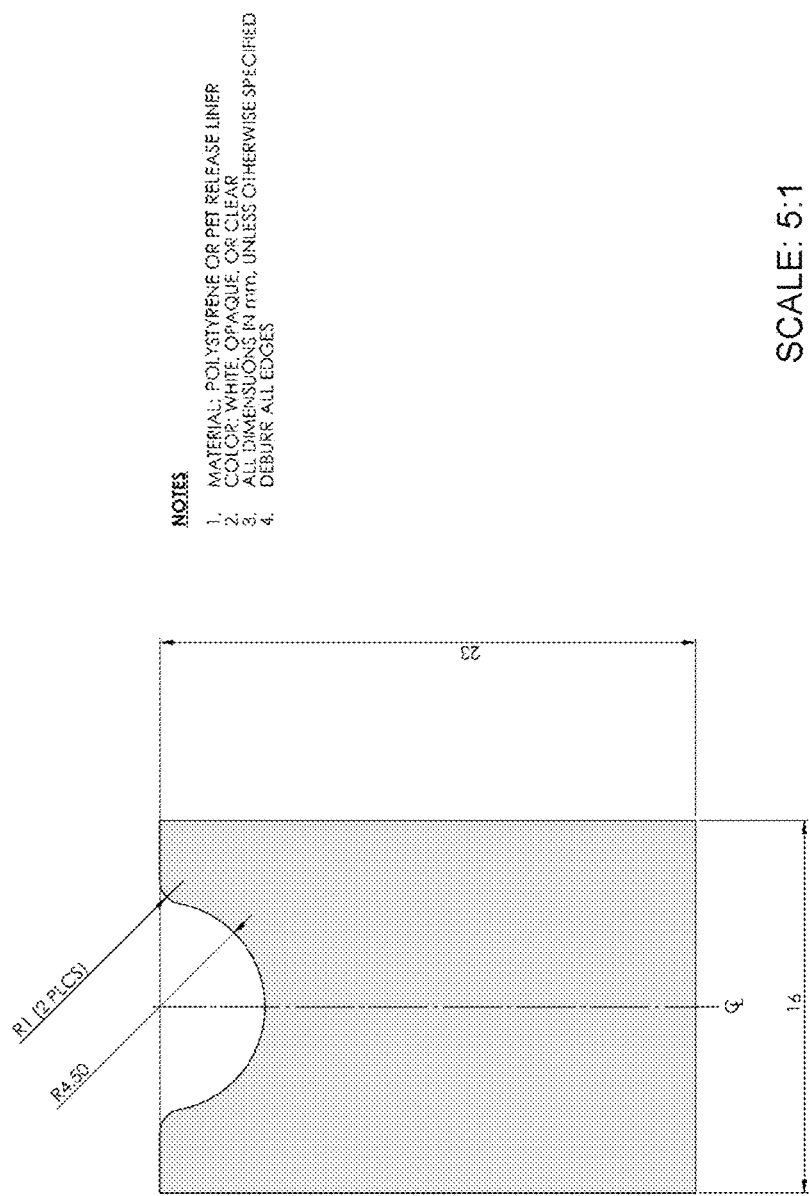
FIG. 46 shows a non-limiting example of an applicator tab ("tab") for use in the present invention.
Figure 47:
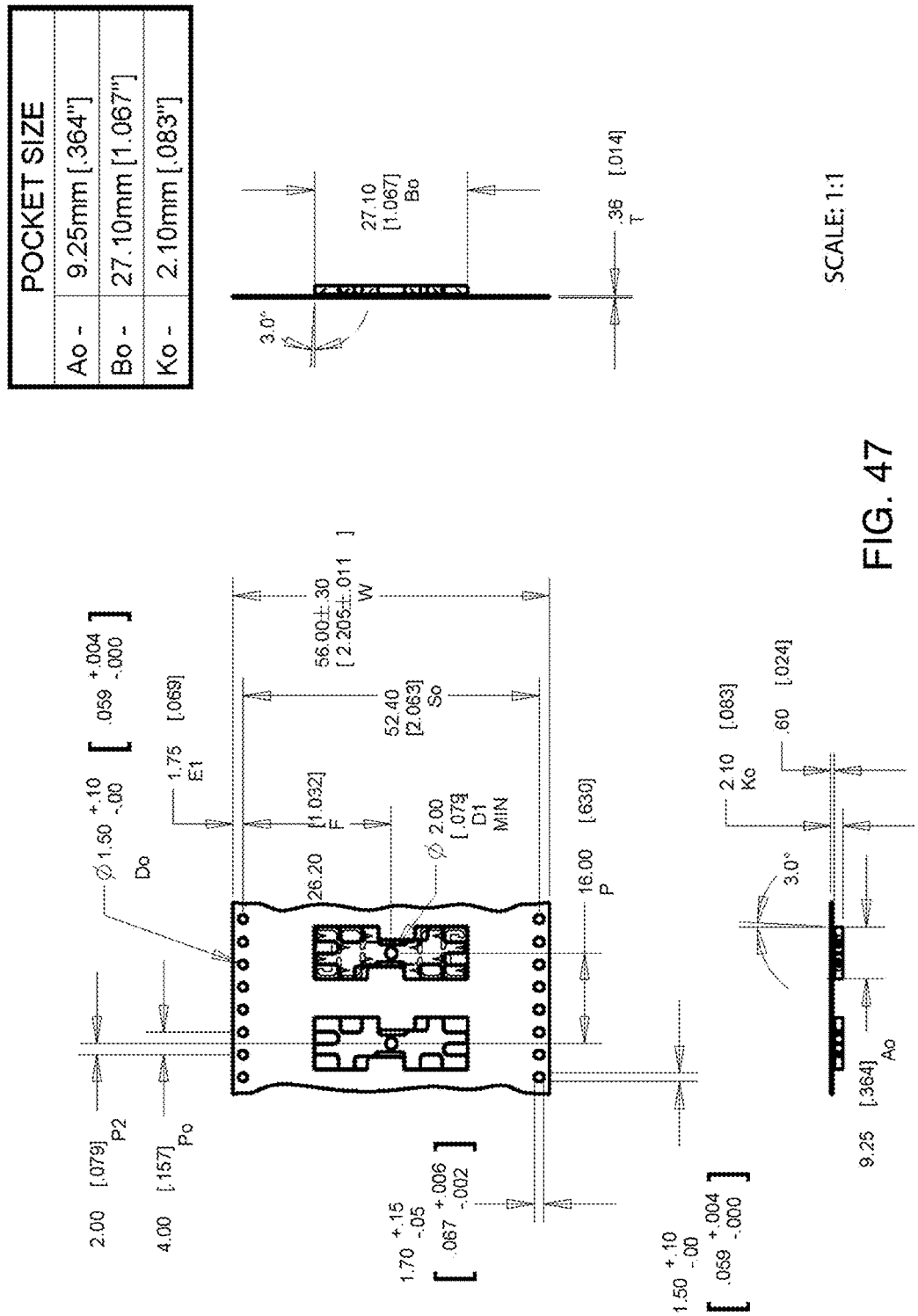
FIG. 47 shows a non-limiting example of a pocketed tray (i.e., "spacer") for use in the wound closure systems disclosed herein.

By "applicator tab" (or "tab," interchangeably") is meant a portion of a microstructure wound closure that protrudes from the device, e.g., to assist in grasping the device and/or applying the device to a subject. The applicator tab may be permanently affixed to the microstructure wound closure device or it may be removably affixed to the microstructure wound closure device (e.g., via a perforated attachment or via a removable adhesive). In particular embodiments tab is removable. The tab may be located anywhere upon the microstructure device provided that the tab does not interfere with the attachment of the microstructures onto a subject's tissue, e.g., the subjects skin. Indicator 3 in FIG. 44 denotes a non-limiting suitable placement of an applicator tab (or "tab"). Any applicator tab disclosed herein may be utilized in the devices contained in such packaging. In some embodiments, the applicator tab is as shown in FIG. 46, which shows a non-limiting applicator tab made of 5 mil polystyrene or poly(ethylene terephthalate) ("PET").

By "approximate" is meant a quantity, level, value, number, frequency, percentage, dimension, size, amount, weight or length that varies by as much as 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "approximate," it is specifically contemplated that the term about can be omitted.

Unless the context requires otherwise, throughout the present specification and claims, the word "comprise" and variations thereof, such as, "comprises" and "comprising" are to be construed in an open, inclusive sense, that is, as "including, but not limited to".

By "consisting of" is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "expandable portion", "reversibly expandable portion", "reversibly expandable structure" and "structure with spring characteristics" are used interchangeably herein.

The terms "expandability" and "strain" are used interchangeably herein to define the amount of extension/original length of the device.

In some embodiments, "microstructures" include, but are not limited to microstaples, microbarbs, microneedles, microblades, microanchors, microhooks, microfishscale, micropillars, microhairs, and combinations thereof.

As used herein, the term "spring characteristic" has its ordinary meaning, i.e., a characteristic that causes an object (e.g., a microstructure device disclosed herein) to exert an opposing force against any stretching force that is applied, wherein the opposing force is related to any change in length of the object such that the object possessing a spring characteristic will retract substantially into its original resting position once the stretching force is removed. For example, in various embodiments, when a wound closure device disclosed herein as having spring characteristics is stretched (e.g., longitudinally across a wound), the spring characteristics of the device will cause the device to retract back into the device's original resting position (or substantially back into its original resting position) once the stretching force is removed. In some embodiments, the stretching and securing of the device longitudinally across a wound (see, e.g., FIG. 37B) results in the retraction of the device back into its resting state after the stretching force is removed, and the result of the retraction is that the tissue (e.g., skin) to which the device is secured is stretched in a direction that opposes a tension of the tissue or skin that naturally pulls the wound apart, thus, resulting in the closure of the wound.

The term "substantially" means nearly totally or completely, for instance, 95% or greater of some given quantity (e.g., 96%, 97%, 98%, 99%, or greater than 99%, including all integers, decimals, and percent ranges between).

As used herein, the term "wound closure device" as used generally means a device used for closing a wound, a device used for covering a wound, a device used for protecting a wound, a wound dressing, a bandage, etc.

As used herein, the term "wound" means an injury to tissue or skin caused by scrapes, cuts, abrasion, surgical procedures (e.g., caused by minimally invasive surgery, laparoscopic surgery, robotic surgery, incisional biopsies, general surgery, and cosmetic surgery), denuded skin, burns, ulcers (e.g., diabetic ulcers, ulcers from vascular insufficiency, pressure sores, and burns), or other skin problems (e.g., allergies). Wounds may range from superficial (e.g., affecting merely the epidermis) to more traumatic (e.g., lesions which affect layers of skin or tissue at depths which are beneath the epidermis). Wounds may be of any length or shape, e.g., in some embodiments, wounds are straight, jagged or curved.

As used herein, the term "tissue" means any human or other animal tissue including, but not limited to skin, muscle, tendon, bone, heart, lung, kidney, brain, bowel, colon, rectum, stomach, esophagus, etc.

The terms "affixed" and "attached" are used interchangeably throughout, and have their ordinary meaning, for example, a first thing (e.g., a microstructure array) being connected or fastened to a second thing (e.g., a backing). Accordingly, other terms such as, "fastened", and "bound" may also be used in a similar manner.

The term "connected" is used herein to describe when two separate things (e.g., a bridge portion and a microstructure array portion) are in direct proximity with one another and are either affixed together or integrally connected to one another.

The term "integrally connected" is used herein to refer to two separate structures (e.g., a microstructure and a base, or a microstructure array portion and a bridge or bridge portion) that are in direct and seamless contact with one another such that they are a single monolithic structure. Thus, reference to two "integrally connected" structures is purely for descriptive purposes, and the two structures are, in fact, one single structure.

The term "flexible" is meant to describe any material that is capable of sustaining a bending force without being damaged. In some embodiments, a "flexible" material comprises enough flexibility as to allow the device of the present invention to bend so as to fit the contours of the biological barrier, such as, e.g., the skin, vessel walls, or the eye, to which the device is applied. Thus, in some embodiments a material or structure used herein may comprise a material property of flexibility.

The term "grasping" is used herein to describe a microstructure-based anchoring of a wound closure device to its intended location on the surface of the skin or other tissue to which it is applied. The anchoring does not require penetration into the skin or tissue by the microstructures. For example, the wound closure device can be anchored via friction generated by the contact of the microstructures with the skin or other tissue. In some embodiments, the wound closure device is anchored by grasping, optionally with or without the assistance of the other various components of the present wound closure devices and systems, such as, for example, an adhesive.

The term "longitudinally" (or "along the longitudinal axis") is used herein to describe a direction on the device that extends across a wound (e.g., a laceration) when appropriately applied. For example, markers 127 and 128 in FIG. 1 illustrate extending portions that run in the direction of the device that would extend across a laceration when appropriately applied according to the present disclosure (see, e.g., FIG. 37B for a representative example of such an appropriately applied device, which is applied perpendicular to a wound). In some such embodiments, wherein the device comprises a length and a width that differs, longitudinally may describe a direction running parallel to the longer side of the device. For example, longitudinally extending portions 127 and 128 described above each run in a direction parallel to the lengthwise direction of device. Conversely, the term "laterally" (or "along the lateral axis") means the axis of the device that is perpendicular to the longitudinal axis, e.g., an axis of a device that extends parallel to a wound (e.g., a laceration) when appropriately applied according to the present disclosure.

The term "material property" means a physical property of a material making up or comprised in a wound closure device described herein. So, said another way, e.g., but not to be limited in any way, a material having a material property of elasticity is an elastic material; a material having a material property of liner spring characteristic is a material that stretches; and a material having a material property of flexibility is a flexible material.

The term "penetration" or "penetrate" is meant herein to refer to the action of piercing the skin or tissue, for example, with one or more of the microstructures disclosed herein.

The term "inflammation" is meant to have its ordinary medical meaning, i.e., a biological response of a tissue to a harmful stimulus. Common signs of inflammation include pain, heat, redness (erythema), swelling (edema), and loss of function.

The term "rigid" is used herein to mean that the rigid object (e.g., a bridge portion of a microstructure would closure device disclosed herein) does not expand.

The term "stretchable" as used herein is meant to encompass any material that can be elongated in any direction, e.g., as a result of a pulling force. "Stretchable" encompasses the term "elastic" and, thus, an object that is said to be stretchable should be understood to optionally comprise elasticity. Thus, in some embodiments, if an object is said to be stretched, this is meant to include at least two embodiments; the first being that the stretching force will be counteracted by a retractile force, and thus once the stretching force is removed, the object will inherently attempt to retract (e.g., as is the case with an elastic object). The second embodiment is one in which the object does not inherently comprise elasticity, and thus no such retractile force is inherent. In various embodiments, the devices of the present disclosure comprise both flexibility and stretchability. In particular embodiments, such devices are stretchable longitudinally. In particular embodiments, the devices are stretchable and elastic longitudinally and they are flexible.

Overview

Examples of wound closure devices utilizing microstructures are described in International Patent Application No. PCT/US2013/046181, entitled "Microstructure-Based Wound Closure Devices," the entire disclosure of which is hereby incorporated by reference.

The embodiments of the present disclosure relate to improved wound closure devices comprising reversibly expandable portions ("expandable portions") that enable the wound closure device to elongate (e.g., if a stretching force is applied) and to retract after elongation (e.g., once a stretching force is removed). These new devices are referred to herein generically as "microMend" wound closure devices.

In various embodiments, the "stretchability" (ability to stretch if a force is applied) and/or "elasticity" (ability to retract once a stretching force is removed) of the expandable portion is due, in part, to the configuration of the expandable portion (as opposed to the stretchability and/or elasticity being due to a property of the material(s) from which the device was made). In some embodiments, substantially all of the stretchability and/or elasticity of the expandable portion is due to the configuration of the expandable portion. In some embodiments, all of the stretchability and/or elasticity of the expandable portion is due to the configuration of the expandable portion.

In various embodiments, the wound closure devices (or "apparatus") of the present disclosure comprise one or more microstructures (e.g., one or more microstructure arrays) and one or more reversibly expandable portions. The expandable portions have a spring constant that is tunable by changing the geometry of the device. In embodiments, the microstructures are configured to grasp and/or penetrate tissue, e.g., tissue on either side of a wound to enable wound closure.

In some embodiments, the wound closure device of the present disclosure comprises a microstructure array that includes a bridge portion (e.g., a rigid bridge portion) connecting a plurality of additional portions, each additional portion comprising one or more microstructure, wherein at least one (e.g., at least 1, 2, 3, 4, or more) of the additional portions comprises an expandable portion. In some embodiments, no such bridge portion is included in the device (e.g., in such embodiments, the portions comprising the one or more microstructure can be in direct connection with one another, without any bridge portion). In some embodiments, at least two of the additional portions comprise an expandable portion. In some embodiments, the bridge portion keeps the edges of the wound approximated during movement, which will avoid opening of the wound, known as dehiscence, and damage to the skin. This reduces the risks of infection, inflammation and scarring during any external stress, such as ones that occur during movement.

In some embodiments, a wound closure device apparatus of the present disclosure includes a microstructure array and, optionally, a backing.

In some particular embodiments, the microstructure array of the present disclosure includes a first portion, a second portion, and a bridge portion. In one such embodiment, the bridge portion connects the first and the second portion. In some such embodiments, the bridge portion does not expand substantially (i.e., it is "rigid"). The microstructure array may include a base that includes at least a portion of the first portion, at least a portion of the second portion, and at least a portion of the bridge portion. In some embodiments, the base includes the entire first, second, and bridge portions. The microstructure array may also define an aperture in the base of the microstructure array. In some embodiments, the microstructure array defines a single aperture in the base of the microstructure array. In some such embodiments, a first portion and a second portion each include one or more microstructures configured to grasp and/or penetrate tissue.

In some particular embodiments, the microstructure array of the present disclosure includes a first portion and a second portion, wherein no bridge portion connects the first and the second portion. In some such embodiments, the device may optionally comprise a portion that does not expand substantially (i.e., it is "rigid"). The microstructure array may include a base that includes at least a portion of the first portion and at least a portion of the second portion. In some embodiments, the base includes the entire first and second portions. The microstructure array may also define an aperture in the base of the microstructure array. In some embodiments, the microstructure array defines a single aperture in the base of the microstructure array. In some such embodiments, a first portion and a second portion each include one or more microstructures configured to grasp and/or penetrate tissue.

Additionally, in some such embodiments, each of the first portion and the second portion of the microstructure array include one or more expandable portions such that the wound closure device is configured to expand in length. In other embodiments, either one of the first portion or the second portion of the microstructure array include one or more expandable portions such that the wound closure device is configured to expand in length. In some embodiments, at least one of the microstructures of the first portion is capable of securing the wound closure device on one side of a wound and at least one of the microstructures of the second portion is capable of securing the wound closure device to the other side of the wound. In some embodiments, such microstructure arrays are additionally or alternatively configured to include one or more expandable portions configured to expand in width.

For example, FIGS. 1-7 show various views of a wound closure device 100 according to one non-limiting embodiment. FIG. 1 is an isometric view of the wound closure device 100. The wound closure device 100 includes a backing 110 and a microstructure array 120. As shown in FIG. 1, the microstructure array 120 is coupled to the backing 110. In some implementations, the microstructure array 120 can be attached to the backing 110 via an adhesive.

In various embodiments, the wound closure devices of the present disclosure range in size, shape, and configuration.

For example, in some embodiments, the wound closure devices of the present disclosure may be any suitable length or width. In some embodiments, the present disclosure provides a wound closure device that ranges from approximately 10 mm to approximately 150 mm in length. In some embodiments, the present disclosure provides a wound closure device that ranges from approximately 20 mm to approximately 100 mm in length. In some embodiments, the present disclosure provides a wound closure device that ranges from approximately 30 mm to approximately 60 mm in length. In some embodiments, the present disclosure provides a wound closure device that ranges from approximately 1 mm to approximately 100 mm in width. In some embodiments, the present disclosure provides a wound closure device that ranges from approximately 2 mm to approximately 100 mm in width. In some embodiments, the present disclosure provides a wound closure device that ranges from approximately 3 mm to approximately 30 mm in width. In some embodiments, the present disclosure provides a wound closure device that ranges from approximately 5 mm to approximately 20 mm in width.

In various embodiments, the wound closure devices described herein are applied to tissue surrounding a wound by a method comprising, (i) securing one or more microstructures comprised on a first portion of a wound closure device to the tissue on a first side of a wound; (ii) stretching the device longitudinally across the wound, thereby expanding one or more expandable portions comprised on the device; (iii) securing one or more microstructures comprised on a second portion of a wound closure device to the tissue on a second side of the wound; and (iv) releasing the stretching force, thereby allowing the expandable portions to retract. In some embodiments, the retraction of the expandable portion pulls the skin surrounding the wound together; thus, effectively closing the wound. In some embodiments, the closure of the wound by the above method results in wound eversion.

In some embodiments, a wound closure device includes expandable portions that minimize irritation and/or inflammation of a subject's skin as compared to conventional wound closure devices and bandages that are inelastic. In some embodiments, the irritation and/or inflammation is minimized because the expandable portions allow the device to stretch with a subject's skin. In some embodiments, a wound closure device includes microstructure anchoring devices to prevent creep of the wound closure device.

In some embodiments, a wound closure device enables simple, minimally invasive, wound closure without the need for follow-up care. The wound closure devices described herein are easily applied and removed, often with little to no pain, thus obviating reliance on trained specialists or specialized equipment for application and removal. In some embodiments, the wound closure devices described herein can achieve wound closure, induce little to no inflammation, and cause little to no scarring (e.g., the railroad track effect that results from staples and sutures). Furthermore, in certain embodiments the wound closure devices described herein may be secured to the skin of a patient in the absence of adhesive, thus, avoiding potential allergic complications. Thus, the wound closure devices described herein provide an attractive and versatile alternative to traditional wound closure devices.

In some embodiments, wound closure devices are capable of performing a variety of functions. For example, in some embodiments, the wound closure devices described herein protect a wound from its surrounding environment, prevent infection, close a wound, and/or increase the delivery of therapeutic compounds through skin or through the external surface of a tissue.

Additionally, the wound closure devices described herein are suitable for treating internal and external wounds alike. In some embodiments, the wound closure devices are applied to a subject's skin. In some embodiments, the wound closure devices are applied to a subject's tissue (e.g., internal tissue). Accordingly, the wound closure devices described herein find utility in a variety of settings including, but not limited to, the treatment of wounds in urgent care settings (e.g., surgery or trauma centers including emergency rooms, operating rooms, ambulances, battlefields, and accident sites), in hospitals and clinics, and in over-the-counter settings (e.g., for use at home).

In some embodiments, the wound closure devices described herein have alternative utilities in addition to, or instead of, their wound closing properties. For example, in some embodiments, the wound closure devices described herein are used to enable delivery of bioactive compounds, e.g., drugs, vaccines, or other therapeutic agents. Some embodiments incorporate microstructures coated with drugs, microstructures with open internal structure in which drugs can be incorporated, or combinations of both microstructures coated with drugs and microstructures with open internal structure. In some embodiments, microstructures with open internal structures enable sampling of tissue or bodily fluids. The bodily fluids can be transported through the open internal structure of a microstructure by any suitable means known in the art including, but not limited to, capillary action, suction (e.g., via application of a vacuum force), pumping, etc. In some embodiments, tissue or bodily fluids sampled using the devices disclosed herein are used for laboratory diagnostic tests.

In some embodiments, the wound closure devices described herein may also be used in cosmetics, wherein microstructures of the wound closure devices may be used to penetrate the skin. The skin penetration can produce skin rejuvenation via acute injury resulting in stimulation of the dermis and collagen formation-inducing effects similar to those achieved with cosmetic laser procedures and/or skin rollers made of microneedles. This stimulation achieves improvement in the appearance of the skin by reducing wrinkles and increasing skin volume. In contrast to cosmetic laser procedures, application of the wound closure devices described herein does not produce symptomatic inflammation resulting in pain, redness, swelling and temporary disfigurement, which can present for up to a few days after the laser procedure. In contrast to rollers made of microneedles, the wound closure devices described herein can be applied to regions of the skin that are not easily accessible to microneedles, such as between the nose and mouth. In addition, the wound closure devices described herein can be applied and left in place overnight or for several days potentially providing more stimulation to the dermis than is achieved with short-term treatment with a microneedle roller. Additionally, the wound closure devices described herein generate more uniform distribution of points of contact for more evenly distributed tension to reduce inflammation and scarring in the skin than can be achieved with a microneedle roller which is rolled onto the skin surface.

In some instances, components of the various devices are designed, accordingly to the specifications disclosed herein, to specifically optimize a device for treating a particular wound, tissue type, or location of the body. Accordingly, various specifications, e.g., the microstructure type, geometry, size, specifications, spacing within an array, array structure, number of arrays, location of arrays, dimension of arrays, bridge, expandable portions, materials of the various components, etc., may in some instances be carefully chosen to design a wound closure device e.g., to treat a specific type of wound, or for treatment of any wound located on a particular type of tissue or location on the patient. For example, but not to be limited in any way, treatment of wounds on the palm or back may need longer needles than would be required to treat a wound on the face, due to the inherent variety of skin thickness that exists in these (and other) different sites of the body. In addition, the treatment of wounds may require shorter needles in patients, who are elderly or have chronic medical conditions or skin conditions, or patients treated with drugs, such as steroids, that are known to result in thinning of the skin. As such, the wound closure devices may comprise any suitable shape and size to adequately cover a variety of wounds. Additionally, the devices may be of any length or width suitable to cover a single wound, or optionally a plurality of wounds (such as, e.g., a tape bandage).

As will be clear to the skilled artisan, the microstructure wound closure devices of the present disclosure comprise several optional and mandatory components (e.g., including some or all of the components selected from one or more microstructure array and/or microstructure array portions; microstructures, backing, bridge portions, expandable portions, tabs, packaging components including spacers, and so forth), which are described in the following embodiments. It is contemplated that these embodiments may be combined together, according to the disclosure, to produce the wound closure devices and systems of the present disclosure.

Backing

In some embodiments, the wound closure device of the present disclosure comprises a microstructure array affixed directly to a backing, e.g., via an adhesive (optionally, an adhesive that is suitable for application to skin or tissue). In some embodiments, the backing is flexible and/or stretchable. In some embodiments, the wound closure device of the present disclosure comprises a microstructure array that is not affixed to a backing.

In some embodiments, the wound closure device of the present disclosure comprises a backing including a top layer and a bottom layer. An adhesive coating may be included on the bottom side of the top layer. An adhesive coating may be included on the top side and the bottom side of the bottom layer. The top layer and the bottom layer of the backing may be arranged such that a microstructure array is disposed between the top layer and the bottom layer and secured in place via the adhesive coatings of the bottom side of the top layer and the top side of the bottom layer. The bottom layer may define one or more apertures such that microstructures of the microstructure array can protrude from the bottom layer via the apertures. For example, the bottom layer may define a first aperture that is the same size as a first portion of a microstructure array and a second aperture that is the same size as a second portion of a microstructure array.

In some embodiments, the backing includes a first backing portion, a second backing portion, and, optionally, a bridge portion (the "bridge portion backing"). The backing also includes a top surface and a bottom surface. The backing can be any suitable size and shape, and is, optionally, configurable to match the specifications of any microstructure array to which it is to be attached (e.g., any one of the microstructure arrays described herein).

In some embodiments, the top surface of the backing is coated in a continuous layer of adhesive to assist in the application and/or the stabilization of the wound closure device upon the skin or other tissue. In some embodiments, the top surface of the backing is coated in a discontinuous and/or patterned layer of adhesive.

In some embodiments, the first backing portion, the second backing portion, and/or the bridge portion backing of the backing include no adhesive intended for contact with skin or tissue. In some embodiments, the first backing portion, the second backing portion, and optionally the bridge portion backing include adhesive, which affixes backing to a microstructure array. Suitable adhesives include those disclosed herein.

In some embodiments, the backing includes rounded edges to prevent premature delamination (i.e., premature and unintentional peeling of the device from the skin or tissue upon which it is affixed or peeling of the microstructure array off of the backing) during application. In some such embodiments, all edges of the backing are rounded (see, e.g., 110 illustrated on FIG. 2). However, in other embodiments, the backing is formed in different shapes, sizes or geometries including, optionally, with non-rounded edges.

The length of the backing may vary in the various embodiments. For example, in some embodiments, the length of the backing ranges from about 10 mm to about 150 mm or more. In some embodiments, the length of the backing ranges from about 20 mm to about 100 mm or more. In some embodiments, the length of the backing ranges from about 30 mm to about 60 mm or more. Accordingly, in various embodiments, the length of the backing ranges from approximately 30 mm, 31 mm, 32 mm, 33 mm, 34 mm, 35 mm, 36 mm, 37 mm, 38 mm, 39 mm, 40 mm, 5 cm, 6 cm, 7 cm, 8 cm, 9 cm, 10 cm, 11 cm, 12 cm, 13 cm, 14 cm, and 15 cm, including all integers (e.g., 45 mm, 46 mm, 47 mm, etc.) and ranges (e.g., 10 mm-50 mm, 20 mm-35 mm, 30 mm-40 mm, 35 mm-50 mm, 35-60 mm, etc.) in between the backing lengths set forth herein.

The width of the backing in at least the regions of the first backing portion and/or the second backing portion may also vary in the various embodiments. For example, in some embodiments, the width of the backing ranges from about 1 mm to about 100 mm or more. In some embodiments, the width of the backing ranges from about 2 mm to about 50 mm or more. In some embodiments, the width of the backing ranges from about 3 mm to about 30 mm or more. In some embodiments, the width of the backing ranges from about 5 mm to about 20 mm or more. Accordingly, in various embodiments, the width of the backing ranges from approximately 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, including all decimals (e.g., 9.5 mm, 10.5 mm, 10.6 mm, etc.) and ranges (e.g., 5 mm-10 mm, 5 mm-18 mm, 7 mm-15 mm, etc.) in between the backing widths set forth herein.

The backing can be any suitable thickness. In some embodiments, the backing is about 8-10 MIL thick. As used herein, MIL has it ordinary meaning, i.e., one thousandth of an inch (or 0.0254 mm).

Figure 33A:
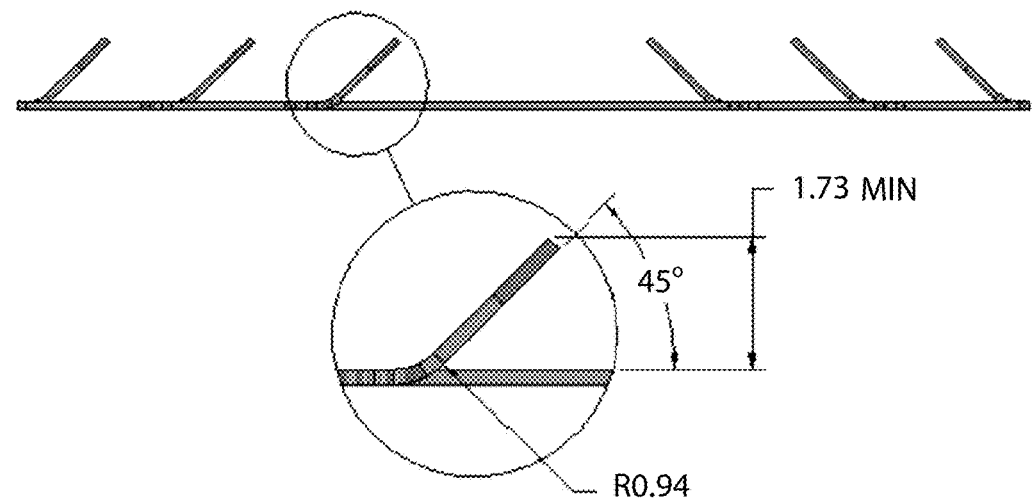
Figure 1:
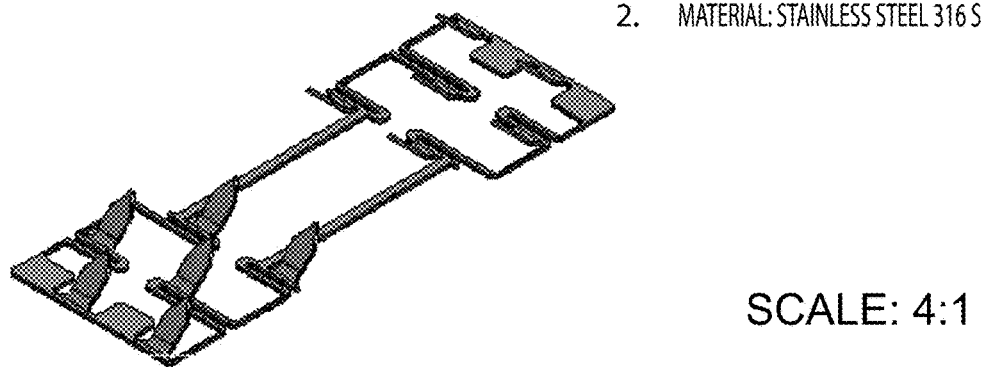
Figures 2, 33A:
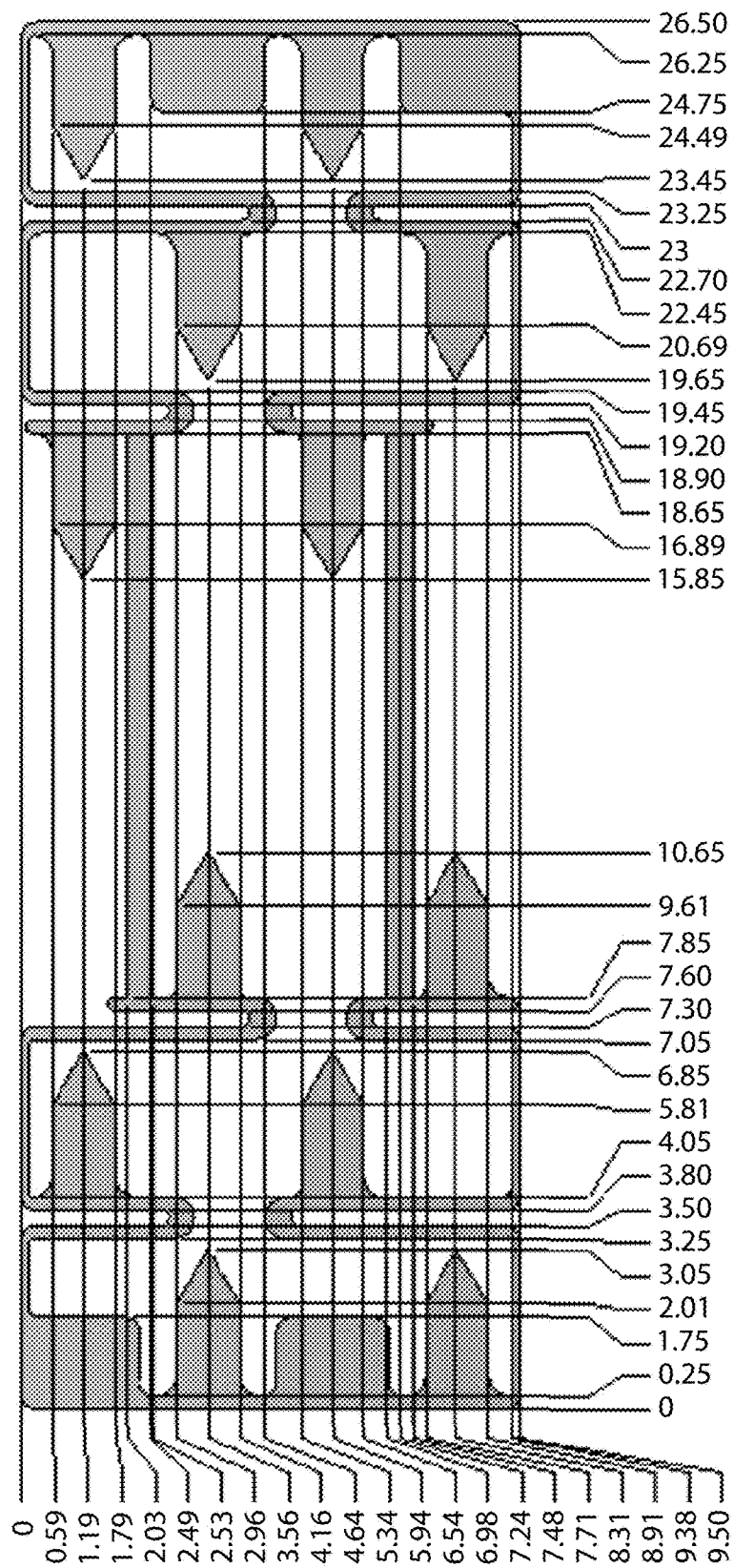

For example, FIG. 2 shows an exploded isometric view of an exemplary wound closure device 100 with the microstructure array 120 and the backing 110 shown as separate components for illustrative purposes. The backing 110 includes a first backing portion 112, a second backing portion 114, and a bridge portion 116 (the "bridge portion backing"). The backing 110 also includes a top surface 111 and a bottom surface indicated at 113. In this example, the top surface 111 of the backing 110 is coated in a continuous layer of adhesive to assist in the application and/or the stabilization of the wound closure device 100 upon the skin or other tissue. Further, the backing 110 has rounded edges. The first backing portion 112 and the second backing portion 114 are shown in FIG. 2 as being the same shape and size, and the bridge portion backing 116 is shown in FIG. 2 as being narrower than the first backing portion 112 and the second backing portion 114.

First and Second Backing Portions

In some embodiments, the first backing portion and/or the second backing portion can be any suitable shape, size, and geometry, e.g., depending on the desired use and/or intended target tissue. In some embodiments, the first backing portion and the second backing portion are the same shape and size. In some embodiments, the first backing portion and the second backing portion are have different shapes, sizes, and/or geometries, e.g., depending on the desired use and/or intended target tissue. In some embodiments, the bridge portion backing is narrower than the first backing portion and/or the second backing portion; and in some implementations the bridge portion backing is the same width as, or wider than, the first backing portion and/or the second backing portion.

Bridge Portion Backing

In some embodiments, the bridge portion backing can be any suitable shape, size, or geometry, e.g., depending on the desired use and/or intended target tissue. In some embodiments, the length, width, and/or shape of the bridge portion backing is determined by the length and width of the microstructure array bridge portion, e.g., to ensure that the entire (or substantially the entire) microstructure array bridge portion is contacted by (e.g., affixed to or covered by) the bridge portion backing.

In some embodiments, the bridge portion backing ranges, for example, from about 1 mm in length to about 50 mm in length. Accordingly, in some embodiments, the bridge portion backing is 1 mm in length; 2 mm; 3 mm; 4 mm; 5 mm; 6 mm; 7 mm; 8 mm; 9 mm; 10 mm; 11 mm; 12 mm; 13 mm; 14 mm; 15 mm; 2 cm; 3 cm; 4 cm; 5 cm in length, including all decimals (e.g., 10.5 mm, 10.6 mm, 10.7 mm, etc.) and ranges (e.g., 1-50 mm, 20-50 mm, 1-15 mm, 5-10 mm, 10-15 mm, 3-4 mm, 5-6 mm, 6-8 mm, etc.) in between the bridge portion backing lengths set forth herein. In one embodiment, the bridge portion backing ranges from 3 mm in length to 30 mm in length. In one embodiment, the bridge portion backing ranges from 13 mm in length to 25 mm in length. In one embodiment, the bridge portion backing ranges from 5 mm in length to 10 mm in length. In one embodiment, the bridge portion backing ranges from 6 mm in length to 9 mm in length. In one embodiment, the bridge portion backing ranges from 5 mm in length to 25 mm in length.

For example, FIG. 15A and FIG. 15B are a top and a side view of a wound closure device 400, respectively. As shown in FIG. 15A, the wound closure device 400 includes a backing 410 and a microstructure array 420. The backing 410 includes a first backing portion 412, a second backing portion 414, and a bridge portion backing 416. The backing 410 has a length $D_{20}$. The length $D_{20}$ can be any suitable length. For example, the length $D_{20}$ may range from about 30 mm to about 60 mm. In other embodiments, the length $D_{20}$ may range from about 20 mm to about 100 mm. In other embodiments, the length $D_{20}$ may range from about 10 mm to about 150 mm.

Also, as described above, the width of the bridge portion backing may vary. In some embodiments, the width of the bridge portion backing ranges from about 1 mm to about 100 mm or more. Accordingly, in these embodiments, the width of bridge portion backing may range from approximately 1 mm, 2 mm, 3 mm, 4 mm, 5 mm, 6 mm, 7 mm, 8 mm, 9 mm, 1 cm, 2 cm, 3 cm, 4 cm, 5 cm, 6 cm, 7 cm, 8 cm, 9 cm, 10 cm, including all integers (e.g., 11 mm, 12 mm, 13 mm, etc.) and ranges (e.g., 2 mm-50 mm, 5 mm-15 mm, 3 mm-30 mm, 5 mm-10 mm, 5-20 mm, etc.) in between of the bridge portion backing widths set forth herein. In one embodiment, the bridge portion backing ranges from 5 mm in width to 25 mm in width. In one embodiment, the bridge portion backing ranges from 7 mm in width to 20 mm in width. In one embodiment, the bridge portion backing ranges from 10 mm in width to 20 mm in width. In one embodiment, the bridge portion backing ranges from 2 mm in width to 50 mm in width. In one embodiment, the bridge portion backing ranges from 3 mm in width to 30 mm in width. In one embodiment, the bridge portion backing ranges from 5 mm in width to 20 mm in width.

For example, as shown in FIG. 15A, the width $D_{22}$ of the bridge portion backing 416 may range from about 5 mm to about 20 mm. In other embodiments, the width $D_{22}$ ranges from about 3 mm to about 30 mm. In other embodiments, the width $D_{22}$ ranges from about 2 mm to about 50 mm. In still other embodiments, the width $D_{22}$ ranges from about 1 to about 100 mm.

In some embodiments, the bridge portion backing comprises a width that is less than the width of the first backing portion and the second backing portion. In some embodiments, the bridge portion backing comprises a width that is greater than the width of the first backing portion and the second backing portion.

For example, as shown in FIG. 15A, the width $D_{21}$ of the first backing portion 412 and the second backing portion 414 may range from about 5 mm to about 20 mm. In other embodiments, the width $D_{21}$ ranges from about 3 mm to about 30 mm. In other embodiments, the width $D_{21}$ ranges from about 2 mm to about 50 mm. In still other embodiments, the width $D_{21}$ ranges from about 1 to about 100 mm.

In some embodiments, as described above, the bridge portion backing includes rounded edges. In some embodiments, the presence of the rounded edges prevents or reduces premature delamination of the device as compared to a similar device having unrounded edges (e.g., square edges). In some embodiments, the bridge portion backing comprises straight lines with rounded edges. In some embodiments, the bridge portion backing comprises a width that is less than the width of the first backing portion and the second backing portion and the bridge portion backing includes a transition portion with sloped edges between the first backing portion and the bridge portion backing and between the second backing portion and the bridge portion backing. For example, as shown in FIG. 15A, an angle $\theta_6$ measured between a sloped edge of a transition portion between the first backing portion 412 and the bridge portion backing 416 and a sloped edge of a transition portion between the second backing portion 414 and the bridge portion backing 416 on the same side of the backing 410 can range, for example, between 0° and 180°. In some embodiments, the angle $\theta_6$ can range from about 20° to about 120°. In some embodiments, the angle $\theta_6$ can range from about 40° to about 100°. In some embodiments, regardless of the angle $\theta_6$, corners of the wound closure device 400 are always rounded with a constant radii to reduce the chances of premature or unintentional delamination locally.

Backing Materials

The backing can be made of a stretchable and breathable polyurethane-based film. Alternatively, the backing can be made of any suitable material. In some embodiments, for example, the backing can be made of a material that is transparent, or substantially transparent, thus allowing for non-invasive monitoring of wound healing. In other embodiments, the backing can be made of a material that is not transparent. In some embodiments, backings of embodiments described herein are in the form of sheets; bandages; rolls; films; cloths; woven materials; or other permeable, semi-permeable, or impermeable coverings. Backings of embodiments described herein may be made from natural, synthetic, and/or artificial materials; and in some particular embodiments, they comprise a polymeric substance (e.g., a silicone, a polyurethane, or a polyethylene). Backings of embodiments described herein may be comprised of materials that are nontoxic, biodegradable, bioresorbable, or biocompatible. In some embodiments, backings of embodiments described herein comprise inert materials, and in other embodiments, the backing comprises activated materials, (e.g., activated carbon cloth to remove microbes, as disclosed in WO2013028966A2, incorporated herein in its entirety). In some embodiments, backings of embodiments described herein comprise a material singularly, or in combination, selected from the group consisting of medical tape, white cloth tape, surgical tape, tan cloth medical tape, silk surgical tape, clear tape, hypoallergenic tape, silicone, elastic silicone, polyurethane, elastic polyurethane, polyethylene, elastic polyethylene, rubber, latex, Gore-Tex, plastic and plastic components, polymers, biopolymers, and natural materials. In some embodiments, wound closure devices, as disclosed herein, can comprise one or more microstructures affixed to a commercially available backing selected from the group consisting of 3M Transpore Surgical Tape, 3M Blenderm Surgical Tape, Coverlet Fabric, Dynarex Silk Surgical Tape, KENDALL™ Hypoallergenic Clear Tape, TENDERFIX™ Hypoallergenic Cloth Tape, CURASILK™ Cloth Tape, Curapont, Leukosan Skinlink, Leukosan Strip, Leukostrip, Steri-Strip, Steri-Strip S, Urgo strip, and combinations thereof. The flexibility and/or stretchability of the backing may be uniform throughout. Alternatively, the flexibility and/or stretchability of the backing may vary across, or along, the device. Further, in some embodiments, backings of embodiments described herein can comprise elastic properties, wherein the elasticity may optionally be similar throughout the device. Alternatively, the elasticity may be varied along or across the device.

Tabs

Figure 24:
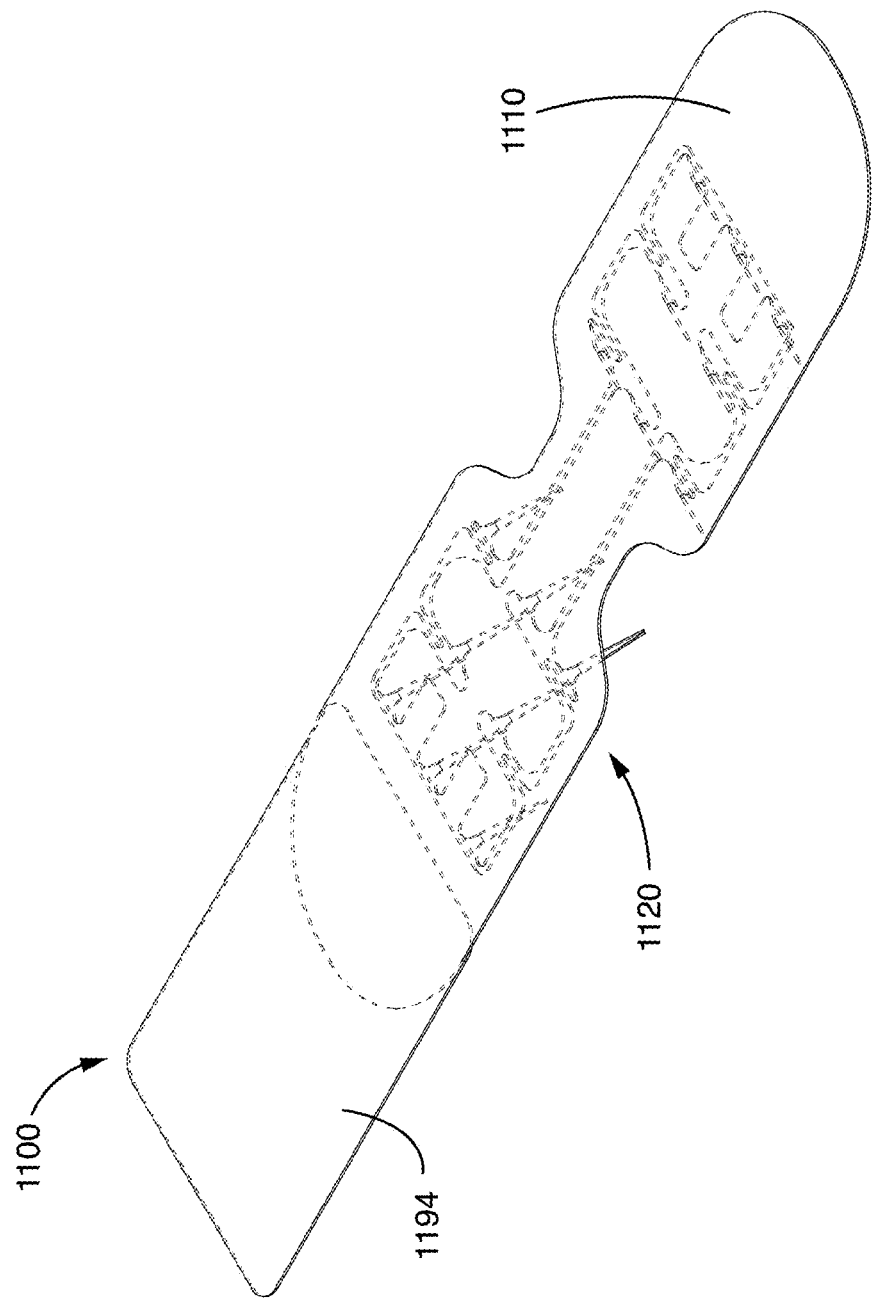
FIG. 24 is an isometric view of a wound closure device according to an embodiment.

In some embodiments, the wound closure devices disclosed herein include one or more tab (e.g., an applicator tab). Such a tab may be located in any suitable position on the device. In some embodiments, the tab is located on one or more end of the device (e.g., on one of the longitudinal ends of the device). For example, marker 1194 in FIG. 24 shows a non-limiting example of one such tab, which is located at a longitudinal end of a wound closure device disclosed herein. Of course, one of skill in the art would understand the tab's location may be altered in any desirable way. In embodiments, the tab may be any shape. The tab may assist in the application of the device, e.g., in the handling and/or placement of the wound closure device on tissue (e.g., skin). The tab may allow the person applying the wound closure device to avoid touching the adhesive during application. The tab may optionally be attached to the device via a perforated edge, so as to permit easy removal of the tab after application of the device.

In some embodiments, the tab is disposable.

In embodiments, the tab may be made of any suitable material. In some embodiments, the tab is made of a backing material disclosed herein. In some embodiments, the tab is made of a backing material disclosed herein, wherein the tab backing material and the backing material to which the microstructure array is affixed are the same. In other embodiments, the tab is made of a backing material disclosed herein, wherein the tab backing material and the backing material to which the microstructure array is affixed differ. In particular embodiments, the tab may be made of a material that has low surface energy, e.g., such as those typically used in the art for release liners. Example materials of such low surface energy materials include, but are not limited to Polyethylene terephthalate (PET) and Polystyrene.

Positioning of a Microstructure Array on a Backing

In some embodiments, the wound closure device includes a microstructure array positioned on the backing, wherein an outer edge of the backing surrounds some, or all, of the outer edge of the microstructure array (see, e.g., FIGS. 1-2). Said another way, in some embodiments, the length and width of the backing is longer and wider than the length and width of the microstructure array, e.g., so as to ensure that all portions of the array's bottom surface are contacted with backing and to ensure that excess backing surrounds the array on all sides. For example, in FIG. 15A, the exemplified array 420 is surrounded by backing 410 on all sides. The distance $D_{11}$ to the outer edge from the edge of the microstructure array 420 is larger on the longitudinal ends of the device than is the distance $D_{12}$ to the outer edge from the edge of the microstructure array 420 on the sides, and the outer edge is rounded around the bridge portion backing 116.

In some embodiments, the distance to the outer edge of the backing from the edge of the microstructure array is substantially uniform around the device. In some embodiments, the distance to the outer edge of the backing from the edge of the microstructure array is longer on the longitudinal ends of the device (e.g., distance $D_{11}$ in FIG. 15A) than the distance to the outer edge of the bridge portion backing from a bridge portion of the microstructure array. In some embodiments, the distance to the outer edge of the backing from the edge of the microstructure array is longer on the longitudinal ends of the device (e.g., the distance $D_{11}$ in FIG. 15A) than the distance to the outer edge of the sides of the backing from the edge of the microstructure array. In some embodiments, a distance, e.g., from an outside edge of the microstructure array to an outside edge of the backing (such as, e.g., distance $D_{11}$ shown in FIG. 15A), ranges from about 1 mm to about 100 mm. In some embodiments, a distance from an outside edge of the microstructure array to an outside edge of the backing (such as, e.g., distance $D_{11}$ shown in FIG. 15A), e.g., ranges from about 2.5 mm to about 25 mm. In some embodiments, a distance from an outside edge of the microstructure array to an outside edge of the backing (such as, e.g., distance $D_{11}$ shown in FIG. 15A), e.g. ranges from about 5 mm to about 15 mm.

In some embodiments, a distance from an outside edge of the microstructure array to an outside edge of the backing (such as, e.g., a distance from an edge of the bridge portion of the microstructure array to an edge of the bridge portion backing), e.g., ranges from about 0.1 mm to about 10 mm. In some embodiments, a distance from an outside edge of the microstructure array to an outside edge of the backing (such as, e.g., a distance from an edge of the bridge portion of the microstructure array to an edge of the bridge portion backing), e.g., ranges from about 0.5 mm to about 5 mm. In some embodiments, a distance from an outside edge of the microstructure array to an outside edge of the backing (such as, e.g., a distance from an edge of the bridge portion of the microstructure array to an edge of the bridge portion backing), e.g., ranges from about 1 mm to about 3 mm. In some embodiments, a distance from an outside edge of the microstructure array to an outside edge of the backing (such as, e.g., distance $D_{12}$ shown in FIG. 15A) e.g., ranges from about 0.1 mm to about 10 mm. In some embodiments, a distance from an outside edge of the microstructure array to an outside edge of the backing (such as, e.g., distance $D_{12}$ shown in FIG. 15A), e.g., ranges from about 0.5 mm to about 5 mm. In some embodiments, a distance from an outside edge of the microstructure array to an outside edge of the backing (such as, e.g., distance $D_{12}$ shown in FIG. 15A), e.g., ranges from about 1 mm to about 3 mm.

Adhesive

In some embodiments, an adhesive that is suitable for application to skin or tissue covers portions of the backing that contact the array and portions of the backing that contact a spacer apparatus (e.g., a thermoformed spacer, as disclosed herein) in which the wound closure device is packaged (e.g., for storage, transit, etc). In some embodiments such as this, when an individual removes the device from its packaging, the adhesive that had contacted the spacer apparatus of the packaging will be exposed ("free contact adhesive") and, upon application of the device to the skin or tissue of a patient, the same free contact adhesive will then contact the patient's skin or tissue. The presence of the free contact adhesive is, in some embodiments, necessary for the appropriate application and/or maintenance of the device on its target tissue or skin. In some embodiments, the presence of the free contact adhesive improves the ability of the wound closure device to be appropriately applied and/or maintained on its target tissue or skin. In other embodiments, free contact adhesive is not included in the device and is not necessary for that application or maintenance of the device on its target tissue or skin. In some embodiments, the spacer apparatus is sterile.

The adhesive can include any medical grade adhesive, such as, for example, an acrylate (such as, e.g., is used on the Steri-Strips or Steri-Strip S isthmus) or hydrogel-based adhesives that can stick to wet surfaces (e.g., Polyethylene glycol (PEG) hydrogel). In other implementations, the adhesive component comprises nanostructures that provide glueless adhesion. Adhesion of a wound closure device (e.g., wound closure device 100) to skin or tissue induced by such adhesives may last for as little as a minute (e.g., when the adhesive is utilized to help apply the device) or may last for 10 days or more. Accordingly, adhesion to the skin or tissue as the result of an adhesive may last for 5 min, 10 min, 15 min, 20 min, 30 min, 60 min, 2 hr, 4 hr, 6 hr, 12 hr, 24 hr, 2 days, 4 days, 6 days, 8 days, 10 days, 14 days, or more, including all integers (e.g., 31 min, 32 min, 33 min, 13 hr, 14 hr, 15 hr, 3 day, 5 days, etc.) and ranges (e.g., 1 min-10 days, 1 min-1 hr, 5 min-20 min, etc.) of the adhesion durations set forth herein.

Microstructure Arrays

In embodiments, the microstructure arrays of the present disclosure comprise one or more microstructure, as disclosed herein. In some embodiments, the microstructure arrays include a plurality of portions, wherein at least two of said plurality of portions includes one or more microstructure and wherein at least one of said plurality includes an expandable portion.

In some embodiments, the microstructure arrays of the wound closure devices disclosed herein include a first portion, a second portion, and a bridge portion (see, e.g., FIGS. 1 and 2, which show a non-limiting example of a microstructure array of the present disclosure, which includes a first portion 122, a second portion 124, and a bridge portion 126). In some embodiments, the bridge portion connects the first portion and the second portion.

In some embodiments, the microstructure arrays of the wound closure devices disclosed herein include a first portion and a second portion, but no bridge portion.

As shown in FIGS. 1-7, in some embodiments, the first portion 122 and the second portion 124 are substantially identical. In some implementations, however, the first portion 122 and the second portion 124 can have different arrangements.

Bridge Portions

In some embodiments, a microstructure array of the present disclosure includes a bridge portion connecting two or more array portions. In some embodiments, the bridge portion comprises one longitudinally extending portion that connects a first portion and a second portion of a microstructure array (i.e., a bridge portion that connects a first microstructure "array portion" and a second microstructure "array portion"). In some embodiments, the bridge portion comprises at least one longitudinally extending portion that connects a first portion and a second portion of a microstructure array. In some embodiments, the bridge portion comprises two longitudinally extending portions that connect a first and a second portion of a microstructure array. In some embodiments, the bridge portion comprises a plurality of longitudinally extending portions (e.g., 2 or more longitudinally extending portions or 3, 4, 5, 6, 7, 8, 9 or more than 10 longitudinally extending portions).

For example, with respect to the wound closure device 100 shown in FIGS. 1 and 2, the bridge portion 126 includes a first longitudinally extending portion 127 and a second longitudinally extending portion 128.

In some embodiments, the bridge portion enables easier alignment for manufacturing of the wound closure device. In some embodiments, the bridge portion reduces the risk of the microstructure array dislodging from the skin as a result of skin movement.

In some such embodiments, the bridge portion does not expand substantially (i.e., it is "rigid"). In various embodiments, the bridge portion is configured to not stretch. Said another way, e.g., in reference to the embodiment presented in FIGS. 1-7, the first longitudinally extending portion 127 and the second longitudinally extending portion 128 are configured to not substantially elongate under the force resultant on the wound closure device 100 from the longitudinal tension caused by tissue naturally separating from a wound. In some embodiments, the first longitudinally extending portion 127 and the second longitudinally extending portion 128 are substantially rigid.

Similarly, in some embodiments, microstructure arrays of the present disclosure comprise one, two, or more than two substantially rigid longitudinally extending portions. As shown in FIGS. 1 and 5, the first longitudinally extending portion 127 extends from the first expandable portion 140A to the sixth expandable portion 140F. The second longitudinally extending portion 128 extends from the second expandable portion 140B to the fifth expandable portion 140E.

The longitudinally extending portions may be any suitable length. In some embodiments, the one or more longitudinally extending portions are all substantially the same length. In some embodiments, a longitudinally extending portion of the microstructure array ranges from, for example, about 1 mm in length to about 50 mm in length. In some embodiments, a longitudinally extending portion of the microstructure array ranges from about 3 mm in length to about 30 mm in length. Accordingly, in these embodiments, the longitudinally extending portion 126 can be 1 mm in length; 2 mm; 3 mm; 4 mm; 5 mm; 6 mm; 7 mm; 8 mm; 9 mm; 10 mm; 11 mm; 12 mm; 13 mm; 14 mm; 15 mm; 16 mm; 17 mm; 18 mm; 19 mm; 20 mm; 21 mm; 22 mm; 23 mm; 24 mm; 25 mm; 26 mm; 27 mm; 28 mm; 29 mm; 30 mm; 31 mm; 32 mm; 33 mm; 34 mm; 35 mm; 36 mm; 37 mm; 38 mm; 39 mm; 40 mm; 41 mm; 42 mm; 43 mm; 44 mm; 45 mm; 46 mm; 47 mm; 48 mm; 49 mm; or 50 mm in length, including all decimals (e.g., 1.5 mm, 1.6 mm, 1.7 mm, etc.) and ranges (e.g., 1-15 mm, 5-25 mm, 10-15 mm, 3-4 mm, 5-6 mm, 6-8 mm, etc.) in between, of the longitudinally extending portion lengths set forth herein. In one embodiments, the longitudinally extending portion of the microstructure array ranges from about 5 mm in length to 25 mm in length.

The longitudinally extending portions may be any suitable width. In some embodiments, the one or more longitudinally extending portions are all substantially the same width. In some embodiments, the width of a longitudinally extending portion of the microstructure array ranges from, for example, about 0.05 mm in width to about 3 mm in width. In some embodiments, a longitudinally extending portion of the microstructure array ranges from about 0.1 mm in width to about 2 mm in width. Accordingly, in these embodiments, the longitudinally extending portion can be, e.g., 0.1 mm in width; 0.15 mm; 0.2 mm; 0.25 mm; 0.3 mm; 0.35 mm; 0.4 mm; 0.45 mm; 0.5 mm; 0.55 mm; 0.6 mm; 0.65 mm; 0.7 mm; 0.75 mm; 0.8 mm; 0.85 mm; 0.9 mm; 0.95 mm; and 1 mm in width, including all decimals (e.g., 0.15 mm, 0.16 mm, 0.17 mm, etc.) and ranges (e.g., 0.2-1.0 mm, 0.3-0.9 mm, 0.5-0.7 mm, etc.) in between, of the longitudinally extending portion widths set forth herein. In one embodiment, the longitudinally extending portion of the microstructure array ranges from about 0.1 mm in width to about 1 mm in width.

The bridge portion (e.g., feature 126 in FIG. 2) of the microstructure array may be any suitable length. In some embodiments, the bridge portion of the microstructure array ranges from, for example, about 1 mm in length to about 50 mm in length. In some embodiments, the bridge portion 126 of the microstructure array 120 ranges from about 3 mm in length to about 30 mm in length. Accordingly, in these embodiments, the bridge portion 126 can be 1 mm in length; 2 mm; 3 mm; 4 mm; 5 mm; 6 mm; 7 mm; 8 mm; 9 mm; 10 mm; 11 mm; 12 mm; 13 mm; 14 mm; 15 mm; 16 mm; 17 mm; 18 mm; 19 mm; 20 mm; 21 mm; 22 mm; 23 mm; 24 mm; 25 mm; 26 mm; 27 mm; 28 mm; 29 mm; 30 mm; 31 mm; 32 mm; 33 mm; 34 mm; 35 mm; 36 mm; 37 mm; 38 mm; 39 mm; 40 mm; 41 mm; 42 mm; 43 mm; 44 mm; 45 mm; 46 mm; 47 mm; 48 mm; 49 mm; or 50 mm in length, including all decimals (e.g., 1.5 mm, 1.6 mm, 1.7 mm, etc.) and ranges (e.g., 1-15 mm, 5-25 mm, 10-15 mm, 3-4 mm, 5-6 mm, 6-8 mm, etc.) in between, of the bridge portion 126 lengths set forth herein. In one embodiments, the bridge portion 126 of the microstructure array 120 ranges from about 5 mm in length to 25 mm in length.

The width of the bridge portion may vary. In some embodiments the width of the bridge portion is the same as the width of the backing. In other embodiments, the bridge portion is wider or narrower than the backing of the device. Thus, in some embodiments, the width of the bridge portion ranges from as small as 0.5 mm to as large as 100 mm or more. Accordingly, in some embodiments, the width of bridge portion 126 is approximately 1 mm, 2 mm, 3 mm, 4 mm, 5 mm, 6 mm, 7 mm, 8 mm, 9 mm, 10 mm; 11 mm; 12 mm; 13 mm; 14 mm; 15 mm; 16 mm; 17 mm; 18 mm; 19 mm; 20 mm; 21 mm; 22 mm; 23 mm; 24 mm; 25 mm; 26 mm; 27 mm; 28 mm; 29 mm; 30 mm; 31 mm; 32 mm; 33 mm; 34 mm; 35 mm; 36 mm; 37 mm; 38 mm; 39 mm; 40 mm; 41 mm; 42 mm; 43 mm; 44 mm; 45 mm; 46 mm; 47 mm; 48 mm; 49 mm; 50 mm; 51 mm; 52 mm; 53 mm; 54 mm; 55 mm; 56 mm; 57 mm; 58 mm; 59 mm; 60 mm; 61 mm; 62 mm; 63 mm; 64 mm; 65 mm; 66 mm; 67 mm; 68 mm; 69 mm; 70 mm; 71 mm; 72 mm; 73 mm; 74 mm; 75 mm; 76 mm; 77 mm; 78 mm; 79 mm; 80 mm; 81 mm; 82 mm; 83 mm; 84 mm; 85 mm; 86 mm; 87 mm; 88 mm; 89 mm; 90 mm; 91 mm; 92 mm; 93 mm; 94 mm; 95 mm; 96 mm; 97 mm; 98 mm; 99 mm; 100 mm, or longer, including all decimals (e.g., 11.5 mm, 11.6 mm, 11.7 mm, etc.) and ranges (e.g., 1 mm-50 mm, 2 mm-30 mm, 5 mm-15 mm, 5 mm-10 mm, etc.) in between of the bridge portion widths set forth herein. In one embodiment, the bridge portion width ranges from about 3 mm to about 20 mm.

Base

In various embodiments, the microstructure arrays of the present disclosure comprise a base that includes at least a portion of the first portion, at least a portion of the second portion, and at least a portion of the bridge portion. In some embodiments, the base includes the entire first, second, and bridge portions. The base may define an aperture in the microstructure array.

Alternatively, in other embodiments, the base can define a plurality of apertures of the microstructure array of the device. In some embodiments, the terms "base" and "support base" are used interchangeably herein.

In some embodiments, the microstructure arrays of the present disclosure comprise a base that includes at least a portion of the first portion and at least a portion of the second portion, wherein no bridge portion is included. In some embodiments, the base includes the entire first and second portions. The base may define an aperture in the microstructure array. Alternatively, in other embodiments, the base can define a plurality of apertures of the microstructure array of the device.

In some embodiments, the base includes the entire first portion, the entire second, and the entire bridge portions. For example, FIG. 5 shows a side view of the wound closure device 100 of FIG. 1, and FIG. 2 shows an exploded isometric view of the microstructure array 120 and the wound backing 110 for the wound closure device 100 of FIG. 1. In this non-limiting example, the microstructure array 120 comprises a base 121 that includes the entire first portion 122, the entire second portion 124, and the entire bridge portion 126 (see FIG. 2 for the identifiers for portions 122, 124, and 126). In this embodiment, the base 121 includes a first longitudinally extending portion 127 and a second longitudinally extending portion 128 of the bridge portion 126. In other embodiments, the base 121 includes only one such longitudinally extending portion (not shown) of the bridge portion 126. In still further embodiments, the base 121 includes a plurality of such longitudinally extending portions (e.g., 3 or more longitudinally extending portions or 4, 5, 6, 7, 8, 9 or more than 10 longitudinally extending portions).

In some embodiments, the base defines a single aperture in the microstructure array. For example, the base 121 defines a single aperture of the microstructure array 120 of the device 100 (see e.g., FIGS. 1 and 2).

The base may be made of any suitable material or mixture of materials, and it may be any suitable width. In some embodiments, the base is made of any material or mixture of materials, provided the expandable portion comprises sufficient stretchability and, optionally, elasticity, as described herein. In some embodiments, the material is a natural material, or a mixture of natural materials. In other embodiments, the material is a synthetic material, or a mixture of synthetic materials. In other embodiments, comprising mixtures of one or more synthetic materials and one or more natural materials. In particular embodiments, base are made of a material selected from a polymer, a metal, a biomaterial, and a combination thereof. In some embodiments, the base is comprised of or consists essentially of a metal. In some embodiments, the base is comprised of or consists essentially of a metal composite. In particular embodiments the base is comprised of or consists essentially of a metal or metal composite selected from the group consisting of: aluminum, titanium, stainless steel, magnesium and zinc. In some embodiments, the material is a series 300 stainless steel. In some embodiments, the material is 316 stainless steel.

In some embodiments, the material width of the base (e.g., material width $W_1$ in FIG. 18) (not accounting for any increased width due to the presence of other portions of the device, e.g., contact portions, discussed below) ranges from about 0.01 mm to about 5 mm. In some embodiments, the material width of the base ranges from about 0.05 mm to about 2 mm. In some embodiments, the material width of the base ranges from about 0.1 mm to about 1 mm. Thus, in some embodiments, the material width of the base is about 0.05 mm; 0.06 mm; 0.07 mm; 0.08 mm; 0.09 mm; 0.1 mm; 0.2 mm; 0.3 mm; 0.4 mm; 0.5 mm; 0.6 mm; 0.7 mm; 0.8 mm; 0.9 mm; 1 mm; 1.1 mm; 1.2 mm; 1.3 mm; 1.4 mm; 1.5 mm; 1.6 mm; 1.7 mm; 1.8 mm; 1.9 mm; 2 mm; or greater than 2 mm, including an decimals (e.g., 0.51 mm, 0.52 mm, 0.53 mm, etc.) and ranges (e.g., 0.1 mm to 1 mm, 0.2 mm to 0.9 mm, etc.) between.

In some embodiments, the height of the base (e.g., H2 in FIG. 5 or H4 in FIG. 19B) ranges from about 10 μm to about 1000 μm. Thus, in some embodiments, the thickness of the base is about 10 μm; 20 μm; 30 μm; 40 μm; 50 μm; 60 μm; 70 μm; 80 μm; 90 μm; 100 μm; 110 μm; 120 μm; 130 μm; 140 μm; 150 μm; 160 μm; 170 μm; 180 μm; 190 μm; 200 μm; 210 μm; 220 μm; 230 μm; 240 μm; 250 μm; 260 μm; 270 μm; 280 μm; 290 μm; 300 μm; 500 μm; 700 μm 900 μm, or greater than 900 μm, including an integers (e.g., 101 μm; 102 μm; 103 μm; 104 μm; 105 μm; 106 μm; 107 μm; 108 μm, etc) and ranges (e.g., 50 μm to about 500 μm, 100 μm to about 300 μm, etc.) between.

Expandable Portions

In embodiments, the wound closure devices of the present disclosure comprise expandable portions that enable the wound closure device to elongate (e.g., if a stretching force or "tension" is applied) and to retract after elongation (e.g., once a stretching force or "tension" is removed).

The expandable portion may be any suitable shape and/or material that enables reversible expansion (or "spring characteristic", as used herein interchangeably). In some embodiments, the expandable portion comprises a shape that is: a congruent V-shape, a congruent U-shape, a congruent S-shape, a congruent I-shape, a congruent H-shape, a congruent C-shape, a congruent X-shape, a congruent Y-shape, a congruent M-shape, a congruent N-shape, a congruent T-shape, a congruent W-shape, and a congruent Z-shape. In some embodiments, said shape enables reversible expansion of the expandable portion. In some embodiments, the expandable portion comprises a shape that is a multiple of, combination of, and/or mirror image of a congruent V-shape, a congruent U-shape, a congruent S-shape, a congruent I-shape, a congruent H-shape, a congruent C-shape, a congruent X-shape, a congruent Y-shape, a congruent M-shape, a congruent N-shape, a congruent T-shape, a congruent W-shape, and a congruent Z-shape. In some embodiments, the multiple of, combination of, and/or mirror image of a congruent the congruent shapes enable reversible expansion of the expandable portion. In some embodiments, the reversible expansion is due, at least in part, to a property of the material from which the expandable portion is made.

For example, FIG. 3 shows an embodiment comprising expandable portions (i.e., 140A, 140B, 140C, 140D in FIG. 3) that are U-shaped. Said another way, in this embodiment, each expandable portion includes a first arm, a second arm, and a curved portion coupling the first arm to the second arm. For example, the first expandable portion 140A includes a first arm 142A, a second arm 144A, and a curved portion 146A (FIG. 3). The second expandable portion 140B includes a first arm 142B, a second arm 144B, and a curved portion 146B (FIG. 3). The third expandable portion 140C includes a first arm 142C, a second arm 144C, and a curved portion 146C (FIG. 3). The fourth expandable portion 140D includes a first arm 142D, a second arm 144D, and a curved portion 146D (FIG. 3).

In various embodiments, the first portion and the second portion of the microstructure array may include expandable portions and connecting segments that are included in the base. For example, FIG. 3 is a top view of a portion of the wound closure device 100. In this embodiment, the first portion 122 (and the base 121) includes a first expandable portion 140A, a second expandable portion 140B, a third expandable portion 140C, and a fourth expandable portion 140D, wherein the first portion 122 (and the base 121) also includes a first connecting segment 160, a second connecting segment 161, a third connecting segment 162, a fourth connecting segment 163, and a fifth connecting segment 164.

In other embodiments, the wound closure device may include more than four such expandable portions. In still other embodiments, the wound closure device may include less than four such expandable portions. In some embodiments, the wound closure device comprises at least 1, 2, 3, 4, 5, 6, 7, 8, 9, 10, or more of such expandable portions.

In various embodiments, the radius of the curved portion (e.g., 140A, 140B, 140C, and 140D) ranges from about 0.1-10 MM. Thus, in some embodiments, the expandable portion includes a plurality of curved portions, each having a radius of about 0.1 mm; 0.2; 0.3; 0.4; 0.5; 0.6; 0.7; 0.8; 0.9; 1; 1.5; 2; 2.5; 3; 3.5; 4; 4.5; 5; 5.5; 6; 6.5; 7; 7.5; 8; 8.5; 9; 9.5; 10 mm; or greater, including all decimal (e.g., 1.1 mm, 1.2 mm, 1.3 mm, 1.4 mm, etc.) and ranges (e.g., 0.1 mm-3 mm, 0.2 mm-2 mm, 0.3 mm-1 mm, etc.) in between of the curved portion radii set forth herein. In one embodiment, the curved portion radius 140A, 140B, 140C, and 140D ranges from 0.2 mm-2 mm. In one embodiment, the curved portion radius 140A, 140B, 140C, and 140D ranges from 0.3 mm-1 mm.

In other embodiments, the radius of some of the curved portions may vary as compared to the other curved portion radii. For example, in one embodiment, the present disclosure provides a microstructure array having four or more expandable portions, wherein a curved portion of at least two of the expandable portions has a different radius than at least two other curved portions.

The U-shaped configuration of each expandable portion allows each curved portion to act as a rotational axis. In other words, the second arm of each expandable portion can rotate relative to the first arm of each expandable portion via the curved portion when a force is applied to pull the second arm away from the first arm. For example, a force applied to the second arm 144A away from the first arm 142A will cause the second arm 144A to rotate, or stretch, away from the first arm 142A through bending the curved portion 146A.

Additionally, in various embodiments, the expandable portions are coupled via connecting segments. For example, in FIG. 3, a first connecting segment 160 couples a second arm 144A to a first arm 142C; a second connecting segment 161 couples a second arm 144C to a third connecting segment 162; a fourth connecting segment 163 couples a third connecting segment 162 to a second arm 144D; and a fifth connecting segment 164 couples a first arm 142D to a second arm 144B.

In various embodiments, the expandable portions are stretchable such that the microstructure array can elongate, e.g., if a stretching force is applied. In various embodiments, the expandable portions are also elastic due to the relationship between the expandable portions and the connecting segments such that the microstructure array can retract after elongation, e.g., once a stretching force is removed. For example, the embodiment shown in FIGS. 1-7 is both stretchable and elastic.

In some embodiments, each expandable portion comprises a U-shape that allows each expandable portion to stretch, making the microstructure array expandable. For example, if a force or forces are applied to some or all of the second arms of the first portion 122 (i.e., 144A, 144B, 144C, 144D) in the direction of arrow B (see FIG. 3), the second arms will rotate relative to their respective first arms about their respective curved portions. As a result, the first portion 122 will be elongated in the direction of arrow B.

As indicated in FIG. 2, in some embodiments, the first portion 122 is substantially identical to the second portion 124. Thus, in the non-limiting example of the device 100 exemplified in FIGS. 1-7, the second portion 124 includes a fifth expandable portion 140E, a sixth expandable portion 140F, a seventh expandable portion 140G, and an eighth expandable portion 140H. The fifth expandable portion 140E, the sixth expandable portion 140F, the seventh expandable portion 140G, and the eighth expandable portion 140H are similar in structure and function to the first expandable portion 140A, the second expandable portion 140B, the third expandable portion 140C, and the fourth expandable portion 140D described with reference to FIG. 3, respectively, and will not be further described herein.

Furthermore, in other embodiments, microstructure arrays described herein can comprise more than eight expandable portions or less than eight expandable portions. In such embodiments, the expandable portions may be substantially identical on either side of the bridge portion or they may differ. For example, in some embodiments, one of the first portion 122 or the second portion 124 comprises expandable portions and the other one of the first portion 122 or the second portion 124 comprise no such expandable portions. In other embodiments, the number or structure of the expandable portions comprised in each of the first portion 122 or the second portion 124 may vary. For example, in some non-limiting embodiments, the present disclosure provides a microstructure array for use in the microstructure wound closure devices disclosed herein, comprising a first portion 122 that comprises one or more expandable portion and a second portion 124 that comprises no expandable portions. Thus, application of a force will result in expansion (and optionally retraction once the force is released) only on one side of the array, e.g., on the first portion 122. In other non-limiting embodiments, a microstructure array 120 may include a first portion 122 that comprises one or more expandable portions and a second portion 124 that comprises one or more expandable portions, wherein at least one of the expandable portions comprised in the first portion 122 differs in structure (e.g., differs in radius of one or more curved portion, such as the curved portions exemplified as 140A, 140B, 140C, and 140D in FIG. 3) from at least one expandable portion comprised on the second portion 124.

Additionally, although not identified by reference number, in some embodiments (e.g., as shown in the embodiment illustrated in FIGS. 2 and 3), the second portion 124 includes connecting segments that have the same structure and function as the connecting segments (i.e., 160, 161, 162, 163, 164) of the first portion 122 and will not be further described herein.

Additionally, in some embodiments (e.g., as shown in the embodiment illustrated in FIGS. 1 and 2), the second portion 124 may include a third contact portion 154 and a fourth contact portion 156. The third contact portion 154 and the fourth contact portion 156 are similar in structure and function to the first contact portion 150 and the second contact portion 152 described above with reference to FIG. 3, and will not be further described herein.

As a result of the combination of the first longitudinally extending portion 127, the second longitudinally extending portion 128, the contact portions (i.e., 150, 152, 154, 156), and the expandable portions and connecting portions of the first portion 122 and the second portion 124, the wound closure device 100 defines only one aperture 190, as shown in FIG. 1. The aperture 190 is continuous and bordered by the first longitudinally extending portion 127, the second longitudinally extending portion 128, the contact portions (i.e., 150, 152, 154, 156), and the expandable portions and connecting portions of the first portion 122 and the second portion 124. In other implementations, however, the wound closure device 100 can include additional segments to define additional apertures to provide increased stability.

In some embodiments, the ability of the expandable portions to expand and/or retract (i.e., the stretchability and/or the elasticity of the expandable portion) is varied, e.g., by altering the type and/or thickness of the material used for the microstructure array (i.e. by varying the base material and/or thickness thereof), the shape or thickness of the U-shape configuration of the expandable portion (e.g., by varying the radius of the U-shape portions), or by varying the length (or the shape or thickness) of the connecting segments that link two or more expandable portions (e.g., second connecting segment 161).

For example, FIG. 20 shows one embodiment in which the length of a connecting segment is equal to the length of another connecting segment and the width of a gap separating two arms of an expandable portion. FIG. 20 is a top view of a microstructure array 520. As shown in FIG. 20, the length L13 and the length L14 can be similar/equal. In other embodiments, the length L13 or the length L14 may be changed such that these lengths are not equal, thus, causing these two expandable portions to comprise different expandability properties. Furthermore, the width of the gap (e.g., gap Si shown in FIG. 20) separating two arms of an expandable portion that are connected by a curved portion can be varied to modulate the local elasticity of the array. In some embodiments, the width of the gap 51 ranges from about 0.1 mm to about 3 mm. In some embodiments, the width of the gap 51 ranges from about 0.2 mm to about 2 mm. In some embodiments, the width of the gap 51 ranges from about 0.3 mm to about 1 mm. Additionally, the length $D_{19}$ of the curved portion between the gap and an inner edge of the curved portion can be varied to alter the expandability properties of the array. For example, the length $D_{19}$ may range from about 0.3 to about 1 mm. In other embodiments, the length $D_{19}$ may range from about 0.2 to about 2 mm. In other embodiments, the length $D_{19}$ may range from about 0.1 mm to about 3 mm.

In some embodiments, as shown in enlarged region E of FIG. 23, the distances X, Y, and Z are substantially similar, so as to allow for even tension distribution. In some embodiments, X, Y, and Z are substantially similar lengths that range from about 1 mm to about 16 mm. In some embodiments, X, Y, and Z are substantially similar lengths that range from about 2 mm to about 14 mm. In some embodiments, X, Y, and Z are substantially similar lengths that range from about 3 mm to about 12 mm. However, in other embodiments, the spacing between X, Y, and Z is varied (i.e., not substantially similar).

In some embodiments, the wound closure devices described herein comprise two or more expandable portions having different properties of expandability and/or elasticity. In one embodiment, the expandability and/or elasticity of a wound closure device varies longitudinally across the device (i.e., one or two first expandable portions closest to the wound will expand and or retract due to their elasticity to a lesser degree or a greater degree than one or more expandable portion located farther away from the wound). In one embodiment, the wound closure device as disclosed herein includes four or more expandable portions, wherein a first set of two expandable portions are positioned on opposite sides of a bridge portion and a second set of two expandable portions are positioned on opposite sides of the bridge portion, wherein the second set of two expandable portions are positioned further away from the bridge portion than the first set of two expandable portions, and wherein the first set of two expandable portions is (i) more stretchable and less elastic than the second set of expandable portions or (ii) less stretchable and more elastic than the second set of expandable portions.

In some embodiments, the expandable portion enables expansion of the device such that the expanded device is from about 100.1% to 105% the length of the device pre-expansion. Thus, in some embodiments, the expandable portion enables expansion of the device to a length that is about 100.1% of the devices pre-expansion length, to about; 100.2%; 100.3%; 100.4%; 100.5%; 100.6%; 100.7%; 100.8%; 100.9%; 101.0%; 101.1%; 101.2%; 101.3%; 101.4%; 101.5%; 101.6%; 101.7%; 101.8%; 101.9%; 102.0%; 102.1%; 102.2%; 102.3%; 102.4%; 102.5%; 102.6%; 102.7%; 102.8%; 102.9%; 103.0%; 103.1%; 103.2%; 103.3%; 103.4%; 103.5%; 103.6%; 103.7%; 103.8%; 103.9%; 104.0%; 104.1%; 104.2%; 104.3%; 104.4%; 104.5%; 104.6%; 104.7%; 104.8%; 104.9%; or about 105.0% of the devices pre-expansion length. In some embodiments, the device expands to a length that is more than 105% the length of the device pre-expansion. In some embodiments, the elasticity of the expandable portion enables retraction of the device post-expansion such that the length of the device in its resting state post-expansion is substantially identical to the length of the device pre-expansion.

Figure 7:
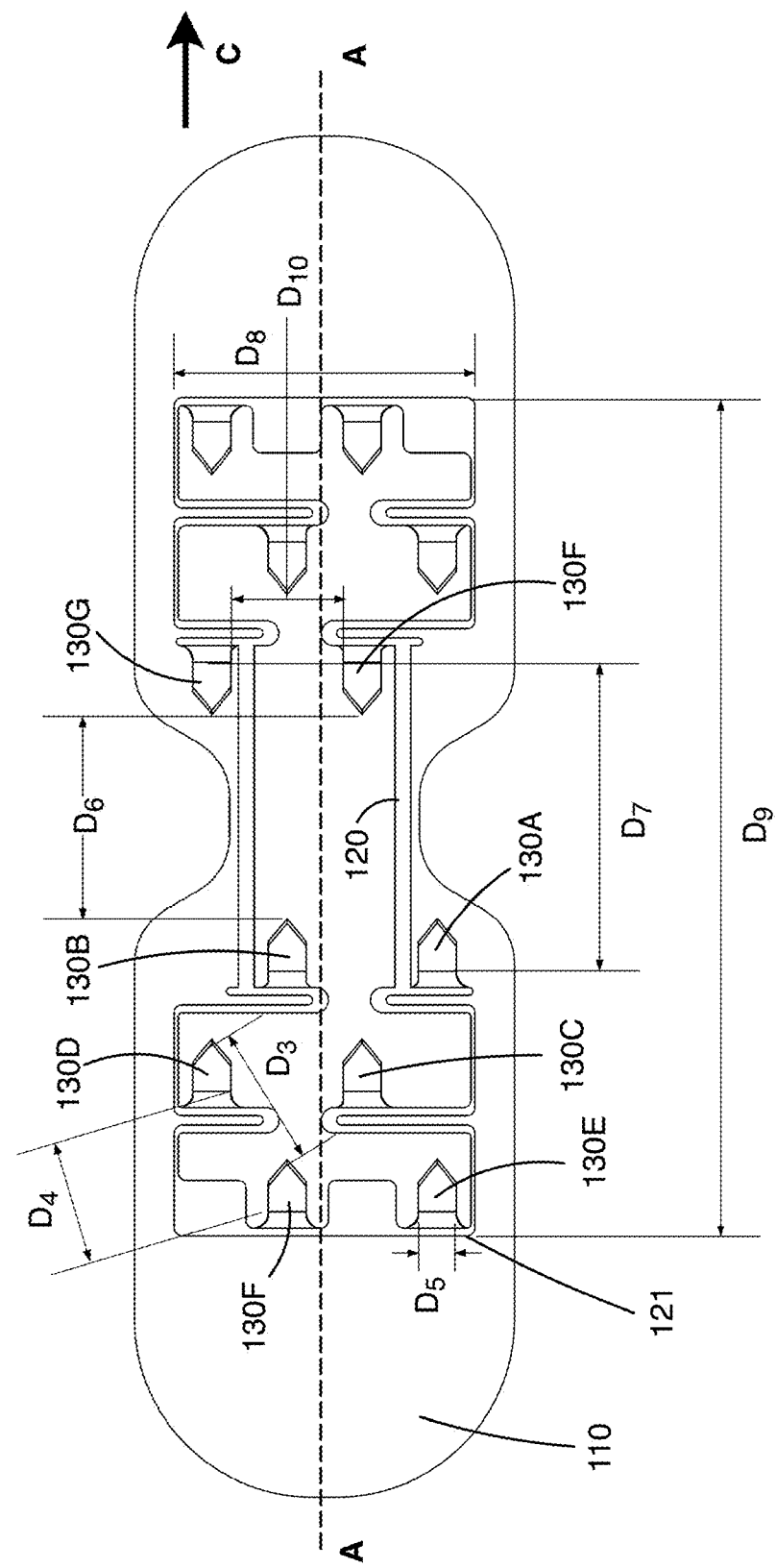
FIG. 7 is a top view of the wound closure device of FIG. 1.
Figure 8:
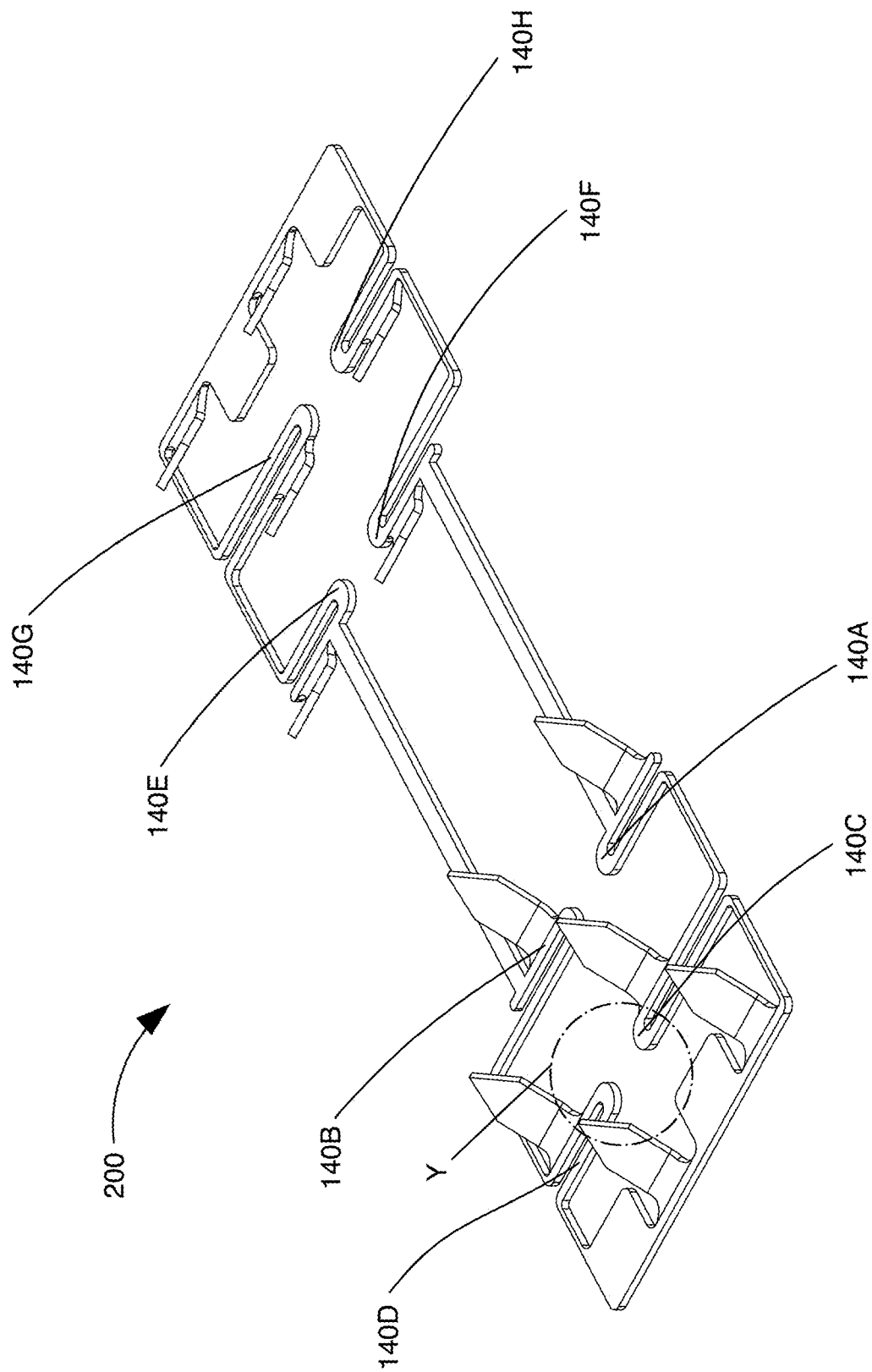
FIG. 8 is an isometric view of a microstructure array of a wound closure device according to an embodiment of the present invention.

Although the expandable portions (e.g., 140A, 140B, 140C, 140D, 140E, 140F, 140G, 140H) are shown in FIGS. 1, 2, 3, and 7 as having a curved portion (e.g., 146A) with a greater thickness than the arm portions (e.g., 142A, 144A), in some implementations the curved portion can have a smaller thickness than the arm portions. For example, FIG. 8 is a wound closure device 200 according to an embodiment. Similarly to the wound closure device 100, the wound closure device 200 includes a first expandable portion 240A, a second expandable portion 240B, a third expandable portion 240C, a fourth expandable portion 240D. The wound closure device 200 also includes a fifth expandable portion 240E, a sixth expandable portion 240F, a seventh expandable portion 240G, and an eighth expandable portion 240H. With the exception of the shape of the expandable portions, the wound closure device 200 is similar in structure and function to the wound closure device 100 described above with reference to FIGS. 1-7 and will not be further described herein.

Figure 9:
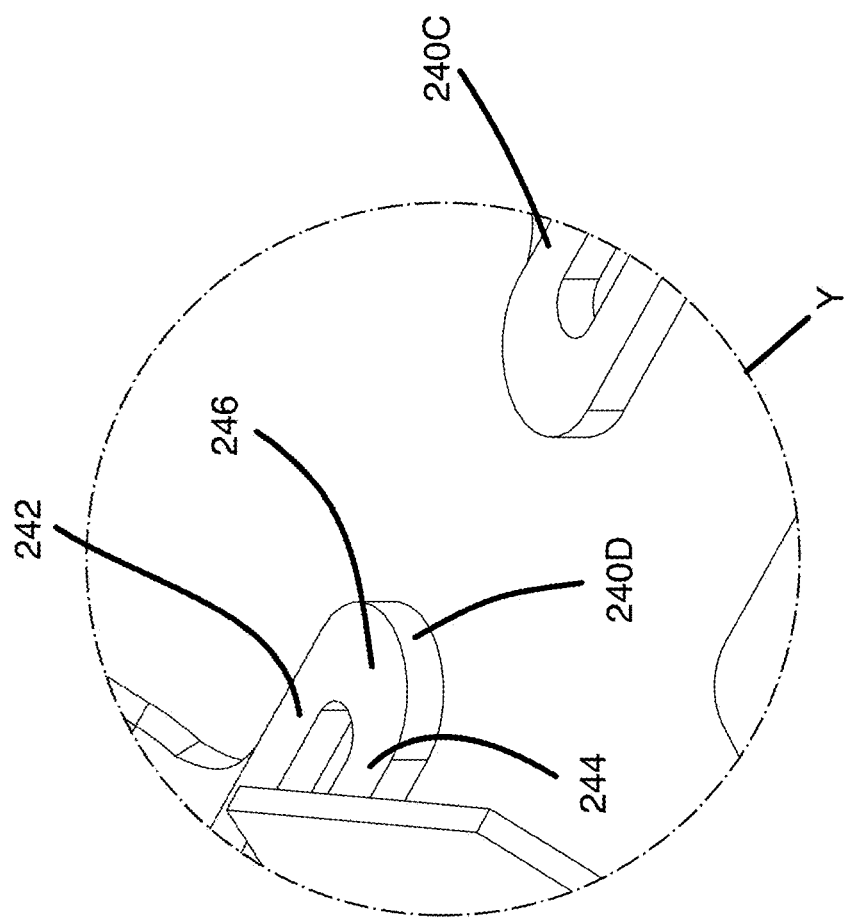
FIG. 9 is an enlarged isometric view of the portion identified as region Y in FIG. 8.

FIG. 9 shows an enlarged portion of region Y identified in FIG. 8. As shown in FIG. 9, the fourth expandable portion 240D includes a first arm 242, a second arm 244, and a curved portion 246. The curved portion 246 is thinner than the first arm 242 and the second arm 244. Generally, the smaller the thickness of the curved portion 246, the greater the flexibility and the lower the elasticity of the fourth expandable portion 240D. Similarly, the expandable portions (i.e., 240A, 240B, 240C, 240D, 240E, 240F, 240G, 240H) can be more flexible and less elastic than if the curved portions have a greater thickness. Said another way, the elasticity of each expandable portion is, in some embodiments, controlled by the thickness of each respective curved portion.

Contact Portions

In some embodiments, the wound closure devices comprise microstructure arrays comprising one or more contact portions (see, e.g., FIG. 1, indicators 150 and 152), which increase the surface area of the microstructure array to facilitate increased contact between the array and a backing.

The contact portions may be any suitable size, shape, or location on the device. In some embodiments, suitable sizes, shapes, or locations of the contact portions are those which effectively allow adhesion to the backing and/or those which permit the device to expand and, optionally, retract after expansion due to the device's elasticity. In various embodiments, a suitable size, shape, or location of a contact portion is such that the bottom surface of the contact portion is flat with respect to the bottom surface of the microstructure array (see, e.g., FIG. 1, in which the bottom surface of 120, 150, and 152 are all on an even plane). Such an arrangement enables even contact with the backing (e.g., 110 in FIG. 1).

In some embodiments, the contact portions have straight edges. In some embodiments, the contact portions have curved edges. In some embodiments, the contact portions are located within the internal aperture(s) created by the microstructure array (e.g., 120 in FIGS. 1-3). In other embodiments, the contact portions are located outside of the aperture(s) created by the microstructure array (embodiments not shown). In other embodiments, contact portions are positioned both within and without of the apertures created by the microstructure array.

For example, with respect to the non-limiting example of wound closure device 100 shown in FIGS. 1-7, the first portion 122 (and the base 121) includes a first contact portion 150 and a second contact portion 152. The first contact portion 150 and the second contact portion 152 are shaped and sized to increase attachment between the microstructure array 120 and the backing 110, in addition to the rest of the contact surfaces of the base 121. Said another way, the first contact portion 150 and the second contact portion 152 include a contact surface (not shown) for the application of adhesive.

For clarity, it should be understood that, unless indicated otherwise, the numbering "first contact portion" or "second contact portion" or any other numbering of such a contact portion described herein is not intended to imply that the contact portions are contacted to something sequentially; this label is merely for the purpose of discussing the contact portions separately.

In some embodiments, a microstructure array of the present disclosure comprises no such contact portions; thus, the microstructure array is attached to the backing via the contact surfaces of the base, alone. In some embodiments, the first portion (e.g., 122 shown in FIG. 2) includes only one, only two, or more than two such contact portions. In one embodiment, the first portion (e.g., 122 shown in FIG. 2) includes two contact portions. In some embodiments, the second portion (e.g., 124 shown in FIG. 2) includes only one, only two, or more than two such contact portions. In one embodiment, the second portion (e.g., 124 shown in FIG. 2) includes two contact portions.

The application of adhesive to the first contact portion (e.g., 150 in FIG. 1) and the second contact portion (e.g., 152 in FIG. 1) (or in other embodiments, to any other number of contact portions included on the device) before attachment of the microstructure array (e.g., 120 in FIG. 1) to the backing (e.g., 110 in FIG. 1) increases the attachment strength between the microstructure array and the backing. In the non-limiting embodiment shown in FIGS. 1-7, the first contact portion 150 extends from the third connecting segment 162; the second contact portion 152 extends from the third connecting segment 162 and the fourth connecting segment 163. Of course, as mentioned previously, in other embodiments, the contact portion is located in other suitable positions. In some embodiments, contact between the microstructure array and the backing comprises contact via the top surface of the backing and the bottom surface of the array, wherein the contact comprises both contact with the contact portions and contact with other surfaces of the base (e.g., contact between the backing and other contact surfaces of base such as the first portion, the second portion, and/or the bridge portion).

Microstructures

The microstructure arrays comprised on the wound closure devices disclosed herein may comprise any suitable number of microstructures. For example, as discussed further herein, in some embodiments, the arrays comprise from 1 to about 1000 or more microstructures.

The wound closure devices disclosed herein may comprise microstructures of any desired size, dimension, and geometry. Additionally, microstructures may optionally comprise surfaces which are substantially smooth, or which comprise uneven surfaces, e.g., a microstructure comprising sides which are wavy, or which comprise protrusions, indentations, or depressions.

In one aspect, the microstructure includes a foundation adjacent to a base, a tip, and a body connecting the foundation to the tip.

In some embodiments, the microstructures of the present disclosure are angled. As used herein, the term "angled" refers to a microstructure that is not perpendicular to the base. Angled microstructures are described in PCT/US2013/046181, and the definition therein of "Angled" is incorporated herein by reference.

In some embodiments, the microstructures of the present disclosure are curved. As used herein, the term "curved" refers to a microstructure having one or more concave or convex surfaces along the body of the microstructure between the foundation and the tip. Curved microstructures are described in PCT/US2013/046181, and the definition therein of "curved" is incorporated herein by reference.

In one embodiment, a line extending from the tip of the microstructure perpendicular to the base does not pass through the foundation of the microstructure. Angled and/or curved microstructures may have a shape that positions the tip beyond the foundation. Examples of some non-limiting microstructures suitable for use in the present disclosure are shown in FIGS. 3, 4, 18, and 19. Additionally, it will be appreciated that any microstructure, no matter the body shape, angle, and/or curvature, that has a tip position as described is contemplated by the present disclosure.

In one embodiment, a line extending from the tip perpendicular to the base passes through the foundation. Angled and/or curved microstructures may have a shape that positions the tip within the perimeter of the foundation. Additionally, it will be appreciated that any microstructure, no matter the body shape, angle, and/or curvature, that has a tip position as described is contemplated by the present embodiment.

In one embodiment, an angle between the body of the microstructure and the base is a constant angle. In such an embodiment, the center point angle and the face angle are constant.

In one embodiment, two or more different angles are formed between the body and the base between the foundation and the tip. Curved or articulated microstructures are examples of such a microstructure.

The body of the microstructures can have concave surfaces, convex surfaces, and a combination of concave and convex surfaces. In one embodiment, the body comprises at least one concave surface. In one embodiment, the body comprises at least one convex surface. In one embodiment, the body comprises at least one concave surface and at least one convex surface.

FIG. 3 shows an embodiment of the microstructure arrays disclosed herein. In this embodiment, the first portion 122 and the second portion 124 (not shown in FIG. 3) include microstructures extending from the base 121. In particular, the first portion 122 includes a first microstructure 130A, a second microstructure 130B, a third microstructure 130C, a fourth microstructure 130D, a fifth microstructure 130E, and a sixth microstructure 130F. Further, in this embodiment (i.e., the wound closure device 100) the second portion 124 (shown in FIG. 1) includes a seventh microstructure 130G, an eighth microstructure 130H, a ninth microstructure 130I, a tenth microstructure 130J, an eleventh microstructure 130K, and a twelfth microstructure 130L.

As shown in the embodiment illustrated in FIG. 3, the first microstructure 130A extends from the first arm 142A. The second microstructure 130B extends from the first arm 142B. The third microstructure 130C extends from the first arm 142C. The fourth microstructure 130D extends from the first arm 142D. The fifth microstructure 130E and the sixth microstructure 130F both extend from the third connecting segment 162 and are separated by the first contact portion 150.

Each microstructure (e.g., 130A, 130B, 130C, 130D, 130E, 130F) is a three-dimensional structure projecting from or connected to the base 121. In some implementations, each microstructure is integrally formed with the base (i.e., the microstructure and the base are monolithic). Alternatively, in other implementations, each microstructure may be made separately from the base but joined to the base (e.g., through adhesive, bonding, etc.). Each microstructure typically has dimensions on the micron size scale, although certain dimensions may extend in the millimeter size scale (e.g., length) and certain dimensions may be smaller than one micron (e.g., nano scale tip width).

Figure 4:
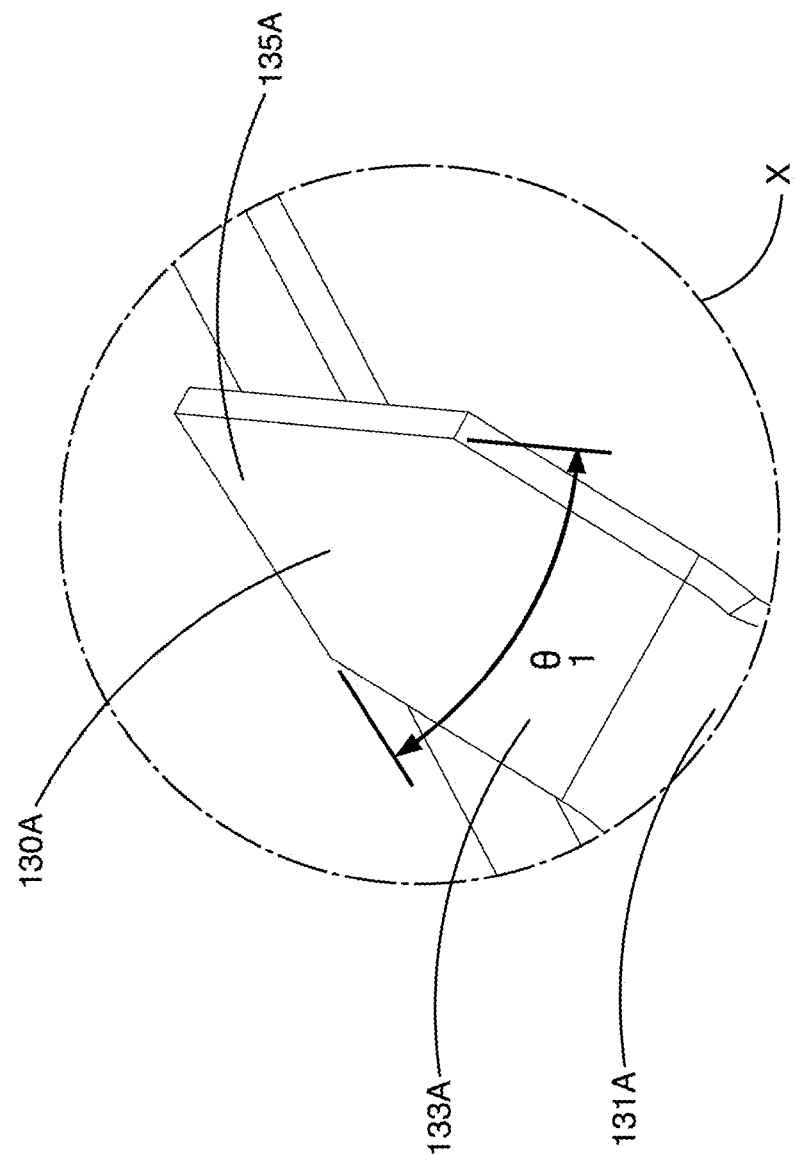
FIG. 4 is an enlarged view of the portion identified as region X in FIG. 1 from a slightly lower isometric view than the isometric view shown in FIG. 1.

In embodiments, each microstructure (e.g., 130A, 130B, 130C, 130D, 130E, 130F) includes a foundation, a tip, and a body joining the foundation with the tip. In some embodiments, a microstructure is joined to the foundation at a center point. The term "center point" is described in PCT/US2013/046181, and the definition therein of "center point" is incorporated herein by reference. For example, FIG. 4 is an enlarged view of the portion identified as region X in FIG. 1 from a slightly lower perspective. FIG. 4 shows the microstructure 130A having a foundation 131A, a tip 135A, and a body 133A. The foundation 131A is the two-dimensional area where the base 121 intersects with the plane of the microstructure 130A. Although the foundation 131A is shown as being substantially rectangular in shape, in other implementations the foundation 131A can be any two dimensional shape. In certain embodiments, the foundation is a circle, oval, ellipse, triangle, rectangle, square, quadrilateral, or higher-order polygon. The tip 135A is the end of the microstructure 130A distal to the foundation 131A and base 121. The tip 135A can be formed as a single point (e.g., a needle), a line (e.g., a blade), or other shape. The body 133A is the portion of the microstructure 130A between the foundation 131A and the tip 135A. The body 133A has a length that is equal to the distance connecting the center point on the foundation 131A to the tip 135A.

Figure 18:
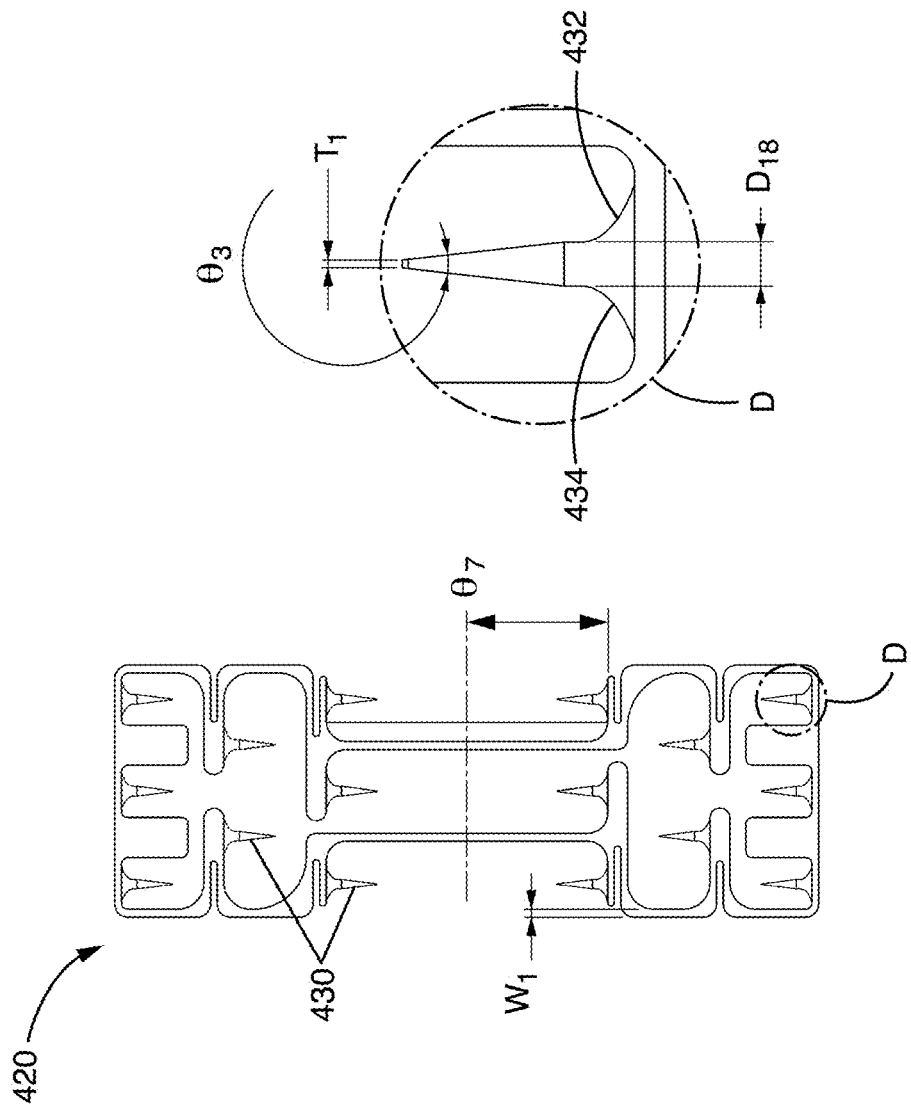
FIG. 18 is a top view of a the microstructure array of the wound closure device of FIGS. 15A and 15B.

FIG. 18 shows another example of a microstructure design suitable for use in wound closure devices disclosed herein. As shown in FIG. 18, the microstructure array 420 includes microstructures 430, which each include a foundation, a tip, and a body joining the foundation with the tip. In various embodiments, the microstructures comprise a staple draft angle (e.g., staple draft angle $\theta_3$ shown in the enlarged region D of FIG. 18) ranging from about 0° to about 80°. Thus, in embodiments the draft angle of the microstructures comprised on the microstructure arrays is selected from about 0°, 1°; 2°; 3°; 4°; 5°; 6°; 7°; 8°; 9°; 10°; 11°; 12°; 13°; 14°; 15°; 16°; 17°; 18°; 19°; 20°; 21°; 22°; 23°; 24°; 25°; 26°; 27°; 28°; 29°; 30°; 31°; 32°; 33°; 34°; 35°; 36°; 37°; 38°; 39°; 40°; 41°; 42°; 43°; 44°; 45°; 46°; 47°; 48°; 49°; 50°; 51°; 52°; 53°; 54°; 55°; 56°; 57°; 58°; 59°; 60°; 61°; 62°; 63°; 64°; 65°; 66°; 67°; 68°; 69°; 70°; 71°; 72°; 73°; 74°; 75°; 76°; 77°; 78°; 79°; or 80°, including all decimals (e.g., 10.5°, 10.6°, 10.7°, etc) and ranges (e.g., from about 1° to about 60°, from about 3° to about 45°, etc). In some particular embodiments, the draft angle ranges from 4°-20°.

In some embodiments, the body of one or more microstructure comprised on a microstructure array is straight. In some embodiments, the body of one or more microstructure comprised on a microstructure array is curved. In some embodiments, the body of one or more microstructure comprised on a microstructure array is not curved. In some embodiments, the body of one or more microstructure comprised on a microstructure array is articulated. As used herein, the term "articulated" refers to a microstructure that does not curve continuously but instead curves via one or more joints connecting straight portions. An articulated microstructure may also be referred to as "beveled." Curved microstructure bodies may be convex or concave. As used herein, the term "convex" refers to a microstructure having at least one line along the outer surface of the body that deviates outwardly from a straight line between the foundation and the tip. As used herein, the term "concave" refers to a microstructure having at least one line along the outer surface of the body that deviates inwardly from a straight line between the foundation and the tip. In certain embodiments, the microstructures (e.g., 130A, 130B, 130C, 130D, 130E, 130F) include an angled tip. For example, as shown in FIG. 4, the microstructure 130A has a tip with a first angle $\theta_1$. In some implementations, the first angle $\theta_1$ is selected from about 1° to about 160° including all decimals (e.g., 35.1, 35.1, 35.3, etc.) and ranges (e.g., from about 10° to about 90°, from about 20° to about 70°, etc.) in between. In particular embodiments, the first angle $\theta_1$ is selected from about 45° and about 75°. In particular embodiments, the first angle $\theta_1$ is selected from about 30° and about 60°. In some implementations, the first angle $\theta_1$ is about 60°. In various embodiments the microstructures have a tip with a first angle $\theta_1$ that is about 1° or about 2°; 3°; 4°; 5°; 6°; 7°; 8°; 9°; 10°; 11°; 12°; 13°; 14°; 15°; 16°; 17°; 18°; 19°; 20°; 21°; 22°; 23°; 24°; 25°; 26°; 27°; 28°; 29°; 30°; 31°; 32°; 33°; 34°; 35°; 36°; 37°; 38°; 39°; 40°; 41°; 42°; 43°; 44°; 45°; 46°; 47°; 48°; 49°; 50°; 51°; 52°; 53°; 54°; 55°; 56°; 57°; 58°; 59°; 60°; 61°; 62°; 63°; 64°; 65°; 66°; 67°; 68°; 69°; 70°; 71°; 72°; 73°; 74°; 75°; 76°; 77°; 78°; 79°; 80°; 81°; 82°; 83°; 84°; 85°; 86°; 87°; 88°; 89°; 90°; 91°; 92°; 93°; 94°; 95°; 96°; 97°; 98°; 99°; 100°; 101°; 102°; 103°; 104°; 105°; 106°; 107°; 108°; 109°; 110°; 111°; 112°; 113°; 114°; 115°; 116°; 117°; 118°; 119°; 120°; 121°; 122°; 123°; 124°; 125°; 126°; 127°; 128°; 129°; 130°; 131°; 132°; 133°; 134°; 135°; 136°; 137°; 138°; 139°; 140°; 141°; 142°; 143°; 144°; 145°; 146°; 147°; 148°; 149°; 150°; 151°; 152°; 153°; 154°; 155°; 156°; 157°; 158°; 159°; or 160°. In some implementations, all of the microstructures (i.e., 130A, 130B, 130C, 130D, 130E, 130F, 130G, 130H, 130I, 130J, 130K, 130L) of the first portion 122 and the second portion 124 have the same tip angle. In other implementations, the microstructures of the first portion 122 and the second portion 124 have varying suitable tip angles.

In embodiments, the microstructures (e.g., 130G, 130H, 130I, 130J, 130K, 130L in FIG. 1) of the second portion (e.g., 124 in FIG. 2) have the same structure and function as described above with reference to the microstructures (e.g. 130A, 130B, 130C, 130D, 130E, 130F in FIG. 1) of the first portion (e.g., 122 in FIG. 2) and will not be separately described herein.

In some embodiments, the wound closure devices of the present disclosure comprise microstructures at an angle relative to the backing or base. In various embodiments, the angle of the microstructures is such that it is angled towards a wound when the wound closure device is appropriately applied to a subject. The microstructures may be positioned at any suitable angle. In some embodiments the microstructures are positioned at an angle relative to a backing or base, wherein the angle is approximately 15, 30, 45, 60, 75, or 90 degrees, including all integers (e.g., 16°, 17°, 18°, etc.) and ranges (e.g., 15°-90°, 30°-90°, 45°-70°, etc.) in between, of the angles set forth. In one embodiment, the microstructures are at an angle of greater than 50 degrees relative to the backing or base. In one embodiment, the microstructures are at an angle of from 45 to 70 degrees relative to the backing or base. In one embodiment, the microstructures are at an angle of from 50 to 70 degrees relative to the backing or base. In some embodiments, the microstructures are at an angle that is about 10°; 11°; 12°; 13°; 14°; 15°; 16°; 17°; 18°; 19°; 20°; 21°; 22°; 23°; 24°; 25°; 26°; 27°; 28°; 29°; 30°; 31°; 32°; 33°; 34°; 35°; 36°; 37°; 38°; 39°; 40°; 41°; 42°; 43°; 44°; 45°; 46°; 47°; 48°; 49°; 50°; 51°; 52°; 53°; 54°; 55°; 56°; 57°; 58°; 59°; 60°; 61°; 62°; 63°; 64°; 65°; 66°; 67°; 68°; 69°; 70°; 71°; 72°; 73°; 74°; 75°; 76°; 77°; 78°; 79°; 80°; 81°; 82°; 83°; 84°; 85°; 86°; 87°; 88°; 89°; or about 90° relative to the backing or base.

The area at which the microstructures intersect with the base can be straight or it can be curved (i.e., thus, comprising a bend radius). In some embodiments, the bend radius of the area at which the microstructures intersect the base ranges from about 0.1 mm to about 3 mm. In some embodiments, the bend radius ranges from about 0.3 mm to about 2 mm. In some embodiments, the bend radius ranges from about 0.5 mm to about 1 mm.

In embodiments, microstructures are angled (i.e., they extend from the base or backing at an angled other than 90°). For example, FIG. 5 is a side view of the wound closure device 100. As shown in FIG. 5, in some embodiments, the microstructures (e.g., 130A, 130C, 130E, 130H, 130J, 130L) extend at an angle relative to the base 121 of the microstructure array 120. For example, the microstructure 130A extends at a second angle $\theta_2$ relative to the base 121 of the microstructure array 120. In some implementations, the second angle $\theta_2$ is selected from about 10° to 90°; from about 20° to 80°, from about 30° to 70°, or from about 30° to 50°. In one non-limiting embodiment, the second angle $\theta_2$ is about 45°. Accordingly, in some embodiments, the second angle is about 10°; 11°; 12°; 13°; 14°; 15°; 16°; 17°; 18°; 19°; 20°; 21°; 22°; 23°; 24°; 25°; 26°; 27°; 28°; 29°; 30°; 31°; 32°; 33°; 34°; 35°; 36°; 37°; 38°; 39°; 40°; 41°; 42°; 43°; 44°; 45°; 46°; 47°; 48°; 49°; 50°; 51°; 52°; 53°; 54°; 55°; 56°; 57°; 58°; 59°; 60°; 61°; 62°; 63°; 64°; 65°; 66°; 67°; 68°; 69°; 70°; 71°; 72°; 73°; 74°; 75°; 76°; 77°; 78°; 79°; 80°; 81°; 82°; 83°; 84°; 85°; 86°; 87°; 88°; 89°; or about 90°, including all decimals (e.g., 45.1°, 45.2°, 45.3°, 45.4°, etc) and ranges (e.g., 35°-45°, 37-47°, 38°-45°, etc.) in between.

In some embodiments, the wound closure devices also include microstructures with an angle relative to the backing or base that is variable depending on its position in any microstructure array. In certain embodiments, the angle of one or more microstructures is approximately constant along the entire length of the microstructure, and in other embodiments, the angle of the microstructure varies along the length of the microstructure.

In embodiments, microstructures may be angled in any direction. In some embodiments, all microstructures in a particular array are angled in the same direction, or in approximately the same direction; while in other embodiments they are not. In certain embodiments, all microstructures on a device are angled towards a wound (i.e., the microstructure tips are angled towards the bridge portion, e.g., as shown in FIG. 5). In some particular embodiments, the microstructures in an array comprise subsets of microstructures angled in different directions.

In some embodiments, microstructures (e.g., 130A, 130B, 130C, 130D, 130E, 130F, 130G, 130H, 130I, 130J, 130K, 130L) are angled in such a way that, when attached to the tissue surrounding a wound, the microstructures can translate the longitudinal tension resultant from the natural condition in which the skin pulls the wound apart into a force that pushes the wound closure device toward the tissue. Thus, the wound closure device is effectively anchored onto or into the tissue. Although the microstructures of the wound closure devices exemplified in the various figures herein are shown as extending at substantially the same angle relative to the base (e.g., 121 in FIG. 5), in some implementations the microstructures can extend at variable angles relative to the base. For example, in some non-limiting embodiments, some microstructures may protrude from the base at an angle of 45°, while other microstructures may protrude from the base at an angle of 60°. As another non-limiting example, some microstructures may protrude from the base at an angle of 45°, while other microstructures may protrude from the base at an angle of 90°. Additionally, individual microstructure protrusion angle and length may vary based upon the position of the individual microstructure in the microstructure array and/or on the wound closure device.

In some embodiments, the microstructures (e.g., 130A, 130B, 130C, 130D, 130E, 130F, 130G, 130H, 130I, 130J, 130K, 130L) may be shaped, sized, and/or angled to penetrate into the superficial epidermis, epidermis, superficial dermis, or deep dermis. In other implementations, the microstructures may be shaped, sized, and/or angled to attach to the skin surface or other tissue surface without penetrating the skin or other tissue surface. The microstructures may include microstaples, microbarbs, microneedles, microblades, microanchors, microhooks, microfishscale, micropillars, microhairs, and combinations thereof. Additionally, although certain exemplified embodiments show the wound closure devices as including twelve microstructures, the microstructure arrays may include any suitable number of microstructures, such as, for example, four microstructures or more than one thousand microstructures. In some embodiments, the microstructure array includes from 1 to 100 microstructures. In some embodiments, the microstructure array includes from 2 to 50 microstructures. In some embodiments, the microstructure array includes from 3 to 30 microstructures. In some embodiments, the microstructure array includes from 5 to 15 microstructures.

In certain embodiments, the microstructure array includes 1 microstructure; or 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46;

47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; 190; 191; 192; 193; 194; 195; 196; 197; 198; 199; 200; 201; 202; 203; 204; 205; 206; 207; 208; 209; 210; 211; 212; 213; 214; 215; 216; 217; 218; 219; 220; 221; 222; 223; 224; 225; 226; 227; 228; 229; 230; 231; 232; 233; 234; 235; 236; 237; 238; 239; 240; 241; 242; 243; 244; 245; 246; 247; 248; 249; 250; 251; 252; 253; 254; 255; 256; 257; 258; 259; 260; 261; 262; 263; 264; 265; 266; 267; 268; 269; 270; 271; 272; 273; 274; 275; 276; 277; 278; 279; 280; 281; 282; 283; 284; 285; 286; 287; 288; 289; 290; 291; 292; 293; 294; 295; 296; 297; 298; 299; 300; 301; 302; 303; 304; 305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; 350; 351; 352; 353; 354; 355; 356; 357; 358; 359; 360; 361; 362; 363; 364; 365; 366; 367; 368; 369; 370; 371; 372; 373; 374; 375; 376; 377; 378; 379; 380; 381; 382; 383; 384; 385; 386; 387; 388; 389; 390; 391; 392; 393; 394; 395; 396; 397; 398; 399; 400; 401; 402; 403; 404; 405; 406; 407; 408; 409; 410; 411; 412; 413; 414; 415; 416; 417; 418; 419; 420; 421; 422; 423; 424; 425; 426; 427; 428; 429; 430; 431; 432; 433; 434; 435; 436; 437; 438; 439; 440; 441; 442; 443; 444; 445; 446; 447; 448; 449; 450; 451; 452; 453; 454; 455; 456; 457; 458; 459; 460; 461; 462; 463; 464; 465; 466; 467; 468; 469; 470; 471; 472; 473; 474; 475; 476; 477; 478; 479; 480; 481; 482; 483; 484; 485; 486; 487; 488; 489; 490; 491; 492; 493; 494; 495; 496; 497; 498; 499; 500; 501; 502; 503; 504; 505; 506; 507; 508; 509; 510; 511; 512; 513; 514; 515; 516; 517; 518; 519; 520; 521; 522; 523; 524; 525; 526; 527; 528; 529; 530; 531; 532; 533; 534; 535; 536; 537; 538; 539; 540; 541; 542; 543; 544; 545; 546; 547; 548; 549; 550; 551; 552; 553; 554; 555; 556; 557; 558; 559; 560; 561; 562; 563; 564; 565; 566; 567; 568; 569; 570; 571; 572; 573; 574; 575; 576; 577; 578; 579; 580; 581; 582; 583; 584; 585; 586; 587; 588; 589; 590; 591; 592; 593; 594; 595; 596; 597; 598; 599; 600; 601; 602; 603; 604; 605; 606; 607; 608; 609; 610; 611; 612; 613; 614; 615; 616; 617; 618; 619; 620; 621; 622; 623; 624; 625; 626; 627; 628; 629; 630; 631; 632; 633; 634; 635; 636; 637; 638; 639; 640; 641; 642; 643; 644; 645; 646; 647; 648; 649; 650; 651; 652; 653; 654; 655; 656; 657; 658; 659; 660; 661; 662; 663; 664; 665; 666; 667; 668; 669; 670; 671; 672; 673; 674; 675; 676; 677; 678; 679; 680; 681; 682; 683; 684; 685; 686; 687; 688; 689; 690; 691; 692; 693; 694; 695; 696; 697; 698; 699; 700; 701; 702; 703; 704; 705; 706; 707; 708; 709; 710; 711; 712; 713; 714; 715; 716; 717; 718; 719; 720; 721; 722; 723; 724; 725; 726; 727; 728; 729; 730; 731; 732; 733; 734; 735; 736; 737; 738; 739; 740; 741; 742; 743; 744; 745; 746; 747; 748; 749; 750; 751; 752; 753; 754; 755; 756; 757; 758; 759; 760; 761; 762; 763; 764; 765; 766; 767; 768; 769; 770; 771; 772; 773; 774; 775; 776; 777; 778; 779; 780; 781; 782; 783; 784; 785; 786; 787; 788; 789; 790; 791; 792; 793; 794; 795; 796; 797; 798; 799; 800; 801; 802; 803; 804; 805; 806; 807; 808; 809; 810; 811; 812; 813; 814; 815; 816; 817; 818; 819; 820; 821; 822; 823; 824; 825; 826; 827; 828; 829; 830; 831; 832; 833; 834; 835; 836; 837; 838; 839; 840; 841; 842; 843; 844; 845; 846; 847; 848; 849; 850; 851; 852; 853; 854; 855; 856; 857; 858; 859; 860; 861; 862; 863; 864; 865; 866; 867; 868; 869; 870; 871; 872; 873; 874; 875; 876; 877; 878; 879; 880; 881; 882; 883; 884; 885; 886; 887; 888; 889; 890; 891; 892; 893; 894; 895; 896; 897; 898; 899; 900; 901; 902; 903; 904; 905; 906; 907; 908; 909; 910; 911; 912; 913; 914; 915; 916; 917; 918; 919; 920; 921; 922; 923; 924; 925; 926; 927; 928; 929; 930; 931; 932; 933; 934; 935; 936; 937; 938; 939; 940; 941; 942; 943; 944; 945; 946; 947; 948; 949; 950; 951; 952; 953; 954; 955; 956; 957; 958; 959; 960; 961; 962; 963; 964; 965; 966; 967; 968; 969; 970; 971; 972; 973; 974; 975; 976; 977; 978; 979; 980; 981; 982; 983; 984; 985; 986; 987; 988; 989; 990; 991; 992; 993; 994; 995; 996; 997; 998; 999; or 1000 or more than 1000 microstructures. In some embodiments, the microstructure arrays comprise less than about 50 microstructures, less than about 40 microstructures, or less than about 20 microstructures. In one embodiment, the microstructure array comprises 18 microstructures. In one embodiment, the microstructure array comprises 16 microstructures. In one embodiment, the microstructure array comprises 12 microstructures.

The microstructures disclosed herein extend a height from the base. For example, as shown in FIG. 5, the microstructure 130C can extend a first height $H_1$ from the base 121. The first height $H_1$ can be any suitable height. In some embodiments, microstructures have heights ranging from approximately 0.1 mm to approximately 8 mm. Thus, in some embodiments, the microstructures comprised on the microstructure arrays have heights of approximately 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 mm, 1.5 mm, 2 mm, 3 mm, including all integers (e.g., 1.6 mm, 1.7 mm, 1.8 mm, etc.) and ranges (e.g., 500-5000 μm, 500-2000 μm, 700 μm to 1600 μm, 100-3000 μm, 1500-2500 μm, 700-1000 μm, 950-1000 μm, etc.) in between, of the microstructure heights set forth herein. For example, in certain embodiments, the first height $H_1$ may be about 1.73 mm. In other implementations, the first height $H_1$ may be, for example, about 1.5 mm or about 1.05 mm. Although the microstructures of the wound closure devices exemplified in the figures (e.g., 100 in FIG. 1) are shown as all extending the same height from the base, in some implementations the microstructures can extend varying heights from the base (i.e., not all microstructures on an array must have the same height).

In other embodiments, microstructure heights exceed 3 mm. For example, in some embodiments, longer (e.g., 8 mm or longer) microstructures may be more effective, or necessary, for treatment areas that include thicker dermal tissue (e.g., the back). Thus, the skilled artisan can configure a microstructure with a height that exceeds 8 mm, e.g., for use in a thicker tissue.

Additionally, the base (e.g., 121 in FIG. 5) has a second height $H_2$. In some embodiments, the second height $H_2$ is from 10 um to 2000 um. In some embodiments, the second height $H_2$ is from 50 um to 1500 um. In some embodiments, the second height $H_2$ is from 100 um to 1000 um. Thus, in certain non-limiting embodiments, the second height $H_2$ is, for example, about 200 μm (about 0.008"). In other implementations, the second height $H_2$ can be any suitable height. In certain embodiments, the second height $H_2$ is selected from about 10 um or about 11 um; 12 um; 13 um; 14 um; 15 um; 16 um; 17 um; 18 um; 19 um; 20 um; 21 um; 22 um; 23 um; 24 um; 25 um; 26 um; 27 um; 28 um; 29 um; 30 um; 31 um; 32 um; 33 um; 34 um; 35 um; 36 um; 37 um; 38 um; 39 um; 40 um; 41 um; 42 um; 43 um; 44 um; 45 um; 46 um; 47 um; 48 um; 49 um; 50 um; 51 um; 52 um; 53 um; 54 um; 55 um; 56 um; 57 um; 58 um; 59 um; 60 um; 61 um; 62 um; 63 um; 64 um; 65 um; 66 um; 67 um; 68 um; 69 um; 70 um;

71 um; 72 um; 73 um; 74 um; 75 um; 76 um; 77 um; 78 um; 79 um; 80 um; 81 um; 82 um; 83 um; 84 um; 85 um; 86 um; 87 um; 88 um; 89 um; 90 um; 91 um; 92 um; 93 um; 94 um; 95 um; 96 um; 97 um; 98 um; 99 um; 100 um; 101 um; 102 um; 103 um; 104 um; 105 um; 106 um; 107 um; 108 um; 109 um; 110 um; 111 um; 112 um; 113 um; 114 um; 115 um; 116 um; 117 um; 118 um; 119 um; 120 um; 121 um; 122 um; 123 um; 124 um; 125 um; 126 um; 127 um; 128 um; 129 um; 130 um; 131 um; 132 um; 133 um; 134 um; 135 um; 136 um; 137 um; 138 um; 139 um; 140 um; 141 um; 142 um; 143 um; 144 um; 145 um; 146 um; 147 um; 148 um; 149 um; 150 um; 151 um; 152 um; 153 um; 154 um; 155 um; 156 um; 157 um; 158 um; 159 um; 160 um; 161 um; 162 um; 163 um; 164 um; 165 um; 166 um; 167 um; 168 um; 169 um; 170 um; 171 um; 172 um; 173 um; 174 um; 175 um; 176 um; 177 um; 178 um; 179 um; 180 um; 181 um; 182 um; 183 um; 184 um; 185 um; 186 um; 187 um; 188 um; 189 um; 190 um; 191 um; 192 um; 193 um; 194 um; 195 um; 196 um; 197 um; 198 um; 199 um; 200 um; 201 um; 202 um; 203 um; 204 um; 205 um; 206 um; 207 um; 208 um; 209 um; 210 um; 211 um; 212 um; 213 um; 214 um; 215 um; 216 um; 217 um; 218 um; 219 um; 220 um; 221 um; 222 um; 223 um; 224 um; 225 um; 226 um; 227 um; 228 um; 229 um; 230 um; 231 um; 232 um; 233 um; 234 um; 235 um; 236 um; 237 um; 238 um; 239 um; 240 um; 241 um; 242 um; 243 um; 244 um; 245 um; 246 um; 247 um; 248 um; 249 um; 250 um; 251 um; 252 um; 253 um; 254 um; 255 um; 256 um; 257 um; 258 um; 259 um; 260 um; 261 um; 262 um; 263 um; 264 um; 265 um; 266 um; 267 um; 268 um; 269 um; 270 um; 271 um; 272 um; 273 um; 274 um; 275 um; 276 um; 277 um; 278 um; 279 um; 280 um; 281 um; 282 um; 283 um; 284 um; 285 um; 286 um; 287 um; 288 um; 289 um; 290 um; 291 um; 292 um; 293 um; 294 um; 295 um; 296 um; 297 um; 298 um; 299 um; or about 300 um, including all decimals (e.g., 200.5 um, 200.6 um, 200.7 um) and ranges (e.g., 150 um to 220 um, 170 um to 210 um, etc.) in between.

Microstructure Materials

The microstructures disclosed herein may be made of any material or mixture of materials. In some implementations, the material is a natural material, or a mixture of natural materials. In other implementations, the material is a synthetic material, or a mixture of synthetic materials. In other implementations, comprising mixtures of one or more synthetic materials and one or more natural materials. In particular implementations, microstructures are made of a material selected from a polymer, a metal, a biomaterial, and a combination thereof. In some implementations, a microstructure is comprised of nanostructures, (e.g., nanofibers). In some implementations, the microstructures are coated with nanostructures (e.g., nanofibers). In some implementations the microstructures are comprised of, or consist essentially of, biodegradable materials. This prevents complications such as inflammation, tissue damage, and infection due to broken needles from occurring. In other implementations, the microstructures do not comprise biodegradable materials. In other implementations, the microstructures comprise biodegradable materials and non-biodegradable materials.

In some implementations, the microstructures are comprised of or consist essentially of a metal. In some implementations, the microstructures are comprised of or consist essentially of a metal composite. In particular embodiments the microstructures are comprised of or consist essentially of a metal or metal composite selected from the group consisting of: aluminum, titanium, stainless steel. In some embodiment, the microstructures are comprised of or consist essentially of a 300 series stainless steel alloy. In some embodiment, the microstructures are comprised of or consist essentially of 316 stainless steel alloy.

In some implementations, the microstructures are made from a material or include a material selected from a polymer such as, for example, poly(methyl methacrylate) (also known as Poly(methyl2-methylpropenoate (IUPAC name), polymethyl methacrylate, or more commonly known as PLEXIGLASS™), silicon, and chitin. The wound closure device 100 can include other components such as, but not limited to, nanostructures (e.g., nanostructure arrays or nanofibers) and bioactive compounds (e.g., drugs, therapeutics, hydrogels, healing substances, and combinations thereof). In some implications, the material is selected from the group consisting of PMMA, silicone, chitin, chitosan, ecoflex, titanium, glass, metal, steel, silicon, silk, catgut, chromic catgut, polyglycolic acid, polydioxanone, polytrimethulene carbonate, nylon, polypropylene, polyester, polybutester, poly(lactic-co-glycolic acid), polylactone, elastin, resilin, collagen, cellulose, polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluoroethylene (TEFLON™), polyesters. and any combination thereof. In some implementations, the wound closure device 100 also includes chitin (e.g., chitin nanofibers). In some implementations, the wound closure devices include a hydrogel.

Microstructure Dimensions and Geometries

Microstructures may be any suitable length, width, shape or geometry. In some embodiments, all microstructures comprised on a microstructure would closure device are the same size, shape, and or geometry. In some embodiments, at least two microstructures on a microstructure would closure device are a different size, shape, or geometry. Microstructures can be any suitable height off of the base. In various embodiments, the microstructures of the microstructure array are designed to penetrate the skin. For example, in one implementation, the microstructures are long enough to penetrate the skin, but not deep enough to reach nerve endings that cause pain. In some embodiments, the microstructures are designed to grasp skin. In some embodiments, the microstructures are designed to enable delivery of drugs or other therapeutic agents. In some implementations, the microstructures are coated with drugs. In other implementations, the microstructures have an open internal structure in which drugs can be incorporated.

Figure 25:
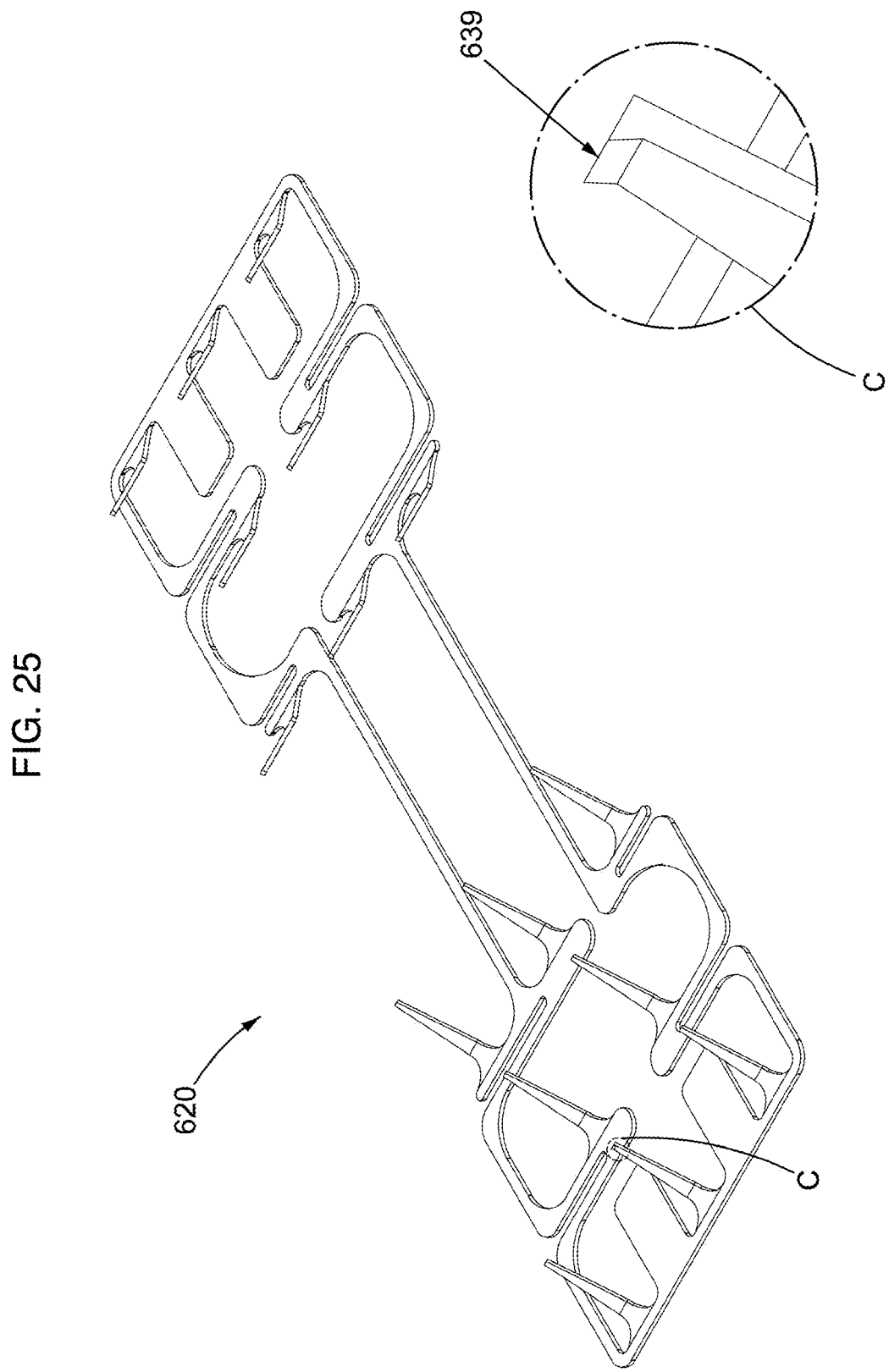
FIG. 25 is an isometric view of a microstructure array according to an embodiment.

In some embodiments, the microstructures comprise a permanent burr such as is shown in FIG. 25. FIG. 25 is an isometric view of a microstructure assembly 620. A permanent burr 639 is shown in the enlarged view of region C. In some embodiments, the burr is any suitable size and shape. In some embodiments, the burr is created by stamping. In some embodiments, tip sharpness is created by use of progressive and overlapping dies.

FIG. 6 is a front view of the wound closure device 100. As shown in FIG. 6, the microstructures (e.g., 130A, 130B, 130C, 130D, 130E, 130F) can include curved transition portions for curved transitions between each microstructure and the base 121. In some embodiments, the curved transition portions increase the strength of the connection between the microstructure and the base. In some embodiments, the curved transition portions reduce local stress to the microstructures caused by the extending force applied during application or the longitudinal tension caused by tissue naturally separating from a wound. For example, the microstructure 130E can include curved transition portions 132E and 134E. In various embodiments, the microstructure arrays can include microstructures with such curved transition portions of any suitable radius. An alternative example of a curved transition portion can be seen in FIG. 18. As shown in region D, microstructures 430 may include curved transition portions 132 and 134. In some embodiments, the radius of the curved transition portions range from 0.05 to 2 mm. In some embodiments, the radius of the curved transition portions range from 0.1 to 2.5 mm. In some embodiments, the radius of the curved transition portions range from 0.1 to 1 mm. In some embodiments, the radius of the curved transition portions range from 0.25 to 0.75 mm.

The microstructure base width $D_5$ (see FIG. 7) of the microstructures (e.g., 130E) can be any suitable dimension. In some embodiments, the width $D_5$ of the microstructure ranges from about 0.05 mm to about 5 mm. In some embodiments, the width $D_5$ of the microstructure ranges from about 1 mm to about 6 mm. In some embodiments, the width $D_5$ of the microstructure ranges from about 2 mm to about 5 mm. In some embodiments, the width $D_5$ of the microstructure ranges from about 0.1 mm to about 2.5 mm. In some embodiments, the width $D_5$ of the microstructure ranges from about 0.5 mm to about 1.5 mm. In one particular embodiment, the width $D_5$ of the microstructure ranges from about 0.5 mm to about 2.5 mm. In one embodiment, the width $D_5$ of the microstructure is about 1.20 mm. In other implementations, however, the width $D_5$ of the microstructure 130E can range, for example, from about 0.7 mm to about 1.7 mm. Similarly, the microstructures 430 shown in FIG. 18 can also have any suitable width $D_{18}$. For example, in some embodiments, the width $D_{18}$ of the microstructure shown in region D ranges from about 0.2 mm to about 1.5 mm. In other embodiments, the width $D_{18}$ of the microstructure shown in region D ranges from about 0.05 mm to about 5 mm. In still other embodiments, the width $D_{18}$ ranges from about 0.1 mm to about 2.5 mm. In some embodiments, the width $D_{18}$ of the microstructure is about 0.4 mm.

In some embodiments, the microstructures can include a tip having a width. The tip width of the microstructures can be any suitable length. For example, region D of FIG. 18 shows a microstructure 430 having a tip width $T_1$. In some embodiments, tip width $T_1$ of the microstructure ranges from about 0.0001 mm to about 2 mm. In some embodiments, tip width $T_1$ of the microstructure ranges from about 0.0005 mm to about 0.5 mm. In some embodiments, tip width $T_1$ of the microstructure ranges from about 0.001 mm to about 0.12 mm. In some embodiments, tip width $T_1$ of the microstructure ranges from about 0.001 mm to about 0.2 mm.

Microstructure Positioning

The position of the microstructures on the microstructure arrays can be in any suitable location. In some embodiments, it is desirable to optimize the spacing between the microstructures. This optimization attempts to maximize the spacing between the microstructures to reduce inflammation and hyperpigmentation while also including an adequate number of microstructures to maintain attachment with the tissue. In some embodiments, such optimization involves consideration of the number of microstructures and the size of various components of the wound closure device. Thus, in some embodiments, the present invention provides microstructure arrays with optimized spacing.

In some embodiments, the microstructures are evenly distributed longitudinally along one or more array portions of the microstructure wound closure device. In some embodiments, the microstructures are evenly distributed laterally (i.e., the axis of the device perpendicular to the longitudinal axis of the device) along the array portions of the microstructure wound closure device. In some embodiments, the microstructures are evenly distributed both longitudinally and laterally along the array portions of the microstructure wound device.

In some embodiments, the microstructures are unevenly distributed longitudinally along one or more array portion of the microstructure wound closure device. In some embodiments, the microstructures are unevenly distributed laterally (i.e., along the axis of the device perpendicular to the longitudinal axis of the device) along the array portions of the microstructure wound closure device. In some embodiments, the microstructures are unevenly distributed both longitudinally and laterally along the array portions of the microstructure wound device.

In certain embodiments, the position of the microstructures on the microstructure arrays is staggered. For example, FIG. 7 is a top view of the wound closure device 100. As shown in FIG. 7, the locations of the microstructures (e.g., 130A, 130B, 130C, 130D, 130E, 130F, 130G, 130H, 130I, 130J, 130K, 130L) on the base 121 are staggered. Said another way, the microstructures 130C and 130D are offset from the microstructures 130A and 130B and from the microstructures 130E and 130F relative to a central longitudinal axis AA of the wound closure device 100. In certain embodiments, when the wound closure device (e.g., device 100 in FIG. 7) is attached to tissue, the staggered arrangement of microstructures distributes the force applied to the tissue, aiding in the prevention of scarring. In other embodiments, the locations of the microstructures on the base are not staggered. In still other embodiments, the locations of some of the microstructures are staggered and some of the microstructures are not staggered.

The distance $D_3$ from the tip of one microstructure to the tip of the next adjacent microstructure can be any suitable length. For example, as shown in the embodiment illustrated in FIG. 7, the distance $D_3$ from the tip of microstructure 130D to the tip of microstructure 130F may be about 4.48 mm. In other implementations, however, the distance $D_3$ can range, for example, from between about 0.5 mm to about 15 mm. In some embodiments, $D_3$ ranges from about 1 mm to about 10 mm. In some embodiments, $D_3$ ranges from about 1 mm to 6 mm. In some embodiments, $D_3$ ranges from about 3 mm to about 6 mm. In some embodiments, $D_3$ ranges from about 2.5 mm to about 5 mm. In some embodiments, $D_3$ ranges from about 2 mm to about 5 mm. In some embodiments, $D_3$ ranges from about 3 to about 4 mm.

The distance $D_4$ (see FIG. 7) from an edge of a microstructure to an edge of an adjacent microstructure can any suitable length. For example, as shown in the embodiment illustrated in FIG. 7, the distance $D_4$ from the edge of 103D to the edge of 130F may be about 3.98 mm. In other embodiments, however, the distance $D_4$ ranges from, for example, between about 0.5 mm to about 15 mm. In some embodiments, $D_4$ ranges from about 1 mm to about 10 mm. In some embodiments, $D_4$ ranges from about 1 mm to 6 mm. In some embodiments, $D_3$ ranges from about 3 mm to about 6 mm. In some embodiments, $D_4$ ranges from about 2.5 mm to about 5 mm. In some embodiments, $D_4$ ranges from about 2 mm to about 5 mm. In some embodiments, $D_4$ ranges from about 3 to about 4 mm.

The distance $D_{10}$ (see FIG. 7) from an edge of the microstructure (e.g., 130F) to an edge of an adjacent microstructure (e.g., 130G) can any suitable length. For example, in some embodiments, the distance $D_{10}$ ranges from, for example, between about 0.5 mm to about 15 mm. In some embodiments, $D_{10}$ ranges from about 1 mm to about 10 mm. In some embodiments, $D_{10}$ ranges from about 1 mm to 6 mm. In some embodiments, $D_{10}$ ranges from about 3 mm to about 6 mm. In some embodiments, $D_{10}$ ranges from about 2.5 mm to about 5 mm. In some embodiments, $D_{10}$ ranges from about 2 mm to about 5 mm. In some embodiments, $D_{10}$ ranges from about 3 to about 4 mm.

As a further example, the distance $D_6$ (see FIG. 7) from the tip of a microstructure on one side of the bridge portion (e.g., 130B) to the tip of a microstructure on the other side of a bridge portion (e.g., 130G) across the wound may, in some embodiments, vary depending on the size of the intended tissue and/or wound. In some embodiments, $D_6$ ranges from about 1 mm to about 50 mm. In some embodiments, $D_6$ ranges from about 3 mm to about 30 mm. In some embodiments, $D_6$ ranges from about 5 mm to about 25 mm. For example, in certain embodiments, the distance $D_6$ can be about 6.73 mm. In other implementations, however, the distance $D_6$ can range, for example, from about 4 mm to about 10 mm. Similarly, in some embodiments, the distance $D_7$ from an edge of the microstructure 130A to an edge of the microstructure 130F can vary depending on the size of the intended tissue and/or wound. In some embodiments, $D_7$ ranges from about 1 mm to about 50 mm. In some embodiments, $D_7$ ranges from about 3 mm to about 30 mm. In some embodiments, $D_7$ ranges from about 5 mm to about 25 mm. For example, in certain embodiments, the distance $D_7$ can be about 9.76 mm. In other implementations, however, the distance $D_7$ can range, for example, from about 6 mm to about 12 mm.

The microstructure array may comprise any suitable dimensions. In some implementations, the width $D_8$ may be any suitable length. In one embodiment, the width $D_8$ (see FIG. 7) of the microstructure array may be, for example, about 9.50 mm. In certain embodiments, the width $D_8$ ranges, for example, from between about 1 mm and about 100 mm. In some embodiments, the width $D_8$ ranges, for example, from between about 2 mm and about 50 mm. In some embodiments, the width $D_8$ ranges, for example, from between about 3 mm and about 30 mm. In some embodiments, the width $D_8$ ranges, for example, from between about 5 mm to about 20 mm. In some embodiments, the width $D_8$ ranges, for example, from between about 7 mm to about 12 mm. Additionally, in certain embodiments, the length $D_9$ (see FIG. 7) may be any suitable length. In some embodiments, for example, the length $D_9$ ranges from about 10 mm to about 150 mm. In some embodiments, the length $D_9$ ranges from about 20 mm to about 100 mm. In some embodiments, the length $D_9$ ranges from about 30 to 60 mm. In some implementations, the length $D_9$ can range, for example, from between about 20 mm to about 35 mm. For example, in certain embodiments, the length $D_9$ is about 26.50 mm.

Figure 19A:
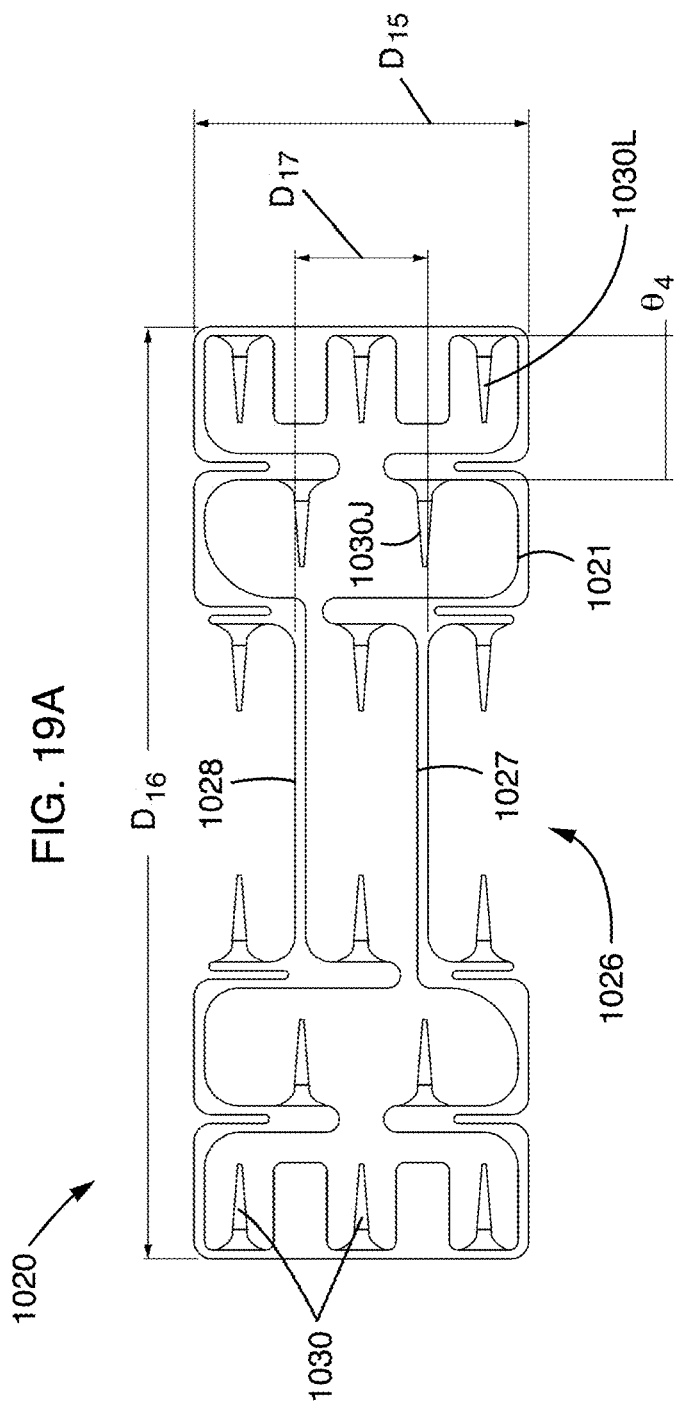
FIG. 19A is a top view of a microstructure array according to an embodiment.
Figure 19B:
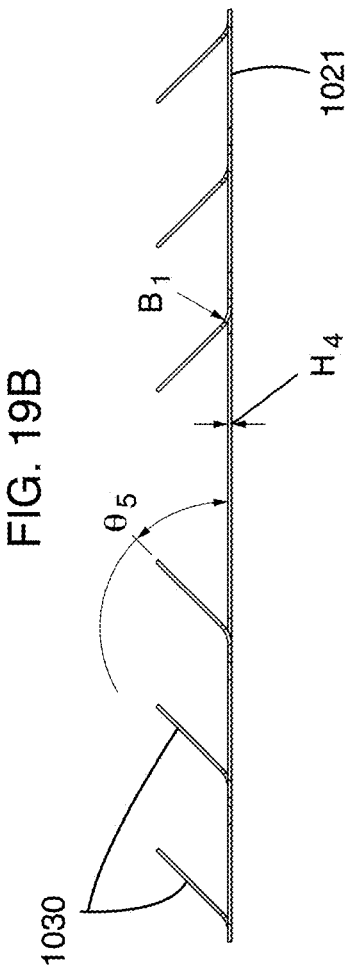
FIG. 19B is a side view of the microstructure array of FIG. 19A.

FIGS. 19A and 19B are a top view and a side view of a microstructure array 1020 according to another embodiment. As shown in FIG. 19A, the microstructure array 1020 can be similar in structure and function to any of the microstructure arrays described herein. Additionally, the microstructure array 1020 can have the same or similar dimensions as any of the microstructure arrays described herein. For example, the distance $D_{15}$ can be the same or similar to the distance $D_{10}$ described above with reference to the microstructure array 120 in FIG. 7. Similarly, the distance $D_{16}$ can be the same or similar to the distance $D_9$ described above with reference to the microstructure array 120 in FIG. 7. Also, as shown in FIG. 19A, the microstructure array 1020 includes a bridge portion 1026, which includes a first longitudinally extending portion 1027 and a second longitudinally extending portion 1028. In some embodiments, the distance $D_{17}$ from an outer edge of the first longitudinally extending portion 1027 to an outer edge of the second longitudinally extending portion 1028 ranges from about 3 mm to about 20 mm. In other embodiments, the distance $D_{17}$ ranges from about 2 mm to about 30 mm. In other embodiments, the distance $D_{17}$ ranges from about 1 mm to about 50 mm. In still other embodiments, the distance $D_{17}$ ranges from about 0.5 mm to about 100 mm.

Although microstructures 1030 of the wound closure device 1000 are shown in FIG. 19A as extending at substantially the same angle relative to a base 1021, in some implementations the microstructures can extend at variable angles relative to the base. For example, the microstructures 430 shown in microstructure array 420 (FIG. 18) are shown as extending at an angle $\theta_7$ of about 0° (i.e., substantially parallel) relative to a longitudinal centerline of the microstructure array 420. The microstructures 430, however, can extend any suitable angle. In some embodiments, the angle $\theta_7$ ranges from about −45° to about 45°. In other embodiments, the angle $\theta_7$ ranges from about −90° to about 90°. Similarly, microstructures can extend at variable angles relative to one another. For example, microstructures 1030J and 1030L are shown in FIG. 19A as extending at an angle $\theta_4$ of 0° relative to each other. Said another way, the microstructures 1030J and 1030L extend parallel relative to each other. In some embodiments, however, the microstructures 1030J and 1030L protrude from the base 1021 at an angle $\theta_4$ ranging from about −30° to about 30°. In other embodiments, the angle $\theta_4$ ranges from about −45° to about 45°. In other embodiments, the angle $\theta_4$ ranges from about −60° to about 60°. In still other embodiments, the angle $\theta_4$ ranges from about −90° to about 90°.

Microstructures 1030 of the wound closure device 1000 can have a bend radius $B_1$ in the area at which the microstructures 1030 intersect the base 1021. As shown in FIG. 19B, the bend radius $B_1$ may be 0.74 mm. In other embodiments, the bend radius $B_1$ ranges from about 0.1 mm to about 3 mm. In other embodiments, the bend radius $B_1$ ranges from about 0.3 mm to about 2 mm. In other embodiments, the bend radius $B_1$ ranges from about 0.5 mm to about 1 mm.

As shown in FIG. 19B, the microstructures 1030 of the wound closure device 1000 may extend from the base 1021 at an angle $\theta_5$ of 45° relative to the base 1021. Additionally, similar to the microstructures 130 described above with reference to FIG. 5, the microstructures 1030 of the wound closure device 1000 can extend from the base 1021 at any suitable angle. For example, the angle $\theta_5$ can be selected from about 10° to about 90°; from about 20° to about 80°, from about 30° to about 70°, or from about 30° to about 50°. Additionally, the base 1021 has a height $H_4$, as shown in FIG. 19. Similar to height $H_2$ described above with respect to FIG. 5, the height $H_4$ can be any suitable height. For example, in some embodiments, the height $H_4$ is from about 10 um to about 300 um. In some embodiments, the height $H_4$ is from about 50 um to about 500 um. In other embodiments, the height $H_4$ is from about 10 um to 1000 um.

In some embodiments, the array portion arms of the reversibly expandable structure comprise any suitable number of microstructures. In some embodiments, each array portion arm of the reversibly expandable structures comprise less than about 10 microstructures or less than about 5 microstructures. In one embodiment, the array portion arms of the reversibly expandable structure comprise more than 1 microstructure. In one embodiment, the array portion arms of the reversibly expandable structure comprise 1, 2, 3, or 4 microstructures.

Tension Indicators

In some embodiments, the wound closure devices described herein comprise one or more expansion or tension indicators that notifies the person applying the device when the device has been stretched (i.e., expanded) to the optimum length or tension. In some embodiments, the indicator is a selected figure or combination of figures or other indicia that are imprinted on or otherwise applied or affixed to the surface of a wound closure device disclosed herein (e.g., imprinted on, applied to, or affixed to the backing). One or more indicators may be present on the wound closure device. In some embodiments, the indicator is present in a single location on the wound closure device. In some embodiments, the wound closure device comprises a plurality of tension indicators. In some embodiments, the wound closure device includes at least one indicator on each of the first backing portion (e.g., 112) and the second backing portion (e.g., 114). In some embodiments, the wound closure device comprises a plurality of tension indicators spaced lengthwise along the backing of the wound closure device. In some embodiments, the indicator is an integral portion of the backing (e.g., it may be woven or otherwise incorporated into the fabric or material of the backing).

Many tension and expansion indicators are known in the art and are suitable for use in the present invention. For example, U.S. Pat. No. 3,613,679, incorporated herein by reference in its entirety, discloses tension indicators that are suitable for use in the present invention. Thus, in some embodiments, the wound closure devices disclosed herein comprise one or more tension indicator such as, e.g., a tension indicator disclosed in U.S. Pat. No. 3,613,679. In some embodiments, the indicator comprises a geometric shape. In some embodiments, the indicator comprises a color. In various embodiments, the indicator comprises a particular first geometric shape and/or first color in its resting state, and the shape and/or color of the indicator changes to a predetermined second geometric shape and/or second color upon stretching to a desired length and or tension. In some embodiments, the indicator identifies the appropriate stretching/tension for a particular type of wound. In some embodiments, the indicator identifies the appropriate stretching/tension to achieve a beneficial effect, such as, e.g., wound closure, sustained wound closure, increased healing rate, decreased scarring, decreased irritation, etc. In some embodiments, the indicator identifies the appropriate stretching/tension to induce eversion of a wound.

Application and Use of Wound Closure Devices

In some embodiments, when the wound closure devices described herein are attached to the tissue surrounding a wound, the microstructures of the first portion can be attached to tissue on a first side of the wound and the microstructures of the second portion can be attached to tissue on a second side of the wound. As the tissue, for example skin, naturally creates longitudinal tension by pulling apart at the wound site, the microstructures engage the tissue with more force and anchor the wound closure device into or onto the tissue.

For example, when the wound closure device 100, which is shown in FIGS. 1-7, is attached to the tissue surrounding a wound, the microstructures of the first portion 122 can be attached to tissue on a first side of the wound and the microstructures of the second portion 124 can be attached to tissue on a second side of the wound. As the tissue, for example, skin, naturally creates longitudinal tension by pulling apart at the wound site, the microstructures engage the tissue with more force and anchor the wound closure device 100 into or onto the tissue.

In some embodiments, the wound closure devices described herein firmly anchor onto the layer of the skin such as the epidermis. In some embodiments, a wound closure device described herein firmly anchors onto the stratum basale layer of the epidermis. In some embodiments, a wound closure device described herein firmly anchors onto the stratum spinosum layer of the epidermis. In some embodiments, a wound closure device described herein firmly anchors onto the stratum granulosum layer of the epidermis. In some embodiments, a wound closure device described herein firmly anchors onto the stratum lucidum layer of the epidermis. In some embodiments, a wound closure device described herein firmly anchors onto the stratum corneum layer of the epidermis.

In some embodiments, the wound closure devices described herein firmly anchors onto the deeper layer of the skin such as the dermis. In some embodiments, a wound closure device described herein firmly anchors onto the papillary layer of the dermis. In some embodiments, a wound closure device described herein firmly anchors onto the reticular layer of the dermis.

In various embodiments, the wound closure device is designed to provide the ability to achieve optimal eversion of the wound. Sutures and staples are characterized by variable wound eversion depending on the operator's skills and abilities. In embodiments, because the wound closure devices disclosed herein are much simpler and easier to use, wound eversion may be achieved much more consistently; this by simply pulling on the distal portion of one side of the device after the other side has been placed on the skin. The amount of eversion may be achieved based on simply observing the degree of tension that has been placed on the skin and then applying the other portion of the device onto the skin (e.g., by observing a tension indicator disclosed herein).

When applying a wound closure device described herein (e.g., wound closure device 100) to tissue surrounding a wound, the expandable portions allow for the wound closure device to slightly stretch into position. As a result, the wound closure device can be slightly stretched longitudinally along the wound closure device, and then engaged with the tissue. When released, the elasticity of the expandable portions will cause the expandable portions to attempt to return to their initial configurations, causing the microstructures to engage the tissue with more force as the expandable portions relax. In some embodiments, the presence of one or more expandable portion reduces or eliminates inflammation as compared to a similar device lacking such an expandable portion. The expandable portions can be configured to have suitable elasticities. For example, in some embodiments, the expandable portions have an elasticity that ranges from about 0.5 N/mm to about 10 N/mm. In some embodiments the expandable portions have an elasticity that ranges from about 2.8 N/mm to about 5 N/mm. In some embodiments, the expandable portions have an elasticity that is similar to skin, for example, of about 0.17 N/mm. In some embodiments the expandable portions have an elasticity that ranges from about 2 N/mm to about 5.5 N/mm. In some embodiments the expandable portions have an elasticity that ranges from about 1 N/mm to about 10 N/mm.

For example, when applying the wound closure device 100, which is shown in FIGS. 1-7, to tissue surround a wound, the expandable portions allow for the wound closure device 100 to slightly stretch into position. As a result, the wound closure device 100 can be slightly stretched along arrow C, shown in FIG. 7, and then engaged with the tissue. When released, the elasticity of the expandable portions will cause the expandable portions to attempt to return to their initial configurations, causing the microstructures to engage the tissue with more force as the expandable portions relax.

Figure 14:
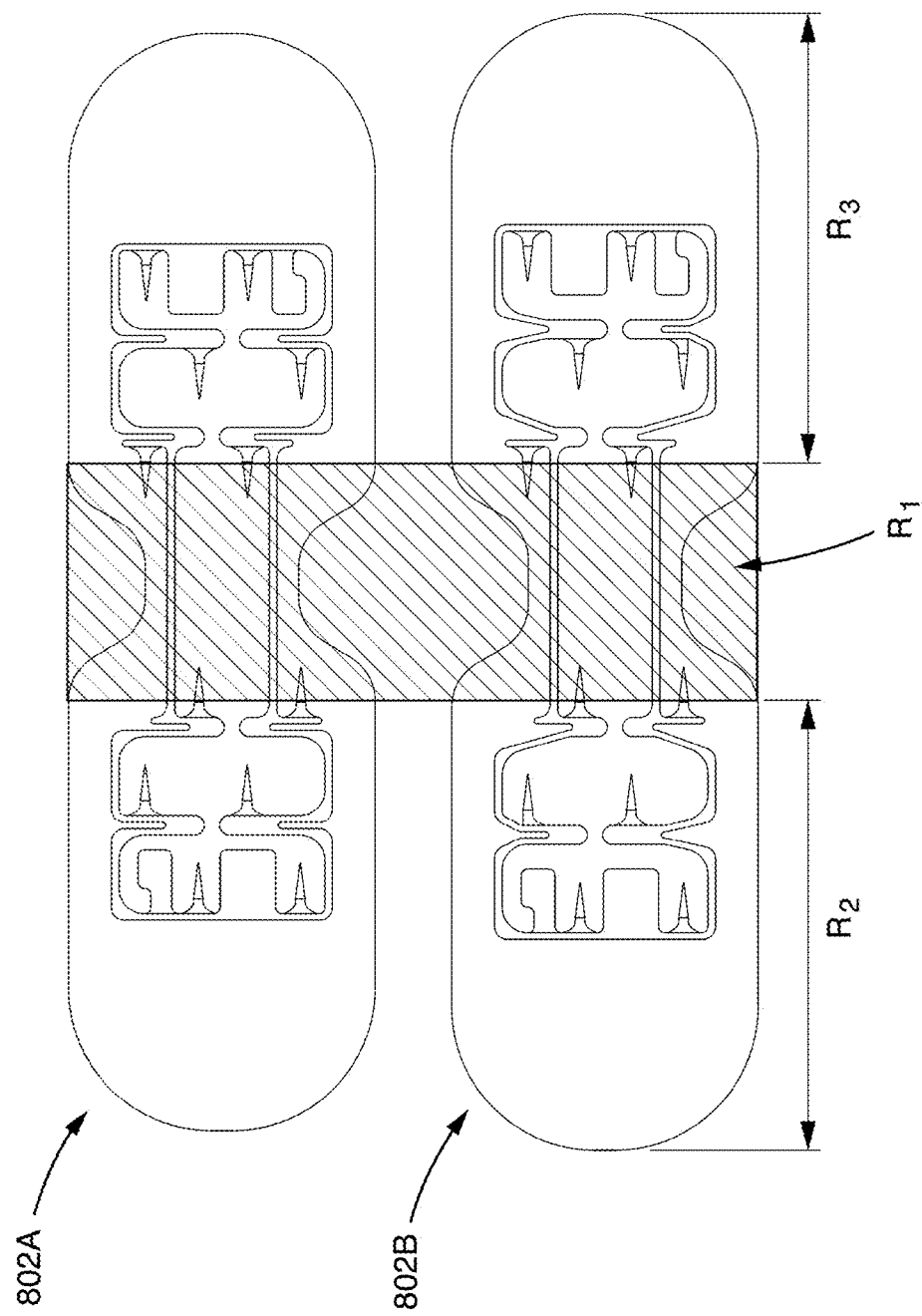
FIG. 14 is a top view of a first wound closure device in a first configuration (i.e., in its resting state) and a second identical wound closure device in a second configuration (i.e., in an expanded state) according to an embodiment.

For example, FIG. 14 shows a first wound closure device 802A and a second wound closure device 802B. The first wound closure device 802A and the second wound closure device 802B are identical to each other, and may have the same or similar features to any of the wound closure devices described herein. However, in the configurations shown in FIG. 14, the first wound closure device 802A is in an undeformed state (i.e., it's resting state) and the second wound closure device 802B is in a deformed state under longitudinal tension. As illustrated, the portions of the first wound closure device 802A and the second wound closure device 802B in the shaded region $R_1$ are inelastic and do not expand when the second wound closure device 802B is placed under tension. The portions of the first wound closure device 802A and the second wound closure device 802B in the regions between the boundaries indicated by $R_2$ and $R_3$ are elastic. Said another way, as shown in FIG. 14, both the backing and the microstructure array of the wound closure device 802B stretch when under tension. When the tension is released, the wound closure device 802B may be configured to return to the dimensions of the wound closure device 802A.

Figure 17:
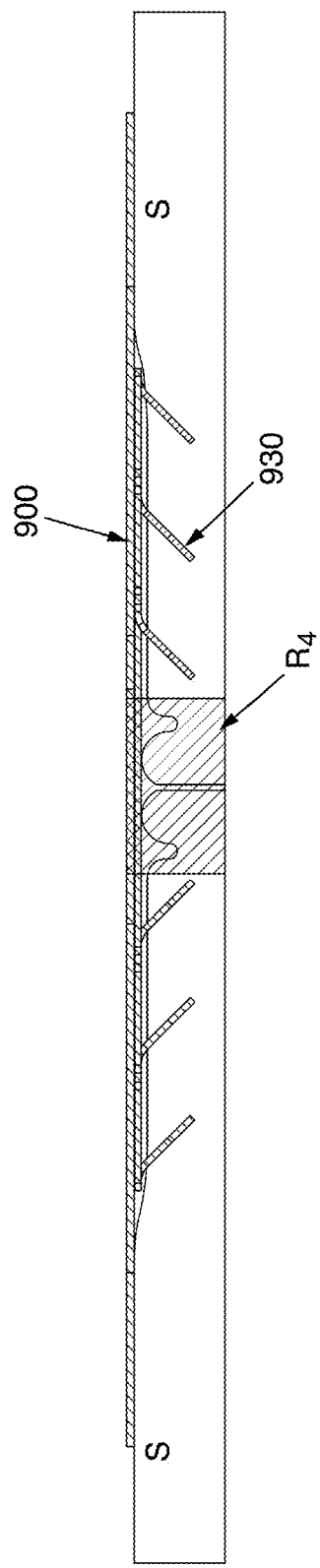

FIGS. 16 and 17 are cross-sectional illustrations of a wound closure device 900 in a configuration in which the wound closure device 900 is engaged with skin tissue S. The wound closure device 900 can be the same or similar in structure and function to any of the wound closure devices described herein. As shown in FIG. 16, the wound closure device 900 is applied to the skin tissue S around a wound W such that skin eversion V is achieved at the site of the wound W. As shown in FIG. 17, the skin eversion is achieved as a result of the compression of the skin tissue S in the region $R_4$, which also includes an inelastic region of the wound closure device 900. The wound closure device 900 maintains skin compression in the region $R_4$ via microstructures 930 anchoring into the skin tissue S in an elastic region outside of the region $R_4$. The base of a microstructure array and the backing of the wound closure device 900 may stretch with the elastic skin tissue S such that compression is maintained on the wound W in region $R_4$.

Additionally, as shown in the enlarged region F of FIG. 16, the microstructures 930 can extend any suitable distance $D_{13}$ into the skin tissue S. For example, in some embodiments, the distance $D_{13}$ can range from about 1.5 mm to about 2.5 mm. In other embodiments, the distance $D_{13}$ can range from about 1 mm to about 3 mm. In other embodiments, the distance $D_{13}$ can range from about 0.5 mm to about 5 mm. In still other embodiments, the distance $D_{13}$ can range from about 0.1 mm to about 8 mm. Additionally, the distance $D_{14}$ between the base of the microstructures closest to the wound W can be any suitable distance. For example, in some embodiments, the distance $D_{14}$ can range from about 5 mm to about 25 mm. In other embodiments, the distance $D_{14}$ can range from about 3 mm to about 30 mm. In other embodiments, the distance $D_{14}$ can range from about 1 mm to about 50 mm.

In some embodiments, the wound closure devices described herein can be applied to the skin without the use of an applicator or instrument. In other embodiments, the wound closure devices described herein can be applied to the skin using an applicator or instrument, such as a forceps or tweezers, to hold the device or to provide assistance in delivering force during the application and/or stretching of the device over the wound.

Microstructure Array Manufacturing

The microstructure arrays comprised in the wound closure devices disclosed herein may be manufactured using any method available to the skilled artisan. In some embodiments, the microstructures are made by microfabrication processes that are based on established methods e.g., those used to make integrated circuits, electronic packages and other microelectronic devices, augmented by additional methods used in the field of micromachining and micromolding.

Microstructure arrays can be fabricated, e.g., using replica molding; injection molding; microlithography; die cutting and etching; cutting; laser cutting; etching, or combinations thereof, such as have been described, e.g., in WO2007127976A2; WO2002072189A2; WO2002-064193A2; U.S. Pat. Nos. 6,503,231 and 6,334,856, WO1999064580 and WO2000074763; WO2012167162, all of which are incorporated herein by reference. For example, but not to be limited, microstructures can be fabricated by (i) etching the microstructure directly, (ii) etching a mold and then filling the mold with a melt or solution comprising the microstructure material to form the microstructure product, or (iii) etching a microstructure master, using the master to make a mold, and then filling the mold to form the microstructure replica (of the master).

In various embodiments, the microstructure arrays 120 are manufactured monolithically. For example, in some embodiments, the microstructure array 120 is stamped from one piece of metal. Methods for utilizing this process, sometimes called microstamping (or stamping of small parts), are known in the art (e.g., with respect to the mass production of delicate electric circuit components, such as connectors), and, in some embodiments, they comprise using a permanent tool or a progressive die, where material (e.g., sheet metal) is fed continuously into the tool which is set up in a stamping machine. Features of the stamping machine, including cutting means (and means for removal of materials) and forming (bending) of the microstructure array are created in multiple number of steps, or progressively. The machinery used to produce the microstructure array 120 can include a male component and a female component used to bend the microstructures to the desired angle. The microstructures can be bent to the desired angle either during the stamping of the microstructure array 120 from a sheet of metal or after the microstructure array 120 has been stamped. Thus, in some embodiments, the entire microstructure array (e.g., including all of the one or more microstructure array portions, all of the one or more microstructures included on each microstructure array portion, all of the one or more bridge portions including all of the one or more longitudinally extending portions contained therein) is monolithic. As used herein "monolithic" means produced from the same material (i.e., not individually produced and then attached), and if a structure (e.g., a microstructure array) is said to be "produced monolithically" it is intended that this mean the structure (e.g., a microstructure array) is produced from the same material and is not individually produced and then attached or connected. For example, in some embodiments, the entire microstructure array (including all of the one or more microstructure array portions, all of the one or more microstructures included on each microstructure array portion, all of the one or more bridge portions including all of the one or more longitudinally extending portions contained therein) is produced monolithically (e.g., from a single sheet of metal, optionally via stamping).

In other embodiments, the microstructure array 120 is manufactured by etching, such as, e.g., photochemical etching. In this process, raw material is masked with materials to be removed exposed. The process involves a photochemical reaction that removes the exposed materials and leaves the materials that were protected with the mask, i.e., the material with the desired geometry in two-dimensional piece. The final array is then formed by a secondary forming process. The secondary forming process can include the use of a custom fixture to bend the microstructures to the desired bend radius, angle, and height.

Wound Closure Systems

The present invention also includes wound closure systems, comprising two or more of the wound closure devices disclosed herein, wherein at least two wound closure devices are coupled to one another via one or more attachment portions included on the backing of the devices.

Figure 10:
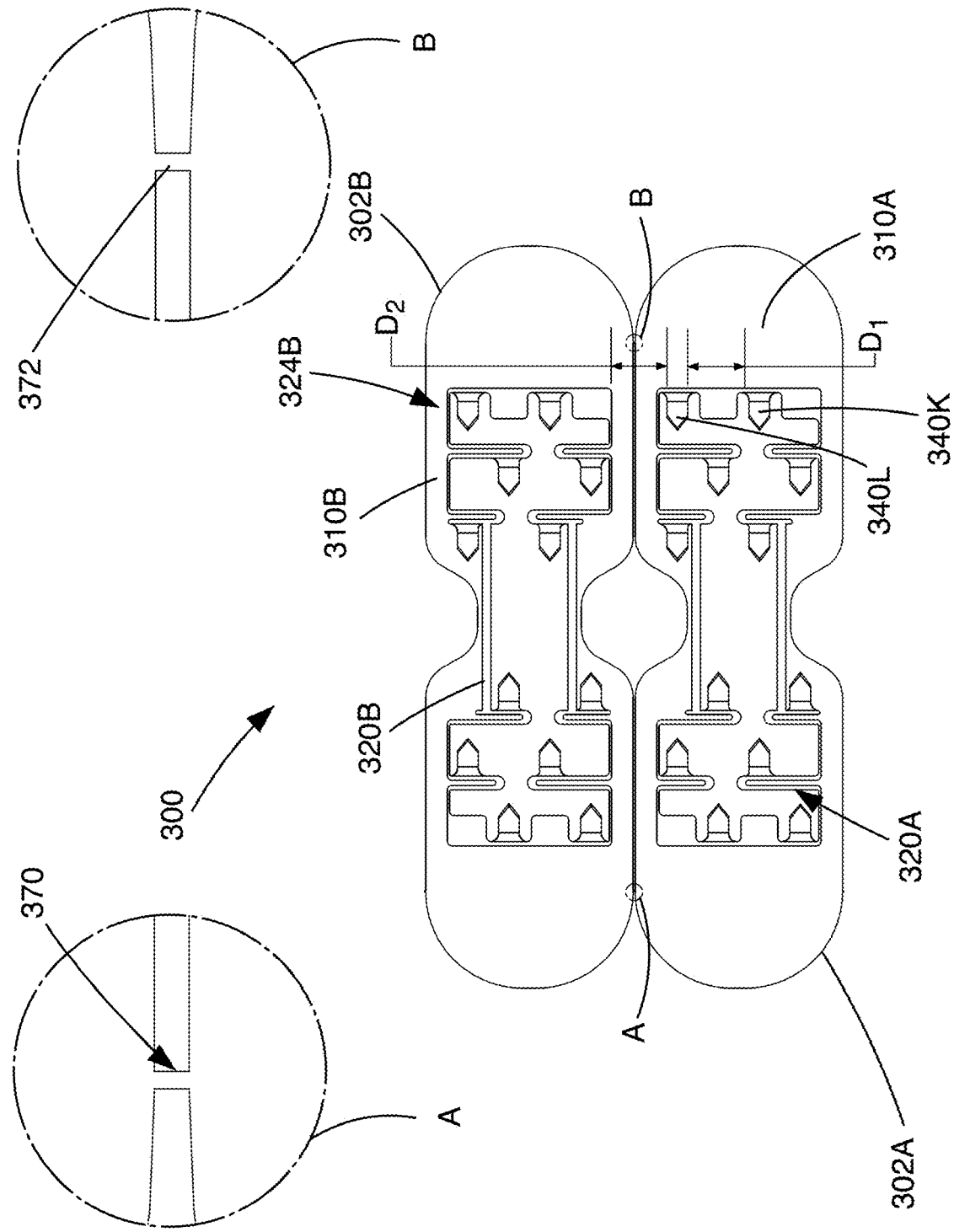
FIG. 10 is top view of a wound closure system according to one embodiment. The large circles A and B in the upper left and right corners of this figure depict enlarged top views of the smaller circles A and B shown on the wound closure system in the lower middle of this figure.

For example, FIG. 10 shows a non-limiting example of a wound closure system 300 according to an embodiment. The wound closure system 300 includes a first wound closure device 302A and a second wound closure device 302B. The first wound closure device 302A includes a first microstructure array 320A and a first backing 310A. The second wound closure device 302B includes a second microstructure array 320B and a second backing 310B. The first microstructure array 320A and the second microstructure array 320B are substantially identical in structure and function to the microstructure array 120 described above with reference to FIGS. 1-7 and will not be further described herein.

The first backing 310A and the second backing 310B are substantially identical in structure and function to the backing 110 described above, except that the first backing 310A is coupled to the second backing 310B via a first attachment portion 370 and a second attachment portion 372. The first attachment portion 370 and the second attachment portion 372 are shown in the enlarged view of region A and region B, respectively. The first attachment portion 370 and the second attachment portion 372 are frangible such that the first backing 310A and the second backing 310B can be separated under force by the user. For example, if only the first wound closure device 302A is desired for use, the attachment portions 370 and 372 can be broken via manual tearing by the user so that the first wound closure device 302A can be separated from the second wound closure device 302B.

Although the wound closure system 300 is shown in FIG. 10 as having two attachment portions, in some embodiments, the wound closure system can include any suitable number of attachment portions, such as, for example, three or four. In some embodiments, the wound closure systems include more than four attachment portions. The attachment portions can be in two or more places for pre-alignment of the two devices. As a result, the wound closure device can be used to close a larger wound by leaving the attachment portions intact such that the first wound closure device (e.g., 302A) and the second wound closure device (e.g., 302B) are applied to target tissue while still attached to each other. Additionally, although the wound closure system 300 is shown in FIG. 10 as including two wound closure devices, the wound closure system can include any suitable number of wound closure devices attached in series similarly to the manner in which the first wound closure device 302A and the second wound closure device 302B are attached. Any desirable amount of wound closure devices may be attached in a wound closure system disclosed herein. In some embodiments, the wound closure systems include about 2, 4, 6, 8, 10, or more wound closure devices attached according to the present disclosure. In some embodiments, the wound closure systems include from 2 to 10 individual wound closure devices attached according to the present disclosure.

Although the first wound closure device 302A and the second wound closure device 302B are shown and described as being coupled together via attachment portions, in some embodiments the first backing 310A and the second backing 310B may be formed such that the transition from the first backing 310A to the second backing 310B is continuous along a common edge. In some embodiments, the common edge of the first backing 310A and the second backing 310B may be perforated such that the first wound closure device 302A and the second wound closure device 302B can be easily separated. In other embodiments, the common edge of the first backing 310A and the second backing 310B may have a reduced thickness (e.g., less than about 1 mil) such that the first wound closure device 302A and the second wound closure device 302B can be easily separated.

In one non-limiting example, FIG. 23 shows a configuration of two microstructure wound closure devices, wherein the two devices are attached to one another. In some such embodiments, the distances X, Y, and Z are substantially similar, so as to allow for even tension distribution when two or more, e.g., 3, 4, 5, 6, 7, 8, 9, 10, or more microstructure wound closure devices are used together. In some embodiments, X, Y, and Z are substantially similar lengths that range from about 1 mm to about 16 mm. In some embodiments, X, Y, and Z are substantially similar lengths that range from about 2 mm to about 14 mm. In some embodiments, X, Y, and Z are substantially similar lengths that range from about 3 mm to about 12 mm. Although this figure shows identical devices attached to one another, in some embodiments, two devices having different dimensions are attached to one another. For example, devices of difference sizes and shapes may be attached to one another for application to an irregular wound shape.

Additionally, when using more than one wound closure device on a target tissue, the staggering of the microstructures of each microstructure array increases the consistency of the tension applied to the target tissue and increases the tensile strength of the system of multiple wound closure devices. Specifically, the microstructures can be arranged such that there are similar distances between microstructures of adjacent wound closure devices as between microstructures of the same wound closure device. For example, as shown in FIG. 10, a first edge of microstructure 340K and a second edge of microstructure 340L are separated by a first distance $D_1$. A first edge of microstructure 340L of the first microstructure 320A and a second edge of a second portion 324B of the second microstructure array 320B are separated by a second distance $D_2$. The microstructures of the first wound closure device 302A and the second wound closure device 302B can be arranged such that the first distance $D_1$ is similar to the second distance $D_2$ so that the application of force to tissue is consistent in use when two or more wound closure devices are being used together. In some implementations, for example, the first distance $D_1$ is about 3.55 mm and the second distance $D_2$ is about 3.66 mm.

Wound Closure Device Packaging

Figure 11:
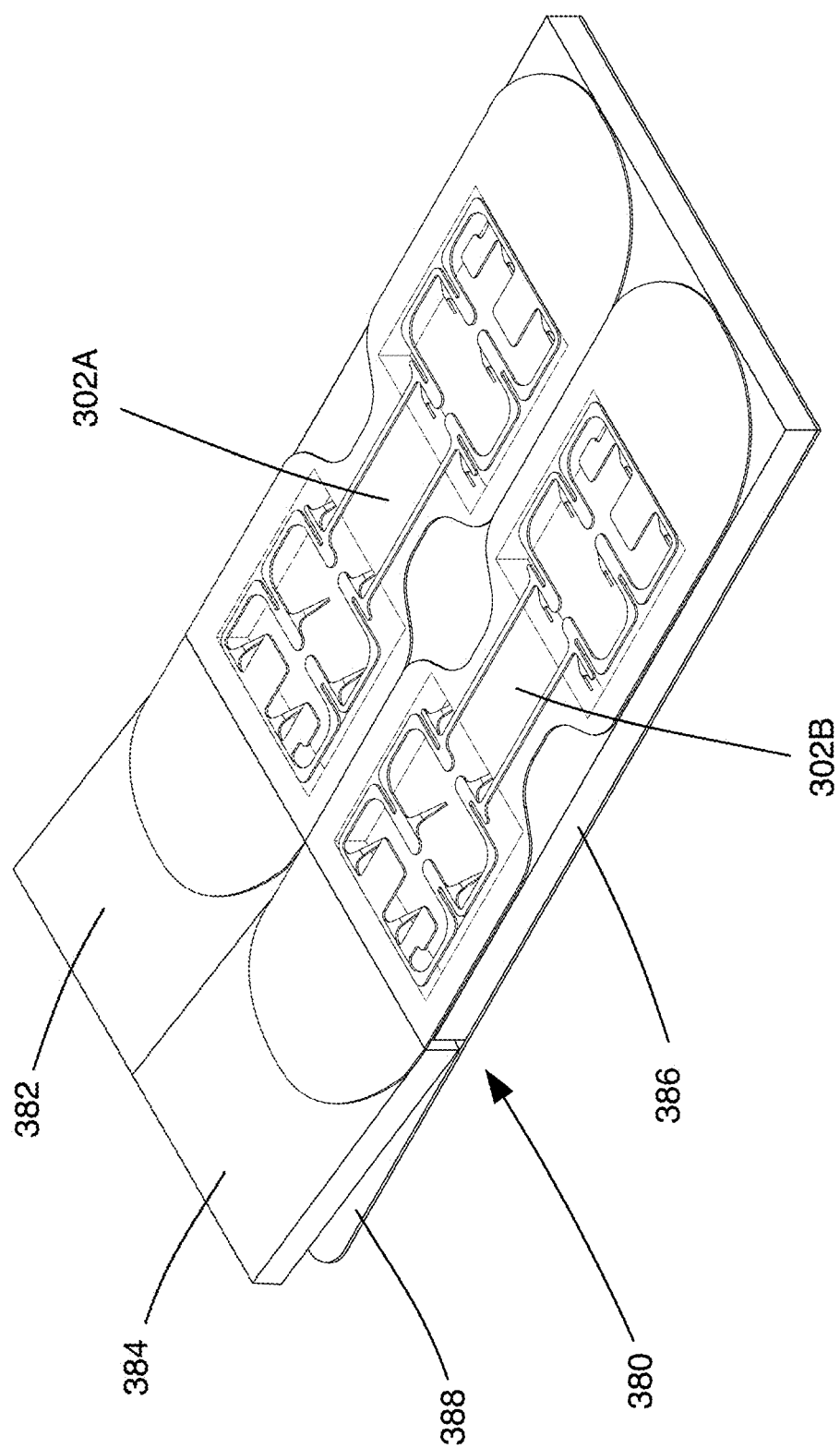
FIG. 11 is an isometric view of the wound closure system of FIG. 10 in a first configuration.

The wound closure devices described herein (e.g., 100, 200, 302A, 302B) may be manufactured in a sterile environment, and may be packaged so as to maintain sterility until being removed from the packaging. The wound closure devices described herein may be packaged in a single package comprising only one such wound closure device. Alternatively, the wound closure devices may be contained in packages comprising a plurality of wound closure devices. For example, FIG. 11 is a perspective view of the wound closure system 300 including one embodiment of the packaging 380 in a first configuration. The packaging 380 includes a first foam portion 382, a second foam portion 384, a third foam portion 386, and a base 388. The third foam portion 386 is attached to the base 388. The first foam portion 382 and the second foam portion 384 are releasably attached to the base 388 and/or the third foam portion 386 indirectly via their attachment to the wound closure devices. Once the wound closure devices are removed from the packaging (i.e., lifted out of the third foam portion 386), the first foam portion 382 and the second foam portion 384 may be released from the microstructure array, e.g., optionally after application of the device to skin or tissue. The first wound closure device 302A is configured to engage with the first foam portion 382 and the third foam portion 386. The second wound closure device 302B is configured to engage with the second foam portion 384 and the third foam portion 386. In some embodiments, adhesive holds the first wound closure device 302A and the second wound closure device 302B in contact with the first foam portion 382 and the second foam portion 384, respectively. This adhesive is suitable for application to skin or tissue, and, thus, the same adhesive holding the devices in place with the third foam portion assist in the applying and/or maintaining of the wound closure device on the target tissue or skin. In other embodiments, no adhesive holds the wound closure devices in place.

Figure 12:
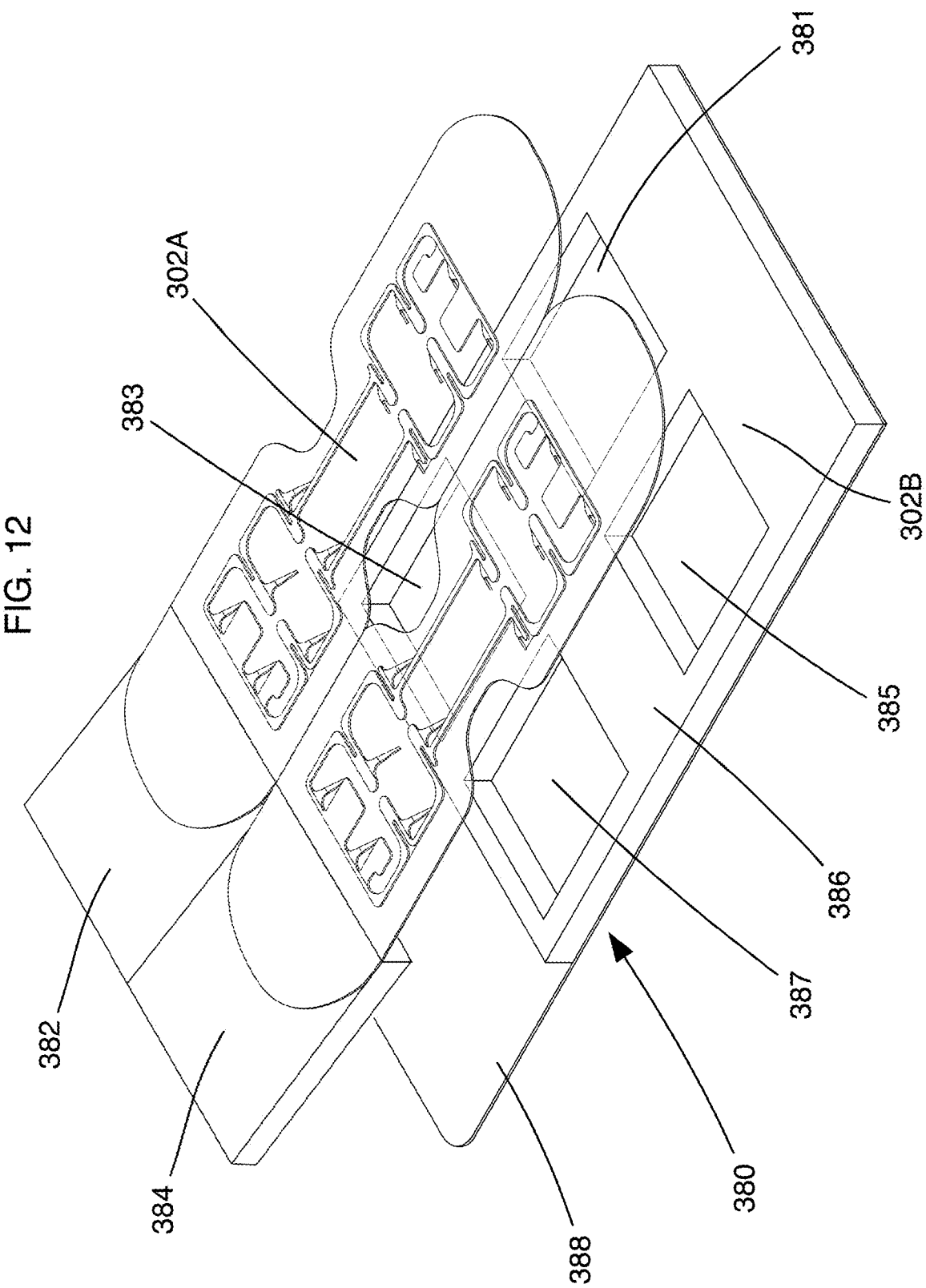
FIG. 12 is an isometric view of the wound closure system of FIG. 10 in a second configuration.

FIG. 12 is a perspective view of the wound closure system 300 in a second configuration. As shown in FIG. 12, the third foam portion 386 defines a first opening 381, a second opening 383, a third opening 385, and a fourth opening 387. The first wound closure device 302A and the second wound closure device 302B are configured to engage with the packaging 380 such that the microstructures of the first wound closure device 302A and the second wound closure device 302B are positioned within the openings. In other words, in the first configuration shown in FIG. 11, the microstructures associated with a first portion of the first wound closure device 302A are positioned within the first opening 381 and the microstructures associated with a second portion of the first wound closure device 302A are positioned within the second opening 383. Similarly, in the first configuration, the microstructures associated with a first portion of the second wound closure device 302B are positioned within the third opening 385 and the microstructures associated with a second portion of the second wound closure device 302B are positioned within the fourth opening 387.

In the second configuration, as shown in FIG. 12, the first wound closure device 302A and the second wound closure device 302B have been simultaneously separated from the base 388 and the third foam portion 386. This is accomplished as a result of lifting the first foam portion 382 and the second foam portion 384, which remain coplanar, away from the base 388 and the third foam portion 386, thus, lifting the first wound closure device 302A and the second wound closure device 302B from the third foam portion 386. After being separated from the third foam portion 386, the first wound closure device 302A and the second wound closure device 302B are configured to be separated from the first foam portion 382 and the second foam portion 384 optionally before or after application to the target tissue or skin of the patient as a set of wound closure devices in parallel.

Figure 13:
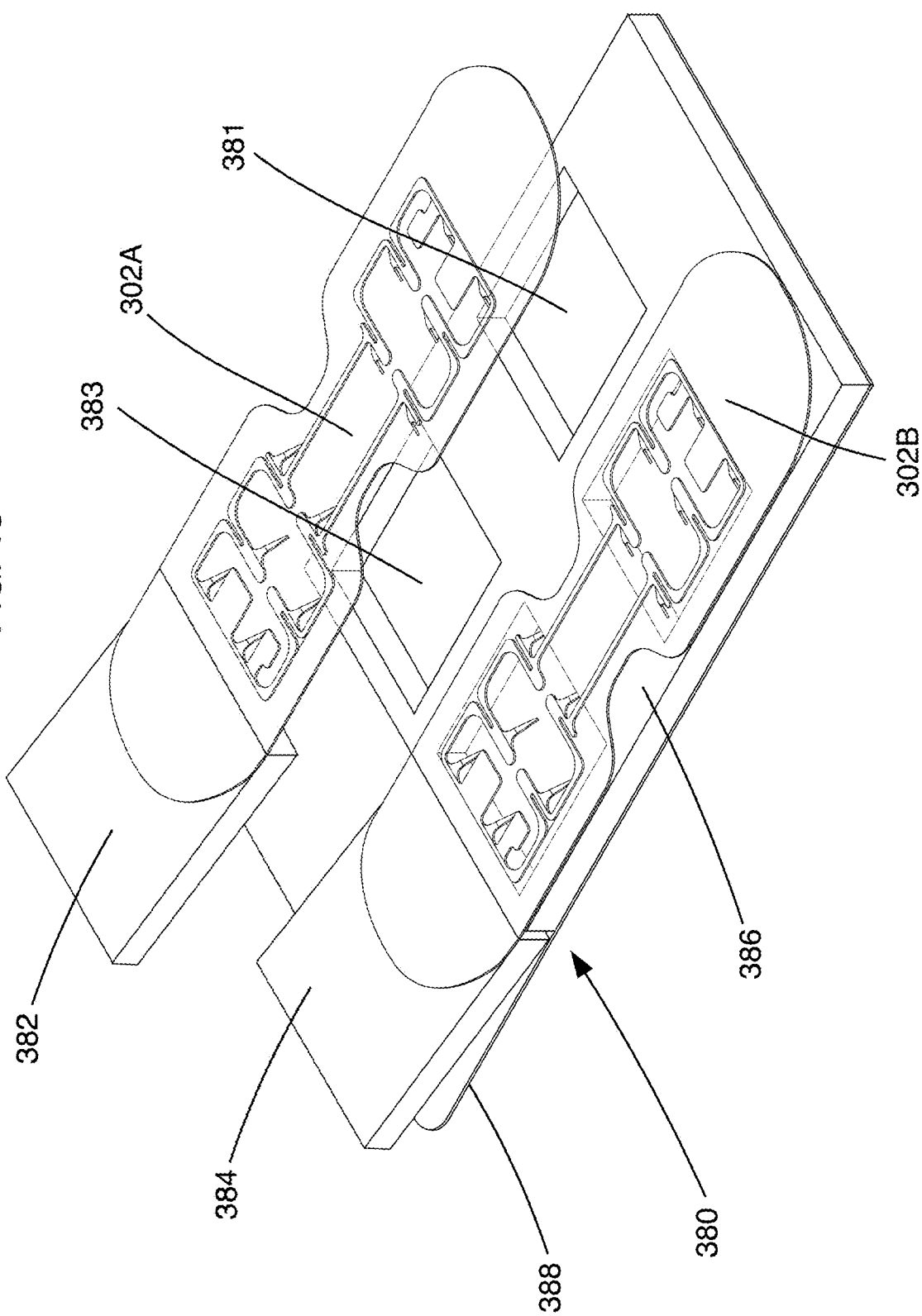
FIG. 13 is an isometric view of the wound closure system of FIG. 10 in a third configuration.

FIG. 13 is a perspective view of the wound closure system 300 in a third configuration. In the third configuration, the first wound closure device 302A has been lifted from the third foam portion 386 by lifting the first foam portion 382 away from the third foam portion 386. The second wound closure device 302B remains engaged with the third foam portion 386. After being separated from the third foam portion 386, the first wound closure device 302A is configured to be separated from the first foam portion 382 optionally before or after application to a treatment site of a subject or patient (i.e., the target tissue or skin).

In some embodiments, the present invention provides wound closure systems that are substantially identical to the wound closure system 300, except that the foam portion 386 and the base 388 are replaced with an alternative material, e.g., a thermoformed spacer. Some such embodiments are shown in FIGS. 21A, 21B, and 22A-C. Some such embodiments are shown in FIGS. 44-47. As was the case for the wound closure system 300, the alternative embodiments that utilize alternative spacers, e.g., thermoformed spacers, are also configured to optionally hold a single device or a plurality of devices, each of which may be individually removed from the packaging in some embodiments. In other embodiments, one or more first wound closure device can be removed from the packaging simultaneously with one or more second wound closure device to which the first device is attached. Additionally, the thermoformed wound closure systems may include tabs, made of any suitable material, for use in removing the wound closure devices from their packaging and for assisting in the application of the device to its target skin or tissue.

FIGS. 21A and 21B are a top view and a side view of a spacer 780A, respectively. In some embodiments, the spacer 780A defines apertures 791. Additionally, the spacer 780A includes a surface 793 that is flat and configured to be in abutting contact with an adhesive surface of a wound closure device, such as any of the wound closure devices described herein, for packaging and protection of the wound closure device prior to use. Optionally, the spacer 780A may also include support locations 792 for additional support of a microstructure array of a wound closure device. In some embodiments, the width W2 of the spacer 780A is equal to or greater than the width of a wound closure device intended to be packaged with the spacer 780A. In some embodiments, the length $L_{15}$ of the spacer 780A is equal to or greater than the length of a wound closure device intended to be packaged with the spacer 780A. In some embodiments, the height $H_3$ of the spacer 780A is equal to or greater than the height of the microstructures of a wound closure device intended to be packaged with the spacer 780A.

FIGS. 22A-22C are a top view, a perspective view in a first configuration, and a perspective view in a second configuration of a wound closure system 700. The wound closure system 700 includes a first wound closure device 702A engaged with a first spacer 780A and a second wound closure device 702B engaged with a second spacer 780B. The first wound closure device 702A and the second wound closure device 702B can be substantially identical in structure and function to any of the wound closure devices described herein and will not be further described herein. Additionally, the first wound closure device 702A and the second wound closure device 702B can be releasably attached along common edge 795 via any suitable means, such as those described above with respect to wound closure system 300. The wound closure system 700 includes a first tab 794A and a second tab 794B. The first tab 794A and the second tab 794B can be releasably coupled to the first wound closure device 702A and the second wound closure device 702B, respectively. The first tab 794A and/or the second tab 794B can be used to remove the first wound closure device 702A and/or the second wound closure device 702B from the first spacer 780A and the second spacer 780B. As shown in FIG. 22B, the first tab 794A and/or the second tab 794B can be used to remove the first wound closure device 702A and the second wound closure device 702B simultaneously from the first spacer 780A and the second spacer 780B. Alternatively, as shown in FIG. 22C, the first tab 794A and the second tab 794B can be used to remove the first wound closure device 702A and the second wound closure device 702B separately from the first spacer 780A and the second spacer 780B.

FIG. 24 is a perspective view of another wound closure system 1100 with components of the wound closure device 1100 shown as transparent. The wound closure device 1100 includes a backing 1110, a microstructure array 1120, and a tab 1194. The wound closure device 1100 can be the same or similar in structure or function to any of the wound closure devices described herein.

Figure 35B:
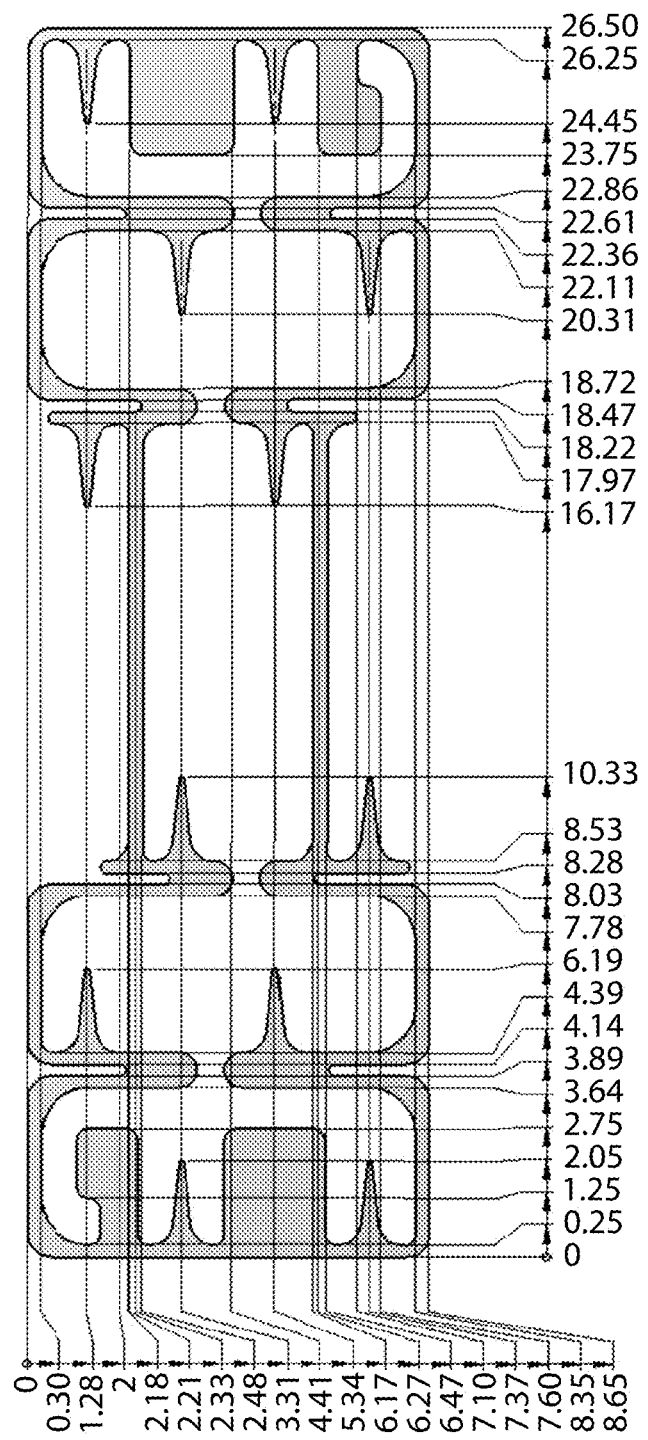
Figure 44:
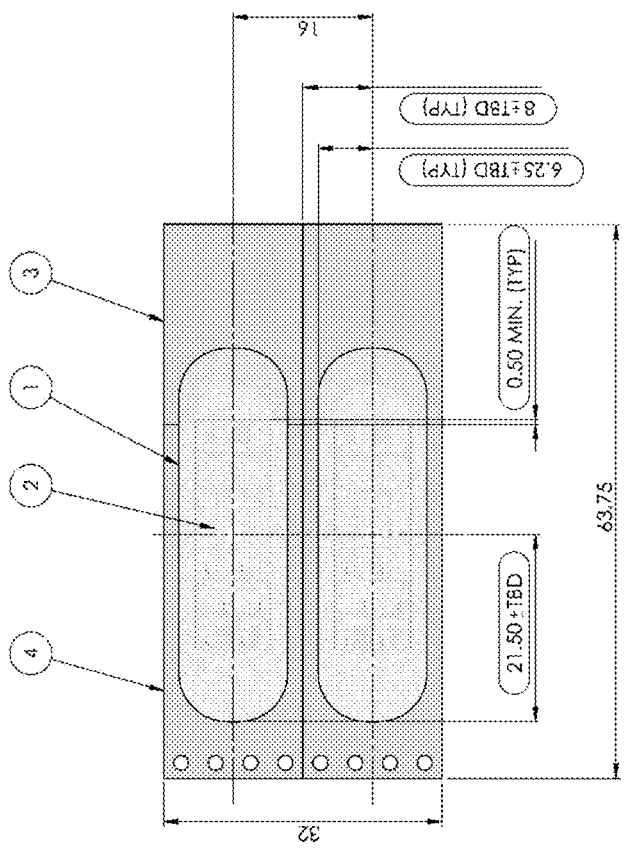
FIG. 44 shows a non-limiting example of design parameters for a microMend multipack. In this example, two wound closure devices are shown individually packaged, and the individual packages are connected together, e.g., optionally via a perforated edge. Indicator 1 denotes the backing film (see, e.g., FIG. 45) to which the microstructure array (see, e.g., FIGS. 35A and 35B) is affixed, and Indicator 2 denotes the positioning of the microstructure array in the center of the backing. Indicator 3 denotes the positioning of the applicator tab (FIG. 46) on the wound closure device (the presence and/or location of such applicator tabs are optional). Indicator 4 denotes a pocketed tray in which the microstructure array is seated (FIG. 47).
Figure 45:
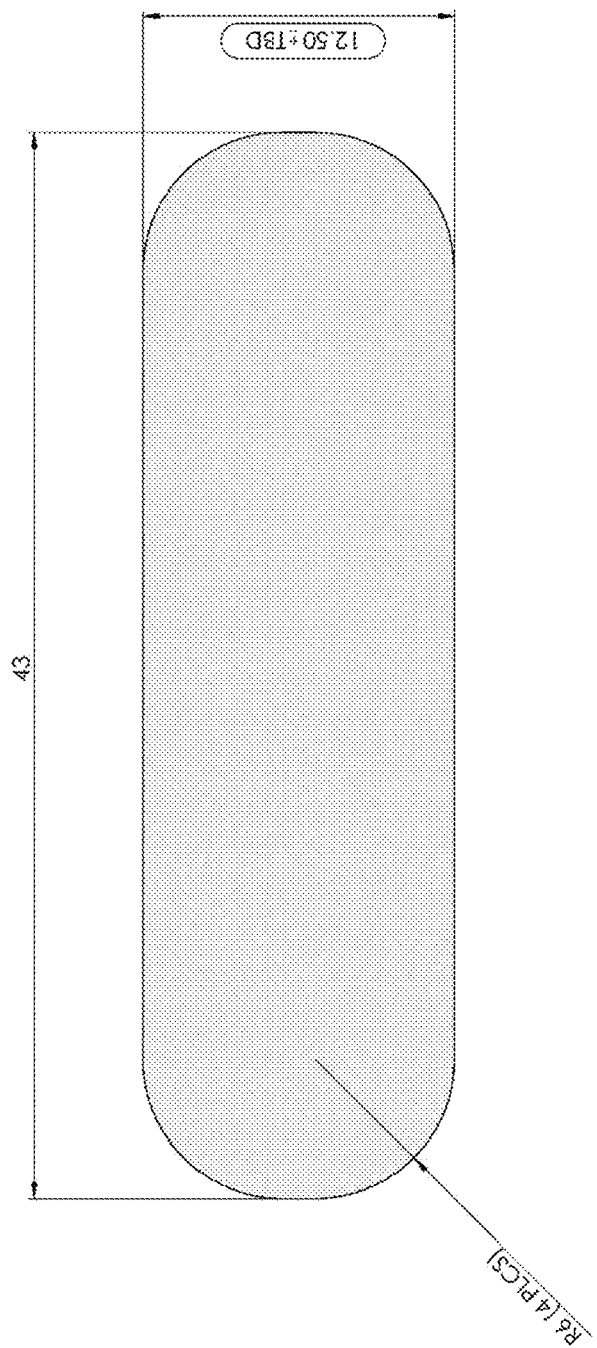
FIG. 45 shows a non-limiting example of a backing for use in the present invention.

FIG. 44 shows a top view schematic of a wound closure system. In this embodiment, the shape of the backing to which the microstructure arrays are attached omits the bridge portion indentation that is present in the device shown in FIG. 22. As shown, two wound closure devices may be packaged together in separate packaging housings (e.g., separate spacers made of any suitable material disclosed herein), and each of the separate spacers are configured to contain one microMend device. In this embodiment (FIG. 44), the spacers are configured in a side-by-side arrangement, connected together, optionally, via a perforated edge (e.g., to facilitate easy manual disconnection by tearing); however other configurations are contemplated, e.g., top to bottom connection and/or both top to bottom and side-by side configurations (e.g., when a packaging comprises 4 or more microstructure housing). Indicator 1 in FIG. 44 denotes the backing film. Any backing disclosed herein may be utilized in a wound closure system such as is presented in FIG. 44. In some embodiments the backing is as shown in FIG. 45, which shows a non-limiting backing made of DERMAMED material (4034, 4 MIL Polyurethane single coated tape). The non-limiting example of a backing shown in FIG. 44 comprises rounded edges and is approximately 43 mm long and 12.5 mm wide (tolerance of +/−0.5 mm), however, the skilled artisan will appreciate that the dimensions of this device may be altered to suit the purpose of the device, e.g., for larger wounds, the device may be widened and/or lengthened, either proportionally or non-proportionally. Indicator 2 in FIG. 44 denotes the positioning of the microstructure array in the package housing. Any microstructure array disclosed herein may be packaged in such a housing. In some embodiments the microstructure array is as shown in FIGS. 35A and 35B. In some embodiments, the microstructure array is as shown in FIG. 18. In some embodiments, the microstructure array is as shown in FIG. 19. In some embodiments, the microstructure array is as shown in FIG. 20. In some embodiments, the microstructure array is as shown in FIGS. 33A-1 and 33A-2. Indicator 3 in FIG. 44 denotes a suitable placement of an applicator tab (or "tab"). Any applicator tab disclosed herein may be utilized in the devices contained in such packaging. In some embodiments, the applicator tab is as shown in FIG. 46, which shows a non-limiting applicator tab made of 5 mil polystyrene or poly(ethylene terephthalate) ("PET"). Such applicator tabs may be any shade or color, e.g., in some embodiments the applicator tab is white; in some embodiments the applicator tab is opaque; in some embodiments the applicator tab is clear; and in some embodiments the applicator tab is colored. Indicator 4 in FIG. 44 denotes the pocketed tray (or "spacer") in which the microstructure array is seated. The pocketed tray may be any size or shape suitable for housing one or more wound closure devices, such as any one or more wound closure devices disclosed herein. In some embodiments, the pocket tray is configured according to FIG. 47. In some embodiments, the width of the pocketed tray is increased or decreased as compared to width of the device shown in FIG. 47 and/or in some embodiments the length of the pocketed tray is increased or decreased as compared to the length of the device shown in FIG. 47.

In one embodiment, the present disclosure provides a wound closure device comprising the backing of FIG. 45, the applicator tab of FIG. 46, and the microstructure array of FIGS. 35A and 35B. In some embodiments, the present disclosure provides a wound closure system comprising are least two microstructure wound closure devices, wherein the wound closure system is configured according to FIG. 44.

In one particular embodiment, the present disclosure provides a wound closure system comprising are least two microstructure wound closure devices, each wound closure device comprising
  (i) the backing of FIG. 45;
  (ii) the applicator tab of FIG. 46;
  (iii) the microstructure array of FIG. 35;
  (iv) each of (i) and (ii);
  (v) each of (i) and (iii);
  (vi) each of (ii) and (iii); or
  (vii) each of (i), (ii), and (iii).

In one particular embodiment, the present disclosure provides a wound closure system comprising are least two microstructure wound closure devices, each wound closure device comprising:
  (i) the backing of FIG. 45;
  (ii) the applicator tab of FIG. 46;
  (iii) the microstructure array of FIG. 35, wherein the microstructure array is made of a metal or metal composite, and wherein preferably the metal or metal composite is selected from the group consisting of: aluminum, titanium, stainless steel, magnesium, zinc, series 300 stainless steel, and 316 stainless steel;
  (iv) each of (i) and (ii);
  (v) each of (i) and (iii);
  (vi) each of (ii) and (iii); or
  (vii) each of (i), (ii), and (iii)

In one particular embodiment, the present disclosure provides a wound closure system comprising are least two microstructure wound closure devices, each wound closure device comprising:
  (i) the backing of FIG. 45;
  (ii) the applicator tab of FIG. 46;
  (iii) the microstructure array of FIG. 35, wherein the microstructure array is made of a metal or metal composite, and wherein preferably the metal or metal composite is selected from the group consisting of: aluminum, titanium, stainless steel, magnesium, zinc, series 300 stainless steel, and 316 stainless steel;
  (iv) each of (i) and (ii);
  (v) each of (i) and (iii);
  (vi) each of (ii) and (iii); or
  (vii) each of (i), (ii), and (iii);

wherein the wound closure system is configured according to FIG. 44.

Figure 26:
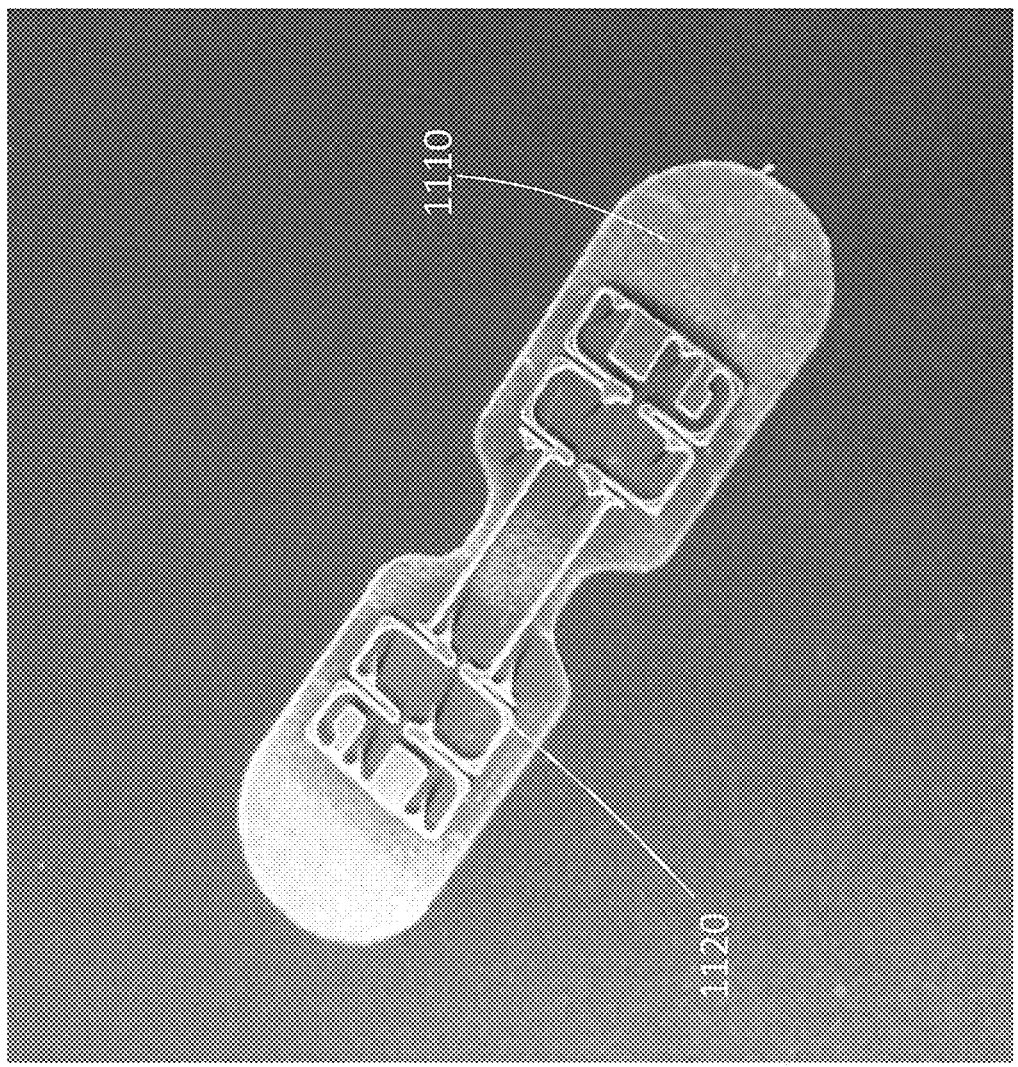
FIG. 26 is a photograph of a wound closure device according to an embodiment.

FIG. 26 is a photograph of a wound closure device 1200. The wound closure device 1200 includes a backing 1210 and a microstructure array 1220. As shown in FIG. 26, the backing 1210 can have an hourglass shape. Additionally, the microstructure array 1220 can be made of, for example, 316 stainless steel.

Of course, the skilled artisan will recognize that the shape, dimensions, etc., of the packages (e.g., length, width, depth, shape, etc.) can be varied to match the shape, dimensions, etc., of the microstructure wound closure devices.

Methods of Use

The wound closure devices of various embodiments can be used to treat any kind of wound including acute and chronic wounds, such as, e.g., lacerations, cuts, scrapes, abrasions, post-operative wounds (e.g., caused by minimally invasive surgery, laparoscopic surgery, robotic surgery, incisional biopsies, general surgery, and cosmetic surgery), denuded skin, burns, ulcers (e.g., diabetic ulcers, ulcers from vascular insufficiency, pressure sores), or other skin problems (e.g., allergies, eczema, dermatitis, and psoriasis). Accordingly, wound closure devices of various sizes can be prepared such that minor wounds as well as larger wounds can be treated using the devices of embodiments. In particular embodiments, the wounds treated with the devices of the present invention range from approximately 0.1 mm in length, to approximately 50 cm in length. Accordingly, in particular embodiments, the wound length is approximately 0.1 mm, 0.2 mm, 0.3 mm, 0.4 mm, 0.5 mm, 0.6 mm, 0.7 mm, 0.8 mm, 0.9 mm, 1 mm, 5 mm, 6 mm, 7 mm, 8 mm, 9 mm, 1 cm, 2 cm, 3 cm, 4 cm, 5 cm, 10 cm, 20 cm, 30 cm, 40 cm, 50 cm, or longer, including all integers and decimals (e.g., 9.1 mm, 9.2 mm, 9.3 mm, etc.) and ranges (e.g., 0.1 mm-50 cm, 0.5 mm-10 cm, 0.5 mm-5 cm, etc.) in between, of the wound lengths set forth.

The wound closure devices can be used to close an entire wound or a portion of a wound. Multiple wound closure devices of the same or different design may be used together to close a given wound. When a plurality of the wound closure devices are used to close a single wound, they may be placed immediately adjacent to one another (either running parallel or perpendicular to the wound), or they may be separated from each other at any suitable distance. Accordingly, the devices may be applied with no space between the arrays of two different devices, or they may be applied approximately 2 cm apart, or more. In particular embodiments, pluralities of wound closure devices are affixed to a wound according to the present disclosure with a spacing that ranges from about 2 mm to about 10 mm.

The wound closure devices can also be used in combination with other wound closure devices, such as sutures, staples, tissue adhesives, and bandages. The wound closure devices can also be used for temporary wound closure prior to closure with other devices, such as staples, sutures, or tissue adhesives. The wound closure devices can also be used after closure with sutures or staples. For example, this could enable earlier removal of sutures and staples, and thus reduce the risk of scarring related to these devices.

The wound closure devices can be used alone or with wound dressings, including transparent films, gauzes, hydrofibers, hydrogels, hydrocolloids, exudative absorbers, collagens, and alginates. The devices can also be used with impregnated dressings containing bismuth, petroleum, silver, and carboxymethylcellulose.

The wound closure devices disclosed herein may be applied in any suitable manner. For example, but not to be limited in any way, in some embodiments, wherein a wound comprises a length to width aspect ratio other than 1 (e.g., a laceration), the wound closure device may in one embodiment be applied perpendicularly, with respect to the longer portion of such a wound, thus bridging the slit of the wound, or alternatively, the devices may be applied parallel to the slit of the wound, e.g., wherein a microstructure array wound bandage roll is rolled over the wound. In still further embodiments, the devices of the present invention may be applied to such a wound at a diagonal, with respect to the slit of the wound. Additionally, as needed, some embodiments provide for the utilization of a plurality of the wound closure devices to treat a particular wound. In such embodiments, the devices may be applied to a wound in any appropriate manner, so as to achieve the desired wound closure effect. Non-limiting examples include, e.g., the application of two or more of the wound closure devices in parallel to one another, perpendicular to one another, or even criss-crossed over one another. In some embodiments the device is stretched across a wound, and in other embodiments the device is applied without stretching. In some embodiments the device is applied by hand, and in some embodiments the device is applied using an applicator or instrument, as described more thoroughly below. In some embodiments, multiple wound closure devices may be used to close an individual wound. Any number of devices may be used to close a given wound, in any orientation, and said devices may be spaced apart from one another at any appropriate distance, so as to achieve the desired wound closing effect.

In general, the wound closure devices of the present invention are capable of closing or protecting a wound, while optionally also enabling efficient and versatile delivery of drugs or therapeutic agents. FIG. 16 shows a schematic representation of a cross sectional view of a wound closure device applied to a wound. In this embodiment, relatively long microstructures are shown penetrating the adjacent skin on either side of the wound. In this way the wound is secured closed. Depending on the desired application, microstructures length can be varied e.g., using shorter microstructures to induce topical drug delivery to the epidermis, systemic delivery via microstructures long enough to penetrate the dermis, or various intermediate lengths to target drug or therapeutic delivery to particular dermal and epidermal sublayers. One skilled in the art is easily able to determine the necessary length of the microstructures to target a specific layer, a property that will vary depending on the location to which the device is intended to be used. For example, if targeting the dermal layer of the eyelid, one must account for microstructure lengths in the range of 0.3 mm. If however, one needs to target the dermal layer of the back, microstructures lengths must be an order of magnitude longer, e.g. 3 mm.

Accordingly, in some embodiments, the wound closure devices of the present invention provide their desired function in the absence of other known drugs or therapeutic agents, and in other embodiments, the devices provide their desired function in combination with other drugs or therapeutic agents. In some particular embodiments, the present invention provides for wound closure devices comprising e.g., hollow microstructures in which drugs or therapeutics can be incorporated e.g., as are described in U.S. Pat. No. 3,964,482, incorporated by reference herein in its entirety; porous microstructures; drug or therapeutic coated microstructures; and microstructures comprising slow release mechanisms for controlled drug or therapeutic delivery.

The wound closure devices described herein can be used to treat wounds on humans or any other animal including, but not limited to, mammals, fish, reptiles, birds, and other creatures. Thus, medical and veterinary uses for the wound closure devices described herein are encompassed by the invention, and such uses can be carried out by trained medical professionals, physicians, veterinarians, nurses, emergency medical technicians, and the like, or by consumers who purchase the devices described herein over the counter.

EXAMPLES

Example 1: Microstructure Optimization

Microstructure shape, size, and number per array were varied to determine optimal wound closing parameters for the wound closure devices disclosed herein (referred to herein as "microMend"). Wound healing was tested on a total of 90 wounds (1.5-2 cm) in neonatal pigs weighing between 35 and 40 kg. The wound closure abilities of the various microMend devices were compared to controls (sutures).

Shape: The microstructure shapes tested were (i) house; (ii) barbed; (iii) and needle. FIGS. 27A, 27B, and 27C illustrate a top view, a front view, and a side view of a barbed microstructure, respectively. FIGS. 28A, 28B, and 28C illustrate a top view, a front view, and a side view of a house-shaped microstructure, respectively. FIGS. 29A, 29B, and 29C illustrate a top view, a front view, and a side view of a needle-shaped microstructure, respectively.

Size: The size of the microstructures was varied from 0.7 mm to 2.0 mm in height (i.e., height from the base, not microneedle length—this is also referred to as "vertical displacement" and refers to the minimum distance from the microstructure tip to the base). The height from the base differs from the microneedle length because the microstructure protruded from the base at an angle of about 45 degrees.

Number: The number of microneedles per array was varied from 2 to 16 per array.

Results:

Variation in microMend design parameters resulted in modification of various properties of the device including strength, ease of use, ease of manufacture, and the resultant inflammation observed during wound closure. These parameters and the resultant effect on the device properties are summarized in Table 1.

TABLE 1

Optimization of microMend design parameters

| | Design Parameter | Effects when increases | Effects when decreases |
|---|---|---|---|
| 1 | Microstructure width (e.g., $D_5$, FIG. 7; $T_1$, FIG. 18) | Increases in strength More difficult to insert | Decreases in strength Easier to insert |
| 2 | Microstructure height (e.g., $H_1$, FIG. 5; $D_{13}$, FIG. 16) | Increases in pain when over 1.2 mm Decreases in strength | Decreases in ability to anchor when below 0.9 mm Increases in strength |
| 3 | Microstructure bend radius (e.g., $B_1$, FIG. 19B) | Increases in strength More difficult to bend accurately | Decreases in strength Easier to manufacture accurately |
| 4 | Microstructure bottom radius (e.g., radius of 132, FIG. 6; radius of 432, FIG. 18) | Increases in strength (limited to not affecting width) | Decreases in strength |
| 5 | Microstructure spacing (e.g., A, B, C, FIG. 20; X, Y, Z, FIG. 23) | Reduces possibility of inflammation Fewer microstructures on device causing less overall strength | Increases possibility of inflammation More microstructures on device increasing overall strength |
| 6 | Material thickness (e.g., $H_2$, FIG. 5; $H_4$, FIG. 19) | Increases in strength Decreases in flexibility Decreases in ability to conform to skin | Decreases in strength Increases in flexibility Increases in ability to conform to skin |
| 7 | Microstructure tip sharpness (e.g., $T_1$, FIG. 18) | Easier to insert Reduced pain | More difficult to insert |
| 8 | Number of microstructures | Increases in strength | Decreases in strength |
| 9 | Spring constant (e.g. of a microstructure array) | Decreases in device strength Reduces stress on adhesive Presence of elasticity, as opposed to inelasticity reduces possibility of inflammation and scarring | Increases in device strength Increases stress on adhesive |
| 10 | Flexible arm length (perpendicular to stretch direction) | Decreases spring characteristics | Increases spring characteristics |
| 11 | Backing film thickness (e.g., thickness of 110) | Improves handling during application Increases the chances for delamination | More difficult to handle during application Less chances of delamination |

Example 2: Microstructure Wound Closure Device Design Process (i) Modeling

In relation to the wound closure device design process, microstructure arrays were modeled on a computer in 3D based on a variety of requirements (e.g., ideal sizes, shapes, and geometries of microstructures, spacing between microstructures, materials, and methods of manufacturing). Next, the forces applied during application of a wound closure device including each microstructure array were simulated using finite element analysis (FEA) to identify areas of structural weaknesses. Examples of FEA software that can be used to identify areas of structural weakness are Solid-Works Simulation, Ansys, and Siemens Solid Edge Simulation. Using the results of the FEA, the geometries of the microstructure array were adjusted. This process of computer simulating forces and adjusting the microstructure array based on the results was repeated until the desired outcome was achieved.

(ii) Wound Closure—Preliminary Human Clinical Study and Porcine Studies

Next, prototypes were created using low volume manufacturing methods to avoid the investments needed for tooling. Said another way, the prototypes were hand assembled and the microstructure arrays were etched. The prototypes were applied on human volunteers (no wounds) to study signs of skin reaction, such as inflammation, pain, or discomfort. Feedback from the human volunteers was used to select a design for a pre-clinical study using a pig model studies described in Example 3. Included in this study was a comparison of wound closure devices containing inelastic microstructure arrays (see, e.g., PCT/US2013/046181) to the elastic arrays disclosed herein to determine whether the expandable portions provide improved wound healing or whether they provide any other added benefits.

Results

Volunteers reported minimum pain/no pain. The preliminary human study showed that rigid devices induce inflammation and hyperpigmentation at the edges of the device 4-5 days after application (FIG. 31A). Surprisingly, the inclusion of the U-shaped spring expandable portion nearly eliminated the hyperpigmentation and resulted in significantly less inflammation 4-5 days after application (FIG. 31B).

Example 3—Wound Closure—Porcine Pre-Clinical Studies

The objective of the pre-clinical studies was to evaluate clinical performance of microMend skin closure devices with and without expandable portions as compared to sutures. To that end, four preclinical studies were conducted in Yorkshire swine, which is a standard animal species used to test wound closure products. In the first of these studies, rigid devices (i.e., inelastic microMend devices that do not expand) and suture controls were compared for various parameters on laparoscopic wounds of 3 cm in length (Study 1). In the other three studies, microMend and suture controls were compared for various parameters on laparoscopic wounds of 1.2 cm in length (Study 2), microMend was tested for its ability to close 12 cm long wounds made with scalpels (Study 3), and microMend was tested for its ability to close trochar wounds (Study 4). Following the pre-clinical study, biocompatibility studies, sterilization validation studies, and clinical/case studies were performed (data not shown).

Study 1: Comparison of Wound Healing, Inflammation, Infection, and Cosmesis after Closure by Rigid microMend Devices or Sutures.

Study 1 had a total of 12 wounds—four 3 cm full-thickness linear incisions on the dorsum of each of 3 juvenile pigs. Nine of the wounds were closed with two rigid (non-expandable) microMend devices such as are disclosed in WO 2013/188884, incorporated herein by reference in its entirety (see FIG. 30D for a picture of a wound closed by two prototypes of such devices), and 3 wounds (suture controls) were closed using three 4.0 sutures.

Evaluations were performed serially via observations over a two-week period, including placement of devices and sutures (Day 0), as well as on subsequent days at intervals of 2-3 days until removal of devices on Day 10. Wounds were assessed for evidence of inflammation, infection, cosmetic results, and any other abnormalities. Photographs were obtained to document healing during these time points.

Results:

Upon application, all of the microMend devices were reported as easy to use by the veterinary surgeon. FIG. 30A shows a representative example of one of the wounds that was closed with either microMend devices or sutures. FIG. 30B and FIG. 30D show such wounds immediately after closure with suture or microMend, respectively. Serial observations showed no evidence of inflammation, infection, wound dehiscence, or other abnormalities in the wounds closed with any of the microMend prototype devices (except for slight inflammation and erythema in one of the devices at Day 4). In contrast, all wounds closed with sutures demonstrated inflammation beginning on the 4th day and continuing until the time of removal of the sutures (on the 10th day after their application). FIG. 30C and FIG. 30E show representative examples of wounds after removal, on Day 10, of the sutures or microMend prototype devices, respectively. Upon removal of the microMend prototype devices, all wounds were documented to be closed with excellent wound approximation and healing, and superior cosmetic results (see FIG. 30C for a representative photo). In contrast, the wounds closed with sutures showed significant erythema and inflammation, slight wound dehiscence, and inferior cosmesis (see FIG. 30E for a representative photo).

Study 2 Comparison of Wound Closure, Cosmesis, Dehiscence, and Wound Tensile Force at Failure after Closure of 1.2 cm Wound with microMend Devices with Expandable Portions or Sutures.

The primary objectives of this study were as follows:
a) Measure the tensile force at failure of closed wounds 9 days after surgery (Day 9) with devices and sutures removed.
b) Estimate suture tension forces required to keep wounds closed on Day 0.
c) Assess efficacy of wound closure on Days 0, and 9 via subjective observations and photographs.

Secondary objectives included making subjective observations on cosmesis and wound conditions such as inflammation, tissue reaction, and wound dehiscence at Days 0 and 9.

Materials and Methods

Figure 32:
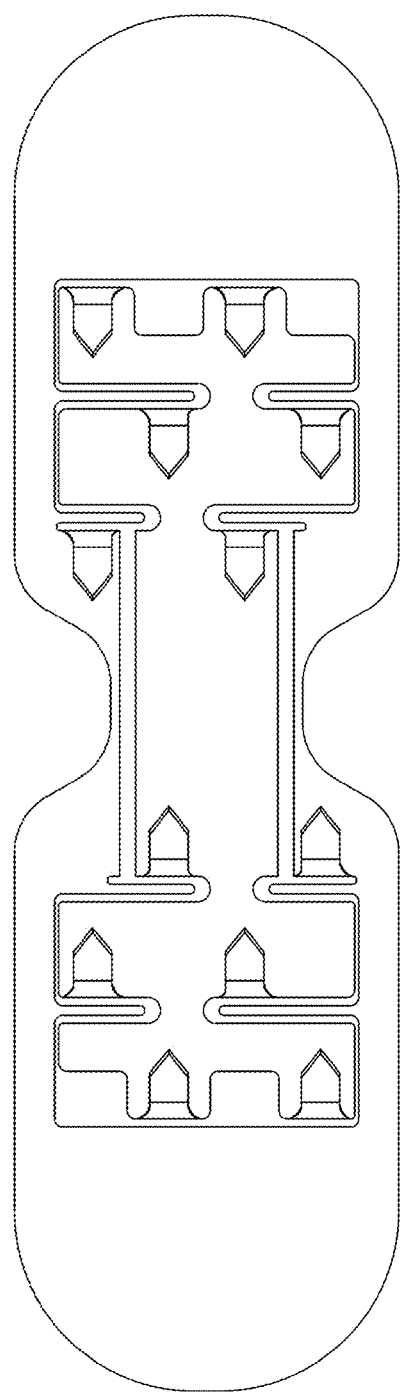
FIG. 32 shows the general structure of the microMend devices utilized in porcine pre-clinical studies 2-4 (see Example 3).

MicroMend: This study utilized microMend devices as shown in FIG. 32, which comprise microstructure arrays having six angled microstructures on either side of a bridge portion, all of which microstructures were disposed with their tips pointed in the direction of the bridge portion. Each microstructure had a vertical displacement of approximately 1.73 mm, and was angled from a planar base at 45°. The entire microstructure array/base portion was formed from a single stainless steel (Grade 316) sheet that was 0.008 inches thick, and the array portion was 26.5 mm in length and 9.5 mm in width. The backing of the device was a 4 mil elastic polyurethane SC Tape (DermaMed Coatings Company LLC, Tallmadge, Ohio, product number DM-4034), which comprised medical grade, pressure-sensitive acrylic adhesive. Further details regarding the specific design parameters of the microstructure arrays, the complete microMend device, and the specifications of the backing materials and adhesives can be found in FIGS. 33A and 33B.

Sutures: Sutures used were 3-0 PROLENE (Ethicon, Somerville, N.J.).

Wound covers: All the wounds sites were covered with TEGADERM® (3M, Maplewood, Minn.) after closure.

Subjects: two Yorkshire swine (range 35-40 kg)

Figure 34:
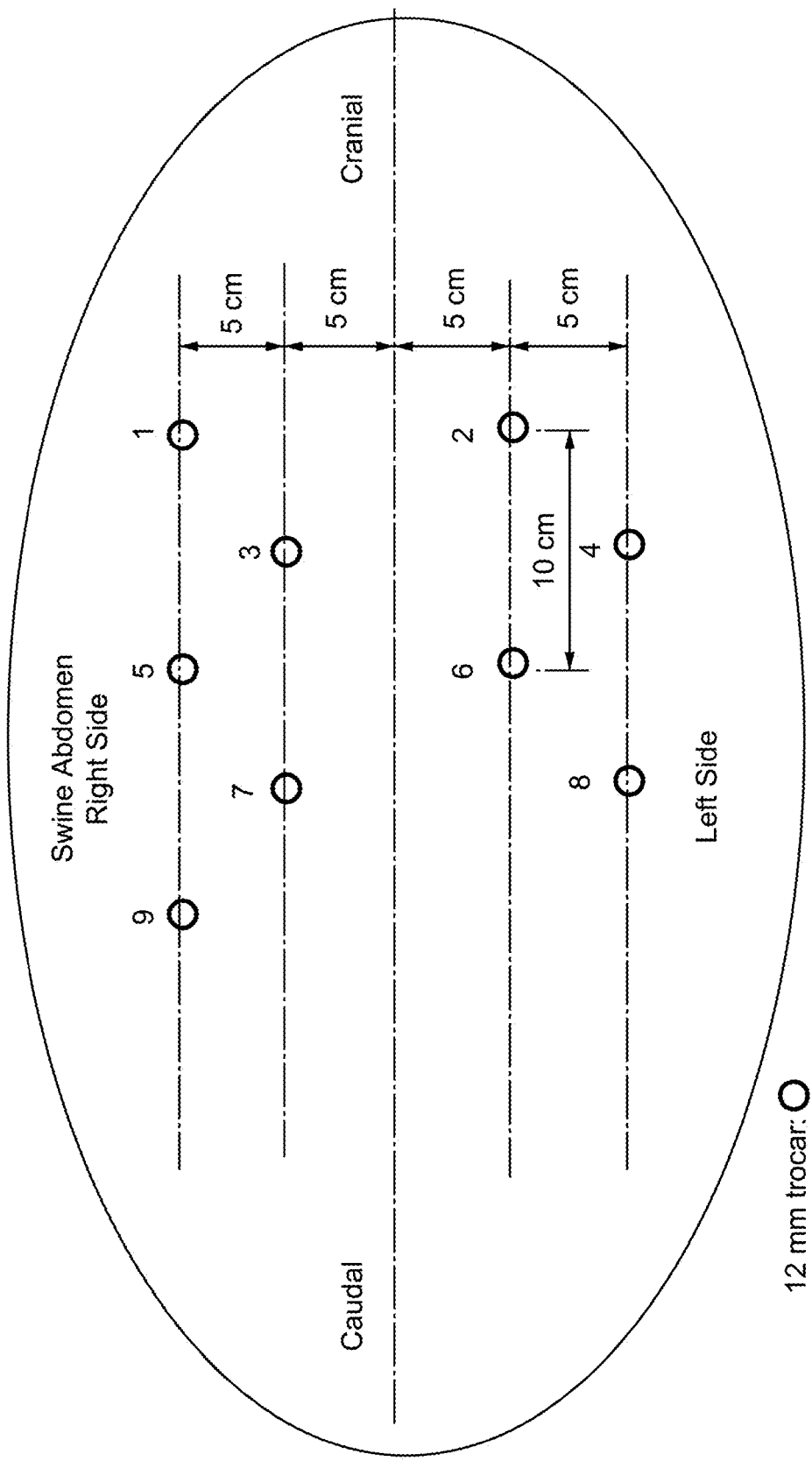
FIG. 34 shows the location of nine 1.2 cm laparoscopic wound incisions made on the abdomen of two Yorkshire swine (range 35-40 kg) according to Example 3.
Figure 36A:
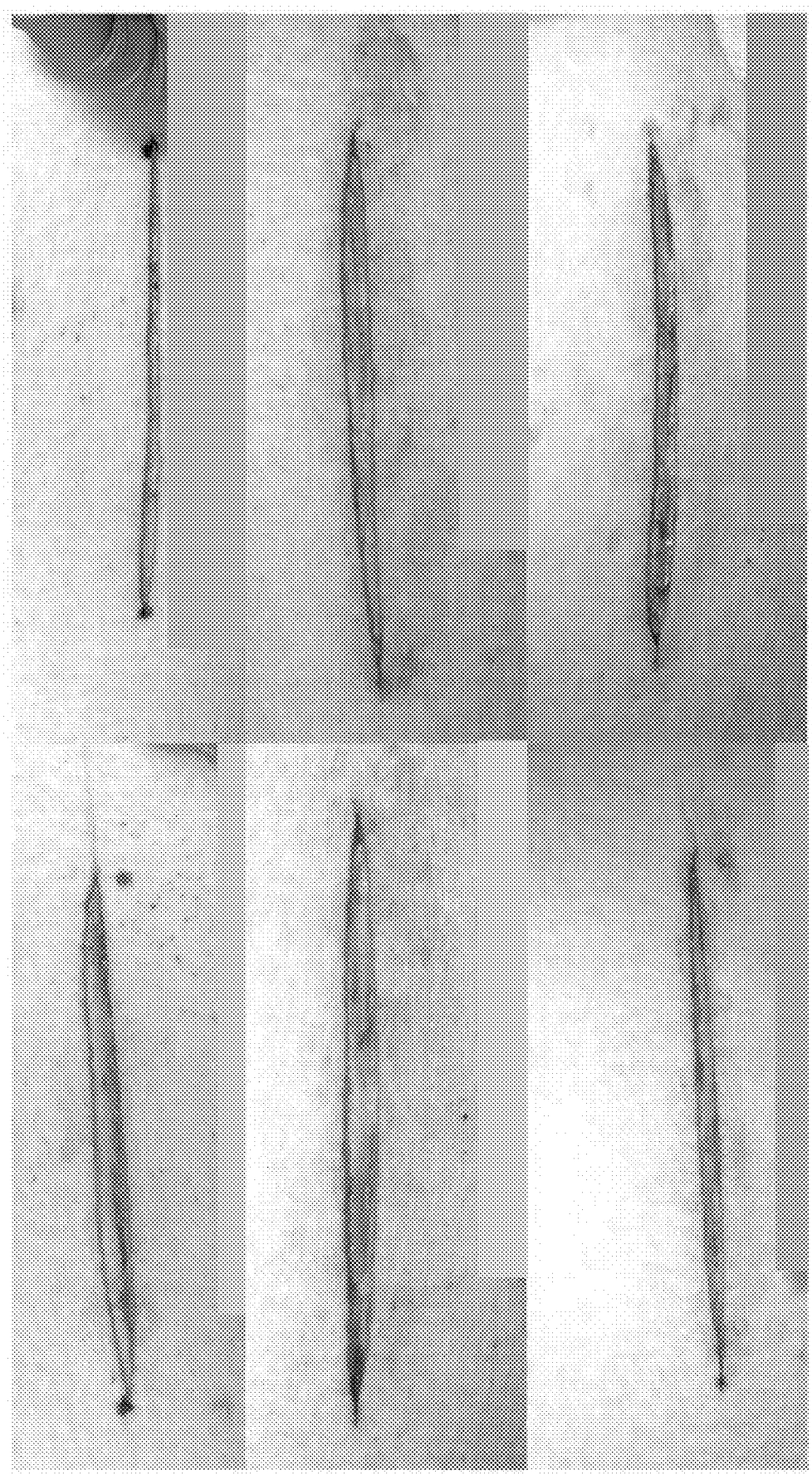
FIGS. 36A, 36B, and 36C show pictures of six 12 cm laparoscopic wounds made on the abdomen of Yorkshire swine (two wounds per animal). Each wound was closed with 10 expandable microMend devices evenly spaced along the wound. microMend devices were removed after 10 days, and 20 days post-surgery, wounds were photographed and tested for tensile force at failure.
Figure 36B:
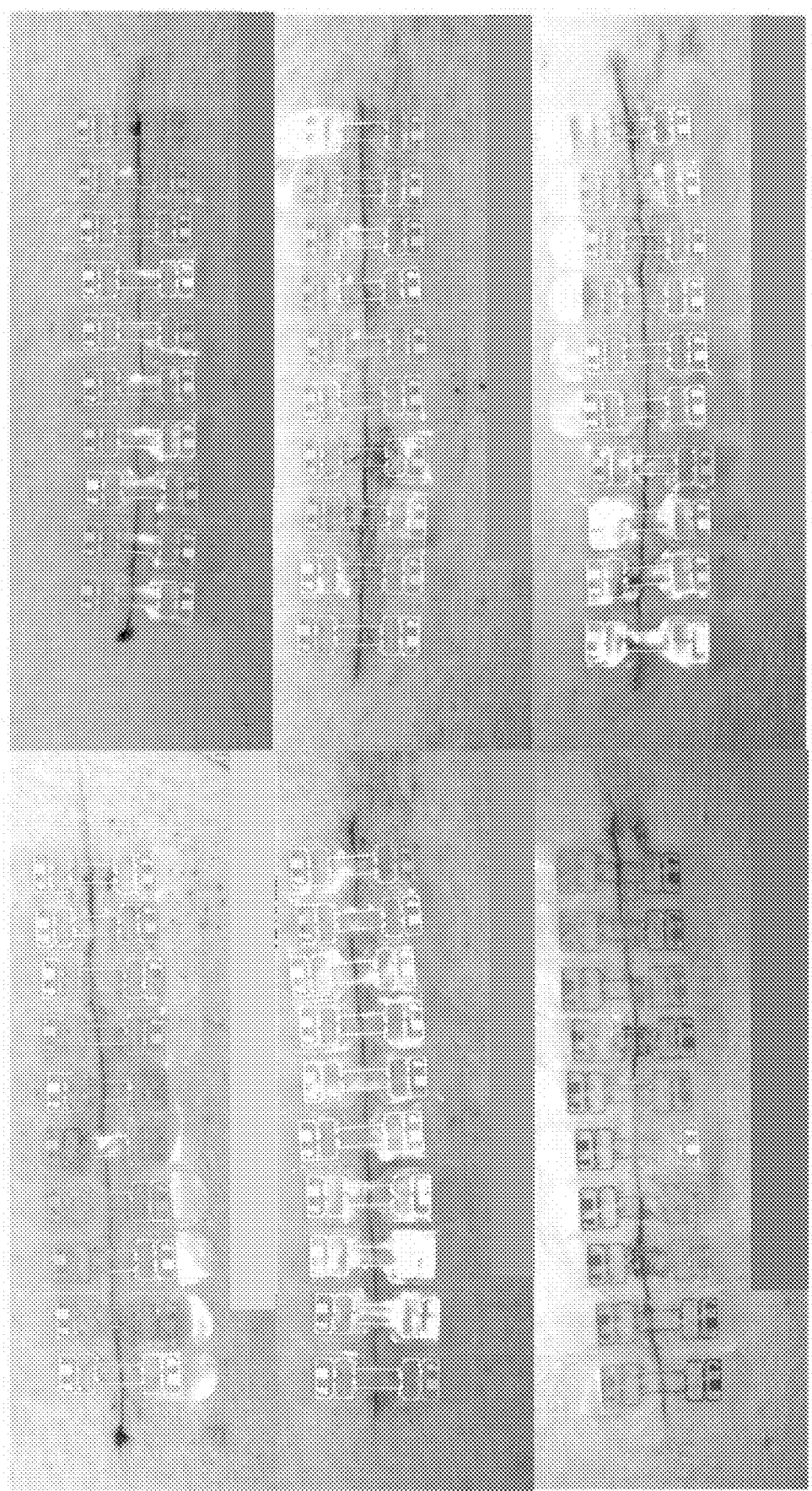

Wounds and wound closure: A total of nine laparoscopic wounds (trochar) were made per swine using a standard laparoscopic instrument that is inserted through all skin layers. Laparoscopic wound incisions of 1.2 cm. in length were spaced evenly on the abdomen of each swine according to the schematic shown in FIG. 34. As shown in Table 2, six of the laparoscopic wounds were closed with a single microMend device and three of the wounds were closed by suture. The individual sites closed by the sutures and the microMend devices were randomized between the two animals. The microMend devices were applied perpendicular to the wound such that the bridge portion of the device crossed the wound (see, e.g., FIG. 36B for a representative example of such a perpendicular application to a wound).

TABLE 2

Incision Site Treatment

| Table 2 | Animal # | |
|---|---|---|
| Site | 775 | 776 |
| 1 | D | D |
| 2 | D | S |
| 3 | S | D |
| 4 | D | D |
| 5 | S | D |
| 6 | D | D |
| 7 | D | S |
| 8 | S | S |
| 9 | D | D |

D—microMend device "D";
S—Suture control

Incision sites were photographed on the day of the surgery both before and after application of before and after applications of microMend Prototypes and Sutures on each wound individually and overall abdomen area of each pig, and again on Day 9, both before and after removals of microMend Prototypes and Sutures for all wounds individually.

Tensile force at failure tests were performed on Day 9 according to the following protocol: microMend devises and sutures were removed from the tissue and tissue was surgically extracted for measuring tensile force at failure using a dogbone template to ensure removal of equal amount of tissue for all samples. Tissue was secured in a calibrated Instron tensile testing machine with flat grips at 85 psi. Load was applied at 40 mm per minute in order to determine the actual strengths of tissues/incision lines. A separate test was also performed to estimate the actual forces required to keep the wounds closed under natural conditions (without introducing an external tensile force). Failure mode (tissue tearing) and maximum load (N) at failure was measured for each skin sample and are shown in Table 3, below. These experiments were video recorded.

Also on Day 9, six new wounds were created on each swine before sacrifice. A template was used to extract the same amount of tissues around the wound. The tissues were mounted on an Instron tensile testing machine with the skin at a tension of 0.05 N, and the wounds were closed by suture (3-0 PROLENE) while recording the tensions generated on the skin samples. After closing the site with suture the tension was measured. The tension difference is the suture wound closure tension.

Results (a) Tensile Forces of Tissue Treated with microMend Devices

The failure mode on Day 9 for all wound sites closed with test microMend devices was at the incision site. Results for the individual measurements at each wound site closed with microMend are shown in Tables 3 and the results for each wound site closed with suture are shown in Table 4.

TABLE 3

Day 9 microMend Device "D" Closed Wound Sites

| Animal | Wound Site Number | Peak Force (N) | Failure Mode |
|---|---|---|---|
| 775 | 1 | 9.0 | At wound site |
| 775 | 2 | 15.1 | At wound site |
| 775 | 4 | 11.0 | At wound site |
| 775 | 6 | 9.9 | At wound site |
| 775 | 7 | 10.7 | At wound site |
| 775 | 9 | 3.5* | At wound site* |
| 776 | 1 | 9.4 | At wound site |
| 776 | 3 | 25.3 | At wound site |
| 776 | 4 | 11.3 | At wound site |
| 776 | 5 | 7.9 | At wound site |
| 776 | 6 | 10.8 | At wound site |
| 776 | 9 | 7.5 | At wound site |
| | Mean | 11.6 | |
| | Std | 4.97 | |

*outlier, not included in statistics

TABLE 4

Day 9 Suture Closed Wound Sites

| Animal | Wound Site Number | Peak Force (N) | Failure Mode |
|---|---|---|---|
| 775 | 3 | 7.0 | At wound site |
| 775 | 5 | 6.4 | At wound site |
| 775 | 8 | 7.1 | At wound site |
| 776 | 2 | 5.5 | At wound site |
| 776 | 7 | 13.0 | At wound site |
| 776 | 8 | 10.0 | At wound site |
| | Mean | 8.2 | |
| | Std | 2.81 | |

The average peak tensile force in Newton (N) on Day 9 for the test microMend device closed wound sites was 11.6±4.97 N (Mean±StDev) (n=12) (n=number of samples). The average peak tensile force for suture closed wound sites was 8.2±2.81 N (n=6). Table 5 summarizes the peak tensile forces measured for Day 9 wound sites treated with microMend device "D" versus sutures, and suture tension forces.

Conclusion. In this study, wounds closed with microMend exhibited increased closure strength as compared to suture, as demonstrated in increased resistance to tearing under tensile force.

(b) Suture Tension Forces Required to Keep Wounds Closed on Day 0.

The average suture wound closure tension for 6 samples was 0.28±0.381 N (n=6). The resultant tensions generated by sutures represent tensions required to maintain closure of wounds. These results and the results of the skin tensile forces measured in (a) above are summarized in Table 5.

TABLE 5

Tensile Forces at Day 9 closed with microMend device "D" or Sutures, and Suture Tension Forces (DB-493)

| Device | Number of Samples | Average Peak Tensile Force in Newton (Mean ± StDev) |
|---|---|---|
| microMend device "D" Day 9 Incision | 12 | 11.6 ± 4.97 |
| Suture Day 9 Incision | 6 | 8.2 ± 2.81 |
| Suture Closure Force | 6 | 0.28 ± 0.381 |

Conclusions

All the animals in both studies completed the in life portion of the study without complications. All the wounds from both studies that were closed with microMend healed well with no evidence of inflammation or infection observed, whereas, evidence of wound separation and inflammation was observed on several of the suture closed wounds.

Study 3: Wound Closure, Cosmesis, Dehiscence, and Wound Tensile Force at Failure after closure of 12 cm wound with microMend devices with expandable portions.

The primary objectives of this study were as follows:
a) Measure the tensile force at failures of closed wounds 20 days after surgery (Day 20) with devices and sutures removed.
b) Assess efficacy of wound closure on Days 0, 10 and 20 via subjective observations and photographs.

Secondary objectives included making subjective observations on cosmesis and wound conditions such as inflammation, tissue reaction, and wound dehiscence at Days 0, 10, and 20.

Materials and Methods microMend: This study utilized microMend devices as shown in FIG. 32, which comprise microstructure arrays having six angled microstructures on either side of a bridge portion, all of which microstructures were disposed with their tips pointed in the direction of the bridge portion. Each microstructure had a vertical displacement of approximately 1.05 mm, and was angled from a planar base at 45°. The entire microstructure array/base portion was formed from a single stainless steel (Grade 316) sheet that was 0.004 inches thick, and the array portion was 26.5 mm in length and 8.65 mm in width. Further details regarding the specific design parameters of the microstructure arrays, the complete microMend device, and the specifications of the backing materials and adhesives can be found in FIG. 35 (i.e., FIG. 35A and FIG. 35B) and FIG. 33B.

Sutures: Sutures used were 3-0 PROLENE (Ethicon, Somerville, N.J.).

Wound covers: All the wounds sites were covered with TEGADERM® (3M, Maplewood, Minn.) after closure.

Subjects: three female Yorkshire swine, age >8 weeks (range 35-40 kg).

Wounds and wound closure: A total of two wounds were made per swine using a scalpel that is inserted through all skin layers to generate linear wounds. Wound incisions of 12 cm in length were located on each of the right and left sides of the abdomen of each swine, and were made in a cephalad to caudal direction, and each wound was closed with ten microMend devices evenly spaced along the wound. The microMend devices were applied perpendicular to the length of the wound such that the bridge portion of the device crossed the wound (see, e.g., FIG. 36B for a representative example of such a perpendicular application to a wound). Excellent wound approximation was achieved using microMend devices. After microMend closure, the devices were covered with TEGADERM® (3M, Maplewood, Minn.).

Figure 36C:
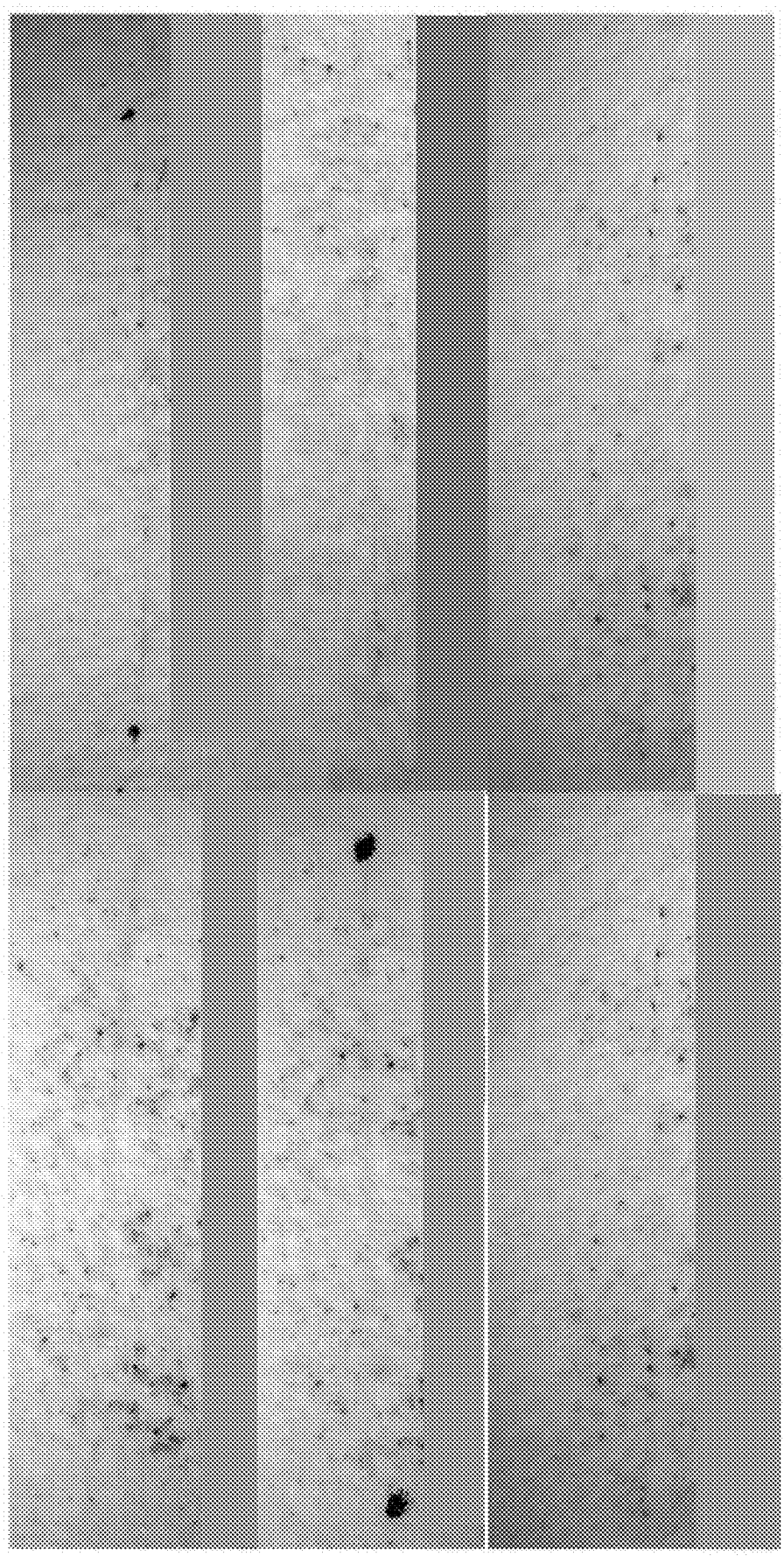

Individual incision sites were photographed on the day of the surgery both before (FIG. 36A) and after application of the microMend Prototypes (FIG. 36B), as were the overall abdomen areas of each pig (data not shown). Individual incision sites and the overall abdomen areas of each pig were photographed again on Day 10, both before and after removal of each microMend Prototypes (data not shown). Wounds were allowed to continue to heal to Day 20 on their own. Overall abdomen areas and individual incision sites were again photographed on Day 20 (FIG. 36C).

Tensile force at failure tests were performed on Day 20 according to the protocol outlined in Study 2 of this Example with the following specific settings: preload was 0.1 N; gap length was 30 mm; and the rate of the applied tension was 40 mm/min.

Results:

Tensile Forces of 12 cm Wounded Tissue Treated with microMend Devices

For analysis, each 12 cm incision was divided into four 25 mm length sections (A-D, cranial to caudal) for mechanical testing in order to maximize consistency of results. Table 6 below summarizes the tensile forces.

TABLE 6

Tensile test results of microMend devices for 12 cm incisions

| Sample | Animal Number | Side | Section | Skin Thickness (mm) | Max Load (N) | Tensile Strength (MPa) | Failure Mode |
|---|---|---|---|---|---|---|---|
| 1 | 784 | Left | A | 1.6 | 67.9 | 8.2 | wound line |
| 2 | 784 | Left | B | 1.6 | 53.1 | 7.8 | wound line |
| 3 | 784 | Left | C | 1.6 | 90.1 | 11.5 | wound line |
| 4 | 784 | Left | D | 1.6 | 57.5 | 7.7 | wound line |
| 5 | 784 | Right | A | 1.6 | 86.6 | 11.3 | wound line |
| 6 | 784 | Right | B | 1.6 | 81.0 | 9.9 | wound line |
| 7 | 784 | Right | C | 1.6 | 49.6 | 6.8 | wound line |
| 8 | 784 | Right | D | 1.6 | 65.4 | 8.3 | wound line |
| 9 | 785 | Left | A | 1.6 | 70.3 | 13.4 | wound line |
| 10 | 785 | Left | B | 1.6 | 73.7 | 10.9 | wound line |
| 11 | 785 | Left | C | 1.6 | 84.8 | 11.6 | wound line |
| 12 | 785 | Left | D | 1.6 | 102.6 | 12.6 | wound line |
| 13 | 785 | Right | A | 1.6 | 89.9 | 12.3 | wound line |
| 14 | 785 | Right | B | 1.6 | 70.5 | 10.6 | wound line |
| 15 | 785 | Right | C | 1.6 | 66.4 | 10.5 | wound line |
| 16 | 785 | Right | D | 1.6 | 40.7 | 7.6 | wound line |
| 17 | 786 | Left | A | 1.6 | 57.5 | 13.0 | wound line |
| 18 | 786 | Left | B | 1.6 | 47.9 | 9.0 | wound line |
| 19 | 786 | Left | C | 1.6 | 44.5 | 8.6 | wound line |
| 20 | 786 | Left | D | 1.6 | 38.9 | 8.9 | wound line |
| 21 | 786 | Right | A | 1.6 | 26.1 | 7.9 | wound line |
| 22 | 786 | Right | B | 1.6 | 59.1 | 9.0 | wound line |
| 23 | 786 | Right | C | 1.6 | 26.4 | 5.0 | wound line |
| 24 | 786 | Right | D | 1.6 | 54.2 | 8.2 | wound line |
| mean | | | | 1.6 | 62.7 | 9.6 | |
| standard deviation | | | | 0.00 | 20.24 | 2.16 | |

| | Skin Thickness (mm) | | | Tensile Force at Failure (Mpa) | | |
|---|---|---|---|---|---|---|
| Animal | 784 | 785 | 786 | 784 | 785 | 786 |
| Mean | 1.6 | 1.6 | 1.6 | 8.9 | 11.2 | 8.7 |
| Std | 0.00 | 0.00 | 0.00 | 1.75 | 1.78 | 2.18 |

TABLE 6-continued

Tensile test results of microMend devices for 12 cm incisions

| | Max Load (N) | | |
|---|---|---|---|
| Animal | 784 | 785 | 786 |
| Mean | 68.9 | 74.9 | 44.3 |
| Std | 15.47 | 18.42 | 13.01 |

The average tensile force at failure for the 25 mm sections on Day 20 were measured 62.7 N, or 30.1 N/12 mm. This is a 26% higher tensile force at failure than was achieved using inelastic devices (24 N/12 mm)(see Example 6).

Conclusions

All the animals in both studies completed the in life portion of the study without complications. The wounds closed with microMend and sutures showed excellent wound closure and cosmetic results. All the wounds from the study healed well with no evidence of wound dehiscence, infection, significant inflammation or other abnormalities observed. Results on Day 20 showed excellent wound healing and appearance for each wound (FIG. 36C). The average tensile force at failure of the 12 cm wounds was estimated to be 30.1 N on Day 20, which translates into approximately 25 N per cm of wound length. The total time to close the 12 cm wounds was a median of 127 seconds (range: 121-187 seconds) while the median time to close each 1 cm of wound length was approximately 11 seconds (range: 12-18).

Study 4 Comparison of Wound Closure, Cosmesis, Dehiscence, and Wound Tensile Force at Failure after Closure of Trochar Wounds with microMend Devices with Expandable Portions or Sutures.

The primary objectives of this study were to add additional subjects to the Study 2 results via an additional experiment with a similar protocol, and to address the following questions:
a) Measure the tensile force at failures of closed trochar wounds 20 days after surgery (Day 20) with microMend devices and sutures removed.
b) Assess efficacy of wound closure on Days 0, 10 and 20 via subjective observations and photographs.

Secondary objectives included making subjective observations on cosmesis and wound conditions such as inflammation, tissue reaction, and wound dehiscence at Days 0, 10, and 20. Results presented in Study 4 include results from Study 2 as well as new data generated from closure of wounds in additional pigs.

Materials and Methods microMend: This study utilized the same microMend devices as in Study 3, above, i.e., as shown in FIG. 32.

Sutures: Sutures used were 3-0 PROLENE (Ethicon, Somerville, N.J.).

Wound covers: All the wounds sites were covered with TEGADERM® (3M, Maplewood, Minn.) after closure.

Subjects: three female Yorkshire swine, age >8 weeks (range 35-40 kg).

Figure 48C:
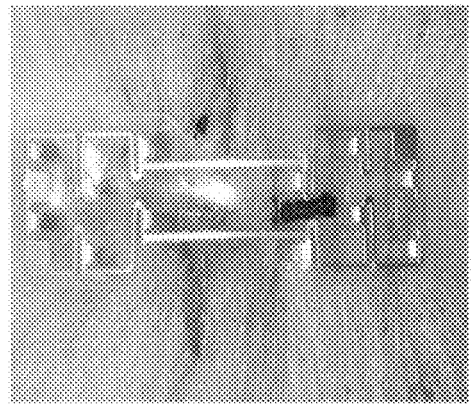
FIG. 48C shows the trocar wound closed with one microMend device.
Figure 48B:
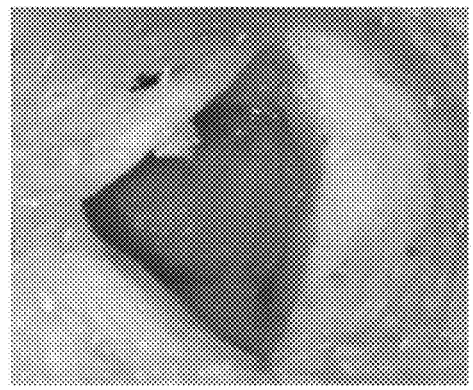
FIG. 48B shows the port site wound caused by insertion of the trocar.
Figure 48A:
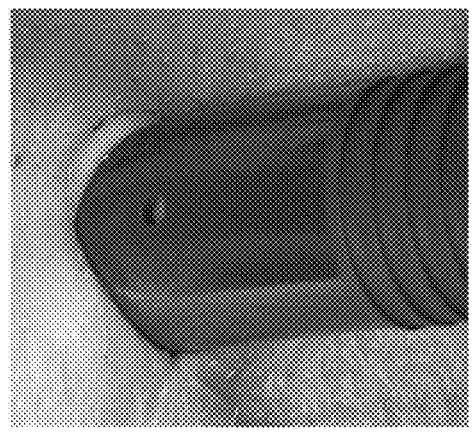
FIG. 48A shows the trocar inserted into the skin.

Wounds and wound closure: Trocar wounds (port site wounds) were made using a standard laparoscopic instrument that was inserted in the lateral dorsal surface of both sides of the abdomen. (FIG. 48A and FIG. 48B). The trocar had a diameter of 1.2 cm and was inserted through all skin layers. The wound was then closed with one microMend device (FIG. 48C) or one suture (3-0 Nylon). Excellent wound approximation was achieved using the microMend device.

A total of 36 wounds were closed with microMend, while 12 wounds were closed with sutures in nine pigs. After microMend closure, the devices were covered with TEGADERM® (3M, Maplewood, Minn.).

Evaluations were performed serially via observations by surgical staff over a three-week period, including placement of devices and sutures (Day 0), as well as on subsequent days at intervals of 2-3 days. Wounds were assessed for evidence of inflammation, wound dehiscence, infection, cosmetic results, and any other abnormalities. Photographs were obtained at Day 0, and on Days 10 and 20 to document healing of the wounds. Wound tensile strength was measured on Days 10 and 20.

Tensile force at failure tests were performed on Day 20 according to the protocol outlined in Study 2 of this Example with the following specific settings: preload was 0.1 N; gap length was 30 mm; and the rate of the applied tension was 40 mm/min.

Figure 49:
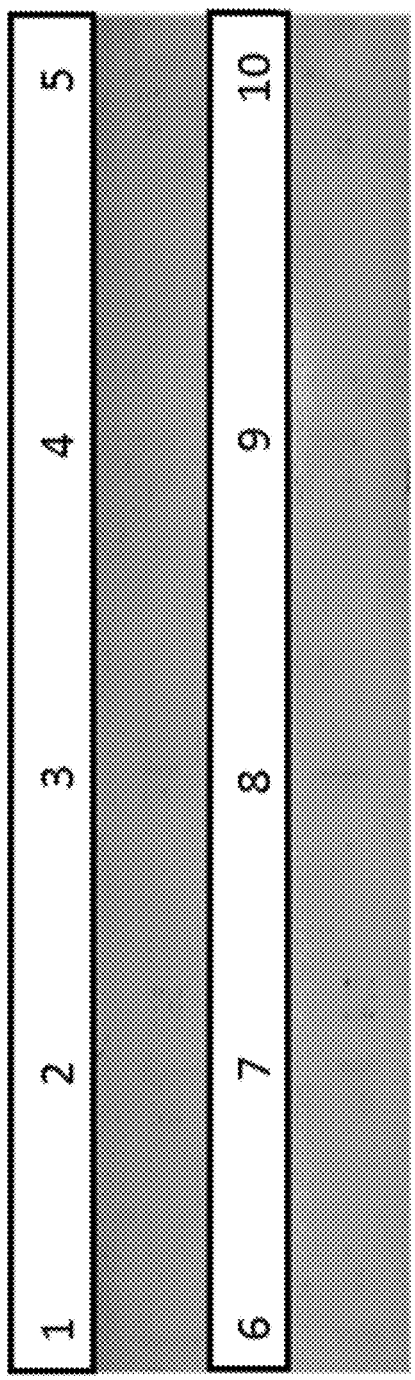
FIG. 49 shows the appearance of ten trocar wounds (port site wounds) that were closed with microMend devices (Day 20) (see Example 4, Study 4).

Results:

Excellent wound closure results were documented in all wounds closed with microMend devices. No wounds showed significant inflammation, and there was no evidence of wound dehiscence or infections in any of the closed wounds. At Days 10 and 20, excellent wound healing and appearance was observed in wounds closed with microMend. (FIG. 49). Comparison of wounds closed with sutures and microMend showed no significant differences in wound healing or appearance (data not shown).

Tensile Forces of Trochar Wounded Tissue Treated with microMend Devices

Wound tensile strength measured in Newtons (N) was equivalent between wounds closed with sutures and staples at Days 10 and 20 (Table 1). At Day 20, microMend closed wounds had approximately 20 N of tensile strength per cm of wound length (note: wounds were approximately 1.2 cm wide). Table 7 below summarizes the tensile forces.

TABLE 7

| | Wound Tensile Strength | |
|---|---|---|
| Time Point | microMend | Suture |
| Day 10 | 12.7 ± 1.3 N (n = 36) | 13.8 ± 2.9 N (n = 18) |
| Day 20 | 23.9 ± 1.4 N (n = 12) | 21.2 ± 4.8 N (n = 6) |

The median time to close each wound (1.2 cm width) with one microMend device was 11 seconds (range: 7-19), while the median time to close each wound with one suture was 32 seconds (range: 20-42). Consequently, wound closure with the microMend device was 3 times faster than with the suture.

Conclusions

The current studies demonstrate that microMend devices can be used to provide effective wound closure for both short and long wounds associated with surgery. These include both port sites due to insertion of trocar instruments in minimally invasive surgeries (laparoscopic and robotic), as well as surgical incisions associated with open surgeries. Reproducible results were observed with excellent wound healing and appearance. There was no evidence of wound dehiscence, infections, or significant inflammation in any wound. Wound approximation was excellent in both studies.

In Study 4 where closure with sutures and microMend were compared, there were no differences in wound healing or appearance In Study 3, close wound approximation across the entire length of the wounds was noteworthy, and likely contributed to the excellent cosmetic results achieved in all long wounds. In addition, wounds closed with microMend achieved equivalent tensile strength to sutures at Days 10 and 20.

The surgeon indicated that closure with microMend devices was simple and straightforward (data not shown) for both short and long wounds. Consistent with this observation, closing port site wounds was 3 times faster with microMend than with sutures. For the long surgical wounds, closure was achieved at a similar speed per cm of wound length to that achieved with closing the shorter port site wounds. The long surgical incisions were closed in approximately 2 minutes. Previous studies have documented that closure of surgical skin incisions takes approximately 30 seconds to a minute for each cm of wound length. If we assume similar closure time in the current study, it would take 6-12 minutes to close the 12 cm long wounds with sutures. microMend is projected to be 3-6 times faster in closing these wounds.

Figure 38B:
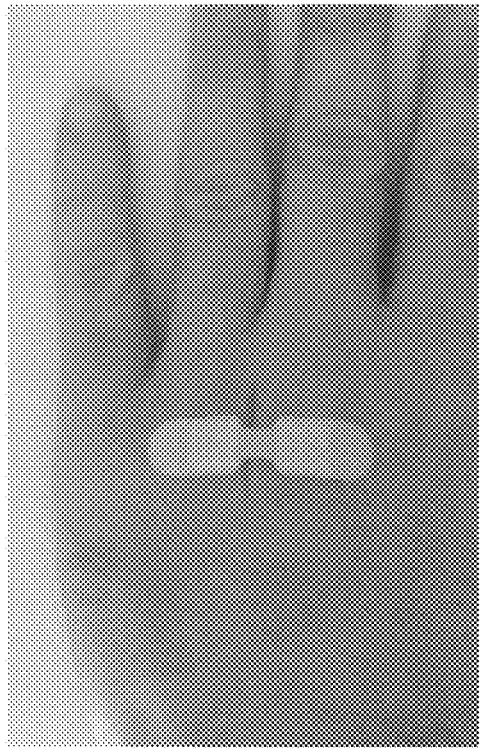
FIGS. 38A, 38B, 38C, and 38D show results of a preliminary human clinical study of microMend closure of a 2 cm laceration.
Figure 38D:
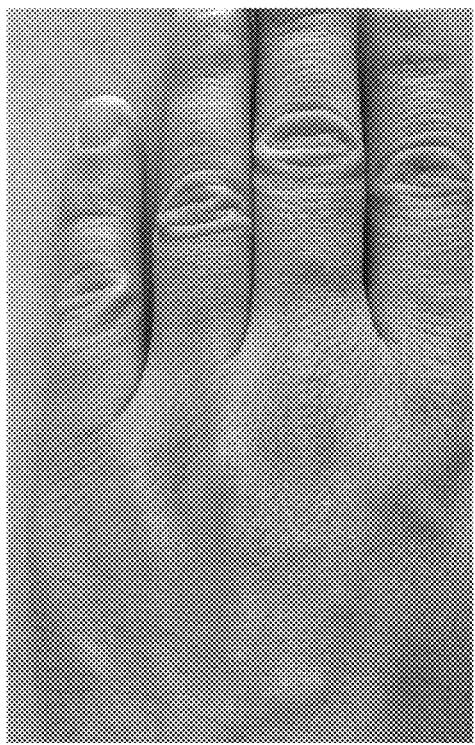
Figure 38A:
Figure 38C:
Figure 39:
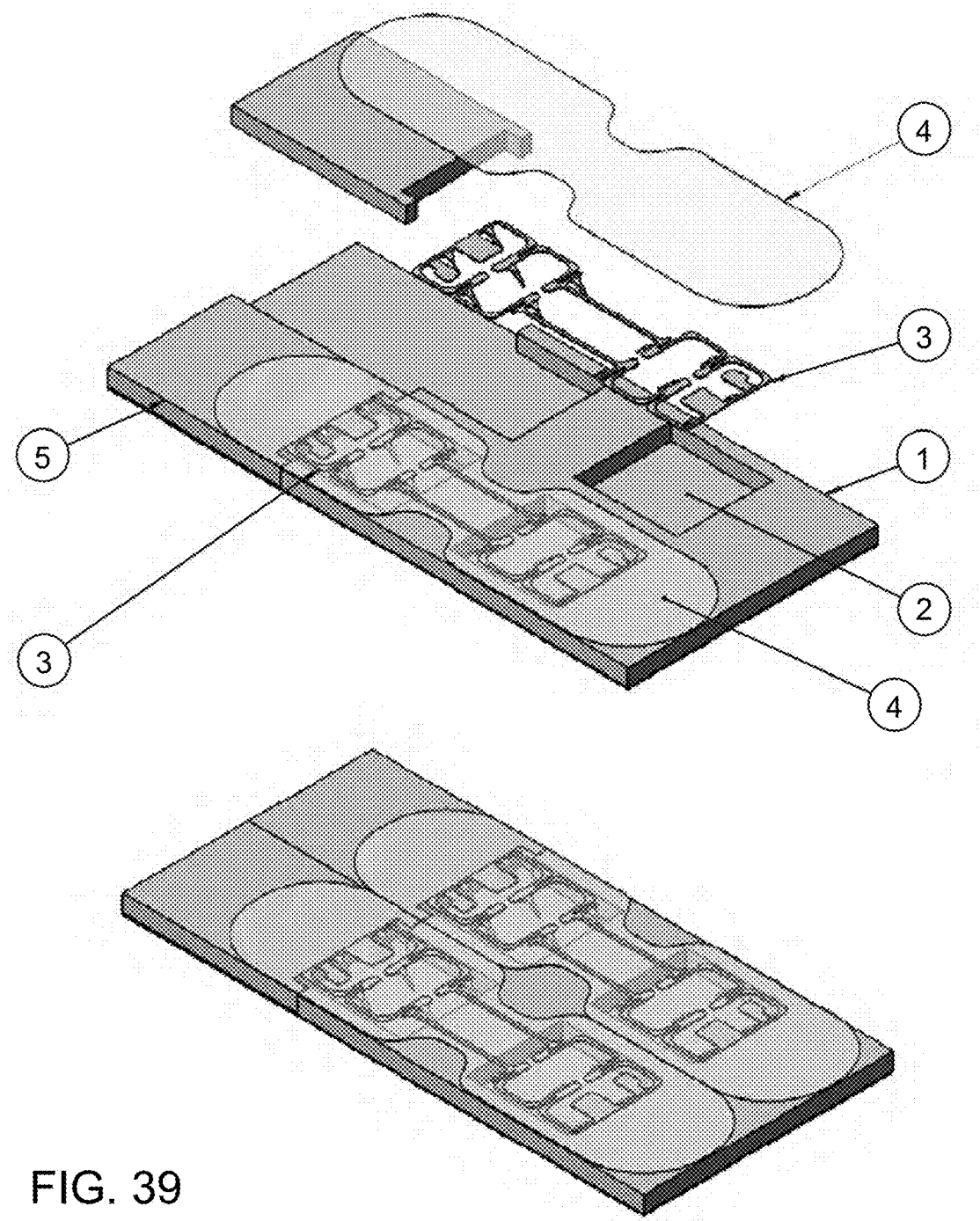
FIG. 39 shows the assembly drawing of the specifications microMend wound closure device utilized in the ongoing open label, single arm human clinical trial discussed in Example 5. 1 shows the foam spacer base; 2 shows the packaging base card; 3 shows the microstructure array (see FIGS. 35A and 35B for specifications of the microstructure array); 4 shows the backing film; and 5 shows the foam tab.
Figure 41B:
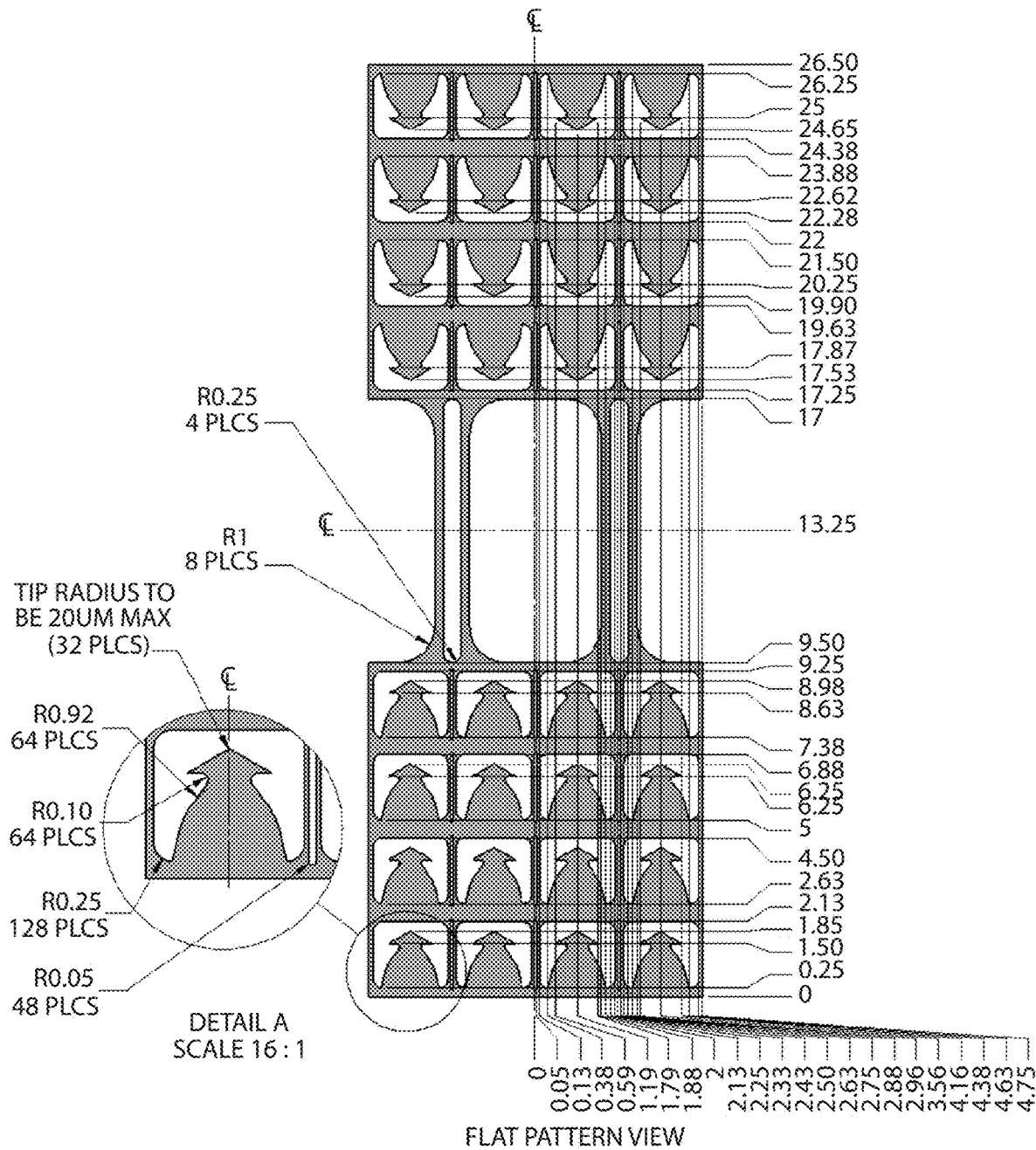

Example 4: Wound Closure—Preliminary Human Clinical Study of Closure of Laceration A 2 cm full thickness laceration to the dorsal surface of the hand of a human subject was closed with a microMend device. FIG. 41 shows the design parameters of the microstructure array included on the microMend devices utilized in this Example. The devices were assembled and packaged as shown in FIG. 39. The backing was made of 2.3 oz/sq.yd. woven polyester cloth with medical-grade acrylic pressure sensitive adhesive coated on one side (backing: Lead-Lok, Inc., Sandpoint, Id.; product #8174-04). FIG. 38 shows pictures of the wound before (FIG. 38A) and after (FIG. 38B) closure with a microMend device. After 7 days, the device was removed and the wound was well-healed with excellent closure (FIG. 38C). Three weeks after wound closure, there was no evidence of inflammation or scar at the wound site (FIG. 38D).

Figure 37:
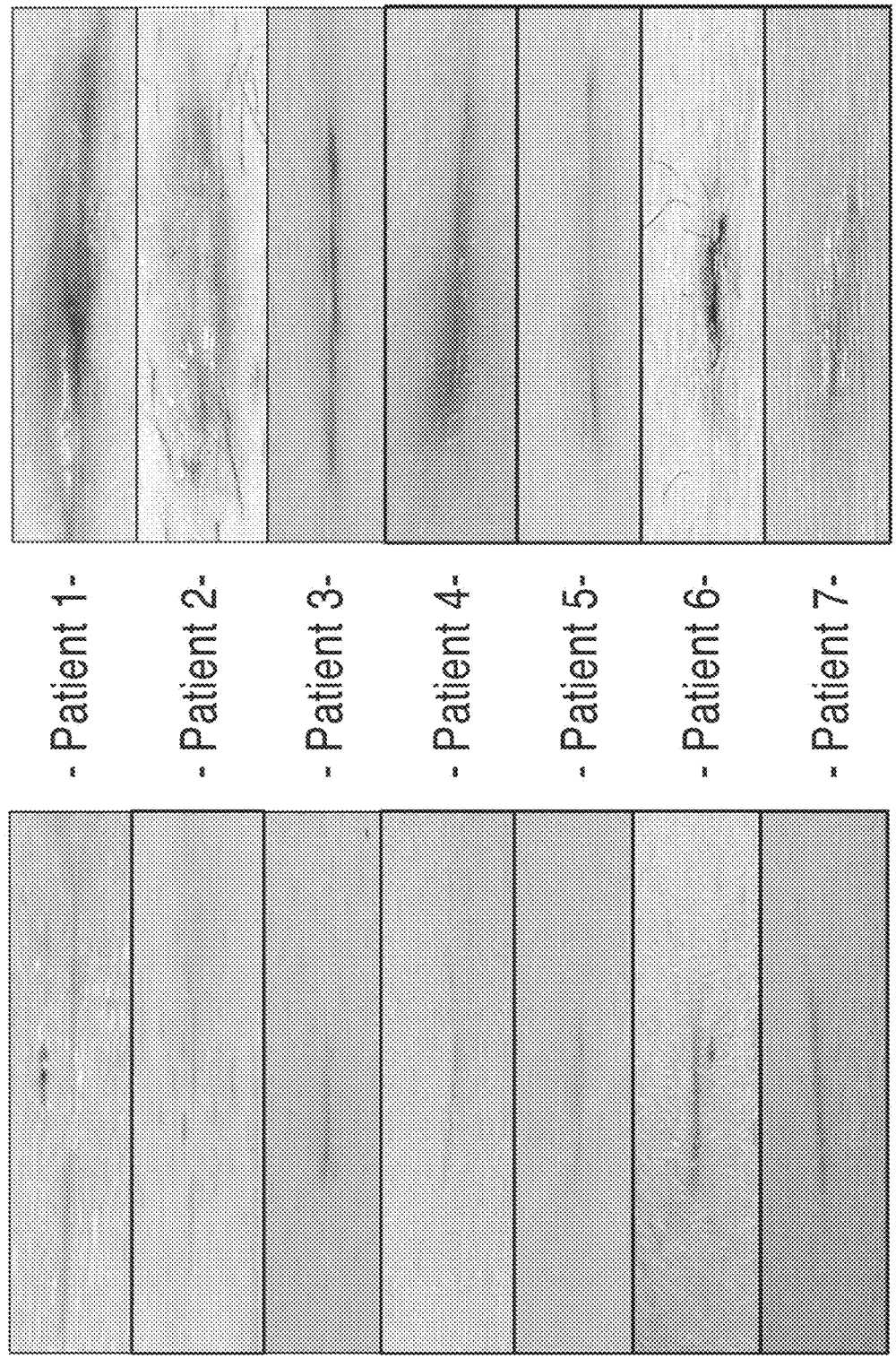
FIG. 37 shows representative human clinical trial results demonstrating that closure of 0.5-2 cm long trochar wounds with microMend devices in 7 human patients results in a pronounced reduction in inflammation and superior wound closure and healing as compared to suture. Photos were taken 30 days after surgery.

Example 5: Wound Closure—Human Clinical Study of Closing Surgical Port Sites after Minimally Invasive Surgeries An open label, single arm study to evaluate closure of skin wounds at port sites using microMend devices in 18 subjects undergoing minimally invasive abdominal and pelvic surgeries (laparoscopic or robotic) was performed, and representative results for the first 7 patients are shown in FIG. 37 and discussed briefly below. Three surgeons in general, gynecologic, and urologic surgery participated in the study.

The intent of the study was to compare skin closure of trochar wounds with microMend to skin closure of trochar wounds with sutures. To do so, one or more skin wounds were closed with suture(s) and one or more wounds closed with microMend in each subject.

Figure 40:
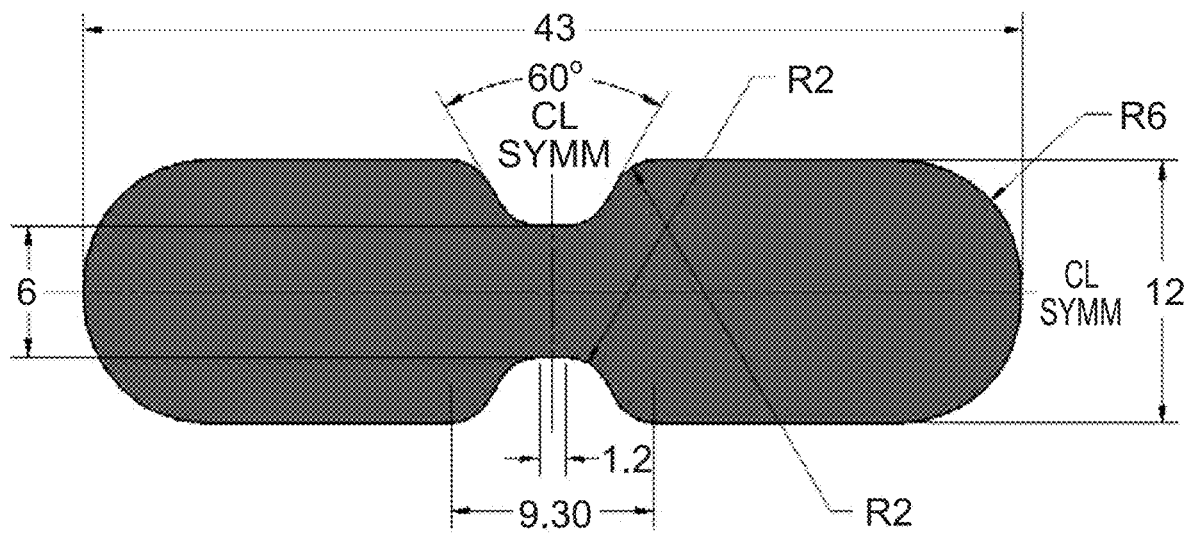
FIG. 40 shows specifications of the backing used in manufacturing the microMend wound closure device utilized in the ongoing open label, single arm human clinical trial discussed in Example 5. Other backings are suitable, such as, e.g., acrylic based adhesive tapes with elastic backing.

A total of 18 evaluable patients enrolled in the study. Evaluations were made via questionnaires completed by surgeons on the day of surgery (Day 0), and by healthcare providers (surgeons and nurses) and patients at 10 days (Day 10) and 30 days (Day 30) after surgery. All collected data on the key parameters were analyzed and included in Table 7 (note: in a small cohort of patients, data were unavailable at some time points).

microMend: This study utilized microMend devices as shown in FIG. 32, which comprise microstructure arrays having six angled microstructures on either side of a bridge portion, all of which microstructures were disposed with their tips pointed in the direction of the bridge portion. Each microstructure had a vertical displacement of approximately 1.05 mm, and was angled from a planar base at 45°. The entire microstructure array/base portion was formed from a single stainless steel (Grade 316) sheet that was 0.004 inches thick, and the array portion was 26.5 mm in length and 8.65 mm in width. Further details regarding the assembly of the device is shown in FIG. 39. Specific design parameters of the microstructure array are shown in FIGS. 35A and 35B. Details regarding the backing of the device are shown in FIG. 40.

For the study, one or more microMend devices are used to close each trocar wound site. The devices and dressings are removed on Day 10 (acceptable range: Days 7-14). Photographs were obtained just prior to and after removal of devices on Day 10 and also at Day 30. Information was also gathered on the surgeon's experience with microMend compared to suture closure as well as on the provider's and patient's subjective assessments of the microMend devices as compared to sutures.

Results

At Day 30, both healthcare providers and patients rated both wound appearance and overall assessment of microMend closure better than sutures in over 90% of the patients. Examples of wound appearance with microMend compared to suture closure at Day 30 are shown in FIG. 37. These data demonstrate that wound closure with microMend leads to a significant reduction in inflammation and superior wound closure and healing resulting in improved appearance and cosmesis as compared to wound closure with suture. Similar results were obtained for the other patients in the study (data not shown).

Patients reported that MicroMend comfort was better than or equal to sutures while wearing and upon removal of the devices. Of note, there was no cases in which microMend was rated worse than sutures by healthcare providers or patients. On Day 0, surgeons rated microMend easier and more rapid to use than sutures for closing wounds in 83% of the patients.

Table 7, below, presents evaluation of surgeons, healthcare providers, and patients that were involved in this clinical study for various parameters including ease of application and removal of the microMend devices, appearance of the healed wounds, comfort of the devices.

TABLE 7

Evaluation of microMend vs. Suture by Healthcare Providers and Patients

|   | Much Better | Somewhat Better | TOTAL BETTER | SAME | WORSE |
|---|---|---|---|---|---|
| SURGEONS (Day 0) | | | | | |
| Ease of use | 28% | 56% | 83% | 0% | 17% |
| Speed | 44% | 34% | 78% | 5% | 17% |
| PROVIDERS (Day 30) | | | | | |
| Appearance | 36% | 57% | 93% | 7% | 0% |
| OVERALL ASSESSMENT | 33% | 58% | 91% | 8% | 0% |
| PATIENTS | | | | | |
| microMend comfort | 19% | 38% | 57% | 43% | 0% |
| Removal comfort | 18% | 29% | 47% | 53% | 0% |

TABLE 7-continued

Evaluation of microMend vs. Suture by Healthcare Providers and Patients

|  | Much Better | Somewhat Better | TOTAL BETTER | SAME | WORSE |
|---|---|---|---|---|---|
| Appearance | 58% | 33% | 91% | 9% | 0% |
| OVERALL ASSESSMENT | 55% | 36% | 91% | 9% | 0% |

Patients reported that MicroMend comfort was better than or equal to sutures while wearing and upon removal of the devices. On Day 0, surgeons rated microMend easier and more rapid to use than sutures for closing wounds in 83% of the patients.

Conclusion:

In this clinical study, healthcare providers and patients strongly preferred microMend to sutures for closing port site wounds associated with minimally invasive surgeries. Importantly, wound appearance was rated better with microMend, which is a benefit for healthcare providers and patients, who can experience scarring with wounds closed with sutures. The comfort with microMend is an advantage for patients in reducing the pain and itching associated with sutures and eliminating the painful process of removing them. Finally, surgeons found microMend easier and more rapid to use than sutures. This study along with the many other benefits of microMend, which include ease of use, time savings, reduced pain, elimination of the need for return clinic visits for device removal and reduced risk of needle sticks, make it an attractive alternative for closing wounds that currently need sutures. Thus, the wound closure devices disclosed herein are superior to traditional wound closure methods.

Example 6: Comparison of Wound Closure, Cosmesis, Dehiscence, and Wound Tensile Force at Failure after Closure of 1.2 cm Wound with Non-Expandable microMend Devices or Sutures This study describes additional variables tested in Study 2 (i.e., closure of 1.2 cm wounds with non-expandable devices A, B, and C), described above in Example 3. All of the experiments described in Example 6 were performed in the same experiment as Study 2 in Example 3.

The primary objectives of this study were as follows:
a) Measure the tensile force at failure of closed wounds 9 days after surgery (Day 9) with devices and sutures removed.
b) Estimate suture tension forces required to keep wounds closed on Day 0.
c) Assess efficacy of wound closure on Days 0, and 9 via subjective observations and photographs.

Secondary objectives included making subjective observations on cosmesis and wound conditions such as inflammation, tissue reaction, and wound dehiscence at Days 0 and 9.

Materials and Methods

Figure 43B:
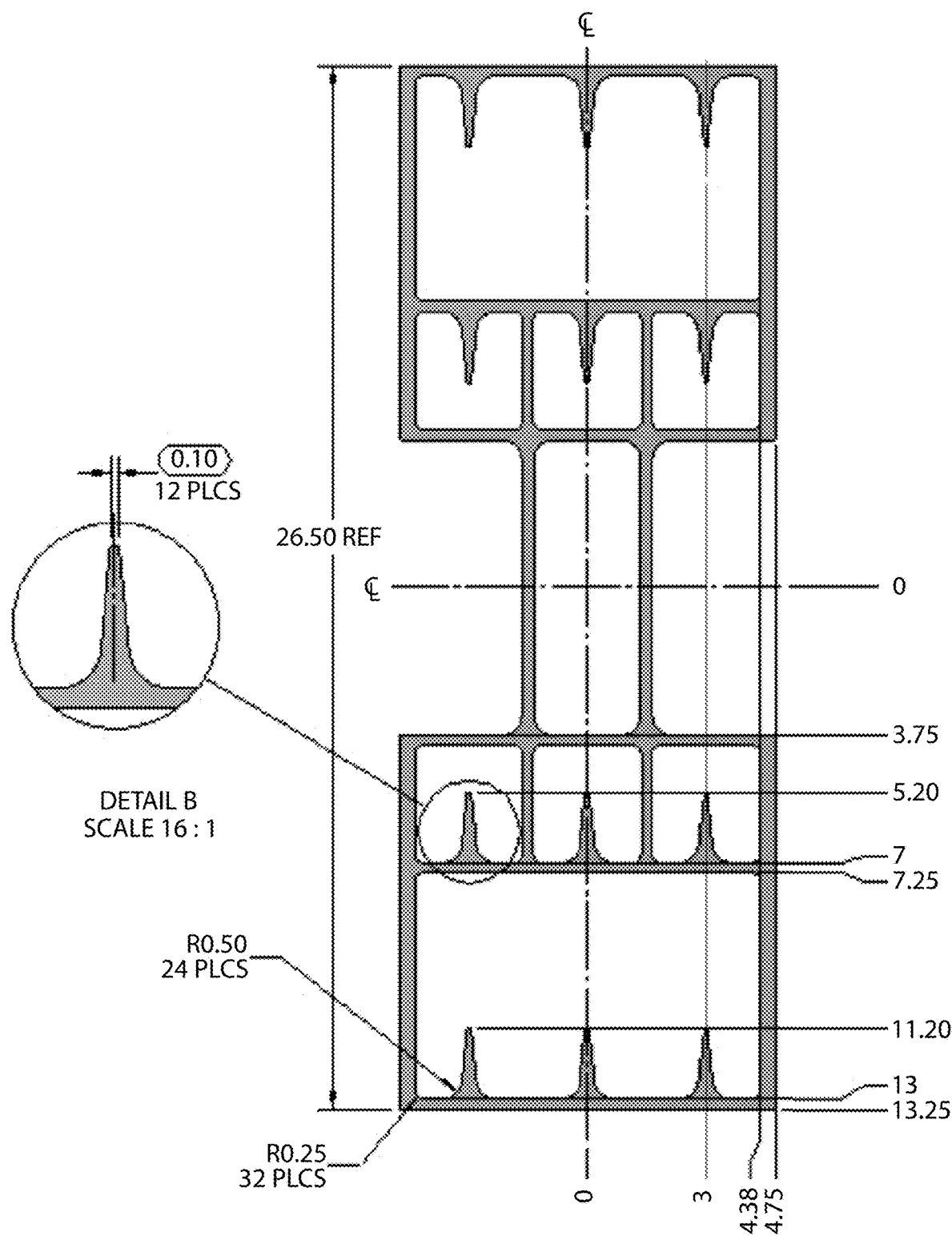

All materials and methods were performed exactly as described in Study 2, Example 3, and simultaneous therewith. The only difference between the studies is the fact that the devices reported on herein in Example 6 were non-expandable. Details regarding these non-expandable microMend devices are described below.

microMend: This study utilized microMend devices as shown in FIG. 42 (Device A—"House" design with 16 microstructures), FIG. 41 (Device B—"Barbed" design with 16 microstructures), and FIG. 43(Device C—"PMMA profile" 6 microstructures). The vertical displacement of the microstructures were as follows: 0.7 mm (Device A); 0.91 mm (Device B), and 1.05 mm (Device C), and all microstructures were angled from a planar base at 45°. The entire microstructure array/base portions were formed from single stainless steel (Grade 316) sheets that were 0.004 inches thick, and the array portion was 26.5 mm in length and 9.5 mm in width. The backing of the devices was inelastic woven polyester cloth with BP 3.5 mil M102 adhesive. Further details regarding the specific design parameters of the microstructure arrays, the complete microMend device, and the specifications of the backing materials and adhesives can be found in FIGS. 41, 42, and 43.

Tensile force at failure tests were performed on Day 9 according to protocol described in Study 2, Example 3.

Results

Tensile Forces of Tissue Treated with microMend Devices

Tensile force at failure of the wounds closed with microMend or sutures are shown in Table 8.

TABLE 8

Tensile force at failure summary - wounds closed by microMend Devices "A", "B", and "C"

| Newtons (N) | Day 0 (N) | Day 0 SD | Day 10 (N) | Day 10 SD | Day 20 (N) | Day 20 SD |
|---|---|---|---|---|---|---|
| Device A | 9.2 | 3.13 | 13.9 | 5.58 | 23.4 | 10.3 |
| Device B | 9.3 | 1.88 | 13.6 | 5.42 | 22.5 | 9.03 |
| Device C | 13.3 | 1.71 | 11.4 | 4.92 | 25.8 | 11.69 |
| Devices A-C Average | 10.6 | 2.24 | 13.0 | 5.31 | 23.9 | 10.34 |
| Sutures | 39.3 | 4.7 | 13.8 | 5.79 | 21.2 | 9.67 |

The average peak tensile force in Newton (N) on Day 20 for the non-expandable microMend device closed wound sites was 23.9 N/12 mm. This was comparable to the peak tensile force on Day 20 of the suture closed wound sites: 21.2 N/12 mm. Notably, as discussed above in Study 2, Example 2, the tensile force at failure of the expandable microMend devices was 26% higher than the strength of the wounds closed with the non-expandable microMend devices and 42% higher than the strength of the wounds closed with sutures.

Conclusions

All the animals in both studies completed the in life portion of the study without complications. All the wounds from both studies that were closed with microMend healed well with no evidence of inflammation or infection observed, whereas, evidence of wound separation and inflammation was observed on several of the suture closed wounds. Expandable microMend devices offer significant improvements in cosmesis and wound closure/strength of healed wound over prior art methods.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

The invention claimed is:

1. A wound closure device for closing a wound in a tissue comprising:
    a microstructure array, the array comprising first and second microstructure array portions fixedly connected at opposite ends of at least one bridge portion that extends in a longitudinal direction extending between the first and second microstructure array portions, wherein the longitudinal direction extends through the first and second microstructure array portions, the first and second microstructure array portions comprising first and second microstructures, respectively, for securing the array to the tissue, and the first and second microstructure array portions at least partially defining first and second structures with spring characteristics, respectively, that lie in-plane with the at least one bridge portion such that the first and second structures with spring characteristics are individually expandable, the at least one bridge portion defining at least one longitudinally extending straight portion without spring characteristics, wherein the at least one bridge portion is longer in the longitudinal direction between the first and second microstructure array portions than in a transverse direction perpendicular to the longitudinal direction, wherein each microstructure comprised on the microstructure array is angled relative to the microstructure array, and wherein each angled microstructure is angled toward the at least one bridge portion.

2. The wound closure device of claim 1, wherein each of the microstructure array portions is integral with the first and second structures with spring characteristics, respectively, and is spaced away from the at least one bridge portion.

3. The wound closure device of claim 1, wherein:
    expandability of at least one of the first and second structures with spring characteristics ranges from about 100.2% to about 105.0% in at least one direction; and
    (i) a spring constant of at least one of the first and second structures with spring characteristics;
    or (ii) a spring constant of the device ranges from about 0.5 N/mm to about 10 N/mm.

4. The wound closure device of claim 1, wherein at least one of the first and second structures with spring characteristics has an approximate shape comprising at least one of a congruent V-shape, a congruent U-shape, a congruent S-shape, a congruent I-shape, a congruent H-shape, a congruent C-shape, a congruent X-shape, a congruent Y-shape, a congruent M-shape, a congruent N-shape, a congruent T-shape, a congruent W-shape, and a congruent Z-shape.

5. The wound closure device of claim 1 wherein at least one of the first and second structures with spring characteristics comprises a first arm portion, a second arm portion, and a curved portion connecting the first arm portion and the second arm portion, the curved portion for operating as a rotational axis such that the first arm rotates relative to the second arm when a force moves the first arm away from the second arm, wherein the first arm portion, the second arm portion, and the curved portion are in-plane with the bridge portion.

6. The wound closure device of claim 5, wherein the microstructure array comprises a support base extending in a plane, and wherein each microstructure, microstructure array portion, structure with spring characteristics, and bridge portion on the wound closure device is monolithically formed from the support base, wherein the first and second microstructures extend transverse to the plane.

7. The wound closure device of claim 6, comprising one bridge portion comprising two longitudinally extending straight portions without spring characteristics, wherein the first and second structures with spring characteristics are configured to expand and contract longitudinally, and wherein a single aperture extends through the support base between the two longitudinally extending straight portions.

8. The wound closure device of claim 6, comprising a backing extending across the support base, wherein the backing is optionally at least one of breathable, stretchable, flexible, elastic, permeable, semi-permeable, impermeable, transparent and opaque.

9. The wound closure device of claim 6, wherein:
    the wound closure device extends along a longitudinal axis;
    the at least one bridge portion extends over a first length in a direction of the longitudinal axis;
    the first and second microstructure array portions each extend over a second length in the direction of the longitudinal axis; and
    the first length is greater than the second length.

10. The wound closure device of claim 1, wherein the expandability of at least one of the first and second structures with spring characteristics is substantially derived from at least one of (i) a geometry of at least one structure with spring characteristics and/or (ii) a material property of at least one structure with spring characteristics, wherein the material property is elasticity.

11. The wound closure device of claim 1, wherein the number of microstructures on each of the first and second microstructure array portions is one of 2, 3, 4, 5, 6, 7, 8, 9, 10, 11, 12, 13, 14, and 15 microstructures.

12. The wound closure device of claim 11, wherein the microstructures on each microstructure array portion are positioned in a staggered arrangement.

13. The wound closure device of claim 1, wherein the microstructure array comprises at least one of a polymer, a metal, a biomaterial, a biodegradable material, and a non-biodegradable material.

14. The wound closure device of claim 13, wherein the microstructure array comprises at least one of aluminum, titanium, stainless steel, a 300 series stainless steel alloy, and 316 stainless steel.

15. The wound closure device of claim 1, wherein at least one of the first and second microstructures is at least one of a microstaple, a microbarb, a microneedle, a microblade, a microanchor, a microhook, a microfishscale, a micropillar, and a microhair.

16. The wound closure device of claim 1, wherein (i) a tip-to-tip distance separating each microstructure on a given microstructure array portion from its nearest microstructure ranges from about 0.5 mm to about 15 mm; (ii) a base-to-tip distance separating each microstructure on a given microstructure array portion from its nearest microstructure ranges from about 0.5 mm to about 15 mm; (iii) at least one microstructure has a height H1 of about 0.1 mm to about 8 mm; about 0.5 mm to about 2 mm; about 1.5 mm or about 3 mm; or about 1.05 mm.

17. The wound closure device of claim 1, wherein:
the wound closure device extends along a longitudinal axis; and
first and second structures with spring characteristics are configured to stretch in a direction of the longitudinal axis.

18. The wound closure device of claim 1, wherein:
the first microstructure array portion comprises a first pair of microstructures;
the second microstructure array portion comprises a second pair of microstructures; and
the first and second microstructure array portions are stretchable such that a first inter-microstructure distance of the first pair of microstructures and a second inter-microstructure distance between the second pair of microstructures are variable.

19. The wound closure device of claim 1, wherein the first microstructure of the first microstructure array portion and the second microstructure of the second microstructure array portion align along a longitudinal centerline of the wound closure device.

20. The wound closure device of claim 1, wherein the first microstructure array portion and the second microstructure array portion each comprise a flexible U-shaped portion projecting toward an interior of the wound closure device such that the flexible U-shaped portion opens toward an exterior of the wound closure device.

21. A wound closure device for closing a wound in a tissue comprising:
a first microstructure array portion comprising:
a first arm portion, a second arm portion, and a first curved portion connecting the first arm portion and the second arm portion to define a first structure with spring characteristics; and
a first microstructure extending from the first arm portion;
a second microstructure array portion comprising:
a third arm portion, a fourth arm portion, and a second curved portion connecting the third arm portion and the fourth arm portion to define a second structure with spring characteristics; and
a second microstructure extending from the third arm portion;
a first longitudinally extending bridge member connecting the first microstructure portion and the second microstructure portion, the first longitudinally extending bridge member comprising a straight portion that defines a first structure without spring characteristics; and
a backing extending across the first microstructure array portion, the second microstructure array portion and the first longitudinally extending bridge member;
wherein the wound closure device extends along a longitudinal axis;
the first longitudinally extending bridge member extends over a first length in a direction of the longitudinal axis between the first microstructure array portion and the second microstructure array portion, the first longitudinally extending bridge member having a width perpendicular to the longitudinal axis that is shorter than the first length;
the first and second microstructure array portions each extend over a second length in the direction of the longitudinal axis from the at least one bridge structure outward, respectively; and
the first length is greater than the second length.

22. A wound closure device comprising:
a first stretchable microstructure portion comprising a first microstructure;
a second stretchable microstructure portion comprising a second microstructure; and
a non-stretchable bridge connecting the first and second stretchable microstructure;
wherein the first stretchable microstructure portion, the first microstructure, the second stretchable microstructure portion, the second microstructure and the non-stretchable bridge comprise a single monolithic structure;
wherein the first microstructure and the second microstructure align along a longitudinal axis of the wound closure device that extends along the non-stretchable bridge;
wherein the first microstructure and the second microstructure are cantilevered from the first stretchable microstructure portion and the second stretchable microstructure portion, respectively; and
wherein the non-stretchable bridge is longer in a longitudinal direction between the first and second stretchable microstructure portions than in a transverse direction perpendicular to the longitudinal direction.

23. The wound closure device of claim 22, wherein the first stretchable microstructure portion and the second stretchable microstructure portion are configured to uniformly stretch along the longitudinal axis.

* * * * *